United States Patent
Casara et al.

(10) Patent No.: US 10,662,173 B2
(45) Date of Patent: May 26, 2020

(54) INDOLE AND PYRROLE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Patrick Casara, Strasbourg (FR); Thierry Le Diguarher, Saint Denis de l'Hôtel (FR); Jean-Michel Henlin, Suresnes (FR); Jérôme-Benoît Starck, Rueil-Malmaison (FR); Arnaud Le Tiran, Croissy sur Seine (FR); Guillaume De Nanteuil, Suresnes (FR); Olivier Geneste, Rueil-Malmaison (FR); James Edward Paul Davidson, Great Shelford (GB); James Brooke Murray, Linton (GB); I-Jen Chen, Cambridge (GB); Claire Walmsley, Ely (GB); Christopher John Graham, Newmarket (GB); Stuart Ray, Milton (GB); Daniel Maddox, Upper Cambourne (GB); Simon Bedford, Harlow (GB)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 15/676,154

(22) Filed: Aug. 14, 2017

(65) Prior Publication Data
US 2017/0342051 A1 Nov. 30, 2017

Related U.S. Application Data

(62) Division of application No. 14/905,877, filed as application No. PCT/FR2014/051884 on Jul. 22, 2014, now Pat. No. 9,765,056.

(30) Foreign Application Priority Data

Jul. 23, 2013 (FR) .................................. 13 57277

(51) Int. Cl.
| | | |
|---|---|---|
| *C07D 401/10* | (2006.01) | |
| *C07D 401/14* | (2006.01) | |
| *C07D 405/14* | (2006.01) | |
| *A61K 31/4709* | (2006.01) | |
| *C07D 471/04* | (2006.01) | |
| *A61K 45/06* | (2006.01) | |
| *A61K 31/4725* | (2006.01) | |
| *A61K 31/496* | (2006.01) | |

(Continued)

(52) U.S. Cl.
CPC ........ *C07D 401/10* (2013.01); *A61K 31/4709* (2013.01); *A61K 31/4725* (2013.01); *A61K 31/496* (2013.01); *A61K 31/5377* (2013.01); *A61K 45/06* (2013.01); *C07D 401/14* (2013.01); *C07D 405/14* (2013.01); *C07D 409/14* (2013.01); *C07D 471/04* (2013.01)

(58) Field of Classification Search
CPC .............. A61K 31/496; A61K 31/4709; A61K 31/4725
See application file for complete search history.

(56) References Cited

U.S. PATENT DOCUMENTS 9,120,791 B2 9/2015 Le Diguarher

FOREIGN PATENT DOCUMENTS

| WO | WO 2006/023778 | 3/2006 |
| WO | WO 2012/162365 | 11/2012 |
| WO | WO 2013/096055 | 6/2013 |

(Continued)

OTHER PUBLICATIONS

Porter (Bioorganic and Medicinal Chemistry Letters, 19 (2009), 230-233).*

(Continued)

*Primary Examiner* — Pancham Bakshi
(74) *Attorney, Agent, or Firm* — Hueschen and Sage

(57) ABSTRACT

Compounds of formula (I):

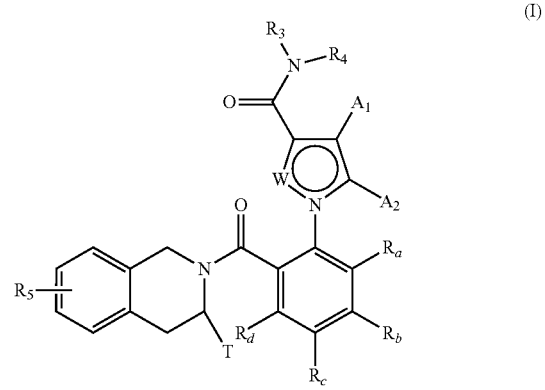

wherein $R_a$, $R_b$, $R_c$, $R_d$, $R_3$, $R_4$, $R_5$, $A_1$, $A_2$, T and W are as defined in the description.
Medicinal products containing the same which are useful in treating conditions requiring a pro-apoptotic agent.

17 Claims, No Drawings

(51) Int. Cl.
*A61K 31/5377* (2006.01)
*C07D 409/14* (2006.01)

(56) References Cited

FOREIGN PATENT DOCUMENTS

WO  WO 2013/096059  6/2013
WO  WO 2013/110890  8/2013

OTHER PUBLICATIONS

International Search Report for PCT/FR2014/051884 dated Nov. 18, 2014.
Porter, et al., Bioorganic and Medicinal Chemistry Letters, vol. 19, No. 1, p. 230-233, Jan. 1, 2009.
Written Opinion for PCT/FR2014/051884, 2014.
Bardwell, et al., Journal of Immunology, 2009, 182, 7482-7489.
Collison, Nature Reviews Rheumatology, 2016, doi: 10.1038/nrrheum.2016.90.
Deng, et al., Cancer Cell, 2007, 12. 171-185.
Hanada, et al., Blood, 1993, 82, 1820-1828.
Juin, et al., Nature Reviews Cancer, 2013, 13, 455-465.
Kelly, et al., Cell Death and Differentiation, 2011, 18, 1414-1424.
Kirkin, et al., Biochimica et Biophysica Acta, 2004, 1644, 229-249.
Letai, et al., Blood, 2005, 106, 5008.
Monnie, et al., Blood, 1997, 90, 1168-1174.
Slavov, et al., Proc. Natl. Acad. Sci. USA, 2009, 106, 4079-4084.
Strasser, et al., Nature Reviews Immunology, 2005, 5, 189-200.
Strasser, et al., Proc. Natl. Acad. Sci. USA, 1991, 88, 8661-8665.
Tsujimoto, et al., Science, 1985, 228, 1440-1443.
Vaux. et al., Nature, 1988, 335, 440-442.
Yip, et al., Oncogene, 2008, 27, 6398-6406.

* cited by examiner

INDOLE AND PYRROLE COMPOUNDS, A PROCESS FOR THEIR PREPARATION AND PHARMACEUTICAL COMPOSITIONS CONTAINING THEM

The present invention relates to new indole and pyrrole compounds, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. and al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colorectal cancer, breast cancer, small-cell lung cancer, non-small-cell lung cancer, bladder cancer, ovarian cancer, prostate cancer, chronic lymphoid leukaemia, follicular lymphoma, myeloma, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer, autoimmune diseases and diseases of the immune system.

The present invention relates more especially to compounds of formula (I):

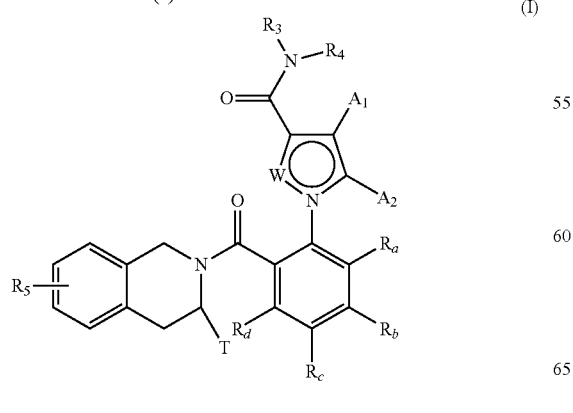

(I)

wherein:
W represents a group $C-A_3$ or a nitrogen atom,
$A_1$, $A_2$ and $A_3$ each independently of the others, represent a hydrogen or halogen atom, a linear or branched polyhalo-$(C_1-C_6)$alkyl, a linear or branched $(C_1-C_6)$alkyl group or a cycloalkyl,
or $A_1$ and $A_2$ form together with the carbon atoms carrying them a cycloalkyl or a benzo ring, these two groups being optionally substituted by a halogen atom, a linear or branched $(C_1-C_6)$alkyl group, a linear or branched polyhalo-$(C_1-C_6)$alkyl group, a hydroxy group, a linear or branched $(C_1-C_6)$alkoxy group or —COOH, it being understood that W necessarily represents a group $C-A_3$ when $A_1$ and $A_2$ independently of one another represent a hydrogen or halogen atom, a linear or branched polyhalo-$(C_1-C_6)$alkyl, a linear or branched $(C_1-C_6)$alkyl group or a cycloalkyl,
T represents a hydrogen atom, a linear or branched $(C_1-C_6)$alkyl group optionally substituted by from one to three halogen atoms, a group $(C_1-C_4)$alkyl-$NR_1R_2$, or a group $(C_1-C_4)$alkyl-$OR_6$,
$R_1$ and $R_2$ independently of one another represent a hydrogen atom or a linear or branched $(C_1-C_6)$alkyl group,
or $R_1$ and $R_2$ form with the nitrogen atom carrying them a heterocycloalkyl,
$R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl moiety is linear or branched, a heterocycloalkyl group, an aryl group or a heteroaryl group, it being understood that one or more carbon atoms of the preceding groups, or carbon atoms of their possible substituents, may be deuterated,
$R_4$ represents an aryl group, a heteroaryl group, a cycloalkyl group or a linear or branched $(C_1-C_6)$alkyl group, it being understood that one or more carbon atoms of the preceding groups, or carbon atoms of their possible substituents, may be deuterated,
$R_5$ represents a hydrogen or halogen atom, a linear or branched $(C_1-C_6)$alkyl group, or a linear or branched $(C_1-C_6)$alkoxy group,
$R_6$ represents a hydrogen atom or a linear or branched $(C_1-C_6)$alkyl group,
$R_a$, $R_b$, $R_c$ and $R_d$, each independently of the others, represent $R_7$, a halogen atom, a linear or branched $(C_1-C_6)$alkoxy group, a hydroxy group, a linear or branched polyhalo-$(C_1-C_6)$alkyl group, a trifluoromethoxy group, —$NR_7R_7'$, nitro, $R_7$—CO—$(C_0-C_6)$alkyl-, $R_7$—CO—NH—$(C_0-C_6)$alkyl-, $NR_7R_7'$—CO—$(C_0-C_6)$alkyl-, $NR_7R_7'$—CO-alkyl$(C_0-C_6)$—O—, $R_7$—$SO_2$—NH—$(C_0-C_6)$alkyl-, $R_7$—NH—CO—NH—$(C_0-C_6)$alkyl-, $R_7$—O—CO—NH—$(C_0-C_6)$alkyl-, a heterocycloalkyl group, or the substituents of one of the pairs $(R_a,R_b)$, $(R_b,R_c)$ or $(R_c,R_d)$ form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched $(C_1-C_6)$alkyl, $R_7$ and $R_7'$ each independently of the other, represent a hydrogen, a linear or branched ($C_1$-$C_6$)alkyl group, a linear or branched ($C_2$-$C_6$)alkenyl group, a linear or branched ($C_2$-$C_6$)alkynyl group, an aryl group or a heteroaryl group, or $R_7$ and $R_7'$ form together with the nitrogen atom carrying them a heterocycle composed of from 5 to 7 ring members, it being understood that when the compound of formula (I) contains a hydroxy group, the latter may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O$]$_n CH_3$), or —PO($O^-M_1^+$)(O[$CH_2CH_2O$]$_n CH_3$), wherein M and M' independently of one another represent a hydrogen atom, a linear or branched ($C_1$-$C_6$)alkyl group, a linear or branched ($C_2$-$C_6$)alkenyl group, a linear or branched ($C_2$-$C_6$)alkynyl group, a cycloalkyl or a heterocycloalkyl, both composed of from 5 to 6 ring members, while $M_1^+$ and $M_2^+$ independently of one another represent a pharmaceutically acceptable monvalent cation, $M_3^{2+}$ represents a pharmaceutically acceptable divalent cation, and n is an integer from 1 to 5, it also being understood that:

- "aryl" means a phenyl, naphthyl, biphenyl or indenyl group,
- "heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
- "cycloalkyl" means any mono- or bi-cyclic, non-aromatic, carbocyclic group containing from 3 to 10 ring members,
- "heterocycloalkyl" means any mono- or bi-cyclic, non-aromatic group composed of from 3 to 10 ring members and containing from 1 to 3 hetero atoms selected from oxygen, sulphur, SO, $SO_2$ and nitrogen, it being possible for the aryl, heteroaryl, cycloalkyl and heterocycloalkyl groups so defined and the groups alkyl, alkenyl, alkynyl and alkoxy to be substituted by from 1 to 3 groups selected from optionally substituted, linear or branched ($C_1$-$C_6$)alkyl, ($C_3$-$C_6$)spiro, optionally substituted linear or branched ($C_1$-$C_6$)alkoxy, ($C_1$-$C_6$)alkyl-S—, hydroxy, oxo (or N-oxide where appropriate), nitro, cyano, —COOR', —OCOR', NR'R'', linear or branched polyhalo-($C_1$-$C_6$)alkyl, trifluoromethoxy, ($C_1$-$C_6$)alkylsulphonyl, halogen, optionally substituted aryl, heteroaryl, aryloxy, arylthio, cycloalkyl, heterocycloalkyl optionally substituted by one or more halogen atoms or alkyl groups, it being understood that R' and R'', each independently of the other, represent a hydrogen atom or an optionally substituted, linear or branched ($C_1$-$C_6$)alkyl group, to their enantiomers and diastereoisomers, and to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred compounds of the invention include the compounds of formula (I) wherein $R_4$ represents a phenyl substituted in the para-position by a group of the formula —OPO(OM)(OM'), —OPO(OM)($O^-M_1^+$), —OPO($O^-M_1^+$)($O^-M_2^+$), —OPO($O^-$)($O^-$)$M_3^{2+}$, —OPO(OM)(O[$CH_2CH_2O$]$_n CH_3$), or —OPO($O^-M_1^+$)(O[$CH_2CH_2O$]$_n CH_3$), wherein M and M' independently of one another represent a hydrogen atom, a linear or branched ($C_1$-$C_6$)alkyl group, a linear or branched ($C_2$-$C_6$)alkenyl group, a linear or branched ($C_2$-$C_6$)alkynyl group, a cycloalkyl or a heterocycloalkyl, both composed of from 5 to 6 ring members, while $M_1^+$ and $M_2^+$ independently of one another represent a pharmaceutically acceptable monovalent cation, $M_3^{2+}$ represents a pharmaceutically acceptable divalent cation, and n is an integer from 1 to 5, it being understood that the phenyl group may be optionally substituted by one or more halogen atoms.

Advantageously, W represents a group C—H, while $A_1$ and $A_2$ represent a hydrogen atom and a methyl group, respectively.

Alternatively, W represents a group C—H, while $A_1$ and $A_2$ together with the carbon atoms carrying them form a cyclohexenyl or a benzo ring optionally substituted by a halogen atom.

In another embodiment of the invention, W represents a nitrogen atom, while $A_1$ and $A_2$ together with the carbon atoms carrying them form a benzo ring.

T preferably represents a group selected from methyl, aminomethyl, dimethylaminomethyl, morpholinylmethyl, (4-methyl-1-piperazinyl)methyl, (3 aR,6aS)-hexahydrocyclopenta-[c]pyrrol-2(1H)-ylmethyl, (4,4-difluoropiperidin-1-yl)methyl, (4-cyclopentylpiperazin-1-yl)methyl, (4-cyclobutylpiperazin-1-yl)methyl, pyrrolidin-1-ylmethyl, piperidin-1-ylmethyl or 2-(morpholin-4-yl)ethyl. Yet more preferably, T represents a morpholinylmethyl or (4-methyl-1-piperazinyl)methyl group.

Advantageously, $R_a$, $R_b$, $R_c$ and $R_d$, each independently of the others, represent $R_7$, a halogen atom, a linear or branched ($C_1$-$C_6$)alkoxy group, a hydroxy group, a linear or branched polyhalo-($C_1$-$C_6$)alkyl group, a trifluoromethoxy group, —$NR_7R_7'$, nitro, or the substituents of one of the pairs ($R_a$,$R_b$), ($R_b$,$R_c$) or ($R_c$,$R_d$) form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched ($C_1$-$C_6$)-alkyl.

In preferred compounds of the invention, $R_a$ and $R_d$ each represent a hydrogen atom and ($R_b$,$R_c$), together with the carbon atoms carrying them, form one of the following groups: optionally substituted 1,3-dioxolane; optionally substituted 1,4-dioxane; cyclopentane; tetrahydrofuran; 2,3-dihydrofuran; or $R_a$, $R_c$ and $R_d$ each represent a hydrogen atom and $R_b$ represents a hydroxy or methoxy group, a halogen atom, a trifluoromethyl or trifluoromethoxy group. Yet more preferably:

$R_a$ and $R_d$ each represent a hydrogen atom and ($R_b$,$R_c$), together with the carbon atoms carrying them, form a 1,3-dioxolane group, or $R_a$, $R_c$ and $R_d$ each represent a hydrogen atom and $R_b$ represents a halogen atom.

Alternatively, one to two of the groups $R_a$, $R_b$, $R_c$, $R_d$ represent a halogen atom, while the others represent a hydrogen atom.

In another embodiment of the invention, $R_a$ and $R_d$ each represent a hydrogen atom, $R_b$ represents a hydrogen, a halogen, a hydroxy or methoxy group, and $R_c$ is selected from one of the following groups: hydroxy, methoxy, amino, 3-phenoxyazetidine, 2-(phenyl-sulphanyl)acetamide or 2-(phenoxy)acetamide.

Preferred groups $R_4$ are the following: butyl; phenyl; 4-hydroxyphenyl; 4-methoxyphenyl; 4-methylphenyl; 3-chloro-4-hydroxyphenyl; 3-fluoro-4-hydroxyphenyl. Yet more preferably, $R_4$ represents a 4-hydroxyphenyl group.

In preferred compounds of the invention, $R_3$ represents a linear $(C_1-C_6)$alkyl (preferably butyl or 2-phenylethyl), cycloalkyl (preferably cyclohexyl), aryl or heteroaryl group, all of which are optionally substituted. The aryl and heteroaryl groups are particularly preferred. Finally, $R_3$ preferably represents a group selected from phenyl, 1H-indole, benzothiophene, benzofuran, 2,3-dihydro-1H-indole, 1H-indazole, 2,3-dihydro-1H-isoindole, 1H-pyrrolo[2,3-b]pyridine, phenoxyphenyl, 2,3-dihydro-1H-pyrrolo[2,3-b]pyridine, 1H-pyrrole, these groups optionally containing one or more substituents selected from halogen, linear or branched $(C_1-C_6)$alkyl, trifluoromethoxy, 4-methylpiperazinyl, linear or branched $(C_1-C_6)$alkoxy, and cyano.

Preferred compounds according to the invention are included in the following group:
N-(4-hydroxyphenyl)-1-{6-[(3S)-3-(morpholin-4-ylmethyl)-1,2,3,4-tetrahydroisoquinoline-2-carbonyl]-2H-1,3-benzodioxol-5-yl}-N-phenyl-1H-indole-3-carboxamide,
N-(4-hydroxyphenyl)-N-(1-methyl-1H-pyrrolo[2,3-b]pyridin-5-yl)-1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indole-3-carboxamide,
1-(5-chloro-2-{[(3S)-3-(morpholin-4-ylmethyl)-3,4-dihydroisoquinolin-2(1H)-yl]carbonyl}phenyl)-N-(4-hydroxyphenyl)-4,5-dimethyl-N-(1-methyl-2,3-dihydro-1H-pyrrolo[2,3-b]pyridin-5-yl)-1H-pyrrole-3-carboxamide,
1-(5-chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-4,5-dimethyl-1H-pyrrole-3-carboxamide,
N-(4-hydroxyphenyl)-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide,
N-(4-hydroxyphenyl)-N-(1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide,
N-(4-hydroxyphenyl)-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide,
1-(5-chloro-2-{[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-5-methyl-1H-pyrrole-3-carboxamide,
1-(5-chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1H-indole-3-carboxamide,
N-(4-hydroxyphenyl)-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide,
their enantiomers and diastereoisomers, and addition salts thereof with a pharmaceutically acceptable acid or base.

The invention relates also to a process for the preparation of a compound of formula (I), which process is characterised in that there is used as starting material the compound of formula (II):

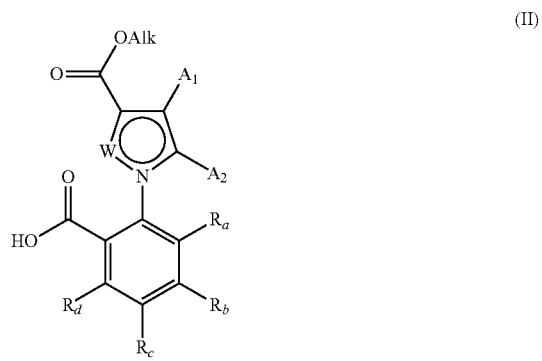

wherein Alk represents a $(C_1-C_6)$alkyl group and W, $A_1$, $A_2$, $R_a$, $R_b$, $R_c$, $R_d$ are as defined for formula (I), which compound of formula (II) is then subjected to peptide coupling with a compound of formula (III):

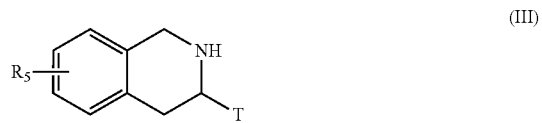

wherein T and $R_5$ are as defined for formula (I),
to yield the compound of formula (IV):

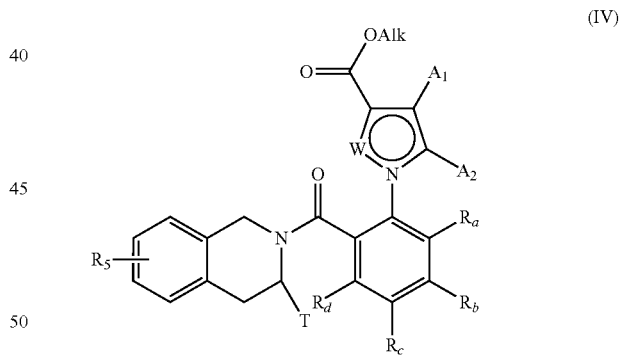

wherein Alk is as defined hereinbefore and W, $A_1$, $A_2$, $R_a$, $R_b$, $R_c$, $R_d$, $R_5$ and T are as defined for formula (I), the ester function of which compound of formula (IV) is hydrolysed to yield the corresponding carboxylic acid or carboxylate, which may be converted into an acid derivative such as the corresponding acyl chloride or anhydride before being coupled with an amine $NHR_3R_4$ wherein $R_3$ and $R_4$ have the same meanings as for formula (I), which may optionally be subjected to the action of a pyrophosphate or phosphonate compound under basic conditions, to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that, at any time considered appropriate in the course of the above-described process, certain groups (hydroxy, amino . . . ) of the reagents or intermediates of synthesis may be protected and then deprotected according to the requirements of synthesis.

More particularly, when one of the groups $R_3$ or $R_4$ of the amine $NHR_3R_4$ is substituted by a hydroxy function, the latter may be subjected beforehand to a protection reaction prior to any coupling with the carboxylic acid formed from the compound of formula (IV), or with a corresponding acid derivative thereof, the resulting protected compound of formula (I) subsequently undergoes a deprotection reaction and is then optionally converted into one of its addition salts with a pharmaceutically acceptable acid or base.

Alternatively, the compounds of formula (I) may be obtained according to the following preparation process, which is characterised in that there is used as starting material the compound of formula (V) as defined below:

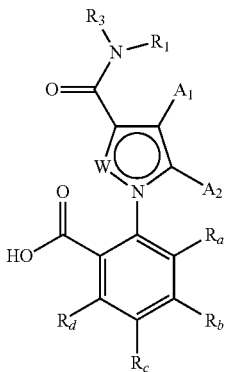

(V)

wherein W, $A_1$, $A_2$, $R_a$, $R_b$, $R_c$, $R_d$, $R_3$ and $R_4$ are as defined for formula (I), which compound of formula (V) is then subjected to peptide coupling with a compound of formula (III):

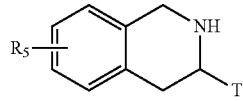

(III)

wherein T and $R_5$ are as defined for formula (I), the compound so obtained optionally being subjected to the action of a pyrophosphate or phosphate compound under basic conditions to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that, at any time considered appropriate in the course of the above-described process, certain groups (hydroxy, amino . . . ) of the reagents or intermediates of synthesis may be protected and then deprotected according to the requirements of synthesis.

The compounds of formulae (II), (III), (V) and the amine $NHR_3R_4$ are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers, auto-immune diseases and diseases of the immune system.

More especially, the compounds according to the invention will be useful in the treatment of chemo- or radio-resistant cancers, and in malignant haemopathies and small-cell lung cancer.

Among the cancer treatments envisaged there may be mentioned, without implying any limitation, the treatment of cancers of the bladder, brain, breast and uterus, chronic lymphoid leukaemias, colorectal cancer, cancers of the esophagus and liver, lymphoblastic leukaemias, non-Hodgkin lymphomas, melanomas, malignant haemopathies, myelomas, ovarian cancer, non-small-cell lung cancer, prostate cancer and small-cell lung cancer.

Among non-Hodgkin lymphomas, there may be mentioned more preferably follicular lymphomas, mantle cell lymphomas, diffuse large B-cell lymphomas, small lymphocytic lymphomas and marginal zone B-cell lymphomas.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, anti-metabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn., 13, 2000, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol., 2001, 74(4):257-75), the protein Z derivative from the domain B of staphylococcal protein A, thioredoxin A or any protein with a repeated domain such as an "ankyrin repeat" (Kohl et al., PNAS, 2003, vol. 100, No. 4, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention without limiting it in any way.

GENERAL PROCEDURES

All reagents and anhydrous solvents are obtained from commercial sources and were used without further purification or drying. Flash chromatography is performed on an ISCO CombiFlash Rf 200i apparatus with pre-packed silica-gel cartridges (SiliaSep™ F60 (40-63 µm, 60 Å). Thin layer chromatography was conducted with 5×10 cm plates coated with Merck Type 60 $F_{254}$ silica gel. Microwave heating was performed with a CEM Discover® SP apparatus.

Analytical LC-MS

The compounds of the invention were characterised by high-performance liquid chromatography coupled with mass spectroscopy (HPLC-MS) on either an Agilent HP1200 rapid-resolution apparatus coupled to a 6140 mass detector with a multi-mode source (m/z range 150 to 1000 atomic mass units or amu) or an Agilent HP1100 apparatus coupled to a 1946D mass detector with an electrospray ionisation source (m/z range 150 to 1000 amu). The conditions and methods listed below are identical for both machines.
Detection: UV detection at 230, 254 and 270 nm.
Injection Volume: 2 µL
Mobile Phases: A—Water+10 mMol/ammonium formate+ 0.08% (v/v) formic acid at pH ca 3.5.
B—95% Acetonitrile+5% A+0.08% (v/v) formic acid
Method a (3.75 Min; Either Positive (Pos) or Positive and Negative (Pos/Neg) Ionisation)
Column: Gemini 5 µm, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 2 |
| 0.25 | 95 | 5 | 2 |
| 2.50 | 95 | 5 | 2 |
| 2.55 | 5 | 95 | 3 |
| 3.60 | 5 | 95 | 3 |
| 3.65 | 5 | 95 | 2 |
| 3.70 | 95 | 5 | 2 |
| 3.75 | 95 | 5 | 2 |

Method B (1.9 Min; Either Positive (Pos) or Positive and Negative (Pos/Neg) Ionisation)
Column: Gemini 5 µm, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 1.1 |
| 0.12 | 95 | 5 | 1.1 |
| 1.30 | 5 | 95 | 1.1 |
| 1.35 | 5 | 95 | 1.7 |
| 1.85 | 5 | 95 | 1.7 |
| 1.90 | 5 | 95 | 1.1 |
| 1.95 | 95 | 5 | 1.1 |

Preparative HPLC

Certain compounds of the invention were purified by preparative HPLC on a Waters FractionLynx MS apparatus with autopurification system, equipped with a Gemini® 5 µm C18(2), 100 mm×20 mm i.d. (Phenomenex) column, operating at a flow of 20 $cm^3 \cdot min^{-1}$ with a diode array UV detector (210-400 nm) and a fraction collector coupled with mass spectroscopy. The gradients used for each of the components are shown in Table 1.

At pH 4: solvent A=10 mM ammonium acetate in HPLC grade water+0.08% v/v formic acid. Solvent B=95% v/v HPLC grade acetonitrile+5% v/v solvent A+0.08% v/v formic acid.

At pH 9: solvent A=10 mM ammonium acetate in HPLC grade water+0.08% v/v ammonia solution. Solvent B=95% v/v HPLC grade acetonitrile+5% v/v solvent A+0.08% v/v ammonia solution.

The mass spectrometer is a Waters Micromass ZQ2000 apparatus, operating by electrospray ionisation in positive or negative mode, with a molecular weight detection range of from 150 to 1000.

Preparation 1: 2-[4-(Ethoxycarbonyl)-2-methyl-1H-pyrrol-1-yl]benzoic Acid

To a solution of 8.3 g of 2-aminobenzoic acid (48 mmol) in acetic acid (20 mL) there are added 8.7 g of ethyl 4-oxopentanoate (prepared according to the method described in WO2005/040128). The whole is then heated at reflux overnight. The reaction mixture is then evaporated to dryness and purified by chromatography over silica gel (dichloromethane/EtOH gradient). The title product is obtained in the form of an oil.

$^1$H NMR: δ (400 MHz; dmso-d6; 300K): 13.0 (m, 1H OH); 7.91 (d, 1H, aryl); 7.70 (t, 1H, aryl); 7.62 (t, 1H, aryl);

7.40 (d, 1H, aryl); 7.30 (s, 1H, pyrrole); 6.30 (s, 1H, pyrrole); 4.18 (q, 2H, OCH$_2$CH$_3$); 1.95 (t, 3H, OCH$_2$CH$_3$).

IR: v: —OH: 2800-2000 cm$^{-1}$ acid; v: C═O 1716 and 1667 cm$^{-1}$; v: C═C 1600 cm$^{-1}$ Preparation 2: 4-(Benzyloxy)-2-[4-(ethoxycarbonyl)-2-methyl-1H-pyrrol-1-yl]-benzoic Acid The title compound is obtained in accordance with the process of Preparation 1, replacing 2-aminobenzoic acid with 2-amino-4-benzyloxy-benzoic acid.

Preparation 3: 2-[4-(Ethoxycarbonyl)-2-methyl-1H-pyrrol-1-yl]-4-(trifluoro-methyl)benzoic Acid The title compound is obtained in accordance with the process of Preparation 1, replacing 2-aminobenzoic acid with 2-amino-4-(trifluoromethyl)benzoic acid.

Preparation 4: 4-Chloro-2-[4-(ethoxycarbonyl)-2-methyl-1H-pyrrol-1-yl]benzoic Acid The title compound is obtained in accordance with the process of Preparation 1, replacing 2-aminobenzoic acid with 2-amino-4-chlorobenzoic acid.

Preparation 5: 4-Fluoro-2-[4-(ethoxycarbonyl)-2-methyl-1H-pyrrol-1-yl]benzoic Acid The title compound is obtained in accordance with the process of Preparation 1, replacing 2-aminobenzoic acid with 2-amino-4-fluorobenzoic acid.

Preparation 6: 4,5-Dibromo-2-[4-(ethoxycarbonyl)-2-methyl-1H-pyrrol-1-yl]-benzoic Acid The title compound is obtained in accordance with the process of Preparation 1, replacing 2-aminobenzoic acid with 2-amino-4,5-dibromobenzoic acid.

Preparation 7: 2-Chloro-6-[4-(ethoxycarbonyl)-2-methyl-1H-pyrrol-1-yl]benzoic Acid The title compound is obtained in accordance with the process of Preparation 1, replacing 2-aminobenzoic acid with 2-amino-6-chlorobenzoic acid.

Preparation 8: 2-[4-(Ethoxycarbonyl)-2-methyl-1H-pyrrol-1-yl]-5-(trifluoro-methoxy)benzoic Acid The title compound is obtained in accordance with the process of Preparation 1, replacing 2-aminobenzoic acid with 2-amino-5-(trifluoromethoxy)benzoic acid.

Preparation 9: 2-[4-(Ethoxycarbonyl)-2-methyl-1H-pyrrol-1-yl]-4,5-difluorobenzoic Acid The title compound is obtained in accordance with the process of Preparation 1, replacing 2-aminobenzoic acid with 2-amino-4,5-difluorobenzoic acid.

Preparation 10: 4-Bromo-2-[4-(ethoxycarbonyl)-2-methyl-1H-pyrrol-1-yl]benzoic Acid The title compound is obtained in accordance with the process of Preparation 1, replacing 2-aminobenzoic acid with 2-amino-4-bromobenzoic acid.

Preparation 11: 6-[4-(Ethoxycarbonyl)-2-methyl-1H-pyrrol-1-yl]-1,3-benzodioxole-5-carboxylic Acid The title compound is obtained in accordance with the process of Preparation 1, replacing 2-aminobenzoic acid with 6-amino-1,3-benzodioxole-5-carboxylic acid (obtained from 6-nitro-1,3-benzodioxole-5-carbaldehyde in accordance with a protocol from the literature: N. Mahindoo et al., Med Chem. Res. 14(6), 347, 2006).

Preparation 12: 4-Chloro-2-[4-(ethoxycarbonyl)-2-methyl-1H-pyrrol-1-yl]-5-fluorobenzoic Acid The title compound is obtained in accordance with the process of Preparation 1, replacing 2-aminobenzoic acid with 2-amino-4-chloro-5-fluorobenzoic acid.

Preparation 13: 5-Bromo-2-[4-(ethoxycarbonyl)-2-methyl-1H-pyrrol-1-yl]-benzoic Acid The title compound is obtained in accordance with the process of Preparation 1, replacing 2-aminobenzoic acid with 2-amino-5-bromobenzoic acid.

Preparation 14: 6-[3-(Methoxycarbonyl)-1H-indol-1-yl]-1,3-benzodioxole-5-carboxylic Acid To a solution of 2 g (7.8 mmol) of methyl 2-(2-bromophenyl)-3-oxopropanoate (prepared in accordance with Heterocycles, 2008 2973-2980) in 20 mL of methanol there are added 1.4 g (7.8 mmol) of 6-amino-1,3-benzodioxole-5-carboxylic acid (obtained in accordance with a protocol from the literature: N. Mahindoo et al., Med Chem. Res. 14(6), 347, 2006). The reaction mixture is stirred for 48 hours at ambient temperature and then evaporated to dryness. There are then added in succession 73 mg of CuI (0.38 mmol), 3.3 g of K$_3$PO$_4$ (15.6 mmol), 0.9 mL (15.6 mmol) of ethylene glycol and 31 mL of dimethylformamide (DMF). The reaction mixture is then heated at 80° C. for 15 hours. The solvents are evaporated off, and 200 mL of a 1M aqueous hydrochloric acid solution are added to the residue. This aqueous phase is extracted with ethyl acetate (3×100 mL). The organic phases are combined and dried over magnesium sulphate and then filtered and evaporated to dryness. The crude product so obtained is then purified by chromatography over silica gel (dichloromethane/methanol gradient) before being triturated in a dichloromethane/diisopropyl ether mixture to yield the expected product in the form of a powder.

$^1$H NMR: δ (400 MHz; dmso-d6; 300K): 12-13 (m, 1H, CO$_2$H); 8.10 (s, 1H, aromatic H); 8.05 (dd, 1H, H indole); 7.45 (s, 1H, aromatic H); 7.25 (m, 2H, H indole); 7.05 (d, 1H, H indole); 6.25 (s, 2H, methylenedioxy); 3.85 (s, 3H, OCH3).

IR: ν OH: 3100-2500 cm$^{-1}$; v: >C═O: 1687 cm$^{-1}$ (split band)

Preparation 15: 4-Bromo-2-[3-(methoxycarbonyl)-1H-indol-1-yl]benzoic Acid

The title compound is obtained in accordance with the process of Preparation 14, replacing 6-amino-1,3-benzodioxole-5-carboxylic acid with 2-amino-4-bromobenzoic acid.

Preparation 16: 4-Chloro-2-[3-(methoxycarbonyl)-1H-indol-1-yl]benzoic Acid

The title compound is obtained in accordance with the process of Preparation 14, replacing 6-amino-1,3-benzodioxole-5-carboxylic acid with 2-amino-4-chlorobenzoic acid.

Preparation 17: 2,4-Dichloro-6-[4-(ethoxycarbonyl)-2-methyl-1H-pyrrol-1-yl]-benzoic Acid The title compound is obtained in accordance with the process of Preparation 1, replacing 2-aminobenzoic acid with 2-amino-4,6-dichlorobenzoic acid.

Preparation 18: 6-[4-(Ethoxycarbonyl)-2-methyl-1H-pyrrol-1-yl]-2,3-dihydro-1H-indene-5-carboxylic Acid This anthranilic acid derivative is prepared in 2 steps in accordance with the protocol from the literature (T. Yoshino et al., *Chemistry letters*, 38(3), 200, 2009) starting from 20 g (150 mmol) of 2,3-dihydro-1H-inden-5-amine. The title product is obtained, as well as 8% of its regioisomer, which is removed by acid-base washing.

$^1$H NMR: δ (400 MHz; dmso-d6; 300K): 9.5-7.5 (m, 1H, COOH); 7.55 (s, 1H, aromatic H); 6.55 (s, 1H, aromatic H); 2.7 (m, 4H, H-indane); 1.95 (m, 2H, H-indane)

IR: ν: NH$_2$: 3494-3384 cm$^{-1}$; ν: OH: 3000-2200 cm$^{-1}$ (OH acid); cm$^{-1}$; ν: >C=O: 1672 cm$^{-1}$

Preparation 19: 6-[3-(Ethoxycarbonyl)-4,5,6,7-tetrahydro-1H-indol-1-yl]-1,3-benzodioxole-5-carboxylic Acid

Step A: Mixture of ethyl (2,2-diethoxycyclohexyl)acetate and ethyl (2-ethoxycyclohex-2-en-1-yl)acetate The title compound mixture is obtained in accordance with the method described in the literature (WO2007/054739) starting from 15 g (81.4 mmol) of ethyl (2-oxocyclohexyl)acetate in solution in 25 mL of anhydrous ethanol in the presence of 40 mL of triethyl orthoformate (244 mmol) and 1.4 g of APTS (8.13 mmol) as catalyst. The reaction mixture is heated overnight at 95° C. and then concentrated to dryness. The mixture of the 2 compounds is obtained in the form of an oil, which is used directly for the following step.

$^1$H NMR: δ (300 MHz; CDCl$_3$; 300K): 4.60 (t, 1H); 4.17-4.09 (m, 4H); 3.76-3.58 (m, 4H); 3.47-3.41 (m, 3H); 3.11 (s, 1H); 2.71-2.63 (m, 2H); 2.58-2.40 (m, 1H); 2.37-2.09 (m, 4H); 2.07-1.97 (m, 4H); 1.91-1.33 (m, 8H); 1.31-1.16 (m, 14H)

R: ν: >C=O: 1740 cm$^{-1}$ ester

Step B: Ethyl 3-oxo-2-(2-oxocyclohexyl)propanoate

To a suspension of 2.15 g (89.5 mmol) of sodium hydride (60% in oil) in 40 mL of anhydrous THF placed at 0° C. under an inert atmosphere there are added, dropwise, 20.6 g (77.8 mmol) of the mixture obtained in Step A and 12.6 mL (155.6 mmol) of ethyl formate in solution in 25 mL of THF. The whole is stirred at 0° C. for 2 h and then for 12 h at ambient temperature. The reaction mixture is hydrolysed. The aqueous phase is acidified by adding a concentrated HCl solution and is then extracted with ethyl acetate. The organic phase is then dried over MgSO$_4$, filtered and concentrated to dryness. The expected product is obtained in the form of an oil.

$^1$H NMR: δ (300 MHz; CDCl$_3$; 300K): 8.4 (s, 1H, CHO); 4.25-4.1 (m, 2H, alphatic Hs, COOCH$_2$CH$_3$); 2.9-2.75 (m, 1H, aliphatic H, CHOCHCOOEt); 2.5-1.45 (m, 9H, aliphatic Hs, cyclohexanone); 1.3 (m, 3H, aliphatic Hs, COOCH$_2$CH$_3$)

Step C: 6-[3-(Ethoxycarbonyl)-4,5,6,7-tetrahydro-1H-indol-1-yl]-1,3-benzodioxole-5-carboxylic Acid To a solution of 4 g (18.84 mmol) of the compound of Step B in 20 mL of acetic acid there are then added, in portions, 3.4 g (18.84 mmol) of 6-amino-1,3-benzodioxole-5-carboxylic acid (obtained in accordance with a protocol from the literature: N. Mahindoo et al., *Med Chem. Res.* 14(6), 347, 2006). The whole is heated at 110° C. for 2 hours. The reaction mixture is then concentrated to dryness while co-evaporating with toluene. The solid so obtained is triturated in a mixture of pentane and diisopropyl ether (50/50), filtered and dried to yield the title product.

$^1$H NMR: δ (300 MHz; CDCl$_3$; 300K): 7.5 (s, 1H, H-pyrrole); 7.20 (s, 1H, aromatic H); 6.70 (s, 1H, aromatic H); 6.12 (s, 2H, O—CH$_2$—O); 4.28 (q, 2H, aliphatic Hs, COOCH$_2$CH$_3$); 2.80 (m, 2H, aliphatic Hs, tetrahydroindole); 2.20 (m, 2H, aliphatic Hs, tetrahydroindole); 1.75 (m, 4H, aliphatic Hs, tetrahydroindole); 1.30 (t, 3H, aliphatic Hs, COOCH$_2$CH$_3$)

IR: ν: OH acid: 2800-2300 cm$^{-1}$; ν: >C=O: 1672 cm$^{-1}$ (split band acid+ester); ν: aromatic >C=C<: 1616 cm$^{-1}$)

Preparation 20: 6-[4-(Ethoxycarbonyl)-2-methyl-1H-pyrrol-1-yl]-2,3-dihydro-1-benzofuran-5-carboxylic Acid The title compound is obtained in accordance with the process of Preparation 1, replacing 2-aminobenzoic acid with 6-amino-2,3-dihydro-1-benzofuran-5-carboxylic acid.

$^1$H NMR: δ (400 MHz; dmso-d6; 300K): 8.00 (s, 1H, H dihydrobenzofuran); 7.25 (d, 1H, H pyrrole); 6.65 (s, 1H, H dihydrobenzofuran); 6.40 (d, 1H, H pyrrole); 4.75 (t, 2H, H dihydrobenzofuran); 4.30 (q, 2H, COOCH$_2$CH$_3$); 3.30 (t, 2H, H dihydrobenzofuran); 2.0 (s, 3H, CH$_3$-pyrrole); 1.30 (t, 3H, COOCH$_2$CH$_3$)

IR: ν: —OH: 3000-2000 cm$^{-1}$; ν: C=O: 1702-1669 cm$^{-1}$

Preparation 21: 6-[4-(Ethoxycarbonyl)-2-methyl-1H-pyrrol-1-yl]-1-benzofuran-5-carboxylic Acid The title compound is obtained in accordance with the process of Preparation 1, replacing 2-aminobenzoic acid with 6-amino-1-benzofuran-5-carboxylic acid.

$^1$H NMR: δ (400 MHz; dmso-d6; 300K): 12.80 (broad s, 1H, COOH); 8.25 (s, 1H, H benzofuran); 8.20 (s, 1H, H pyrrole); 7.75 (s, 1H, H benzofuran); 7.30 (s, 1H, H pyrrole); 7.20 (s, 1H, H benzofuran); 6.30 (s, 1H, benzofuran); 4.20 (q, 2H, COOCH$_2$CH$_3$); 1.9 (s, 3H, CH$_3$-pyrrole); 1.25 (t, 3H, COOCH$_2$CH$_3$)

IR: ν: —OH: 2720-2450 cm$^{-1}$; C=O: 1698-1682 cm$^{-1}$

Preparation 22: 4-Chloro-2-[4-(methoxycarbonyl)-2,3-dimethyl-1H-pyrrol-1-yl]-benzoic Acid 3.35 g (153.18 mmol) of methyl 4,5-dimethyl-1H-pyrrole-3-carboxylate prepared in accordance with the literature (Synthetic uses of tosylmethyl isocyanide (TosMIC)

*Organic Reactions* (Hoboken, N.J., United States) (2001), 57, No 418) and 4.63 g (16.4 mmol) of 4-chloro-2-iodobenzoic acid are dissolved in 50 mL of acetonitrile. There are added thereto copper powder (45μ) (280 mg, 4.37 mmol) as well as caesium carbonate (14.25 g, 43.74 mmol). The reaction mixture is heated at reflux for 12 hours. The progress of the reaction is monitored by liquid chromatography (LC). The suspension is allowed to return to ambient temperature and is then filtered, washed with acetonitrile and evaporated to dryness. The residue is taken up in ethyl acetate. The solution is then washed with 1M hydrochloric acid and then with a saturated sodium chloride solution, it is dried over magnesium sulphate, filtered and then evaporated to dryness. The compound so obtained is purified over a silica gel column using dichloromethane and ethanol as solvents.

Mass Spectroscopy (ESI+):
Empirical formula: $C_{15}H_{14}ClNO_2$
monoisotopic mass=307.07 Da
$[M+H]^+$, measured: 308.12
(isotope ratios consistent with one chlorine atom)

Preparation 1': tert-Butyl [(3S)-1,2,3,4-tetrahydroisoquinolin-3-ylmethyl]-carbamate

Step A: Benzyl (3S)-3-(hydroxymethyl)-3,4-dihydro-1H-isoquinoline-2-carboxylate This compound is obtained using a protocol from the literature (R. B. Kawthekar et al. *South Africa Journal of Chemistry* 63, 195, 2009) starting from 15 g of (3S)-1,2,3,4-tetrahydroisoquinolin-3-ylmethanol (91.9 mmol) in the presence of benzyl chloroformate and triethylamine in solution in dichloromethane. After purification over silica gel (petroleum ether/AcOEt gradient), the title compound is obtained in the form of an oil.

$^1$H NMR: δ (300 MHz; DMSO-d6; 300K): 7.33 (m, 5H, aromatic Hs, O-benzyl); 7.15 (s, 4H, aromatic Hs, H tetrahydroisoquinoline); 5.13 (s, 2H, $CH_2$-Ph); 4.73 (d, 1H, H tetrahydroisoquinoline); 4.47 (m, H, $CH_2OH$); 4.36 (m, 1H, H tetrahydroisoquinoline); 4.28 (d, 1H, H tetrahydroisoquinoline); 3.39 (dd, 1H, $CH_2OH$); 3.23 (dd, 1H, $CH_2OH$); 2.93 (dd, 1H, H tetrahydroisoquinoline); 2.86 (dd, 1H, H tetrahydroisoquinoline)

IR: ν: OH: 3416 $cm^{-1}$; ν: <C=O 1694 $cm^{-1}$; ν: aromatic >C—H: 754 $cm^{-1}$

Step B: Benzyl (3S)-3-(azidomethyl)-3,4-dihydroisoquinoline-2(1H)-carboxylate This compound is obtained using a protocol from the literature (D. Page et al. *J. Med. Chem*, 44, 2387, 2001) starting from 23 g of the compound obtained in Step A (77.3 mmol) in the presence of diphenyl phosphorylazide and triphenylphosphine in solution in THF. After purification over silica gel (petroleum ether/AcOEt gradient), the title product is obtained in the form of an oil.

$^1$H NMR: δ (400 MHz; DMSO-d6; 300K): 7.36 (m, 5H, aromatic Hs, O-benzyl); 7.19 (m, 4H, aromatic Hs, H tetrahydroisoquinoline); 5.16 (s, 2H, $CH_2$-Ph); 4.76 (d, 1H, H tetrahydroisoquinoline); 4.53 (m, 1H, H tetrahydroisoquinoline); 4.30 (m, 1H, H tetrahydroisoquinoline); 3.28 (m, 2H, $CH_2N_3$); 3.06 (dd, 1H, H tetrahydroisoquinoline); 2.78 (dd, 1H, H tetrahydroisoquinoline)

IR: ν: $N_3$: 2095 $cm^{-1}$; ν: <C=O: 1694 $cm^{-1}$; aromatic >C—H: 754 $cm^{-1}$

Step C: Benzyl (3S)-3-(aminomethyl)-3,4-dihydroisoquinoline-2(1H)-carboxylate To a solution of 20.9 g (64.5 mmol) of the azido compound obtained in Step B in 650 mL of THF there are added in succession 25.5 g (97.2 mmol) of triphenylphosphine and 157 mL of water. The whole is refluxed for 212 hours. The reaction mixture is then concentrated to dryness, and then the residual oil is taken up in isopropyl ether. A white precipitate appears; it is filtered off and washed with isopropyl ether. The filtrate is then concentrated to dryness before being purified by chromatography over silica gel ($CH_2Cl_2$/MeOH gradient). The title product is obtained in the form of an oil.

$^1$H NMR: δ (400 MHz; DMSO-d6; 300K): 7.40 (m, 5H, aromatic Hs, O-benzyl); 7.20 (m, 4H, aromatic Hs, H tetrahydroisoquinoline); 5.15 (s, 2H, $CH_2$-Ph); 4.75-4.3 (m, 2H, H tetrahydroisoquinoline); 4.30 (d, 1H, H tetrahydroisoquinoline); 2.90 (m, 2H, $CH_2NH_2$); 2.45 (m, 2H, H tetrahydroisoquinoline); 1.40 (m, 2H, $NH_2$)

IR: ν: $NH_2$: 3400-3300 $cm^{-1}$; ν: <C=O: 1688 $cm^{-1}$

Step D: Benzyl (3S)-3-{[(tert-butoxycarbonyl)amino]methyl}-3,4-dihydroisoquinoline-2(1H)-carboxylate To a solution of 18.4 g (62.1 mmol) of the compound obtained in Step C in 630 mL of dichloromethane there are added in succession 17.5 mL (124 mmol) of triethylamine and, in portions, 14.9 g (68.3 mmol) of di-tert-butyl dicarbonate. The whole is stirred at ambient temperature for 2 hours. The reaction mixture is then concentrated, before ethyl acetate is added. The organic phase is washed in succession with a 1M HCl solution, a saturated NaCl solution, a saturated $NaHCO_3$ solution and then a saturated NaCl solution. After drying, concentration to dryness and purification by chromatography over silica gel (petroleum ether/AcOEt gradient), the title product is obtained in the form of an oil.

$^1$H NMR: δ (400 MHz; DMSO-d6; 300K): 7.35 (m, 5H, aromatic Hs, O-benzyl); 7.15 (m, 4H, aromatic Hs, H tetrahydroisoquinoline); 6.51 (m, 1H, NHBoc); 5.12 (s, 2H, $CH_2$-Ph); 4.76 (d, 1H, H tetrahydroisoquinoline); 4.51 (m, 1H, H tetrahydroisoquinoline); 4.36 (d, 1H, H tetrahydroisoquinoline); 2.95 (m, 3H, H tetrahydroisoquinoline+$CH_2$NHBoc); 2.71 (d, 1H, H tetrahydroisoquinoline); 1.34 (s, 9H, NHBoc)

IR: ν: NH: 3351 $cm^{-1}$; ν: <C=O: 1686 $cm^{-1}$

Step E: tert-Butyl [(3S)-1,2,3,4-tetrahydroisoquinolin-3-ylmethyl]carbamate To a solution of 21 g (53 mmol) of the compound obtained in Step D in 600 mL of ethyl acetate there are added 2.1 g of 10% palladium on carbon. The whole is stirred at ambient temperature under a dihydrogen pressure of 1.3 bar for 5 hours. The reaction mixture is then filtered before being concentrated to dryness. The title product is obtained in the form of a solid.

$^1$H NMR: δ (400 MHz; DMSO-d6; 300K): 7.15 (m, 4H, aromatic Hs, H tetrahydroisoquinoline); 6.85 (t, 1H, NHBoc); 3.90 (m, 2H, H tetrahydroisoquinoline); 3.00 (m, 2H, $CH_2$NHBoc); 2.80 (m, 1H, H tetrahydroisoquinoline); 2.65 (dd, 1H, H tetrahydro isoquinoline); 2.40 (dd, 1H, H tetrahydroisoquinoline); 1.40 (s, 9H, NHBoc)

IR: ν: NH: 3386-3205 cm$^{-1}$ (NH amide); ν: <C=O: 1688 cm$^{-1}$; ν: NH: 1526 cm$^{-1}$ (NH amine)

Preparation 2': (3S)-3-(4-Morpholinylmethyl)-1,2,3,4-tetrahydroisoquinoline

Step A: Benzyl (3S)-3-(4-morpholinylcarbonyl)-3,4-dihydro-2(1H)-isoquinoline Carboxylate To a solution of 5 g of (3S)-2-[(benzyloxy)carbonyl]-1,2,3,4-tetrahydro-3-isoquinolinecarboxylic acid (16 mmol) in 160 mL of dichloromethane there are added 1.5 mL of morpholine (17.6 mmol) and then 9 mL of N,N,N-triethylamine (64 mmol), 3.3 g of 1-ethyl-3-(3'-dimethylaminopropyl)-carbodiimide (EDC) (19.2 mmol) and 2.6 g of hydroxybenzotriazole (HOBT) (19.2 mmol). The reaction mixture is stirred at ambient temperature overnight and then it is poured over an ammonium chloride solution and extracted with ethyl acetate. The organic phase is then dried over magnesium sulphate before being filtered and evaporated to dryness. The crude product so obtained is then purified by chromatography over silica gel (dichloromethane/methanol gradient). The product is obtained in the form of a foam.

$^1$H NMR: δ (400 MHz; dmso-d6; 353° K): 7.30 (m, 5H benzyl); 7.15 (m, 4 aromatic Hs); 5.2-5.0 (m, 3H, 2H benzyl, 1H dihydroisoquinoline); 4.75-4.5 (2 d, 2H dihydroisoquinoline); 3.55-3.3 (m, 8H morpholine); 3.15-2.9 (2dd, 2H dihydroisoquinoline)

IR: ν: >C=O: 1694-1650 cm$^{-1}$

Step B: Benzyl (3S)-3-(4-morpholinylmethyl)-3,4-dihydro-2(1H)-isoquinoline Carboxylate To a solution of 5.3 g of the product obtained in Step A (13.9 mmol) in 278 mL of tetrahydrofuran there are added 14 mL of BH$_3$Me$_2$S (27.8 mmol) at ambient temperature. The whole is heated for 4 hours at 80° C. The mixture is allowed to return to ambient temperature, and then 7 mL (14 mmol) of BH$_3$Me$_2$S are added. The reaction mixture is again heated at 80° C. for 2 hours. The tetrahydrofuran is then evaporated off, and there are then added slowly methanol and then 5.6 mL of 5N hydrochloric acid (27.8 mmol). The mixture is stirred at ambient temperature overnight and then at 80° C. for 1 hour. A saturated NaHCO$_3$ solution is then added to the reaction mixture placed at 0° C. until pH=8 is reached, and then extraction with ethyl acetate is carried out. The organic phase is then dried over magnesium sulphate before being filtered and evaporated to dryness. The title product is obtained in the form of an oil.

$^1$H NMR: δ (400 MHz; dmso-d6; 353° K): 7.43-7.30 (unresolved peak, 5H benzyl); 7.19 (m, aromatic 4Hs); 5.16 (m, 2H, 2H benzyl); 4.79-4.29 (d, 2H dihydroisoquinoline); 4.58 (m, 1H dihydroisoquinoline); 3.50 (m, 4H morpholine); 3.02-2.80 (dd, 2H dihydroisoquinoline); 2.42-2.28 (unresolved peak, 5H, 4H morpholine, 1H morpholine); 2.15 (dd, 1H morpholine)

IR: ν: >CH: 2810 cm$^{-1}$; ν: >C=O: 1694 cm$^{-1}$; ν: >C—O—C<: 1114 cm$^{-1}$; ν: >CH—Ar: 751; 697 cm$^{-1}$

Step C: (3S)-3-(4-Morpholinylmethyl)-1,2,3,4-tetrahydroisoquinoline

To a solution of 4.9 g of the compound of Step B (13.4 mmol) in 67 mL of ethanol there is added 0.980 g of palladium dihydroxide (20% by mass) at ambient temperature. The reaction mixture is placed under 1.2 bar of hydrogen at ambient temperature for 4 hours. It is then passed over a Whatman filter, and then the palladium is rinsed several times with ethanol. The filtrate is evaporated to dryness. The title product is obtained in the form of an oil.

$^1$H NMR: δ (400 MHz; dmso-d6; 300K): 7.12-7.0 (unresolved peak, aromatic 4Hs); 3.92 (s, 2H tetrahydroisoquinoline); 3.60 (t, 4H morpholine); 2.98 (m, 1H tetrahydroisoquinoline); 2.68 (dd, 1H tetrahydroisoquinoline); 2.5-2.3 (unresolved peak, 8H, 1H tetrahydroisoquinoline, 6H morpholine, 1H NH)

IR: ν: >NH: 3322 cm$^{-1}$; ν: >C—O—C<: 1115 cm$^{-1}$; ν: >CH—Ar: 742 cm$^{-1}$

Preparation 3': (3S)-3-[(4-Methyl-1-piperazinyl)methyl]-1,2,3,4-tetrahydroisoquinoline The procedure is in accordance with the process of Preparation 2', replacing the morpholine used in Step A with 1-methyl-piperazine.

Preparation 4': (3S)-3-[(3aR,6aS)-Hexahydrocyclopenta[c]pyrrol-2(1H)-ylmethyl]-1,2,3,4-tetrahydroisoquinoline The procedure is in accordance with the process of Preparation 2', replacing the morpholine used in Step A with (3aR,6aS)-octahydrocyclopenta[c]pyrrole.

$^1$H NMR: δ (400 MHz; DMSO-d6; 300K): 7.05 (m, 4H, aromatic Hs, H tetrahydroisoquinoline); 3.90 (s, 2H, H tetrahydroisoquinoline); 2.85 (m, 1H, H tetrahydroisoquinoline); 2.70 (dd, 1H, H tetrahydroisoquinoline); 2.7-2.3 (m, 6H); 2.4-2.3 (2dd, 2H); 2.2-2.1 (2dd, 2H, bicyclic amine); 1.7-1.3 (2m, 6H, bicyclic amine)

Preparation 5': (3S)-3-[(4,4-Difluoropiperidin-1-yl)methyl]-1,2,3,4-tetrahydroisoquinoline The procedure is in accordance with the process of Preparation 2', replacing the morpholine used in Step A with 4,4-difluoro-1-piperidine.

$^1$H NMR: δ (300 MHz; DMSO-d6; 300K): 10.2 (broad s, 1H, NH$_2$); 7.25 (m, 4H, aromatic Hs, H tetrahydroisoquinoline); 4.40 (s, 2H, H tetrahydroisoquinoline); 4.20 (m, 1H, H tetrahydroisoquinoline); 3.75-3.35 (m, 6H, H difluoropiperidine); 3.3-3.1 (2dd, 2H, H tetrahydroisoquinoline); 2.4 (m, 4H, H difluoropiperidine)

IR: ν: NH$_2$$^+$: 2782-2381 cm$^{-1}$

Preparation 6': (3S)-3-[(4-Cyclopentylpiperazin-1-yl)methyl]-1,2,3,4-tetrahydroisoquinoline The procedure is in accordance with the process of Preparation 2', replacing the morpholine used in Step A with 1-cyclopentylpiperazine.

$^1$H NMR: δ (400 MHz; DMSO-d6; 300K): 7.20 (m, 4H, aromatic Hs, H tetrahydroisoquinoline); 4.30 (broad s, 2H, H tetrahydroisoquinoline); 3.70 (m, 1H, H tetrahydroisoquinoline); 3.50 (m, 3H, H piperazine); 3.10 (m, 4H); 3.1-2.75 (2m, 4H, H piperazine); 2.85 (dd, 1H); 2.60 (m, 1H); 2.00 (m, 2H, H cyclopentyl); 1.75 (m, 4H, H cyclopentyl); 1.55 (m, 2H, H cyclopentyl)

IR: ν: NH$^+$/NH$_2$$^+$: 3550-2000 cm$^{-1}$; ν: aromatic >CH—: 761 cm$^{-1}$

Preparation 7': (3S)-3-[(4-Cyclobutylpiperazin-1-yl)methyl]-1,2,3,4-tetrahydroisoquinoline The procedure is in accordance with the process of Preparation 2', replacing the morpholine used in Step A with 1-cyclobutylpiperazine.

¹H NMR: δ (400 MHz; DMSO-d6; 300K): 7.20 (m, 4H, aromatic Hs, H tetrahydroisoquinoline); 4.20 (2 d, 2H, H tetrahydroisoquinoline); 3.55 (m, 1H, H tetrahydroisoquinoline); 3.00 (dd, 1H, H tetrahydroisoquinoline); 2.85 (m, 1H); 2.75 (dd, 1H, H tetrahydroisoquinoline); 2.7-2.2 (m, 8H, H piperazine); 2.65 (dd, 1H); 2.55 (dd, 1H); 2.1-1.5 (m, 6H, H cyclobutyl)
IR: ν: $NH^+$: 2900-2050 $cm^{-1}$; ν: <C=C<: 1603 $cm^{-1}$; ν: aromatic >C—H: 754 $cm^{-1}$

Preparation 8': (3S)-3-(Pyrrolidin-1-ylmethyl)-1,2,3,4-tetrahydroisoquinoline The procedure is in accordance with the process of Preparation 2', replacing the morpholine used in Step A with pyrrolidine.
¹H NMR: δ (400 MHz; DMSO-d6; 300K): 7.10 (m, 4H, aromatic Hs, H tetrahydroisoquinoline); 3.90 (s, 2H, H tetrahydroisoquinoline); 2.90 (m, 1H, H tetrahydroisoquinoline); 2.70 (dd, 1H, H tetrahydroisoquinoline); 2.5-2.4 (m, 7H); 1.7 (m, 4H, pyrrolidine)
IR: ν: NH: 3400-3300 $cm^{-1}$

Preparation 9': (3R)-3-Methyl-1,2,3,4-tetrahydroisoquinoline Hydrochloride

Step A: {(3S)-2-[(4-Methylphenyl)sulphonyl]-1,2,3,4-tetrahydroisoquinolin-3-yl}methyl 4-methylbenzenesulphonate To a solution of 30.2 g of [(3S)-1,2,3,4-tetrahydroisoquinolin-3-yl]methanol (185 mmol) in 750 mL of dichloromethane there are added in succession 91.71 g of tosyl chloride (481 mmol) and then, dropwise, 122.3 mL of N,N,N-triethylamine (740 mmol). The reaction mixture is then stirred at ambient temperature for 20 hours. It is then diluted with dichloromethane, washed in succession with a 1M HCl solution, a saturated $NaHCO_3$ solution and then with a saturated NaCl solution until neutral. The organic phase is then dried over $MgSO_4$, filtered and concentrated to dryness. The solid obtained is then dissolved in a minimum volume of dichloromethane, and then cyclohexane is added until a precipitate forms. The precipitate is then filtered off and washed with cyclohexane. After drying, the title product is obtained in the form of crystals.
¹H NMR: δ (400 MHz; dmso-d6; 300K): 7.75 (d, 2H, aromatic Hs, ortho O-tosyl); 7.6 (d, 2H, aromatic Hs, ortho N-tosyl); 7.5 (d, 2H, aromatic Hs, meta O-tosyl); 7.3 (d, 2H, aromatic Hs, meta N-tosyl); 7.15-6.9 (m, 4H, aromatic Hs, tetrahydroisoquinoline); 4.4-4.15 (dd, 2H, aliphatic Hs, tetrahydroisoquinoline); 4.25 (m, 1H, aliphatic H, tetrahydroisoquinoline); 4.0-3.8 (2dd, 2H, aliphatic Hs, $CH_2$—O-tosyl); 2.7 (2dd, 2H, aliphatic Hs, tetrahydroisoquinoline); 2.45 (s, 3H, O—$SO_2$-Ph-$CH_3$); 2.35 (s, 3H, N—$SO_2$-Ph-$CH_3$)
IR: ν: —$SO_2$: 1339-1165 $cm^{-1}$

Step B: (3R)-3-Methyl-2-[(4-methylphenyl)sulphonyl]-1,2,3,4-tetrahydroisoquinoline To a suspension of 8.15 g (214.8 mmol) of $LiAlH_4$ in 800 mL of methyl tert-butyl ether (MTBE) there are added 101.2 g of the ditosyl compound obtained in Step A (214.8 mmol) in solution in 200 mL of MTBE. The whole is then heated at 50° C. for 2 hours. The mixture is allowed to cool, placed at 0° C. and there are then added, dropwise, 12 mL of a 5N NaOH solution. The whole is stirred at ambient temperature for 45 minutes. The solid so obtained is then filtered off, washed with MTBE and then with dichloromethane. The filtrate is then concentrated to dryness. The title product is then obtained in the form of a solid.
¹H NMR: δ (400 MHz; dmso-d6; 300K): 7.70 (d, 2H, aromatic Hs, ortho N-tosyl); 7.38 (d, 2H, aromatic Hs, meta N-tosyl); 7.2-7.0 (m, 4H, aromatic Hs, tetrahydroisoquinoline); 4.4 (m, 2H, aliphatic Hs); 4.3 (m, 1H, aliphatic H, tetrahydroisoquinoline); 2.85-2.51 (2dd, 2H, aliphatic Hs, tetrahydroisoquinoline); 2.35 (s, 3H, N—$SO_2$-Ph-$CH_3$); 0.90 (d, 3H, tetrahydroisoquinoline-$CH_3$)
IR: ν: —$SO_2$: 1332-1154 $cm^{-1}$

Step C: (3R)-3-Methyl-1,2,3,4-tetrahydroisoquinoline

To a solution of 31.15 g (103.15 mmol) of the monotosyl compound obtained in Step B in 500 mL of anhydrous methanol there are added, in portions, 3.92 g (161 mmol) of magnesium turnings. The whole is stirred in the presence of ultrasound for 96 hours. The reaction mixture is then filtered and the solid is washed several times with methanol. The filtrate is then concentrated to dryness. After purification by column chromatography over silica gel (dichloromethane/EtOH/$NH_4OH$), the title product is obtained in the form of an oil.
¹H NMR: δ (400 MHz; dmso-d6; 300K): 7.05 (m, 4H, aromatic Hs, tetrahydroisoquinoline); 3.90 (m, 2H, aliphatic Hs, tetrahydroisoquinoline); 2.85 (m, 1H, aliphatic H, tetrahydroisoquinoline); 2.68-2.4 (2dd, 2H, aliphatic Hs, tetrahydroisoquinoline); 1.12 (d, 3H, tetrahydroisoquinoline-$CH_3$); 2.9-2.3 (m, broad, 1H, HN (tetrahydroisoquinoline))
IR: ν: —NH: 3248 $cm^{-1}$

Step D: (3R)-3-Methyl-1,2,3,4-tetrahydroisoquinoline Hydrochloride

To a solution of 14.3 g (97.20 mmol) of the compound obtained in Step C in 20 mL of anhydrous ethanol there are added, dropwise, 100 mL of a 1M solution of HCl in ether. The whole is stirred at ambient temperature for 1 hour and then filtered. The crystals so obtained are washed with ethyl ether. After drying, the title product is obtained in the form of crystals.
¹H NMR: δ (400 MHz; dmso-d6; 300K): 9.57 (m, broad, 2H, $NH_{2+}$ (tetrahydroisoquinoline)); 7.22 (m, 4H, aromatic Hs, tetrahydroisoquinoline); 4.27 (s, 2H, aliphatic Hs, tetrahydroisoquinoline); 3.52 (m, 1H, aliphatic H, tetrahydroisoquinoline); 3.03-2.85 (2dd, 2H, aliphatic Hs, tetrahydroisoquinoline); 1.39 (d, 3H, tetrahydroisoquinoline-$CH_3$)
IR: ν: —$NH_2^+$: 3000-2300 $cm^{-1}$; ν: aromatic —CH: 766 $cm^{-1}$

Preparation 10': (3S)-3-[2-(Morpholin-4-yl)ethyl]-1,2,3,4-tetrahydroisoquinoline Hydrochloride

Step A: tert-Butyl (3S)-3-(2-morpholino-2-oxoethyl)-3,4-dihydro-1H-isoquinoline-2-carboxylate To a solution of 3 g (10.30 mmol) of [(3S)-2-(tert-butoxycarbonyl)-1,2,3,4-tetrahydroisoquinolin-3-yl]acetic acid in 100 mL of dichloromethane there are added dropwise 1.10 mL (11.32 mmol) of morpholine and then, still dropwise, 4.3 mL (30.9 mmol) of triethylamine, 2.20 g (12.40 mmol) of 1,2-dichloromethane and 1.70 g (1.68 mmol) of hydroxybenzotriazole. The whole is stirred at ambient temperature for 15 hours. The reaction mixture is then diluted with dichloromethane, washed in succession with a 1M HCl solution, a saturated NaHCO$_3$ solution and then with a saturated NaCl solution until neutral. The organic phase is then dried over MgSO$_4$, filtered and concentrated to dryness. After purification by column chromatography over silica gel (dichloromethane/MeOH), the title product is obtained in the form of an oil.

$^1$H NMR: δ (400 MHz; dmso-d6; 300K): 7.20-7.10 (m, 4H, aromatic Hs, tetrahydroisoquinoline); 4.70 (m, 1H, aliphatic Hs, CH tetrahydroisoquinoline); 4.75-4.20 (2m, 2H, aliphatic Hs, CH$_2$ alpha to N tetrahydroisoquinoline); 3.60 (m, 8H, aliphatic Hs, morpholine); 3.00 and 2.70 (2dd, 2H, aliphatic H, tetrahydroisoquinoline); 2.50-2.20 (2 d, 2H, aliphatic Hs, CH$_2$CO); 1.40 (s, 9H, $^t$Bu)

IR: ν: C═O: 1687; 1625 cm$^{-1}$

Step B: 1-(Morpholin-4-yl)-2-[(3S)-1,2,3,4-tetrahydroisoquinolin-3-yl]ethanone Hydrochloride To a solution of 2.88 g (7.18 mmol) of the compound obtained in Step A in 16 mL of dichloromethane there are added dropwise 80 mL (80 mmol) of a 1M solution of HCl in ether. The whole is stirred at ambient temperature for 15 hours, and then the suspension is filtered and the precipitate is washed with ether. After drying, the title product is obtained in the form of a solid.

$^1$H NMR: δ (400 MHz; dmso-d6; 300K): 9.80-9.50 (m, 2H, NH$_2^+$); 7.30-7.10 (m, 4H, aromatic Hs, tetrahydroisoquinoline); 4.30 (m, 2H, aliphatic Hs, CH$_2$ alpha to N tetrahydroisoquinoline); 3.80 (m, 1H, aliphatic Hs, CH tetrahydroisoquinoline); 3.70-3.40 (2m, 8H, aliphatic Hs, morpholine); 3.15 and 2.8 (m, 4H, aliphatic H, CH$_2$ tetrahydroisoquinoline and CH$_2$CO)

IR: ν: —NH$_2^+$: 2800-1900 cm$^{-1}$; ν: C═O: 1620 cm$^{-1}$

Step C: (3S)-3-[2-(Morpholin-4-yl)ethyl]-1,2,3,4-tetrahydroisoquinoline Hydrochloride A solution of 2.2 g (7.44 mmol) of the compound obtained in Step B in 22 mL of MTBE and 5 mL of dichloromethane is prepared. After cooling in an ice bath at 0° C., there are added dropwise thereto 15 mL (15 mmol) of a 1M LiAlH$_4$ solution in tetrahydrofuran. The whole is then stirred at ambient temperature for 6 hours. It is placed at 0° C., and then 1 mL of a 5N NaOH solution is added dropwise. The whole is stirred at ambient temperature for 45 minutes. The solid is then filtered off and washed with MTBE and then with dichloromethane, and the filtrate is concentrated to dryness. The oil so obtained is diluted with dichloromethane, and 6.3 mL of a 1M solution of HCl in ether are added dropwise. The whole is stirred at ambient temperature for 1 hour and then filtered. The crystals so obtained are washed with ethyl ether. After drying, the title product is obtained in the form of a solid.

$^1$H NMR: δ (400 MHz; dmso-d6; 300K): 11.35+9.80 (2m, 2H, NH$_2^+$); 10.00 (m, H, NH$^+$); 7.20 (m, 4H, aromatic Hs, tetrahydroisoquinoline); 4.30 (s, 2H, aliphatic Hs, CH$_2$ alpha to N tetrahydroisoquinoline); 4.00+3.85 (2m, 4H, aliphatic Hs, CH$_2$ alpha to N morpholine); 3.70 (m, 1H, aliphatic Hs, CH tetrahydroisoquinoline); 3.55-3.30 (m, 4H, aliphatic Hs, CH alpha to O morpholine and CH$_2$ morpholine); 3.15 (dd, 1H, aliphatic H, CH alpha to O morpholine); 3.10 (m, 2H, aliphatic H, CH alpha to O morpholine); 2.90 (dd, 1H, aliphatic H, CH$_2$ tetrahydroisoquinoline); 2.30+2.15 (2m, 2H, aliphatic H, CH$_2$ tetrahydroisoquinoline)

IR: ν: NH$^+$/—NH$_2$+: between 3500 and 2250 cm$^{-1}$; ν: C═C: weak 1593 cm$^{-1}$; ν: aromatic C—H: 765 cm$^{-1}$

Preparation 11': (3S)-3-(Piperidin-1-ylmethyl)-1,2,3,4-tetrahydroisoquinoline The procedure is in accordance with the process of Preparation 2', replacing the morpholine used in Step A with piperidine.

$^1$H NMR: δ (400 MHz; DMSO-d6; 300K): 7.15 (m, 4H, aromatic Hs, H tetrahydroisoquinoline); 3.85 (s, 2H, H tetrahydroisoquinoline); 2.90 (m, 1H, H tetrahydroisoquinoline); 2.75 (dd, 1H, H tetrahydroisoquinoline); 2.5-2.4 (m, 7H); 1.7 (m, 6H, piperidine)

Preparation 12': N,N-Dimethyl-1-[(3S)-1,2,3,4-tetrahydroisoquinolin-3-yl]-methanamine The procedure is in accordance with the process of Preparation 2', replacing the morpholine used in Step A with N,N-dimethylamine.

Preparation 1″: 4-Benzyloxy-N-phenyl-aniline

To a solution of 4-hydroxy-N-phenyl-aniline (30 g; 162 mmol) in acetonitrile (400 mL) there are added 58 g of Cs$_2$CO$_3$ (178 mmol) and stirring is carried out for 15 minutes at ambient temperature. Benzyl bromide (22.5 mL; 178 mmol) is then added dropwise, and the reaction mixture is heated at reflux for 4 hours. After filtration and rinsing with acetonitrile, the filtrate is concentrated and chromatographed on silica gel (petroleum ether/AcOEt gradient). The title product is then obtained in the form of a colourless solid.

$^1$H NMR: δ (400 MHz; dmso-d6; 300K): 7.80 (m, 1H, NH); 7.45 (m, 2H, aryl); 7.40 (m, 2H, aryl); 7.30 (m, 1H, aryl); 7.15 (s, 2H, aryl); 7.05 (d, 2H, aryl); 6.9-7.0 (m, 4H, aryl); 6.70 (t, 1H, aryl); 5.05 (s, 2H, benzyl)

IR: ν: >NH: 3408 cm$^{-1}$

Preparation 2″: N-(4-{[tert-Butyl(dimethyl)silyl]oxy}phenyl)-1-benzothiophene-5-amine

Step A: 4-{[tert-Butyl(dimethyl)silyl]oxy}aniline

The title compound is obtained starting from 4-aminophenol in THF in the presence of imidazole and tert-butyl (dimethyl)silyl chloride in accordance with the protocol described in the literature (S. Knaggs et al., *Organic & Biomolecular Chemistry*, 3(21), 4002-4010; 2005).

$^1$H NMR: δ (400 MHz; dmso-d6; 300K): 6.45-6.55 (dd, 4H, aromatic Hs); 4.60 (m, 2H, NH$_2$-Ph); 0.90 (s, 9H, Si(CH$_2$)$_2$CH(CH$_3$)$_2$); 0.10 (s, 6H, Si(CH$_2$)$_2$CH(CH$_3$)$_2$)

IR: ν: —NH$_2^+$: 3300-3400 cm$^{-1}$

Step B: N-(4-{[tert-Butyl(dimethyl)silyl]oxy}phenyl)-1-benzothiophene-5-amine To a solution of 6 g (26.9 mmol) of the compound obtained in Step A in 250 mL of anhydrous toluene there are added in succession sodium tert-butylate (2.8 g; 23.5 mmol), Pd(OAc)$_2$ (500 mg; 2.3 mmol), 1,1-bis(diphenylphosphino) ferrocene (2.6 g; 4.7 mmol) and 5-bromobenzothiophene (5 g; 23.5 mmol). The whole is degassed under argon for 30 minutes and then heated at reflux for 17 hours. The mixture is allowed to cool. The reaction mixture is concentrated to dryness and then taken up in dichloromethane, filtered over Celite and then concentrated to dryness again. The residue is then purified by chromatography over silica gel (CHCl$_2$/AcOEt gradient) to provide the expected product in the form of a solid.

$^1$H NMR: δ (400 MHz; dmso-d6; 300K): 7.90 (s, 1H, NH); 7.75 (d, 1H, aromatic CH); 7.65 (d, 1H, CH thiophene); 7.40 (d, 1H, aromatic CH); 7.30 (d, 1H, CH thiophene); 7.05 (d, 2H, aromatic CH); 7.00 (dd, 1H, aromatic CH); 6.80 (d, 2H, aromatic CH); 0.95 (s, 9H, $^t$Bu); 0.20 (s, 6H, SiCH$_3$)

IR: ν>NH: 3397 cm$^{-1}$

Preparation 3": tert-Butyl 5-(phenylamino)-1H-indole-1-carboxylate

The procedure is in accordance with the process of Step B of Preparation 2", replacing the 5-bromobenzothiophene used with tert-butyl 5-bromo-1H-indole-1-carboxylate and the 4-{[tert-butyl(dimethyl)silyl]oxy}aniline with aniline.

$^1$H NMR: δ (400 MHz; dmso-d6; 300K): 8.04 (s, 1H); 7.92 (d, 1H); 7.59 (s, 1H); 7.31 (d, 1H); 7.20 (t, 2H); 7.07 (dd, 1H); 7.03 (d, 2H); 6.76 (t, 1H); 6.61 (d, 1H); 1.63 (s, 9H)

Preparation 4": tert-Butyl 6-(phenylamino)-1H-indole-1-carboxylate

The procedure is in accordance with the process of Step B of Preparation 2", replacing the 5-bromobenzothiophene used with tert-butyl 6-bromo-1H-indole-1-carboxylate and the 4-{[tert-butyl(dimethyl)silyl]oxy}aniline with aniline.

$^1$H NMR: δ (400 MHz; CDCl$_3$; 300K): 8.00 (s, 1H); 7.92 (d, 1H); 7.50 (s, 1H); 7.31 (d, 1H); 7.20-7.03 (m, 4H); 6.76 (t, 1H); 6.80 (d, 1H); 1.65 (s, 9H)

Preparation 5": tert-Butyl 5-[(4-{[tert-butyl(dimethyl)silyl]oxy}phenyl)amino]-1H-indole-1-carboxylate The procedure is in accordance with the process of Preparation 2", replacing the 5-bromobenzothiophene used with tert-butyl 5-bromo-1H-indole-1-carboxylate.

$^1$H NMR: δ (400 MHz; dmso-d6; 300K): 7.85 (d, 1H); 7.78 (s, 1H); 7.55 (d, 1H); 7.15 (d, 1H); 6.95 (m, 3H); 6.75 (d, 2H); 6.58 (d, 1H); 1.65 (s, 9H); 1.00 (s, 9H); 0.2 (s, 6H)

Preparation 6": 4-{[tert-Butyl(dimethyl)silyl]oxy}-3-chloro-N-phenylaniline

The procedure is in accordance with the process of Step B of Preparation 2", replacing the 5-bromobenzothiophene used with bromobenzene and the 4-{[tert-butyl(dimethyl)silyl]oxy}aniline with 4-{[tert-butyl(dimethyl)silyl]oxy}-3-chloroaniline (obtained in accordance with a protocol from the literature: *Bioorg Med Chem Lett* 22(14), 4839-4843).

$^1$H NMR: δ (400 MHz; dmso-d6; 300K): 7.2-7.1 (m, 3H); 7.15-7.05 (m, 2H); 7-6.8 (m, 4H); (s, 9H); 0.20 (s, 6H)

Preparation 7": N-(4-{[tert-Butyl(dimethyl)silyl]oxy}phenyl)-3-phenoxyaniline The procedure is in accordance with the process of Preparation 2", replacing the 5-bromobenzothiophene used in Step B with 1-bromo-3-phenoxybenzene.

$^1$H NMR: δ (400 MHz; dmso-d6; 300K): 7.98 (s, 1H, NH); 7.38 (d, 1H); 7.15 (m, 2H); 7.00 (d, 2H); 6.95 (d, 2H); 6.75 (d, 2H); 6.70 (d, 2H); 6.50 (t, 1H); 6.35 (dd, 1H); 0.95 (s, 9H, $^t$Bu); 0.20 (s, 6H, SiCH$_3$)

IR: ν>NH: 3300 cm$^{-1}$

Preparation 8": 4-{[tert-Butyl(dimethyl)silyl]oxy}-N-(2-phenylethyl)aniline

To a solution of 4-[tert-butyl(dimethyl)silyl]oxyaniline (6 g; 26.9 mmol) and phenylacetaldehyde (4 g; 33.6 mmol) in a mixture of isopropanol (270 mL) and water (27 mL) there are added 17 g of ammonium formate (270 mmol) and Pd/C (2 g). After stirring for 17 hours at ambient temperature, the reaction mixture is filtered over Celite and then concentrated to dryness. The residue is then diluted with a saturated sodium bicarbonate solution before being extracted with dichloromethane. The organic phase is dried over MgSO$_4$, concentrated to dryness, and the residue is purified by chromatography over silica gel (heptane/AcOEt gradient) to provide the expected product in the form of an oil.

IR: ν>NH: 3300 cm$^{-1}$

Preparation 9": N-(4-{[tert-Butyl(dimethyl)silyl]oxy}phenyl)-1-benzofuran-5-amine The procedure is in accordance with the process of Preparation 2", replacing the 5-bromobenzothiophene used in Step B with 5-bromo-1-benzofuran.

$^1$H NMR: δ (400 MHz; dmso-d6; 300K): 7.78 (s, 1H, H furan); 7.70 (s, 1H, NH); 7.40 (d, 1H, aromatic H); 7.20 (s, 1H, aromatic H); 6.95 (dd, 1H, aromatic H); 6.95 (d, 2H, aromatic H); 6.80 (d, 1H, H furan); 6.70 (d, 2H, aromatic H); 0.95 (s, 9H, $^t$Bu); 0.20 (s, 6H, SiCH$_3$)

IR: ν>NH: 3401 cm$^{-1}$

Preparation 10": 4-{[tert-Butyl(dimethyl)silyl]oxy}-N-(4-methoxyphenyl)aniline The procedure is in accordance with the process of Preparation 2", replacing the 5-bromobenzothiophene used in Step B with 1-bromo-4-methoxybenzene.

$^1$H NMR: δ (400 MHz; dmso-d6; 300K): 4.52 (s, 1H, NH); 6.95 (d, 2H, aromatic H); 6.85 (d, (d, 1H, aromatic H); 7.20 (s, 1H, aromatic H); 6.95 (dd, 1H, aromatic H); 6.95 (d, H, aromatic H); 6.85 (d, 2H, aromatic H); 6.70 (d, 2H, aromatic H); 3.70 (s, 3H, OCH$_3$); 1.00 (s, 9H, $^t$Bu); 0.20 (s, 6H, SiCH$_3$)

Preparation 11": 4-{[tert-Butyl(dimethyl)silyl]oxy}-N-[4-(trifluoromethoxy)-phenyl]aniline The procedure is in accordance with the process of Preparation 2", replacing the 5-bromobenzothiophene used in Step B with 4-bromophenyl trifluoromethyl ether.

$^1$H NMR: δ (400 MHz; CDCl$_3$; 300K): 7.1-6.8 (m, 8H); 5.70 (s, 1H); 1 (s, 9H); 0.25 (s, 6H)

Preparation 12": tert-Butyl 5-[(4-methylphenyl)amino]-1H-indole-1-carboxylate The procedure is in accordance with the process of Step B of Preparation 2", replacing the 5-bromobenzothiophene used with tert-butyl 5-bromo-1H-indole-1-carboxylate and the 4-{[tert-butyl(dimethyl)silyl]oxy}aniline with 4-methylaniline.

$^1$H NMR: δ (400 MHz; CDCl$_3$; 300K): 8.0 (s, 1H); 7.5 (m, 1H); 7.1-6.9 (m, 6H); 6.45 (d, 1H); 2.25 (s, 3H); 1.65 (s, 9H)

Preparation 13": N-(4-{[tert-Butyl(dimethyl)silyl]oxy}phenyl)-3-chloro-4-fluoro-aniline The procedure is in accordance with the process of Preparation 2", replacing the 5-bromobenzothiophene used in Step B with 4-bromo-2-chloro-1-fluorobenzene.

$^1$H NMR: δ (400 MHz; dmso-d6; 300K): 8.0 (s, 1H); 7.3 (t, 1H); 7.0-6.7 (m, 6H); 1.00 (s, 9H); 0.20 (s, 6H)

Preparation 14": 4-{[tert-Butyl(dimethyl)silyl]oxy}-3-chloro-N-(4-methylphenyl)-aniline The procedure is in accordance with the process of Step B of Preparation 2", replacing the 5-bromobenzothiophene used with 1-bromo-4-methylbenzene and the 4-{[tert-butyl(dimethyl)silyl]oxy}aniline with 4-{[tert-butyl(dimethyl)silyl]oxy}-3-chloroaniline (obtained in accordance with a protocol from the literature: *Bioorg Med Chem Lett* 22(14), 4839-4843).

$^1$H NMR: δ (400 MHz; dmso-d6; 300K): 7.90 (s, 1H, NH); 7.00 (m, 3H); 6.90 (m, 4H); 2.20 (s, 3H); 1.00 (s, 9H, $^t$Bu); 0.20 (s, 6H, SiCH$_3$)

Preparation 15": 4-{[tert-Butyl(dimethyl)silyl]oxy}-3-chloro-N-[4-(propan-2-yl)-phenyl]aniline The procedure is in accordance with the process of Step B of Preparation 2", replacing the 5-bromobenzothiophene used with 1-bromo-4-(propan-2-yl)benzene and the 4-{[tert-butyl(dimethyl)silyl]oxy}aniline with 4-{[tert-butyl(dimethyl)silyl]oxy}-3-chloroaniline (obtained in accordance with a protocol from the literature: *Bioorg Med Chem Lett* 22(14), 4839-4843).

$^1$H NMR: δ (400 MHz; dmso-d6; 300K): 7.12 (s, 1H, NH); 7.10 (d, 2H); 6.95 (d, 2H); 6.85 (m, 1H); 6.80 (d, 1H); 2.85 (m, 1H); 1.25 (d, 6H); 1.05 (s, 9H, $^t$Bu); 0.25 (s, 6H, SiCH$_3$)

Preparation 16": tert-Butyl 5-[(4-methylphenyl)amino]-1H-indazole-1-carboxylate The procedure is in accordance with the process of Step B of Preparation 2", replacing the 5-bromobenzothiophene used with tert-butyl 5-bromo-1H-indazole-1-carboxylate and the 4-{[tert-butyl(dimethyl)silyl]oxy}aniline with 4-methylaniline.

$^1$H NMR: δ (400 MHz; dmso-d6; 300K): 8.25 (s, 1H); 8.15 (s, 1H); 7.95 (d, 1H); 7.40 (d, 1H); 7.30 (dd, 1H); 7.08 (d, 2H); 7.02 (d, 2H); 2.25 (s, 3H); 1.65 (s, 9H)

Preparation 17": N-(4-{[tert-Butyl(dimethyl)silyl]oxy}-3-chlorophenyl)-1-methyl-1H-indol-5-amine The procedure is in accordance with the process of Step B of Preparation 2", replacing the 5-bromobenzothiophene used with 5-bromo-1-methyl-1H-indole and the 4-{[tert-butyl(dimethyl)silyl]oxy}aniline with 4-{[tert-butyl(dimethyl)silyl]oxy}-3-chloroaniline (obtained in accordance with a protocol from the literature: *Bioorg Med Chem Lett* 22(14), 4839-4843).

$^1$H NMR: δ (400 MHz; dmso-d6; 300K): 7.70 (s, 1H); 7.35 (d, 1H); 7.25 (s, 1H); 7.28 (d, 1H); 6.92 (d, 1H); 6.85 (m, 3H); 6.30 (d, 1H); 3.75 (s, 3H); 1.00 (s, 9H); 0.20 (s, 6H)

Preparation 18": tert-Butyl 5-[(4-{[tert-butyl(dimethyl)silyl]oxy}-3-chlorophenyl)-amino]-1H-indole-1-carboxylate The procedure is in accordance with the process of Step B of Preparation 2", replacing the 5-bromobenzothiophene used with tert-butyl 5-bromo-1H-indole-1-carboxylate and the 4-{[tert-butyl(dimethyl) silyl]oxy}aniline with 4-{[tert-butyl(dimethyl)silyl]oxy}-3-chloroaniline (obtained in accordance with a protocol from the literature: *Bioorg Med Chem Lett* 22(14), 4839-4843).

$^1$H NMR: δ (400 MHz; dmso-d6; 300K): 8.0 (s, 1H); 7.9 (d, 1H); 7.6 (d, 1H); 7.25 (d, 1H); 7.1-6.8 (m, 4H); 6.60 (d, 1H); 1.60 (s, 9H), 1.00 (s, 9H); 0.20 (s, 6H)

Preparation 19": tert-Butyl 4-(4-methylphenylamino)piperidine-1-carboxylate

To a solution of 4 g (20 mmol) of tert-butyl 4-aminopiperidine-1-carboxylate in dichloromethane there are added (4-methylphenyl)boronic acid (5.4 g; 40 mmol), triethylamine (5.6 mL; 40 mmol) and copper acetate (3.6 g; 20 mmol). The reaction mixture is stirred for 24 hours at ambient temperature and then for 17 hours at reflux. After evaporation to dryness, the residue is taken up in ethyl acetate, washed with 1N hydrochloric acid, water and with brine. The organic phase is dried over MgSO$_4$ and then concentrated to dryness and purified by chromatography over silica gel (CH$_2$Cl$_2$/AcOEt gradient). The title product is obtained in the form of a solid.

$^1$H NMR: δ (400 MHz; dmso-d6; 300K): 6.85 (d, 2H); 6.50 (d, 2H); 5.65 (d, 1H); 3.85 (m, 2H); 3.35 (m, 1H); 2.90 (m, 2H); 2.15 (s, 3H); 2.15 (s, 3H); 1.85 (m, 2H); 1.40 (s, 9H), 1.20 (m, 2H)

Preparation 20": N-(4-{[tert-Butyl(dimethyl)silyl]oxy}phenyl)-1-methylpiperidin-4-amine To a solution of 4-[tert-butyl(dimethyl)silyl]oxyaniline (5 g; 22.4 mmol) and 1-methylpiperidin-4-one (2.5 g; 22.4 mmol) in dichloromethane there is added, in portions, sodium triacetoxyborohydride (4.8 g; 22.4 mmol). After stirring for 24 hours at ambient temperature, the reaction mixture is poured slowly over a sodium bicarbonate solution. The aqueous phase is extracted with dichloromethane. The organic phase is dried over MgSO$_4$, concentrated to dryness and the residue is purified by chromatography over silica gel (CH$_2$Cl$_2$/MeOH gradient) to yield the expected product in the form of a solid.

$^1$H NMR: δ (400 MHz; dmso-d6; 300K): 6.62 (2 d, 4H); 3.15 (m, 1H); 2.88-2.18 (m, 4H); 2.30 (s, 3H); 1.98-1.48 (m, 4H); 0.98 (s, 9H); 0.15 (s, 6H).

Preparation 21": N-(4-{[tert-Butyl(dimethyl)silyl]oxy}phenyl)-3-(4-methylpiperazin-1-yl)aniline The procedure is in accordance with the process of Preparation 2", replacing the 5-bromobenzothiophene used in Step B with 1-(3-bromophenyl)-4-methylpiperazine.

$^1$H NMR: δ (400 MHz; dmso-d6; 300K): 7.68 (s, 1H); 7.00 (t, 1H); 6.96 (d, 2H); 6.74 (d, 2H); 6.46 (m, 1H); 6.4-6.35 (m, 2H); 3.04 (m, 4H); 2.42 (m, 4H); 2.20 (s, 3H); 0.95 (s, 9H); 0.16 (s, 6H)

Preparation 22": N-(4-{[tert-Butyl(dimethyl)silyl]oxy}phenyl)-2-methyl-2,3-dihydro-1H-isoindol-5-amine The procedure is in accordance with the process of Preparation 2", replacing the 5-bromobenzothiophene used in Step B with 5-bromo-2-methyl-2,3-dihydro-1H-isoindole.

¹H NMR: δ (400 MHz; dmso-d6; 300K): 7.02 (d, 1H); 6.95 (d, 2H); 6.75 (m, 4H); 5.45 (s, 1H); 3.85 (s, 4H); 2.78 (s, 3H); 1.00 (s, 9H); 0.20 (s, 6H)

Preparation 23": N-(4-{[tert-Butyl(dimethyl)silyl]oxy}phenyl)-1-[2-(morpholin-4-yl)ethyl]-1H-indol-5-amine Step A: 5-Bromo-1-[2-(morpholin-4-yl)ethyl]-1H-indole To a suspension of NaH (4.5 g; 112 mmol) in anhydrous THF (300 mL) there is added at 0° C. and in portions 5-bromoindole (10.4 g; 51 mmol). After stirring for 20 minutes at 0° C., 4-(2-chloroethyl)morpholine hydrochloride (10.4 g; 56 mmol) is added in portions in the course of 1 hour. After stirring overnight at ambient temperature and then for 5 hours at 80° C., the reaction mixture is poured over a mixture of aqueous sodium bicarbonate and dichloromethane. The aqueous phase is extracted with dichloromethane. The organic phase is dried over MgSO₄, concentrated to dryness and the residue is purified by chromatography over silica gel (CH₂Cl₂/MeOH gradient) to provide the expected product in the form of a slightly yellow oil.

¹H NMR: δ (400 MHz; CDCl3; 300K): 7.75 (d, 1H); 7.30 (dd, 1H); 7.20 (d, 1H); 7.15 (d, 1H); 6.40 (d, 1H); 4.20 (t, 2H); 3.70 (m, 4H); 2.75 (t, 2H); 2.45 (m, 4H)

Step B: 5-Bromo-1-[2-(morpholin-4-yl)ethyl]-1H-indole

The procedure is in accordance with the process of Preparation 2", replacing the 5-bromobenzothiophene used in Step B with the compound obtained in Step A.

¹H NMR: δ (400 MHz; dmso-d6; 300K): 7.35 (d, 1H); 7.15 (s, 1H); 6.85 (d, 3H); 6.70 (d, 2H); 7.30 (d, 1H); 6.25 (d, 1H); 4.20 (t, 2H); 3.55 (m, 4H); 2.65 (t, 2H); 2.45 (m, 4H); 1.45 (s, 9H), 0.15 (s, 6H)

Preparation 24": N-(4-{[tert-Butyl(dimethyl)silyl]oxy}phenyl)-1-methyl-1H-pyrrolo[2,3-b]pyridin-5-amine The procedure is in accordance with the process of Preparation 2", replacing the 5-bromobenzothiophene used in Step B with 5-bromo-1-methyl-1H-pyrrolo[2,3-b]pyridine (obtained in accordance with a protocol from the literature: *Heterocycles*, 60(4), 865, 2003).

IR: ν: —NH—: 3278 cm⁻¹; ν: aromatic —C=C— moieties: 1605 cm⁻¹

Preparation 25": 4-{[tert-Butyl(dimethyl)silyl]oxy}-N-phenylaniline

To a solution of 12 g of 4-anilinophenol (64.7 mmol) in 200 mL of acetonitrile there are added at ambient temperature 6.7 g of imidazole (97.05 mmol) and 11.7 g of tert-butyl(chloro)dimethylsilane (77.64 mmol). The whole is stirred at 70° C. for 4 hours. The reaction mixture is then poured over water and extracted with ether. The organic phase is then dried over magnesium sulphate and then filtered and evaporated to dryness. The crude product so obtained is then purified by column chromatography over silica gel (petroleum ether/dichloromethane gradient). The title product is obtained in the form of a powder.

¹H NMR: δ (400 MHz; dmso-d6; 300° K): 7.84 (s, 1H NH); 7.17 (t, 2H aniline); 6.98 (d, 2H phenoxy); 6.94 (d, 2H aniline); 6.76 (d, 2H phenoxy); 6.72 (t, 1H aniline); 0.95 (s, 9H tert-butyl); 0.15 (s, 6H dimethyl)

IR: ν: >NH: 3403 cm⁻¹; ν: >Ar: 1597 cm⁻¹

Preparation 26": 4-({4-[(tert-Butyldimethylsilyl)oxy]phenyl}amino)-1,5-dimethyl-1H-pyrrole-2-carbonitrile Step A: 4-Bromo-1,5-dimethyl-1H-pyrrole-2-carbonitrile A solution of bromine (6.58 mL, 0.13 mol) in acetic acid (60 mL) is added dropwise with the aid of a dropping funnel to a solution of 1,5-dimethyl-1H-pyrrole-2-carbonitrile (15.0 g, 0.12 mol) in acetic acid (300 mL). The whole is stirred at ambient temperature for 24 hours. The reaction mixture is then poured into a beaker containing 300 mL of water. The solid formed is filtered off and rinsed with water. It is then dissolved in dichloromethane (300 mL) and the organic phase is washed with brine, dried over sodium sulphate, filtered and concentrated in vacuo to give the expected product in the form of a solid.

¹H NMR (CDCl₃) δ ppm: 2.25 (s, 3H), 3.67 (s, 3H), 6.74 (s, 1H)

Step B: 4-({4-[(tert-Butyldimethylsilyl)oxy]phenyl}amino)-1,5-dimethyl-1H-pyrrole-2-carbonitrile A solution of the compound of the preceding step (1.5 g, 7.53 mmol), 4-[(tert-butyldimethylsilyl)oxy]aniline (2.02 g, 9.04 mmol), sodium tert-butoxide (1.45 g, 15.06 mmol) and 2-di-tert-butylphosphino-2',4',6'-triisopropylbiphenyl (0.13 g, 0.30 mmol) in toluene (20 mL) is purged with nitrogen. Tris(dibenzylideneacetone)dipalladium(0) (0.28 g, 0.30 mmol) is added, and then the reaction mixture is heated at 90° C. until the reaction is complete (monitored by TLC). Heating is stopped and the mixture is allowed to return to ambient temperature. Water (75 mL) is added and the mixture is extracted with ethyl acetate (3×75 mL). The combined organic phases are washed with brine and then concentrated. The crude product is absorbed on silica gel and purified by flash chromatography over silica gel with a mixture of ethyl acetate and heptane (0 to 30%). The product so obtained is dissolved while hot in heptane and is allowed to precipitate with stirring at ambient temperature and then at 0° C. The solid is filtered off and the operation is repeated on the filtrate to give the expected compound in the form of a solid.

¹H NMR (400 MHz, CDCl₃) δ ppm: 0.15 (s, 6H), 0.97 (s, 9H), 2.13 (s, 3H), 3.66 (s, 3H), 4.68 (br. s, 1H), 6.49 (d, J=8.5 Hz, 2H), 6.64 (s, 1H), 6.66 (d, J=8.7 Hz, 2H)

¹³C NMR (100 MHz, CDCl₃) δ ppm: 4.34, 9.72, 18.30, 25.88, 32.94, 101.27, 114.37, 114.70, 116.41, 120.73, 124.52, 131.23, 141.54, 148.27

MS (ESI+): [M+H]⁺ measured: 342.3

The amines NHR₃R₄ wherein R₃ and R₄, each independently of the other, represent an aryl or heteroaryl group are obtained in accordance with processes described in the literature (Surry D. S. et al., *Chemical Science*, 2011, 2, 27-50, Charles M. D. et al., *Organic Letters*, 2005, 7, 3965-3968). The reaction protecting the hydroxy function of the 4-anilinophenol described in Preparation 25" can be applied to various secondary amines NHR₃R₄ (as defined hereinbefore) having one or more hydroxy functions, when they are available commercially. Alternatively, the secondary amines having at least one hydroxy substituent may be synthesised directly in a protected form, i.e. starting from reagents whose hydroxy function has been protected beforehand. Among the protecting groups, tert-butyl(dimethyl) silyloxy and benzyloxy are especially preferred.

Among the amines $NHR_3R_4$ having a hydroxy substituent that are used for synthesising the compounds of the invention there may be mentioned: 4-(4-toluidino)phenol, 4-(4-chloroanilino)phenol, 4-(3-fluoro-4-methylanilino)phenol, 4-[4-(trifluoromethoxy)anilino]-phenol, 4-[4-hydroxyanilino]phenol, {4-[(1-methyl-1H-indol-6-yl)amino]phenyl}-methanol, 4-(2,3-dihydro-1H-indol-6-ylamino)phenol, 4-[(1-methyl-2,3-dihydro-1H-indol-6-yl)amino]phenol, 4-[(1-methyl-1H-indol-6-yl)amino]phenol, 4-[(1-methyl-1H-indol-6-yl)amino]cyclohexanol, 4-[(1-methyl-1,2,3,4-tetrahydro-6-quinolinyl)amino]phenol, 4-[(4-methyl-3,4-dihydro-2H-1,4-benzoxazin-7-yl)amino]phenol, 4-[4-(diethylamino)anilino]-phenol, 4-(2,3-dihydro-1H-inden-5-ylamino)phenol, 4-[(1-methyl-1H-indazol-5-yl)amino]-phenol, 4-[(1'-methyl-1',2'-dihydrospiro[cyclopropane-1,3'-indol]-5'-yl)amino]phenol, 4-[(1,3,3-trimethyl-2,3-dihydro-1H-indol-5-yl)amino]phenol, 4-[4-methoxy-3-(trifluoromethyl)anilino]phenol, 4-[4-(methylsulphanyl)-3-(trifluoromethyl)anilino]phenol, 2-fluoro-4-[(1-methyl-1H-indol-5-yl)amino]phenol, 4-[(1-ethyl-1H-indol-5-yl)amino] phenol, 4-[(1-ethyl-2,3-dihydro-1H-indol-5-yl)amino] phenol, 4-[(1-isopropyl-2,3-dihydro-1H-indol-5-yl)amino] phenol, 4-(butylamino)phenol, 3-[(1-methyl-1H-indol-5-yl) amino]-1-propanol, 4-[(1-methyl-1H-indol-5-yl)amino]-1-butanol, 4-[(3-fluoro-4-methylphenyl)-amino]phenol, 4-[(3-chloro-4-methylphenyl)amino]phenol, 4-[(4-fluorophenyl) amino]-phenol, 4-[(1-methyl-1H-pyrrolo[2,3-b]pyridin-5-yl)amino]phenol, 4-[(4-fluorophenyl)-amino]phenol, 4-[(2-fluorophenyl)amino]phenol, 4-[(3-fluorophenyl)amino] phenol, 4-[(2,4-difluorophenyl)amino]phenol, 4-[(3,4-difluorophenyl)amino]phenol, 3-[(4-hydroxy-phenyl) amino]benzonitrile, 4-[(3-methoxyphenyl)amino]phenol, 4-[(3,5-difluorophenyl)-amino]phenol, 4-[(3-methylphenyl) amino]phenol, 4-[(4-hydroxyphenyl)amino]benzonitrile, 4-[(3-chlorophenyl)amino]phenol, 4-(pyrimidin-2-ylamino) phenol, 4-[(cyclobutyl-methyl)amino]phenol, 2-[(4-hydroxyphenyl)amino]benzonitrile, 4-{[(1-methyl-1H-pyrazol-4-yl)methyl]amino}phenol, 4-[(cyclopropylmethyl) amino]phenol, 4-{[(1-methyl-1H-pyrazol-3-yl)methyl] amino}phenol, 4-(but-2-yn-1-ylamino)phenol, 4-(pyrazin-2-yl-amino)phenol, 4-(pyridin-2-ylamino)phenol, 4-(pyridazin-3-ylamino)phenol, 4-(pyrimidin-5-ylamino) phenol, 4-(pyridin-3-ylamino)phenol, 4-[(3,5-difluoro-4-methoxyphenyl)-amino]phenol, 4-(pyridin-4-ylamino)phenol, 4-[(3-fluoro-4-methoxyphenyl)amino]phenol, 2-(phenylamino)pyrimidin-5-ol, 5-[(4-hydroxyphenyl) amino]-2-methoxybenzonitrile and 4-{[3-(trifluoromethyl) phenyl]amino}phenol.

The hydroxy function(s) of the secondary amines listed above is (are) protected beforehand by a suitable protecting group prior to any coupling to an acid derivative of the compound of formula (IV) as defined in the preceding general process.

Preparation 2a: N-[4-(Benzyloxy)phenyl]-N-phenyl-1H-indole-3-carboxamide

Step A: Methyl 1-{[2-(trimethylsilyl)ethoxy] methyl}-1H-indole-3-carboxylate

Anhydrous tetrahydrofuran (200 ml) and methyl 1H-indole-3-carboxylate (20 g, 114.17 mmol) are cooled to 0° C., and then 60% sodium hydride in oil (9.12 g, 228 mmol) are added and the whole is stirred for 10 minutes under nitrogen. [2-(Chloromethoxy)ethyl]trimethylsilane (24.25 ml, 137 mmol) is added and the reaction mixture is stirred at ambient temperature under nitrogen for approximately 16 hours. The reaction mixture is rendered inactive with water and extracted with ethyl acetate, dried over magnesium sulphate, filtered and concentrated. The crude product is purified by chromatography over silica gel according to a gradient from isohexane to an isohexane (10%)/ethyl acetate mixture to provide the compound in the form of an oil.

LC/MS ($C_{16}H_{23}NO_3Si$) 306 [M+H]$^+$; RT 2.75 (Method A), it being understood that RT denotes retention time Step B: N-[4-(Benzyloxy)phenyl]-N-phenyl-1-{[2-(trimethylsilyl)ethoxy]methyl}-1H-indole-3-carboxamide To a solution of 4-(benzyloxy)-N-phenylaniline (8.59 g, 31.2 mmol) in tetrahydrofuran (40 ml), cooled to −78° C. under nitrogen, there is added lithium bis(trimethylsilyl) amide (1M, 43 ml, 43 mmol). After 10 minutes, the indole obtained in Step A in 40 ml of tetrahydrofuran is added, and the reaction mixture is allowed to warm to ambient temperature again before being heated to 50° C. under nitrogen over a period of approximately 16 hours. The reaction mixture is distributed according to its solubility between ethyl acetate and water, and the organic phases are dried over magnesium sulphate, filtered and concentrated. The crude product is purified over silica gel according to a gradient from isohexane to an isohexane (20%)/ethyl acetate mixture to provide an oil.

LC/MS ($C_{34}H_{36}N_2O_3Si$) 549 [M+H]$^+$; RT 2.95 (Method A)

Step C: N-[4-(Benzyloxy)phenyl]-N-phenyl-1H-indole-3-carboxamide

TBAF (1M, 78 ml, 78 mmol) is added to a solution of the compound obtained in Step B (14.24 g, 25.95 mmol) and ethylenediamine (5.22 ml, 77.85 mmol) in tetrahydrofuran, and the mixture is heated at reflux under nitrogen for approximately 16 hours. The reaction mixture is concentrated and distributed according to its solubility between ethyl acetate and brine. The organic phases are then dried over magnesium sulphate, filtered and stirred for 1 hour with $CaCO_3$ (6.5 g) and an ion-exchange resin DOWEX 50WX8-100 (5 g). The mixture is then filtered, concentrated and triturated with ether. The solid product is isolated by filtration and dried in vacuo.

LC/MS ($C_{28}H_{22}N_2O_2$) 419 [M+H]$^+$; RT 2.36 (Method A)

Preparation 2b:
N,N-Diphenyl-1H-indole-3-carboxamide

The procedure is the same as in Preparation 2a, replacing the 4-(benzyloxy)-N-phenylaniline used in Step B with N-phenylaniline. The product is obtained in the form of a solid.

LC/MS ($C_{21}H_{16}N_2O$) 313.2 [M+H]$^+$; RT 2.47 (Method A)

Preparation 2c:
N,N-Dibutyl-1H-indole-3-carboxamide

Dibutylamine (3.14 ml, 18.62 mmol), DIPEA (1.95 ml, 11.17 mmol) and HBTU (4.24 g, 11.17 mmol) are added to a solution of 1H-indole-3-carboxylic acid (1.5 g, 9.31 mmol) in N,N-dimethylformamide (60 ml) and the reaction mixture is stirred at ambient temperature for 16 hours. The reaction mixture is concentrated in vacuo, diluted with a saturated aqueous NaHCO$_3$ solution and extracted with ethyl acetate. The organic phases are washed with a saturated NaHCO$_3$ solution, with brine, dried over magnesium sulphate and concentrated in vacuo. The resulting material is dissolved in dichloromethane and stirred with 5 g of pre-washed MP-Carbonate resin for 20 minutes, filtered and washed with dichloromethane and then concentrated in vacuo and purified by chromatography over silica gel in isohexane and then a 3:1 then 3:2 isohexane:ethyl acetate mixture to provide the product in the form of a solid.

LC/MS (C$_{17}$H$_{24}$N$_2$O) 273 [M+H]$^+$; RT 2.53 (Method A)

Preparation 2d: N-[4-(Benzyloxy)phenyl]-5-fluoro-N-phenyl-1H-indole-3-carboxamide The procedure is the same as in Preparation 2a, replacing the methyl 1H-indole-3-carboxylate used in Step A with methyl 5-fluoro-1H-indole-3-carboxylate. The product is obtained in the form of a solid.

LC/MS (C$_{28}$H$_{21}$N$_2$O$_2$F) 437 [M+H]$^+$; RT 2.71 (Method A)

Preparation 2e: 6-(Benzyloxy)-N,N-diphenyl-1H-indole-3-carboxamide

Step A: 1-(Benzenesulphonyl)-6-(benzyloxy)-3-iodo-1H-indole

A solution of n-butyllithium (4.02 ml, 8.44 mmol) is added to a solution of 6-(benzyloxy)-1H-indole (942 mg, 4.22 mmol) in tetrahydrofuran (20 ml), cooled to −78° C., and then the whole is stirred at 0° C. for 1 hour. The resulting solution is then transferred by means of a cannula into a solution of iodine (1.07 g, 4.22 mmol) in tetrahydrofuran (20 ml), cooled to −78° C., and the resulting mixture is stirred at 0° C. for 2 hours. The reaction mixture is inactivated by adding methanol (1 drop), cooled to −78° C., and there is then added a lithium diisopropylamide solution prepared according to the following process: a solution of diisopropylamine (0.596 ml, 4.22 mmol) in 10 ml of tetrahydrofuran, cooled to −78° C., is treated with an n-butyllithium solution (2.01 ml, 4.22 mmol) and the resulting mixture is stirred at ambient temperature for 1 hour.

After addition of the lithium diisopropylamide solution, phenylsulphonyl chloride (0.565 ml, 4.43 mmol) is added and, after 30 minutes, the reaction mixture is allowed to warm to ambient temperature again and is stirred for approximately 16 hours. The reaction mixture is inactivated with water and distributed according to its solubility between ethyl acetate and a saturated aqueous sodium bicarbonate solution, and the organic phases are washed with a sodium thiosulphate solution, dried over magnesium sulphate, filtered and concentrated in vacuo. The crude material is purified by chromatography over silica gel in an ethyl acetate (10%)/isohexane mixture to provide an oil.

LC/MS (C$_{21}$H$_{16}$NO$_3$SI) 490 [M+H]$^+$; RT 2.83 (Method A)

Step B: 1-(Benzenesulphonyl)-6-(benzyloxy)-N,N-diphenyl-1H-indole-3-carboxamide

A solution of n-butyllithium (0.41 ml, 0.82 mmol) is added to a solution of the iodide obtained in Step A (200 mg, 0.41 mmol) in tetrahydrofuran (8 ml) under nitrogen, cooled to −78° C. After 5 minutes, N,N-diphenylcarbamoyl chloride (142 mg, 0.61 mmol) in tetrahydrofuran (4 ml) is added and the reaction mixture is stirred at −78° C. for 90 minutes. The reaction mixture is inactivated with water and extracted with ethyl acetate, dried over magnesium sulphate, filtered and evaporated. The crude material is purified by chromatography over silica gel in an ethyl acetate (10%)/isohexane mixture and then 5:1 isohexane/ethyl acetate to provide a gum.

LC/MS (C$_{34}$H$_{26}$N$_2$O$_4$S) 559 [M+H]$^+$; RT 2.84 (Method A)

Step C: 6-(Benzyloxy)-N,N-diphenyl-1H-indole-3-carboxamide

A solution of TBAF (3.63 ml, 3.63 mmol) is added to a solution of the product obtained in Step B (0.68 g, 1.21 mmol) in tetrahydrofuran (8 ml) and the reaction mixture is heated by microwave irradiation at 100° C. for 45 minutes. The reaction mixture is concentrated in vacuo, distributed according to its solubility between ethyl acetate and water and dried over magnesium sulphate. The solvent is removed in vacuo and the crude product is purified by chromatography over silica gel, eluting with a gradient from isohexane to a 1:2 ethyl acetate/isohexane mixture to provide a solid.

LC/MS (C$_{28}$H$_{22}$N$_2$O$_2$) 419 [M+H]$^+$; RT 2.62 (Method A)

Preparation 2f: N-(4-Fluorophenyl)-N-phenyl-1H-indole-3-carboxamide

The procedure is the same as in Preparation 2a, replacing the 4-(benzyloxy)-N-phenylaniline used in Step B with 4-fluoro-N-phenylaniline. The product is obtained in the form of a solid.

Preparation 2g: N-(4-Methylphenyl)-N-phenyl-1H-indole-3-carboxamide

The procedure is the same as in Preparation 2a, replacing the 4-(benzyloxy)-N-phenylaniline used in Step B with 4-methyl-N-phenylaniline. The product is obtained in the form of a solid.

Preparation 3a: 5-(Benzyloxy)-2-(3-{[4-(benzyloxy)phenyl](phenyl)carbamoyl}-1H-indol-1-yl)-4-methoxybenzoic Acid The N-[4-(benzyloxy)phenyl]-N-phenyl-1H-indole-3-carboxamide obtained in Preparation 2a (1.17 g, 2.79 mmol), 5-benzyloxy-2-bromo-4-methoxybenzoic acid (940 mg, 2.79 mmol) and potassium carbonate (771 mg, 5.58 mmol) are combined and suspended in N,N-dimethylformamide (10 ml). The reaction mixture is degassed with nitrogen, then copper iodide (55 mg, 0.28 mmol) is added and the whole is heated to 80° C. under nitrogen over a period of approximately 16 hours. The reaction mixture is diluted with water and acidified with 2 M aqueous HCl. The resulting precipitate is filtered off and washed with water, dissolved in dichloromethane and dried over magnesium sulphate, filtered and evaporated. The crude material is purified by chromatography over silica gel according to a gradient from isohexane to ethyl acetate to provide the product in the form of a foam.

LC/MS ($C_{43}H_{34}N_2O_6$) 675 [M+H]$^+$; RT 2.89 (Method A)

Preparation 3b: 2-[6-(Benzyloxy)-3-(diphenylcarbamoyl)-1H-indol-1-yl]benzoic Acid The procedure is the same as in Preparation 3a, replacing N-[4-(benzyloxy)phenyl]-N-phenyl-1H-indole-3-carboxamide with N,N-diphenyl-1H-indole-3-carboxamide obtained in Preparation 2b and replacing 5-benzyloxy-2-bromo-4-methoxybenzoic acid with 2-bromobenzoic acid.

Preparation 3c: 5-(Benzyloxy)-2-[3-(diphenylcarbamoyl)-1H-indol-1-yl]-4-methoxybenzoic Acid The procedure is the same as in Preparation 3a, replacing N-[4-(benzyloxy)phenyl]-N-phenyl-1H-indole-3-carboxamide with N,N-diphenyl-1H-indole-3-carboxamide obtained in Preparation 2b.

Preparation 3d: 2-(3-{[4-(Benzyloxy)phenyl](phenyl)carbamoyl}-1H-indol-1-yl)benzoic Acid Step A: 2-[3-(Methoxycarbonyl)-1H-indol-1-yl]benzoic Acid Potassium carbonate (1.3 g, 9.42 mmol) and 2-iodobenzoic acid (1.56 g, 6.28 mmol) are added to a solution of methyl 1H-indole-3-carboxylate (1.1 g, 6.28 mmol) in N,N-dimethylformamide (10 ml) and the reaction mixture is degassed with nitrogen before copper iodide (120 mg, 0.628 mmol) is added. The reaction mixture is heated at 90° C. for approximately 16 hours and is then allowed to cool to ambient temperature, diluted with water and extracted with ethyl acetate. The pH of the aqueous phase is adjusted until it becomes acidic using a 2M aqueous HCl solution, and extraction with ethyl acetate is carried out again. The combined organic extracts are dried over magnesium sulphate, filtered and evaporated, and the crude material is purified by chromatography over silica gel according to a gradient from isohexane to ethyl acetate to provide the product in the form of a solid.

LC/MS ($C_{17}H_{13}NO_4$) 296 [M+H]$^+$; RT 2.25 (Method A)

Step B: 2-(3-{[4-(Benzyloxy)phenyl](phenyl)carbamoyl}-1H-indol-1-yl)benzoic Acid Lithium bis(trimethylsilyl)amide (1M in THF, 3.1 ml, 3.11 mmol) is added to a solution of 4-(benzyloxy)-N-phenylaniline (570 mg, 2.07 mmol) in anhydrous tetrahydrofuran (10 ml), cooled to −78° C. under nitrogen, and the reaction mixture is stirred at −78° C. for 20 minutes. A solution of the compound obtained in Step A (610 mg, 2.07 mmol) in tetrahydrofuran (5 ml) is then added to the reaction mixture, which is allowed to warm to ambient temperature again before being heated to 50° C. over a period of approximately 16 hours, during which time a further 5.1 ml of lithium bis(trimethylsilyl)amide are added in 2 portions. The reaction mixture is allowed to cool to ambient temperature, is diluted with water and is extracted with ethyl acetate. The aqueous phase is acidified and extracted with ethyl acetate again, and the combined organic extracts are dried over magnesium sulphate, filtered and evaporated. The crude material is purified by chromatography over silica gel according to a gradient from dichloromethane to a methanol (5%)/dichloromethane mixture to provide an oil, which is then used without being purified further.

LC/MS ($C_{35}H_{26}N_2O_4$) 539 [M+H]$^+$; RT 2.72 (Method A)

Preparation 3e: 2-(3-{[4-(Benzyloxy)phenyl](phenyl)carbamoyl}-1H-indol-1-yl)-4-methoxybenzoic Acid Step A: Methyl 2-(3-{[4-(benzyloxy)phenyl](phenyl)carbamoyl}-1H-indol-1-yl)-4-methoxybenzoate The procedure is the same as in the process of Preparation 3a, replacing 5-benzyloxy-2-bromo-4-methoxybenzoic acid with methyl 2 bromo-4-methoxybenzoate.

LC/MS ($C_{37}H_{30}N_2O_5$) 583 [M+H]$^+$; RT 2.85 (Method A)

Step B: 2-(3-{[4-(Benzyloxy)phenyl](phenyl)carbamoyl}-1H-indol-1-yl)-4-methoxybenzoic Acid Aqueous NaOH (2 M, 1 ml) is added to a solution of the compound obtained in Step A (314 mg, 0.54 mmol) in tetrahydrofuran/methanol (1:1, 4 ml) and the reaction mixture is stirred at ambient temperature overnight. The resulting solution is acidified with 2 M aqueous HCl and extracted with ethyl acetate, dried over magnesium sulphate, filtered and evaporated to provide the product in the form of an oil, which is used without being purified further.

LC/MS ($C_{36}H_{28}N_2O_5$) 569 [M+H]$^+$; RT 2.74 (Method A)

Preparation 3f: 2-[3-(Diphenylcarbamoyl)-1H-indol-1-yl]benzoic Acid

The procedure is the same as in Preparation 3d, replacing the 4-(benzyloxy)-N-phenyl-aniline of Step B with N-phenylaniline.

Preparation 3g: 2-[3-(Diphenylcarbamoyl)-1H-indol-1-yl]-4-methoxybenzoic Acid

The procedure is the same as in Preparation 3a, replacing N-[4-(benzyloxy)phenyl]-N-phenyl-1H-indole-3-carboxamide with N,N-diphenyl-1H-indole-3-carboxamide obtained in Preparation 2b and replacing 5-benzyloxy-2-bromo-4-methoxybenzoic acid with 2-iodo-4-methoxybenzoic acid.

Preparation 3h: 6-(3-{[4-(Benzyloxy)phenyl](phenyl)carbamoyl}-1H-indol-1-yl)-2H-1,3-benzodioxole-5-carboxylic Acid The procedure is the same as in Preparation 3a, replacing 5-benzyloxy-2-bromo-4-methoxybenzoic acid with 6-bromo-2H-1,3-benzodioxole-5-carboxylic acid.

Preparation 3i: 2-(3-{[4-(Benzyloxy)phenyl](phenyl)carbamoyl}-1H-indol-1-yl)-4-chlorobenzoic Acid The procedure is the same as in Preparation 3a, replacing 5-benzyloxy-2-bromo-4-methoxybenzoic acid with 4-chloro-2-iodobenzoic acid.

Preparation 3j: 6-(3-{[4-(Benzyloxy)phenyl](phenyl)carbamoyl}-1H-indol-1-yl)-2-(2-methylpropyl)-2H-1,3-benzodioxole-5-carboxylic Acid The procedure is the same as in Preparation 3a, replacing 5-benzyloxy-2-bromo-4-methoxybenzoic acid with 6-bromo-2-(2-methylpropyl)-2H-1,3-benzodioxole-5-carboxylic acid.

Preparation 3k: 2-(3-{[4-(Benzyloxy)phenyl](phenyl)carbamoyl}-1H-indol-1-yl)-4-,5-dimethoxybenzoic Acid The procedure is the same as in Preparation 3a, replacing 5-benzyloxy-2-bromo-4-methoxybenzoic acid with 2-bromo-4,5-dimethoxybenzoic acid.

Preparation 3l: 2-(3-{[4-(Benzyloxy)phenyl](phenyl)carbamoyl}-1H-indol-1-yl)-4-chloro-5-methoxybenzoic Acid

Step A: Methyl 2-(3-{[4-(benzyloxy)phenyl](phenyl)carbamoyl}-1H-indol-1-yl)-4-chloro-5-methoxybenzoate The procedure is the same as in the process of Preparation 3e, replacing methyl 2-bromo-4-methoxybenzoate with methyl 2-bromo-4-chloro-5-methoxybenzoate.

Step B: 2-(3-{[4-(Benzyloxy)phenyl](phenyl)carbamoyl}-1H-indol-1-yl)-4-chloro-5-methoxybenzoic Acid The compound obtained in Step A (110 mg, 0.18 mmol) is heated at reflux in tetrahydrofuran (2 ml) and 2M aqueous NaOH (2 ml, 4 mmol) for 1.5 hours. The reaction mixture is distributed according to its solubility between ethyl acetate and water, and the organic phases are dried over magnesium sulphate, filtered and concentrated. The crude material is applied to a PE-AX column, washed with dichloromethane, and the compound is eluted with a formic acid (10%)/dichloromethane mixture and subjected to azeotropic distillation with toluene to provide a gum.
LC/MS ($C_{36}H_{27}N_2O_5Cl$) 603.2 [M+H]$^+$; RT 2.58 (Method A)

Preparation 3m: 7-(3-{[4-(Benzyloxy)phenyl](phenyl)carbamoyl}-1H-indol-1-yl)-3-ethyl-2,3-dihydro-1,4-benzodioxine-6-carboxylic Acid

Step A: Methyl 2-bromo-4,5-dihydroxybenzoate

To a solution of methyl 2-bromo-4,5-dimethoxybenzoate (2.41 g, 10 mmol) in dichloromethane, cooled to −78° C. under nitrogen, there is added boron tribromide (1M; 77 mL, 77 mmol), and the reaction mixture is allowed to return to ambient temperature. The mixture is poured over MeOH (200 mL) cooled in an ice bath and then evaporated and distributed according to its solubility between ethyl acetate and water. The organic phase is dried over magnesium sulphate, filtered and evaporated to yield the expected product, which is used in the following step without being purified.
LC/MS ($C_8H_7BrO_4$) 244 [M−H]$^−$; RT 1.82 (Method A)

Step B: Methyl 7-bromo-3-ethyl-2,3-dihydro-1,4-benzodioxine-6-carboxylate

To a solution of the compound of Step A (200 mg, 0.81 mmol) in DMF (3 mL) there are added caesium carbonate (792 mg, 2.43 mmol) and 1,2-dibromobutane (295 μL, 2.43 mmol). The resulting mixture is heated in a microwave apparatus at 150° C. for 20 minutes. The mixture is distributed according to its solubility between ethyl acetate and water, and the organic phase is dried over magnesium sulphate, filtered and concentrated under reduced pressure. The crude material is purified by flash chromatography over a silica gel column, eluted with hexane to a 4:1 hexane/ethyl acetate mixture to yield the expected product in the form of an oil.
LC/MS ($C_{12}H_{13}BrO_4$) 301 [M+H]$^+$; RT 2.62 (Method A)

Step C: 7-(3-{[4-(Benzyloxy)phenyl](phenyl)carbamoyl}-1H-indol-1-yl)-3-ethyl-2,3-dihydro-1,4-benzodioxine-6-carboxylic Acid The procedure is the same as that of Preparation 3e, replacing methyl 2-bromo-4-methoxybenzoate with the compound of Step B.

Preparation 3n: 3-(Benzyloxy)-6-(3-{[4-(benzyloxy)phenyl](phenyl)-carbamoyl}-1H-indol-1-yl)-2-chloro-4-methoxybenzoic Acid The procedure is the same as in Preparation 3a, replacing 5-benzyloxy-2-bromo-4-methoxybenzoic acid with 3-(benzyloxy)-6-bromo-2-chloro-4-methoxybenzoic acid.

Preparation 3o: 6-(3-{[4-(Benzyloxy)phenyl](phenyl)carbamoyl}-5-fluoro-1H-indol-1-yl)-2H-1,3-benzodioxole-5-carboxylic Acid The procedure is the same as in Preparation 3a, replacing 5-benzyloxy-2-bromo-4-methoxybenzoic acid with 6-bromo-2H-1,3-benzodioxole-5-carboxylic acid and replacing the compound of Preparation 2a with the compound of Preparation 2d.

Preparation 3p: 6-[3-(Diphenylcarbamoyl)-1H-indol-1-yl]-2H-1,3-benzodioxole-5-carboxylic Acid The procedure is the same as in Preparation 3a, replacing 5-benzyloxy-2-bromo-4-methoxybenzoic acid with 6-bromo-2H-1,3-benzodioxole-5-carboxylic acid and replacing the compound of Preparation 2a with the compound of Preparation 2b.

Preparation 3q: 4-Chloro-2-[3-(diphenylcarbamoyl)-1H-indol-1-yl]benzoic Acid The procedure is the same as in Preparation 3a, replacing 5-benzyloxy-2-bromo-4-methoxybenzoic acid with 2-bromo-4-chlorobenzoic acid and replacing the compound of Preparation 2a with the compound of Preparation 2b.

Preparation 3r: 4,5-Bis(benzyloxy)-2-(3-{[4-(benzyloxy)phenyl](phenyl)-carbamoyl}-1H-indol-1-yl)benzoic Acid The procedure is the same as in Preparation 3e, replacing methyl 2-bromo-4-methoxybenzoate with methyl 4,5-bis(benzyloxy)-2-bromobenzoate.

Preparation 3s: 2-[3-(Dibutylcarbamoyl)-1H-indol-1-yl]-5-nitrobenzoic Acid

A solution of the compound of Preparation 2c (250 mg, 0.92 mmol) and methyl 2-fluoro-5-nitrobenzoate (365.5 mg, 1.84 mmol) in N,N-dimethylformamide (5 ml) is treated with potassium carbonate (317.12 mg, 2.29 mmol) and heated at reflux for 20 hours under nitrogen. The reaction mixture is cooled to ambient temperature, concentrated in vacuo, diluted with water, acidified to pH 1 with 2M aqueous HCl and extracted with ethyl acetate. The organic extracts are washed with brine, dried over magnesium sulphate, filtered and concentrated in vacuo. The crude material, isolated in the form of the acid, is applied in the dry state to a 20 g silica column and eluted with isohexane, then with a 1:1 isohexane/ethyl acetate mixture, then with ethyl acetate and finally with a 9:1 ethyl acetate/methanol mixture. The fractions containing the product are combined, concentrated in vacuo and applied to a pre-washed 10 g PEAX cartridge, washing with dichloromethane, then with methanol, then with dichloromethane and eluting the product with a 9:1 dichloromethane/formic acid mixture, which is then concentrated in vacuo, diluted with brine and extracted with ethyl acetate. The organic phases are then washed with brine, dried over magnesium sulphate, filtered and concentrated in vacuo to provide a solid.

LC/MS ($C_{24}H_{27}N_3O_5$) 438 $[M+H]^+$; RT 2.64 (Method A)

Preparation 3t: 5-(Benzyloxy)-2-[3-(diphenylcarbamoyl)-1H-indol-1-yl]-4-methoxybenzoic Acid The procedure is the same as in Preparation 3a, replacing 5-benzyloxy-2-bromo-4-methoxybenzoic acid with 5-(benzyloxy)-2-bromo-4-methoxybenzoic acid and replacing the compound of Preparation 2a with the compound of Preparation 2b.

Preparation 3u: 5-(Benzyloxy)-2-{3-[(4-fluorophenyl)(phenyl)carbamoyl]-1H-indol-1-yl}-4-methoxybenzoic Acid The procedure is the same as in Preparation 3a, replacing the compound of Preparation 2a with the compound of Preparation 2f.

Preparation 3v: 5-(Benzyloxy)-4-methoxy-2-{3-[(4-methylphenyl)(phenyl)-carbamoyl]-1H-indol-1-yl}benzoic Acid The procedure is the same as in Preparation 3a, replacing the compound of Preparation 2a with the compound of Preparation 2g.

The compounds of Preparations 4a, 4b and 4c are synthesised in accordance with procedures analogous to those described in Preparations 1" to 26".

Preparation 4a: 4-[(tert-Butyldimethylsilyl)oxy]-N-cyclohexylaniline

Preparation 4b: 4-(Benzyloxy)-N-butylaniline

Preparation 4c: N-(4-{[tert-Butyl(dimethyl)silyl]oxy}phenyl)-1-methyl-1H-indol-5-amine Preparation 5a: N,N-Diphenyl-1H-indazole-3-carboxamide Step A: 3-Iodo-1H-indazole Iodine (51.56 g, 0.2 mol) and ground KOH (8.62 g, 0.375 mol) are added to a solution of 1H-indazole (12 g, 0.1 mol) in N,N-dimethylformamide (190 ml) and the reaction mixture is stirred at ambient temperature for 1 hour. The reaction mixture is distributed according to its solubility between diethyl ether and a 10% sodium thiosulphate solution, and then the aqueous phase is washed twice with diethyl ether. The organic phases are combined and washed with brine, dried over magnesium sulphate, filtered, evaporated and dried in vacuo to provide the product in the form of a solid.

LC/MS ($C_7H_5N_2I$) 245 $[M+H]^+$; RT 2.13 (Method A)

Step B: 3-Iodo-2-{[2-(trimethylsilyl)ethoxy]methyl}-2H-indazole

N-Methyldicyclohexylamine (18.3 ml, 0.09 mol) and 2-(trimethylsilyl)ethoxymethyl chloride (15.3 ml, 0.09 mol) are added to a solution of 3-iodo-1H-indazole (15 g, 0.06 mol) in tetrahydrofuran (150 ml) and the reaction mixture is stirred at ambient temperature under nitrogen over the weekend. The reaction mixture is distributed according to its solubility between ethyl acetate and 2M NaOH, and then the organic phase is washed with brine, dried over magnesium sulphate, filtered and concentrated. It is purified by flash chromatography over a silica gel column according to a gradient from isohexane to an ethyl acetate (40%)/isohexane mixture to obtain the product in the form of an oil.

LC/MS ($C_{13}H_{19}N_2OSiI$) 375 $[M+H]^+$; RT 2.78 (Method A)

Step C: N,N-Diphenyl-2-{[2-(trimethylsilyl)ethoxy]methyl}-2H-indazole-3-carboxamide A solution of the compound obtained in Step B (5.0 g, 13.36 mmol) in anhydrous tetrahydrofuran (25 ml) is added dropwise to a solution of anhydrous tetrahydrofuran (100 ml) and n-butyllithium (2.2 M, 12.15 ml, 26.72 mmol) cooled to −78° C. under nitrogen. After 5 minutes, a solution of diphenylcarbamyl chloride (4.64 g, 20.04 mmol) in anhydrous tetrahydrofuran (25 ml) is added dropwise and the reaction mixture is allowed to warm to ambient temperature again over a period of 4 hours. The reaction mixture is distributed according to its solubility between water and ethyl acetate, and the organic phases are dried over magnesium sulphate, filtered and concentrated to provide an oil, which is purified by flash chromatography over silica gel according to a gradient from isohexane to an ethyl acetate (25%)/isohexane mixture to provide the product in the form of a solid.

LC/MS ($C_{26}H_{29}N_3O_2Si$) no m/z observed; RT 2.87 (Method A)

Step D: N,N-Diphenyl-1H-indazole-3-carboxamide

Ethylenediamine (0.48 ml, 7.16 mmol) and then a 1M TBAF solution in tetrahydrofuran (7.16 ml, 7.16 mmol) are added to a solution of the compound obtained in Step C (3.03 g, 6.82 mmol) in anhydrous tetrahydrofuran (50 ml), and the reaction mixture is heated at reflux at 80° C. overnight under nitrogen. A further amount of ethylenediamine (0.17 ml, 2.54 mmol) and of TBAF (1.36 ml, 1.36 mmol) is added, and the reaction mixture is heated at reflux for a further one hour. The reaction mixture is allowed to cool to ambient temperature and is then distributed according to its solubility between water and ethyl acetate. The organic phases are dried over magnesium sulphate, filtered and concentrated. They are purified by flash chromatography over silica gel according to a gradient from isohexane to an ethyl acetate (80%)/isohexane mixture to obtain a solid.

LC/MS ($C_{20}H_{15}N_3O$) 314 [M+H]$^+$; RT 2.36 (Method A)

Preparation 5b: 5-(Benzyloxy)-N,N-diphenyl-1H-indazole-3-carboxamide

The procedure is the same as in the process of Preparation 5a, replacing the 1H-indazole of Step A with 5-(benzyloxy)-1H-indazole.

LC/MS ($C_{27}H_{21}N_3O_2$) 420 [M+H]$^+$; RT 2.63 (Method A)

Preparation 5c: 6-Methoxy-N,N-diphenyl-1H-indazole-3-carboxamide

The procedure is the same as in the process of Preparation 5a, replacing the 1H-indazole of Step A with 6-(methoxy)-1H-indazole.

LC/MS ($C_{21}H_{17}N_3O_2$) 344 [M+H]$^+$; RT 2.33 (Method A)

Preparation 5d: N,N-Dibutyl-1H-indazole-3-carboxamide

DIPEA (1.1 ml, 6.16 mmol) and dibutylamine (627 μl, 3.70 mmol), then HBTU (1.4 g, 3.70 mmol), are added to a solution of 1H-indazole-3-carboxylic acid (500 mg, 3.08 mmol) in N,N-dimethylformamide (10 ml) under nitrogen, and the reaction mixture is stirred at ambient temperature for 16 hours. Further dibutylamine (2.61 ml, 15.4 mmol) is added and the reaction mixture is heated at 50° C. for 48 hours. The reaction mixture inactivated with water, concentrated and then diluted with a saturated sodium bicarbonate solution and the organic phases are extracted with ethyl acetate, washed with brine, dried over magnesium sulphate, filtered and concentrated. The crude material is purified by chromatography over silica gel in isohexane, to a 9:1 isohexane/ethyl acetate mixture, then to a 3:1 isohexane/ethyl acetate mixture, to provide the product in the form of a solid.

LC/MS ($C_{16}H_{23}N_3O$) 274 [M+H]$^+$; RT 2.51 (Method A)

Preparation 5e: Ethyl 6-(benzyloxy)-1H-indazole-3-carboxylate

Step A: 6-(Benzyloxy)-3-iodo-2-{[2-(trimethylsilyl)ethoxy]methyl}-2H-indazole

The procedure is the same as in the process of Steps A-B of Preparation 5a, replacing the 1H-indazole used in Step A with 6-(benzyloxy)-1H-indazole.

Step B: 6-(Benzyloxy)-2-{[2-(trimethylsilyl)ethoxy]methyl}-2H-indazole-3-carboxylic Acid A solution of the compound obtained in Step A (0.97 g, 2.02 mmol) in tetrahydrofuran (5 ml) is added to a solution of tetrahydrofuran (10 ml), cooled to −78° C., and of n-butyllithium (2.5 M, 1.62 ml, 4.04 mmol), and then the whole is allowed to warm to ambient temperature again over a period of 30 minutes. A further 0.41 ml of n-butyllithium is added to the reaction mixture, which is stirred for 30 minutes before being cooled to −78° C. again. Ground solid carbon dioxide is added and then the reaction mixture is allowed to warm to ambient temperature again and is stirred overnight. The reaction mixture is inactivated with water and the pH is adjusted to 4 with 2M HCl, the mixture is extracted with ethyl acetate and the organic phases are dried over magnesium sulphate, filtered and evaporated. The crude material is applied to a PE-AX column, washed with methanol, and the compound is eluted with a 5:1 dichloromethane/acetic acid mixture to provide a solid.

LC/MS ($C_{21}H_{26}N_2O_4Si$) 397.1 [M−H]$^-$; RT 2.69 (Method A)

Step C: Ethyl 6-(benzyloxy)-1H-indazole-3-carboxylate

Sulphuric acid (0.25 ml) is added to a solution of the compound obtained in Step B (76 mg, 0.19 mmol) in ethanol (5 ml) and the reaction mixture is heated at reflux overnight. The reaction mixture is rendered alkaline with 2N NaOH and then extracted with ethyl acetate and the organic phases are dried over magnesium sulphate, filtered and concentrated to provide a solid. The product is used in the following step without being purified further.

LC/MS ($C_{17}H_{16}N_2O_3$) 297.1 [M+H]$^+$; RT 2.47 (Method A)

Preparation 6a: 6-[3-(Diphenylcarbamoyl)-1H-indazol-1-yl]-2H-1,3-benzodioxole-5-carboxylic Acid A solution of N,N-diphenyl-1H-indazole-3-carboxamide obtained in Preparation 5a (300 mg, 0.96 mmol), potassium carbonate (200 mg, 1.44 mmol) and 6-bromo-2H-1,3-benzodioxole-5-carboxylic acid (235 mg, 0.96 mmol) is degassed in N,N-dimethylformamide (3 ml) with nitrogen, and then copper(I) iodide (20 mg, 0.096 mmol) is added and the reaction mixture is stirred at 100° C. under nitrogen for 4.5 hours. The reaction mixture is cooled to ambient temperature, diluted with ethyl acetate and washed with water. The organic phases are dried over magnesium sulphate, filtered and evaporated and the crude material is purified by chromatography over a silica gel column according to a gradient from dichloromethane to a methanol (10%)/dichloromethane mixture to provide the product in the form of an oil.

LC/MS ($C_{28}H_{19}N_3O_5$) 478 [M+H]$^+$; RT 2.54 (Method A)

Preparation 6b: 2-[3-(Diphenylcarbamoyl)-1H-indazol-1-yl]-5-nitrobenzoic Acid

Step A: Methyl 2-[3-(diphenylcarbamoyl)-1H-indazol-1-yl]-5-nitrobenzoate

Potassium carbonate (514 mg, 3.72 mmol) is added to a solution of the compound obtained in Preparation 5a (777 mg, 2.48 mmol) and of methyl 2-fluoro-5-nitrobenzoate (593 mg, 2.98 mmol) in N,N-dimethylformamide (30 ml) and the reaction mixture is heated at 100° C. under nitrogen overnight. The reaction mixture is concentrated and taken up in ethyl acetate, washed with brine, then dried over magnesium sulphate, filtered and concentrated. The crude material is purified by chromatography over silica gel in a 6:1 isohexane/ethyl acetate mixture and then in a 2:1 isohexane/ethyl acetate mixture to provide a solid.

LC/MS ($C_{28}H_{20}N_4O_5$) 493 [M+H]$^+$; RT 2.69 (Method A)

Step B: 2-[3-(Diphenylcarbamoyl)-1H-indazol-1-yl]-5-nitrobenzoic Acid

2N NaOH (8 ml) is added to a solution of the compound obtained in Step A (816 mg, 1.66 mmol) in tetrahydrofuran (8 ml) and the reaction mixture is stirred at ambient temperature overnight. The reaction mixture is acidified with 2M HCl and the product is extracted with ethyl acetate, dried over magnesium sulphate, filtered and concentrated to provide a solid, which is used directly, without being purified further, in the following step.

LC/MS ($C_{27}H_{18}N_4O_5$) 479 [M+H]$^+$; RT 2.5 (Method A)

Preparation 6c: 2-[6-(Benzyloxy)-3-(diphenylcarbamoyl)-1H-indazol-1-yl]benzoic Acid

Step A: 2-[6-(Benzyloxy)-3-(ethoxycarbonyl)-1H-indazol-1-yl]benzoic Acid

Copper(I) iodide (15 mg, 0.081 mmol) and 2-bromobenzoic acid (196 mg, 0.973 mmol) are added to the compound obtained in Preparation 5e (240 mg, 0.811 mmol) in N,N-dimethylformamide (10 ml) and potassium carbonate (160 mg, 1.217 mmol) and the reaction mixture is stirred at 140° C. overnight. The reaction mixture is concentrated and the residue is taken up in ethyl acetate and washed in succession with water and with brine before being dried over magnesium sulphate, filtered and concentrated. The crude material is purified by column chromatography in a 96:4 dichloromethane/methanol mixture to provide an oil.

LC/MS ($C_{24}H_{20}N_2O_5$) 417 [M+H]$^+$; RT 2.55 (Method A)

Step B: 2-[6-(Benzyloxy)-3-(diphenylcarbamoyl)-1H-indazol-1-yl]benzoic Acid n-Butyllithium (2.5 M, 0.2 ml, 0.49 mmol) is added to a solution of N-phenylaniline (83 mg, 0.49 mmol) in tetrahydrofuran (5 ml), cooled to −78° C., and the reaction mixture is allowed to warm to ambient temperature again over a period of 1 hour. The compound obtained in Step A (68 mg, 0.163 mmol) dissolved in tetrahydrofuran (5 ml) is cooled to −78° C. and the solution of N-phenylaniline is added. The reaction mixture is allowed to warm to ambient temperature again. After 1.5 hours, the reaction mixture is inactivated with water and neutralised with 2M HCl. The organic phases are extracted with ethyl acetate and then dried over magnesium sulphate, filtered and evaporated. The crude material is purified by column chromatography in a 96:4 dichloromethane/methanol mixture.

LC/MS ($C_{35}H_{26}N_2O_4$) 540 [M+H]$^+$; RT 2.67 (Method A)

Preparation 6d: 2-[3-(Dibutylcarbamoyl)-1H-indazol-1-yl]benzoic Acid

The procedure is the same as in the process of Preparation 6a, replacing the compound of Preparation 5a with the compound of Preparation 5d and 6-bromo-2H-1,3-benzodioxole-5-carboxylic acid with 2-iodobenzoic acid.

Preparation 6e: 2-[3-(Diphenylcarbamoyl)-1H-indazol-1-yl]benzoic Acid

The procedure is the same as in the process of Preparation 6a, using 2-iodobenzoic acid.

Preparation 6f: 2-(3-{[4-(Benzyloxy)phenyl](phenyl)carbamoyl}-1H-indazol-1-yl)benzoic Acid

Step A: 2-[3-(Ethoxycarbonyl)-1H-indazol-1-yl]benzoic Acid

Potassium carbonate (218 mg, 1.58 mmol) and 2-iodobenzoic acid (313 mg, 1.26 mmol) are added to a solution of ethyl 1H-indazole-3-carboxylate (200 mg, 1.05 mmol) in N,N-dimethylformamide (20 ml). The solution is degassed with nitrogen and then copper(I) iodide (20 mg, 0.11 mmol) is added, before the whole is heated at 100° C. overnight. The reaction mixture is distributed according to its solubility between ethyl acetate and 2M HCl and then the organic phases are washed with brine, dried over magnesium sulphate, filtered and evaporated to provide an oil, which is purified by a PE-AX column pre-washed with methanol. The compound is applied in the minimal amount of methanol with several drops of triethylamine. The column is washed with methanol and the product is eluted with a formic acid (10%)/dichloromethane mixture to provide an oil, which is used directly without being purified further.

LC/MS ($C_{17}H_{14}N_2O_4$) 311 [M+H]$^+$; RT 2.22 (Method A)

Step B: 2-(3-{[4-(Benzyloxy)phenyl](phenyl)carbamoyl}-1H-indazol-1-yl)benzoic acid LiHMDS (0.8 ml, 0.8 mmol) is added to a solution of 4-(benzyloxy)-N-phenylaniline (0.15 g, 0.53 mmol) in anhydrous tetrahydrofuran (5 ml), cooled −78° C. under nitrogen, and the reaction mixture is stirred at −78° C. for 10 minutes. A solution of the compound obtained in Step A (0.17 g, 0.53 mmol) in anhydrous tetrahydrofuran (5 ml) is added and the reaction mixture is allowed to warm to ambient temperature again before being heated to 50° C. over the weekend. A further quantity of LiHDMS (0.80 ml) is added and the reaction mixture is heated at 50° C. for a further 4 hours. The reaction mixture is distributed according to its solubility between ethyl acetate and water, and then the organic phases are washed with brine, dried over magnesium sulphate, filtered and concentrated to provide an oil, which is used directly, without being purified further, for the following step.

LC/MS ($C_{34}H_{25}N_3O_4$) 538 [M−H]$^-$; RT 2.72 (Method A)

Preparation 6g: 2-[3-(Diphenylcarbamoyl)-6-methoxy-1H-indazol-1-yl]benzoic Acid The procedure of Preparation 6a is applied to the compound obtained in Preparation 5c in the presence of 2-iodobenzoic acid, heating at 140° C.

Preparation 6h: 2-[3-(Diphenylcarbamoyl)-6-hydroxy-1H-indazol-1-yl]benzoic Acid The compound of Preparation 6g (464 mg, 1 mmol) in dichloromethane (20 ml), cooled to 0° C. under nitrogen, is treated dropwise with boron tribromide (1M, 0.95 ml, 10 mmol) and the reaction mixture is stirred at ambient temperature under nitrogen overnight. The reaction mixture is diluted with methanol and neutralised with triethylamine before being concentrated. The residue is extracted with ethyl acetate and washed with dilute HCl, and the organic phases are dried over magnesium sulphate, filtered and concentrated. The crude material is purified by chromatography over silica gel according to a gradient from dichloromethane to a methanol (8%)/dichloromethane mixture to provide a solid.

LC/MS ($C_{27}H_{19}N_3O_4$) 450 [M+H]$^+$; RT 2.34 (Method A)

Preparation 6i: 2-[3-(Diphenylcarbamoyl)-6-hydroxy-1H-indazol-1-yl]benzoic Acid The procedure is the same as in the process of Preparation 6a using 5-(benzyloxy)-2-bromo-4-methoxybenzoic acid.

Preparation 6j: 2-[5-(Benzyloxy)-3-(diphenylcarbamoyl)-1H-indazol-1-yl]benzoic Acid The procedure is the same as in the process of Preparation 6a, replacing the compound of Preparation 5a with the compound of Preparation 5b and 6-bromo-2H-1,3-benzodioxole-5-carboxylic acid with 2-iodobenzoic acid.

Example 1. 1-(2-{[(3S)-3-(Aminomethyl)-3,4-dihydroisoquinolin-2(1H)-yl]-carbonyl}phenyl)-N,N-dibutyl-5-methyl-1H-pyrrole-3-carboxamide Hydrochloride Step A: tert-Butyl {[(3S)-2-{2-[4-(dibutylcarbamoyl)-2-methyl-1H-pyrrol-1-yl]benzoyl}-1,2,3,4-tetrahydroisoquinolin-3-yl]methyl}carbamate The title compound is obtained in accordance with Steps A-C of the process of Example 8 using tert-butyl [(3S)-1,2,3,4-tetrahydroisoquinolin-3-ylmethyl]carbamate (see Preparation 1') in Step A and N,N-dibutylamine in Step C.

Step B: 1-(2-{[(3S)-3-(Aminomethyl)-3,4-dihydroisoquinolin-2(1H)-yl]carbonyl}phenyl)-N,N-dibutyl-5-methyl-1H-pyrrole-3-carboxamide Hydrochloride Trifluoroacetic acid (10 molar equivalents) is added dropwise to a solution of the NH-Boc compound of Step A in dichloromethane (10 mL/mmol) placed at 0° C. The whole is stirred gradually at ambient temperature for 12 hours. The reaction mixture is then concentrated to dryness, taken up and co-evaporated twice with toluene and then concentrated to dryness. The residue is then dissolved in dichloromethane. This organic phase is washed with a saturated NaHCO$_3$ solution and then with a saturated NaCl solution, dried over MgSO$_4$ and concentrated to dryness. The residue obtained is then dissolved in a minimum volume of dichloromethane. The whole is placed at 0° C. and a 1M HCl/Et$_2$O solution (2 molar equivalents) is added. The reaction mixture is stirred for 1 hour at ambient temperature, concentrated to dryness, taken up in a CH$_3$CN/H$_2$O mixture and lyophilised at low temperature to yield the expected product.

Elemental microanalysis: (%, theoretical:measured)
% C=69.32:69.32; % H=7.69:7.68; % N=10.43:10.43; % Cl=6.6:6.79; % Cl—=6.6:6.66

The compounds of Examples 2 to 4 are obtained in accordance with the process of Example 1 using the suitable NHR$_3$R$_4$ amine.

Example 2. 1-(2-{[(3S)-3-(Aminomethyl)-3,4-dihydroisoquinolin-2(1H)-yl]-carbonyl}phenyl)-N-butyl-5-methyl-N-(2-phenylethyl)-1H-pyrrole-3-carboxamide Hydrochloride Elemental microanalysis: (%, theoretical:measured)
% C=71.84:71.44; % H=7.06:6.73; % N=9.57:9.42; % Cl—=6.06:6.16

Example 3. 1-(2-{[(3S)-3-(Aminomethyl)-3,4-dihydroisoquinolin-2(1H)-yl]-carbonyl}phenyl)-N-butyl-5-methyl-N-(3-phenylpropyl)-1H-pyrrole-3-carboxamide Elemental microanalysis: (%, theoretical:measured)
% C=72.16:70.89; % H=7.23:6.96; % N=9.35:9.21; % Cl—=5.92:8.01

High-resolution mass spectroscopy (ESI+):
Empirical formula: C$_{36}$H$_{42}$N$_4$O$_2$
[M+H]$^+$ calculated: 563.3386
[M+H]$^+$ measured: 563.3373

Example 4. 1-(2-{[(3S)-3-(Aminomethyl)-3,4-dihydroisoquinolin-2(1H)-yl]-carbonyl}phenyl)-N-butyl-5-methyl-N-(4-phenylbutyl)-1H-pyrrole-3-carboxamide Hydrochloride Elemental microanalysis: (%, theoretical:measured)
% C=72.47:73.11; % H=7.4:6.95; % N=9.14:9.03; % Cl—=5.78:5.81

Example 5. 1-(2-{[(3S)-3-(Aminomethyl)-3,4-dihydroisoquinolin-2(1H)-yl]-carbonyl}phenyl)-5-methyl-N,N-diphenyl-1H-pyrrole-3-carboxamide Trifluoroacetate Step A: tert-Butyl {[(3S)-2-{2-[4-(diphenylcarbamoyl)-2-methyl-1H-pyrrol-1-yl]benzoyl}-1,2,3,4-tetrahydroisoquinolin-3-yl]methyl}carbamate The title compound is obtained in accordance with the process of Example 8 using tert-butyl [(3S)-1,2,3,4-tetrahydroisoquinolin-3-ylmethyl]carbamate (see Preparation 1') in Step A and N-phenylaniline in Step C.

Step B: 1-(2-{[(3S)-3-(Aminomethyl)-3,4-dihydroisoquinolin-2(1H)-yl]carbonyl}phenyl)-5-methyl-N,N-diphenyl-1H-pyrrole-3-carboxamide Trifluoroacetate A solution of the NH-Boc compound of Step A in dichloromethane is placed at 0° C. 10 molar equivalents of trifluoroacetic acid are added dropwise thereto. The whole is stirred at ambient temperature for 4 hours until the starting material has disappeared completely. The reaction mixture is then concentrated to dryness, taken up in and co-evaporated twice with toluene before being taken up in an acetonitrile/H$_2$O mixture and finally lyophilised.

High-resolution mass spectroscopy (ESI+):
Empirical formula: C$_{35}$H$_{32}$N$_4$O$_2$
[M+H]$^+$ calculated: 541.2604
[M+H]$^+$ measured: 541.2612

Example 6. 1-(2-{[(3S)-3-(Aminomethyl)-3,4-dihydroisoquinolin-2(1H)-yl]-carbonyl}-5-hydroxyphenyl)-5-methyl-N,N-diphenyl-1H-pyrrole-3-carboxamide Step A: tert-Butyl {[(3S)-2-{4-(benzyloxy)-2-[4-(diphenylcarbamoyl)-2-methyl-1H-pyrrol-1-yl]benzoyl}-1,2,3,4-tetrahydroisoquinolin-3-yl]methyl}carbamate The title compound is synthesised in accordance with the process of Example 8 using in Step A the acid obtained in Preparation 2 and the tert-butyl [(3S)-1,2,3,4-tetrahydroisoquinolin-3-ylmethyl]carbamate obtained in Preparation 1', and N-phenylaniline in Step C.

Step B: tert-Butyl {[(3S)-2-{2-[4-(diphenylcarbamoyl)-2-methyl-1H-pyrrol-1-yl]-4-hydroxybenzoyl}-1,2,3,4-tetrahydroisoquinolin-3-yl]methyl}carbamate The compound of Step A is dissolved in methanol (5 mL/mmol), and Pd/C (10% by mass) is added. After one night under a hydrogen pressure of 1 bar, the reaction mixture is filtered, rinsed with ethanol. The filtrate is concentrated to dryness. The desired product is obtained and is used in the following step without being purified.

Step C: 1-(2-{[(3S)-3-(Aminomethyl)-3,4-dihydroisoquinolin-2(1H)-yl]carbonyl}-5-hydroxyphenyl)-5-methyl-N,N-diphenyl-1H-pyrrole-3-carboxamide Trifluoroacetic acid (10 molar equivalents) is added dropwise to a solution of the NH-Boc intermediate in dichloromethane (10 mL/mmol) placed at 0° C. The whole is then stirred at ambient temperature for 12 hours. The reaction mixture is concentrated to dryness, taken up in and co-evaporated twice with toluene and then concentrated to dryness. The residue is then dissolved in dichloromethane. This organic phase is washed with a saturated NaHCO$_3$ solution and then with a saturated NaCl solution, dried over MgSO$_4$ and concentrated to dryness. The residue obtained is then dissolved in a minimum volume of dichloromethane. The whole is placed at 0° C., and a 1M HCl/EtO$_2$ solution (2 molar equivalents) is added. The reaction mixture is stirred for 1 hour at ambient temperature, concentrated to dryness, taken up in a CH$_3$CN/H$_2$O mixture and lyophilised at low temperature to yield the expected product.
Elemental microanalysis: (%, theoretical:measured)
% C=75.52:74.91; % H=5.79:5.17; % N=10.06:10.07

Example 7. 1-(2-{[(3S)-3-(Aminomethyl)-3,4-dihydroisoquinolin-2(1H)-yl]-carbonyl}-5-hydroxyphenyl)-N-(4-hydroxyphenyl)-5-methyl-N-phenyl-1H-pyrrole-3-carboxamide Hydrochloride The title compound is synthesised in accordance with the process of Example 6, replacing N-phenylaniline with 4-benzyloxy-N-phenyl-aniline.
Elemental microanalysis: (%, theoretical:measured)
% C=69.01:67.55; % H=5.46:4.86; % N=9.2:9.26; % Cl—=5.82:6.56
High-resolution mass spectroscopy (ESI+):
Empirical formula: C$_{35}$H$_{32}$N$_4$O$_4$
[M+H]$^+$ calculated: 573.2502
[M+H]$^+$ measured: 573.2493

Example 8. 1-(2-{[(3S)-3-[(Dimethylamino)methyl]-3,4-dihydroisoquinolin-2(1H)-yl]carbonyl}phenyl)-N-(4-hydroxyphenyl)-5-methyl-N-phenyl-1H-pyrrole-3-carboxamide Step A: Ethyl 1-(2-{[(3S)-3-[(dimethylamino)methyl]-3,4-dihydroisoquinolin-2(1H)-yl]carbonyl}phenyl)-5-methyl-1H-pyrrole-3-carboxylate To a solution of 1.7 g of acid obtained in Preparation 1 (6.3 mmol) in 50 mL of dichloromethane there are added 2 g of N,N-dimethyl-1-[(3S)-1,2,3,4-tetrahydroisoquinolin-3-yl]methanamine (7.6 mmol), 4 mL of N,N,N-triethylamine (28.5 mmol), 1.46 g of 1-ethyl-3-(3'-dimethylaminopropyl)-carbodiimide (EDC) (7.6 mmol), and 1.03 g of hydroxybenzotriazole (HOBT) (7.6 mmol). The reaction mixture is stirred at ambient temperature overnight and is then poured over a saturated aqueous NaHCO$_3$ solution and extracted with methylene chloride. The organic phase is then dried over magnesium sulphate before being filtered and evaporated to dryness. The crude product so obtained is then purified by chromatography over silica gel (dichloromethane/methanol gradient) to give the expected product in the form of a powder.
IR: ν: >C=O 1703 cm$^{-1}$ ester; ν: >C=O 1630 cm$^{-1}$ amide; ν: CHN 2768 cm$^{-1}$ Bolhmann band Step B: Lithium 1-(2-{[(3S)-3-[(dimethylamino)methyl]-3,4-dihydroisoquinolin-2(1H)-yl]carbonyl}phenyl)-5-methyl-1H-pyrrole-3-carboxylate The compound of Step A (0.5 g; 1.1 mmol) is dissolved in 4 mL of dioxane. A solution of LiOH (50 mg; 1.2 mmol) in water (1 mL) is added. The whole is heated in a microwave apparatus for 70 minutes at 140° C. (power 100 W). After returning to ambient temperature, the reaction mixture is evaporated to dryness and used as such for the following step.
RMN$^1$H: δ: (400 MHz; dmso-d6; 353K): 7.6-6.8 (m, 9H, aryls+1H pyrrole); 6.05 (sl, 1H, pyrrole); 5.0-4.0 (m, 3H, C$_{tertiary}$ THIQ+$^2$C$_{secondary}$ THIQ); 2.68 (m, 2H C$_{secondary}$ THIQ); 2.2-1.8 (m, 11H, NMe$_2$+CH$_2$N+CH$_3$pyrrole)
IR: ν: >C=O 1626 cm$^{-1}$ amide; ν: >C=O—O 1573 cm$^{-1}$ Step C: N-[4-(Benzyloxy)phenyl]-1-(2-{[(3S)-3-[(dimethylamino)methyl]-3,4-dihydroisoquinolin-2(1H)-yl]carbonyl}phenyl)-5-methyl-N-phenyl-1H-pyrrole-3-carboxamide To a suspension of 475 mg (1.1 mmol) of the lithium carboxylate obtained in Step B in 10 mL of dichloromethane there are added 0.3 mL (3.4 mmol) of oxalyl chloride and a drop of DMF. After stirring for 3 hours, the reaction mixture is concentrated to dryness and then taken up in dichloromethane (10 ml). This solution is then poured over a dichloromethane solution (10 mL) containing compound from Preparation 1'' (470 mg; 1.7 mmol) and pyridine (0.15 mL; 1.7 mmol). After the addition, the reaction mixture is heated at reflux for 10 hours. After cooling, it is poured over a saturated aqueous NaHCO$_3$ solution and extracted with methylene chloride. The organic phase is then dried over magnesium sulphate before being filtered and evaporated to dryness. The crude product so obtained is then purified by chromatography over silica gel (dichloromethane/methanol gradient) to give the expected product in the form of a foam.
$^1$H NMR: δ (400 MHz; dmso-d6; 350K): 7.6-6.3 (m, 23H, aromatic Hs); 5.5 (sl, 1H, H pyrrole); 5.05 (s, 2H, benzylic Hs); 4.0-5.0 (m, 3H, H THIQ); 2.9-2.5 (m, 2H, H THIQ); 2.3-1.6 (m, 8H, NME$_2$+CH$_2$N); 1.85 (sl, 3H, CH$_3$pyrrole)
IR: ν: >C=O: 1623 cm$^{-1}$ amide Step D: 1-(2-{[(3S)-3-[(Dimethylamino)methyl]-3,4-dihydroisoquinolin-2(1H)-yl]-carbonyl}phenyl)-N-(4-hydroxyphenyl)-5-methyl-N-phenyl-1H-pyrrole-3-carboxamide To a solution of the product obtained in Step C (510 mg; 0.75 mmol) in ethanol (8 mL) there are added cyclohexene (0.5 mL) and Pd/C with 10% Pd (100 mg). The reaction mixture is heated at 80° C. overnight. After cooling and filtration through a Whatman® filter, the filtrate is concentrated to dryness and purified by chromatography over silica gel (dichloromethane/methanol gradient) to give the expected product in the form of a colourless foam.
$^1$H NMR: δ (400 MHz; dmso-d6; 350K): 9.5 (sl, 1H, OH); 7.55-6.3 (m, 14H, aromatic Hs+H pyrrole); 6.9 (d, 2H, aromatic Hs); 6.67 (d, 2H, aromatic Hs); 5.50 (s, 1H, H pyrrole); 4.80 (m, 1H, H THIQ); 4.15 (m, 2H, H THIQ); 2.80 (m, 2H, H THIQ); 2.3-1.6 (m, 11H, NMe$_2$+CH$_2$N+ CH$_3$pyrrole).

IR: ν: OH(H$_2$O) and OH (phenol): 3500-2200 cm$^{-1}$; ν: >C=O: 1630 cm$^{-1}$ amide Elemental microanalysis: (%, theoretical:measured)
% C=76:75.62; % H=6.21:5.83; % N=9.58:9.68

Example 9. 1-(2-{[(3S)-3-[(Dimethylamino) methyl]-3,4-dihydroisoquinolin-2(1H)-yl] carbonyl}phenyl)-N,N-bis(4-methoxyphenyl)-5-methyl-1H-pyrrole-3-carboxamide The compound is obtained in accordance with Steps A-C of the process of Example 8 using 4-methoxy-N-(4-methoxyphenyl)aniline in Step C.

Elemental microanalysis: (%, theoretical:measured)
% C=74.5:73.91; % H=6.41:6.06; % N=8.91:8.9

Example 10. 1-(2-{[(3S)-3-[(Dimethylamino) methyl]-3,4-dihydroisoquinolin-2(1H)-yl] carbonyl}phenyl)-N-(1H-indol-5-yl)-5-methyl-N-phenyl-1H-pyrrole-3-carboxamide The compound is obtained in accordance with Steps A-C of the process of Example 8 using the compound of Preparation 3" in Step C. The 1H-indol-5-yl group is then deprotected by means of methanolic potassium hydroxide in accordance with the protocol of Step B of Example 48.

Elemental microanalysis: (%, theoretical:measured)
% C=77.08:76.34; % H=6.14:5.76; % N=11.52:11.3

Example 11. 1-(2-{[(3S)-3-[(Dimethylamino) methyl]-3,4-dihydroisoquinolin-2(1H)-yl] carbonyl}phenyl)-N-(1H-indol-6-yl)-5-methyl-N-phenyl-1H-pyrrole-3-carboxamide The compound is obtained in accordance with Steps A-C of the process of Example 8 using the compound of Preparation 4" in Step C. The 1H-indol-5-yl group is then deprotected by means of methanolic potassium hydroxide in accordance with the protocol of Step B of Example 48.

Elemental microanalysis: (%, theoretical:measured)
% C=77.08:76.59; % H=6.14:5.63; % N=11.52:11.01

Example 12. 1-[2-{[(3S)-3-[(Dimethylamino) methyl]-3,4-dihydroisoquinolin-2(1H)-yl]carbonyl}-5-(trifluoromethyl)phenyl]-N-(4-hydroxyphenyl)-5-methyl-N-phenyl-1H-pyrrole-3-carboxamide Step A: N-(4-{[tert-Butyl(dimethyl)silyl] oxy}phenyl)-1-[2-{[(3S)-3-[(dimethylamino)-methyl]-3,4-dihydroisoquinolin-2(1H)-yl]carbonyl}-5-(trifluoromethyl)phenyl]-5-methyl-N-phenyl-1H-pyrrole-3-carboxamide The title compound is synthesised in accordance with Steps A-C of the process of Example 8 using in Step A the acid obtained in Preparation 3 and in Step C the compound of Preparation 25".

Step B: 1-[2-{[(3S)-3-[(Dimethylamino)methyl]-3,4-dihydroisoquinolin-2(1H)-yl]-carbonyl}-5-(trifluoromethyl)phenyl]-N-(4-hydroxyphenyl)-5-methyl-N-phenyl-1H-pyrrole-3-carboxamide To a solution of 2.3 mmol of the compound obtained in Step A in 4 mL of methanol there is added 0.646 g (11.5 mmol) of potassium hydroxide dissolved in 8 mL of methanol. The whole is stirred at ambient temperature for 30 minutes. The reaction mixture is then diluted in dichloromethane and washed in succession with a 1N HCl solution, a saturated NaHCO$_3$ solution and then with a saturated NaCl solution until a neutral pH is reached. The organic phase is then dried over magnesium sulphate, filtered and evaporated. The crude product so obtained is purified over silica gel (dichloromethane/methanol gradient) to yield the title product.

Elemental microanalysis: (%, theoretical:measured)
% C=69.93:69.34; % H=5.4:5.09; % N=8.58:8.09

Example 13. 1-(5-Chloro-2-{[(3S)-3-[(dimethyl-amino)methyl]-3,4-dihydroisoquinolin-2(1H)-yl] carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 4.

Elemental microanalysis: (%, theoretical:measured)
% C=71.78:69.85; % H=5.7:5.39; % N=9.05:8.54

High-resolution mass spectroscopy (ESI+):
Empirical formula: C$_{37}$H$_{35}$$^{35}$ClN$_4$O$_3$
[M+H]$^+$ calculated: 619.2476
[M+H]$^+$ measured: 619.2458

Example 14. 1-(2-{[(3S)-3-[(Dimethylamino) methyl]-3,4-dihydroisoquinolin-2(1H)-yl]carbonyl}-5-fluorophenyl)-N-(4-hydroxyphenyl)-5-methyl-N-phenyl-1H-pyrrole-3-carboxamide The title compound is synthesised in accordance with the process of Example 12 using in Step A the acid obtained in Preparation 5.

Elemental microanalysis: (%, theoretical:measured)
% C=73.74:72.75; % H=5.85:5.73; % N=9.3:9

Example 15. 1-(5-Hydroxy-2-{[(3S)-3-(morpholin-4-ylmethyl)-3,4-dihydroisoquinolin-2(1H)-yl] carbonyl}phenyl)-N-(4-hydroxyphenyl)-5-methyl-N-phenyl-1H-pyrrole-3-carboxamide The title compound is synthesised in accordance with the process of Example 7 using the (3S)-3-(4-morpholinylmethyl)-1,2,3,4-tetrahydroisoquinoline obtained in Preparation 2'.

Elemental microanalysis: (%, theoretical:measured)
% C=68.97:68.74; % H=5.79:5.65; % N=8.25:8.16; % Cl—=5.22:4.74

Example 16. 1-(4,5-Dibromo-2-{[(3S)-3-[(4-methyl-piperazin-1-yl)methyl]-3,4-dihydroisoquinolin-2 (1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 6 and the (3S)-3-[(4-methyl-1-piperazinyl) methyl]-1,2,3,4-tetrahydroisoquinoline obtained in Preparation 3'.

Elemental microanalysis: (%, theoretical:measured)
% C=60.24:59.6; % H=4.93:4.56; % N=8.78:8.31; % Br=20.04:19.65

Example 17. 1-(5-Hydroxy-2-{[(3S)-3-[(4-methyl-piperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 7 using in Step A the (3S)-3-[(4-methyl-1-piperazinyl)methyl]-1,2,3,4-tetrahydroisoquinoline obtained in Preparation 3'.

Elemental microanalysis: (%, theoretical:measured)
% C=65.93:66.7; % H=5.95:5.61; % N=9.61:9.72; % Cl—=9.73:7.55

Example 18. 1-(3-Chloro-2-{[(3S)-3-[(dimethyl-amino)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 7.

Elemental microanalysis: (%, theoretical:measured)
% C=71.78:70.82; % H=5.7:5.31; % N=9.05:8.89

Example 19. N-(4-Hydroxyphenyl)-5-methyl-1-[2-{[(3S)-3-[(4-methylpiperazin-1-yl)methyl]-3,4-dihydroisoquinolin-2(1H)-yl]carbonyl}-4-(trifluoromethoxy)phenyl]-N-phenyl-1H-pyrrole-3-carboxamide The title compound is synthesised in accordance with the process of Example 12 using in Step A the acid obtained in Preparation 8 and the (3S)-3-[(4-methyl-1-piperazinyl)methyl]-1,2,3,4-tetrahydroisoquinoline obtained in Preparation 3'.

Elemental microanalysis: (%, theoretical:measured)
% C=68.04:67.57; % H=5.57:5.48; % N=9.68:9.73

Example 20. 1-(4,5-Difluoro-2-{[(3S)-3-[(4-methyl-piperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 9 and the (3S)-3-[(4-methyl-1-piperazinyl)methyl]-1,2,3,4-tetrahydroisoquinoline obtained in Preparation 3'.

Elemental microanalysis: (%, theoretical:measured)
% C=71.09:70.09; % H=5.82:5.28; % N=10.36:10.24

Example 21. 1-(5-fluoro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 5 and the (3S)-3-[(4-methyl-1-piperazinyl)methyl]-1,2,3,4-tetrahydroisoquinoline obtained in Preparation 3'.

Elemental microanalysis: (%, theoretical:measured)
% C=73.04:72.28; % H=6.13:5.73; % N=10.65:10.52

Example 22. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 10 and the (3S)-3-[(4-methyl-1-piperazinyl)methyl]-1,2,3,4-tetrahydroisoquinoline obtained in Preparation 3'.

Elemental microanalysis: (%, theoretical:measured)
% C=66.85:66.38; % H=5.61:5.41; % N=9.74:9.73; % Br=11.12:11.09

Example 23. 1-(2-{[(3S)-3-[(Dimethylamino)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Step A: tert-Butyl 5-[(4-{[tert-butyl(dimethyl)silyl]oxy}phenyl){1-(2-{[(3S)-3-[(dimethyl-amino)methyl]-3,4-dihydroisoquinolin-2(1H)-yl]carbonyl}phenyl)-5-methyl-1H-pyrrol-3-yl]carbonyl}amino]-1H-indole-1-carboxylate The title compound is synthesised in accordance with Steps A-C of the process of Example 8, replacing the compound of Preparation 1" with the compound of Preparation 5".

Step B: 1-(2-{[(3S)-3-[(Dimethylamino)methyl]-3,4-dihydroisoquinolin-2(1H)-yl]-carbonyl}phenyl)-N-(4-hydroxyphenyl)-N-(1H-indol-5-yl)-5-methyl-1H-pyrrole-3-carboxamide The product of Step A is deprotected in accordance with the protocol of Step B of Example 48.
Elemental microanalysis: (%, theoretical:measured)
% C=75.1:72.56; % H=5.98:5.42; % N=11.23:10.71
High-resolution mass spectroscopy (ESI+):
Empirical formula: $C_{39}H_{37}N_5O_3$
$[M+H]^+$ calculated: 624.2975
$[M+H]^+$ measured: 624.2994

Example 24. N-(4-Hydroxyphenyl)-5-methyl-1-(6-{[(3S)-3-[(4-methylpiperazin-1-yl)methyl]-3,4-dihydroisoquinolin-2(1H)-yl]carbonyl}-1,3-benzodioxol-5-yl)-N-phenyl-1H-pyrrole-3-carboxamide The title compound is synthesised in accordance with the process of Example 12 using in Step A the acid obtained in Preparation 11 and the (3S)-3-[(4-methyl-1-piperazinyl)methyl]-1,2,3,4-tetrahydroisoquinoline obtained in Preparation 3'.
High-resolution mass spectroscopy (ESI+):
Empirical formula: $C_{41}H_{41}N_5O_5$
$[M+H]^+$ calculated: 684.3186
$[M+H]^+$ measured: 684.3163

The compounds of Examples 25 to 27 are obtained in accordance with the process of Example 13 using the suitable 1,2,3,4-tetrahydroisoquinoline compound and the suitable $NHR_3R_4$ amine.

Example 25. 1-(4-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide Elemental microanalysis: (%, theoretical:measured)
% C=71.26:69.72; % H=5.98:5.35; % N=10.39:10.09
High-resolution mass spectroscopy (ESI+):
Empirical formula: $C_{40}H_{40}{}^{35}ClN_5O_3$
$[M+H]^+$ calculated: 674.2898
$[M+H]^+$ measured: 674.2873

Example 26. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide Elemental microanalysis: (%, theoretical:measured)
% C=71.26:70.06; % H=5.98:5.19; % N=10.39:10.05; % Cl=5.26:5.49
High-resolution mass spectroscopy (ESI+):
Empirical formula: $C_{40}H_{40}{}^{35}ClN_5O_3$
$[M+H]^+$ calculated: 674.2898
$[M+H]^+$ measured: 674.2878

Example 27. N-(3-Chloro-4-hydroxyphenyl)-1-(5-chloro-2-{[(3S)-3-[(4-methylpiperazin-1-yl)methyl]-3,4-dihydroisoquinolin-2(1H)-yl]carbonyl}phenyl)-5-methyl-N-phenyl-1H-pyrrole-3-carboxamide Hydrochloride Elemental microanalysis: (%, theoretical:measured)
% C=64.48:65.67; % H=5.41:5.4; % N=9.4:9.45; % Cl=14.27:11.82
High-resolution mass spectroscopy (ESI+):
Empirical formula: $C_{40}H_{39}{}^{35}Cl_2N_5O_3$
$[M+H]^+$ calculated: 708.2508
$[M+H]^+$ measured: 708.2509

Example 28. 1-(5-Chloro-4-fluoro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 12 and the (3S)-3-[(4-methyl-1-piperazinyl)methyl]-1,2,3,4-tetrahydroisoquinoline obtained in Preparation 3'.
Elemental microanalysis: (%, theoretical:measured)
% C=69.4:68.27; % H=5.68:5.08; % N=10.12:9.81
High-resolution mass spectroscopy (ESI+):
Empirical formula: $C_{40}H_{39}{}^{35}ClFN_5O_3$
$[M+H]^+$ calculated: 692.2804
$[M+H]^+$ measured: 692.2818

Example 29. 1-(4-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 13 and the (3S)-3-[(4-methyl-1-piperazinyl)methyl]-1,2,3,4-tetrahydroisoquinoline obtained in Preparation 3'.
Elemental microanalysis: (%, theoretical:measured)
% C=66.85:64.98; % H=5.61:5.2; % N=9.74:9.38
High-resolution mass spectroscopy (ESI+):
Empirical formula: $C_{40}H_{40}{}^{79}BrN_5O_3$
$[M+H]^+$ calculated: 718.2393
$[M+H]^+$ measured: 718.2380

Example 30. N,N-bis(4-Chlorophenyl)-1-(6-{[(3S)-3-[(4-methylpiperazin-1-yl)-methyl]-3,4-dihydroisoquinolin-2(1H)-yl]carbonyl}-1,3-benzodioxol-5-yl)-1H-indole-3-carboxamide The title compound is synthesised in accordance with the process of Example 12 using in Step A the acid obtained in Preparation 14 and the (3S)-3-[(4-methyl-1-piperazinyl)methyl]-1,2,3,4-tetrahydroisoquinoline obtained in Preparation 3', and the suitable $NHR_3R_4$ amine.
High-resolution mass spectroscopy (ESI+):
Empirical formula: $C_{44}H_{39}Cl_2N_5O_4$
$[M+H]^+$ calculated: 772.2457
$[M+H]^+$ measured: 772.2477

Example 31. N-(4-Chlorophenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Step A: Methyl 1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxylate The process described in Step A of Example 8 is applied using the acid obtained in Preparation 14 and the (3S)-3-[(4-methyl-1-piperazinyl)methyl]-1,2,3,4-tetrahydroisoquinoline obtained in Preparation 3'.

Step B: N-(4-{[tert-Butyl(dimethyl)silyl]oxy}phenyl)-N-(4-chlorophenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide The process described in Steps B and C of Example 8 is applied, replacing in Step C 4-benzyloxy-N-phenyl-aniline with 4-[tert-butyl(dimethyl)silyl]oxy-N-(4-chlorophenyl)-aniline.

Step C: N-(4-Chlorophenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide 0.32 mL of a molar solution of tetrabutylammonium fluoride (0.32 mmol) is added to a suspension of 250 mg (0.29 mmol) of the product obtained in Step B in 1.5 mL of THF. After stirring for 2 hours, the reaction mixture is concentrated to dryness and purified by chromatography over silica gel (dichloromethane/methanol gradient) to give the expected product in the form of a foam.
Elemental microanalysis: (%, theoretical:measured)
% C=70.06:69.54; % H=5.34:4.93; % N=9.28:9.29

The compounds of Examples 32 to 36 are obtained in accordance with the process of Example 31 using the suitable $NHR_3R_4$ amine.

Example 32. N-(4-Hydroxyphenyl)-N-(4-methyl-phenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=73.65:73.41; % H=5.91:5.47; % N=9.54:9.58

Example 33. N-Butyl-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=72.08:71; % H=6.48:6.06; % N=10.01:10.02
High-resolution mass spectroscopy (ESI+):
Empirical formula: $C_{42}H_{45}N_5O_5$
[M+H]$^+$ calculated: 700.3499
[M+H]$^+$ measured: 700.3495

Example 34. N-(3-Fluoro-4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-phenyl-1H-indole-3-carboxamide Elemental microanalysis: (%, theoretical:measured)
% C=71.63:69.22; % H=5.46:4.77; % N=9.49:9.36
High-resolution mass spectroscopy (ESI+):
Empirical formula: $C_{44}H_{40}FN_5O_5$
[M+H]$^+$ calculated: 738.3092
[M+H]$^+$ measured: 738.3083

Example 35. N-(4-Fluorophenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=71.63:69.88; % H=5.46:4.72; % N=9.49:9.5
High-resolution mass spectroscopy (ESI+):
Empirical formula: $C_{44}H_{40}FN_5O_5$
[M+H]$^+$ calculated: 738.3092
[M+H]$^+$ measured: 738.3086

Example 36. N-(4-Chlorophenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-(2-phenylethyl)-1H-indole-3-carboxamide Elemental microanalysis: (%, theoretical:measured)
% C=72.1:71.1; % H=5.79:5.25; % N=9.14:9.34

Example 37. N-(4-Hydroxyphenyl)-N-(1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Step A: tert-Butyl 5-[(4-{[tert-butyl(dimethyl)silyl]oxy}phenyl){1-(6-{[(3S)-3-[(4-methylpiperazin-1-yl)methyl]-3,4-dihydroisoquinolin-2(1H)-yl]carbonyl}-1,3-benzodioxol-5-yl)-1H-indol-3-yl]carbonyl}amino]-1H-indole-1-carboxylate The title compound is synthesised in accordance with Steps A-B of the process of Example 31, replacing the compound of Preparation 6" with the compound of Preparation 5".

Step B: N-(4-Hydroxyphenyl)-N-(1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide 135 mg (2.5 mmol) of KOH are added to a solution of 0.49 mmol of the product obtained in Step A in 5 mL of methanol. After stirring for 3 hours at ambient temperature, the reaction mixture is concentrated, treated with a saturated aqueous NaHCO$_3$ solution and extracted with methylene chloride. The organic phase is then dried over magnesium sulphate, filtered and evaporated to dryness. The crude product so obtained is then purified by chromatography over silica gel (dichloromethane/methanol gradient) to give the expected product in the form of a foam.
Elemental microanalysis: (%, theoretical:measured)
% C=72.81:72.42; % H=5.58:5.34; % N=11.07:10.84

Example 38. 1-(5-Bromo-2-{[(3S)-3-[(3aR,6aS)-hexahydrocyclopenta[c]pyrrol-2(1H)-ylmethyl]-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 13 and the (3S)-3-[(3aR,6aS)-hexahydrocyclopenta[c]pyrrol-2(1H)-ylmethyl]-1,2,3,4-tetrahydroisoquinoline obtained in Preparation 4'.
Elemental microanalysis: (%, theoretical:measured)
% C=69.13:67.94; % H=5.66:5.25; % N=7.68:7.46; % Br=10.95:10.49
High-resolution mass spectroscopy (ESI+):
Empirical formula: $C_{42}H_{41}{}^{79}BrN_4O_3$
[M+H]$^+$ calculated: 729.2440
[M+H]$^+$ measured: 729.2454

The compounds of Examples 39 to 41 are obtained in accordance with the process of Example 31 using the suitable NHR$_3$R$_4$ amine.

Example 39. N-(4-Hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-(3-phenoxyphenyl)-1H-indole-3-carboxamide Hydrochloride Elemental microanalysis: (%, theoretical:measured)
% C=73.97:71.81; % H=5.59:5.26; % N=8.63:8.1
High-resolution mass spectroscopy (ESI+):
Empirical formula: $C_{50}H_{45}N_5O_6$
[M+H]$^+$ calculated: 812.3448
[M+H]$^+$ measured: 812.3431

Example 40. N-(4-Hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-(2-phenylethyl)-1H-indole-3-carboxamide Elemental microanalysis: (%, theoretical:measured)
% C=73.88:72.92; % H=6.06:5.64; % N=9.36:9.38

Example 41. N,N-bis(4-Hydroxyphenyl)-1-(6-{[(3S)-3-[(4-methylpiperazin-1-yl)-methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=71.82:70.67; % H=5.62:5.33; % N=9.52:8.97
High-resolution mass spectroscopy (ESI+):
Empirical formula: $C_{44}H_{41}N_5O_6$

[M+H]$^+$ calculated: 736.3135
[M+H]$^+$ measured: 736.3138

Example 42. 1-(5-Bromo-2-{[(3S)-3-(morpholin-4-ylmethyl)-3,4-dihydroisoquinolin-2(1H)-yl]carbonyl}phenyl)-N-(4-hydroxyphenyl)-5-methyl-N-phenyl-1H-pyrrole-3-carboxamide The title compound is synthesised in accordance with the process of Example 12 using in Step A the acid obtained in Preparation 10 and the (3S)-3-(4-morpholinylmethyl)-1,2,3,4-tetrahydroisoquinoline obtained in Preparation 2'.
Elemental microanalysis: (%, theoretical:measured)
% C=66.38:65.51; % H=5.28:4.91; % N=7.94:7.95; % Br=11.32:10.2

The compounds of Examples 43 to 45 are obtained in accordance with the process of Example 31 using the suitable NHR$_3$R$_4$ amine.

Example 43. N-(1-Benzothiophene-5-yl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=71.21:66.87; % H=5.33:4.87; % N=9.03:8.3; S=4.13:5.03
High-resolution mass spectroscopy (ESI+):
Empirical formula: C$_{46}$H$_{41}$N$_5$O$_5$S
[M+H]$^+$ calculated: 776.2907
[M+H]$^+$ measured: 776.2922

Example 44. N-(1-Benzofuran-5-yl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=72.71:70.11; % H=5.44:5.08; % N=9.22:8.78
High-resolution mass spectroscopy (ESI+):
Empirical formula: C$_{46}$H$_{41}$N$_5$O$_6$
[M+H]$^+$ calculated: 760.3135
[M+H]$^+$ measured: 760.3135

Example 45. N-(4-Hydroxyphenyl)-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=73.04:70.78; % H=5.74:5.26; % N=10.87:10.28
High-resolution mass spectroscopy (ESI+):
Empirical formula: C$_{47}$H$_{44}$N$_6$O$_5$
[M+H]$^+$ calculated: 773.3451
[M+H]$^+$ measured: 773.3459

Example 46. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide The title compound is synthesised in accordance with the process of Example 12 using in Step A the acid obtained in Preparation 10, the (3S)-3-[(4-methyl-1-piperazinyl)methyl]-1,2,3,4-tetrahydroisoquinoline obtained in Preparation 3' and the compound of Preparation 5".
Elemental microanalysis: (%, theoretical:measured)
% C=66.58:64.54; % H=5.45:4.96; % N=11.09:10.48; % Br=10.55:10.02
High-resolution mass spectroscopy (ESI+):
Empirical formula: C$_{42}$H$_{41}$$^{79}$BrN$_6$O$_3$
[M+H]$^+$ calculated: 757.2502
[M+H]$^+$ measured: 757.2480

Example 47. N-(2,3-Dihydro-1H-indol-5-yl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide The title compound is synthesised in accordance with the process of Example 31 using the suitable NHR$_3$R$_4$ amine.
Elemental microanalysis: (%, theoretical:measured)
% C=72.61:70.73; % H=5.83:5.16; % N=11.05:10.51
High-resolution mass spectroscopy (ESI+):
Empirical formula: C$_{46}$H$_{44}$N$_6$O$_5$
[M+H]$^+$ calculated: 761.3451
[M+H]$^+$ measured: 761.3418

Example 48. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1H-indole-3-carboxamide Step A: tert-Butyl 5-[{[1-(5-bromo-2-{[(3S)-3-[(4-methylpiperazin-1-yl)methyl]-3,4-dihydroisoquinolin-2(1H)-yl]carbonyl}phenyl)-1H-indol-3-yl]carbonyl}(4-{[tert-butyl-(dimethyl)silyl]oxy}phenyl)amino]-1H-indole-1-carboxylate The title compound is synthesised in accordance with the process of Example 37 using the acid obtained in Preparation 15.

Step B: 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1H-indole-3-carboxamide 135 mg (2.5 mmol) of KOH are added to a solution of 495 mg (0.49 mmol) of the product obtained in Step A in 5 mL of methanol. After stirring for 3 hours at ambient temperature, the reaction mixture is concentrated, treated with a saturated aqueous NaHCO$_3$ solution and extracted with methylene chloride. The organic phase is then dried over magnesium sulphate, filtered and evaporated to dryness. The crude product so obtained is then purified by chromatography over silica gel (dichloromethane/methanol gradient) to give the expected product in the form of a foam.
Elemental microanalysis: (%, theoretical:measured)
% C=68.09:66.77; % H=5.21:4.73; % N=10.59:10.29; % Br=10.07:9.76
High-resolution mass spectroscopy (ESI+):
Empirical formula: C$_{45}$H$_{41}$$^{79}$BrN$_6$O$_3$
[M+H]$^+$ calculated: 793.2502
[M+H]$^+$ measured: 793.2539

Unless otherwise mentioned, the compounds of the following Examples are synthesised in accordance with the process of Example 31 using in Step A: (i) the appropriate acid obtained in accordance with one of Preparations 1 to 22 and (ii) the appropriate tetrahydroisoquinoline compound obtained in accordance with one of Preparations 1' to 12' and, in Step B: (iii) the suitable $NHR_3R_4$ amine (a non-exhaustive list is proposed in Preparations 1" to 26"). The compounds so obtained can be isolated in the form of a hydrochloride using the salt formation protocol using methanolic ether presented at the end of Step C of Example 1.

Example 49. N-(4-Hydroxyphenyl)-N-(4-methoxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=72.08:71.86; % H=5.78:5.49; % N=9.34:9.31

Example 50. 1-(5-Bromo-2-{[(3S)-3-[(4-methylpiperazin-1-yl)methyl]-3,4-dihydroisoquinolin-2(1H)-yl]carbonyl}phenyl)-N-(4-fluorophenyl)-N-(4-hydroxyphenyl)-5-methyl-1H-pyrrole-3-carboxamide Elemental microanalysis: (%, theoretical:measured)
% C=65.22:65.4; % H=5.34:4.89; % N=9.51:9.53; % Br=10.85:10.86

Example 51. N-(4-Hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-[4-(trifluoro-methoxy)phenyl]-1H-indole-3-carboxamide Elemental microanalysis: (%, theoretical:measured)
% C=67.24:67.28; % H=5.02:4.73; % N=8.71:8.78

Example 52. N-(3-Fluoro-4-methylphenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical: measured)
% C=71.89:71.45; % H=5.63:5.15; % N=9.31:9.34

Example 53. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-(4-methylphenyl)-1H-pyrrole-3-carboxamide Elemental microanalysis: (%, theoretical:measured)
% C=67.21:67.28; % H=5.78:5.62; % N=9.56:9.49; % Br=10.91:10.87

Example 54. 1-(5-Bromo-2-{[(3S)-3-[(4-methylpiperazin-1-yl)methyl]-3,4-dihydroisoquinolin-2(1H)-yl]carbonyl}phenyl)-N,N-bis(4-hydroxyphenyl)-1H-indole-3-carboxamide Elemental microanalysis: (%, theoretical:measured)
% C=67.01:66.03; % H=5.23:5.23; % N=9.09:8.74

Example 55. N-(1H-Indol-5-yl)-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical: measured)
% C=74.58:73.82; % H=5.86:5.69; % N=11.1:10.87

Example 56. N-(3,4-Difluorophenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical: measured)
% C=69.92:69.53; % H=5.2:4.98; % N=9.27:9.07

Example 57. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-N-(4-methylphenyl)-1H-indole-3-carboxamide Elemental microanalysis: (%, theoretical: measured)
% C=68.75:68.42; % H=5.51:5.88; % N=9.11:8.83; % Br=10.39:10.16

Example 58. N-(3-Chloro-4-fluorophenyl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical: measured)
% C=65.35:66.91; % H=4.99:4.83; % N=8.66:8.8; % Cl=8.77:7.03; % Cl—=4.38:2.37

Example 59. 1-(5-Bromo-2-{[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-1H-indole-3-carboxamide Elemental microanalysis: (%, theoretical:measured)
% H=4.98:5.64; % N=8.87:8.4; % C=65.45:65.99

Example 60. 4-[(4-Methylphenyl){1-(6-{[(3S)-3-[(4-methylpiperazin-1-yl)methyl]-3,4-dihydroisoquinolin-2(1H)-yl]carbonyl}-1,3-benzodioxol-5-yl)-1H-indol-3-yl]-carbonyl}amino]phenyl Acetate Elemental microanalysis: (%, theoretical: measured)
% C=72.76:71.25; % H=5.85:5.71; % N=9.03:8.92
High-resolution mass spectroscopy (ESI+):
Empirical formula: $C_{47}H_{45}N_5O_6$
$[M+H]^+$ calculated: 776.3448
$[M+H]^+$ measured: 776.3398

Example 61. 1-(5-Bromo-2-{[(3S)-3-[(4-methylpiperazin-1-yl)methyl]-3,4-dihydroisoquinolin-2(1H)-yl]carbonyl}phenyl)-N,N-bis(4-hydroxyphenyl)-5-methyl-1H-pyrrole-3-carboxamide Elemental microanalysis: (%, theoretical: measured)
% C=65.39:63.91; % H=5.49:5.43; % N=9.53:9.12
High-resolution mass spectroscopy (ESI+):
Empirical formula: $C_{40}H_{40}{}^{79}BrN_5O_4$
$[M+H]^+$ calculated: 734.2342
$[M+H]^+$ measured: 734.2298

Example 62. 1-(5-Bromo-2-{[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-5-methyl-1H-pyrrole-3-carboxamide Elemental microanalysis: (%, theoretical:measured)
% C=63.79:63.87; % H=5.22:5.13; % N=9.3:9.58

Example 63. N-(3-Chloro-4-hydroxyphenyl)-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical:measured)
% C=64.25:64.13; % H=5.27:5.01; % N=8.33:8.18; % Cl—=8.43:7.25

Example 64. N-(3-Chloro-4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-[4-(propan-2-yl)phenyl]-1H-indole-3-carboxamide Hydrochloride Elemental microanalysis: (%, theoretical: measured)
% C=64.94:65.36; % H=5.57:5.2; % N=8.06:7.95; % Cl—=8.16:6.8

Example 65. 1-(5-Chloro-2-{[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-5-methyl-1H-pyrrole-3-carboxamide Elemental microanalysis: (%, theoretical: measured)
% C=67.79:67.6; % H=5.55:5.52; % N=9.88:9.98

Example 66. 1-(5-Chloro-2-{[(3S)-3-[(4-methylpiperazin-1-yl)methyl]-3,4-dihydroisoquinolin-2(1H)-yl]carbonyl}phenyl)-N-(4-fluorophenyl)-N-(4-hydroxyphenyl)-5-methyl-1H-pyrrole-3-carboxamide Elemental microanalysis: (%, theoretical: measured)
% C=69.4:68.97; % H=5.68:5.64; % N=10.12:10.08

Example 67. 1-(5-Chloro-2-{[(3S)-3-[(4-methylpiperazin-1-yl)methyl]-3,4-dihydroisoquinolin-2(1H)-yl]carbonyl}phenyl)-N,N-bis(4-hydroxyphenyl)-5-methyl-1H-pyrrole-3-carboxamide Elemental microanalysis: (%, theoretical: measured)
% C=69.6:69.52; % H=5.84:5.73; % N=10.15:10.31

Example 68. N-(1H-Indazol-5-yl)-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical: measured)
% C=66.5:66.14; % H=5.46:5.3; % N=11.8:11.86; % Cl—=8.53:8.06

Example 69. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1-methyl-1H-indol-5-yl)-1H-indole-3-carboxamide Hydrochloride Elemental microanalysis: (%, theoretical:measured)
% C=62.73:63.57; % H=5.15:5.04; % N=9.54:9.64; % Cl—=8.05:6.7

Example 70. 1-(5-Bromo-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-(1-methyl-1H-indol-5-yl)-1H-pyrrole-3-carboxamide Hydrochloride Elemental microanalysis: (%, theoretical:measured)
% C=61.14:62.23; % H=5.37:5.27; % N=9.95:10.13; % Cl—=8.39:7

High-resolution mass spectroscopy (ESI+):
Empirical formula: $C_{43}H_{43}{}^{79}BrN_6O_3$
$[M+H]^+$ calculated: 771.2658
$[M+H]^+$ measured: 771.2645

Example 71. 1-(5-Bromo-2-{[(3S)-3-[(4-methylpiperazin-1-yl)methyl]-3,4-dihydroisoquinolin-2(1H)-yl]carbonyl}phenyl)-N-(4-fluorophenyl)-N-(4-hydroxyphenyl)-1H-indole-3-carboxamide Elemental microanalysis: (%, theoretical:measured)
% C=66.84:66.66; % H=5.09:5.23; % N=9.06:8.81; % Br=10.34:9.95

Example 72. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1H-indole-3-carboxamide The title compound is synthesised in accordance with the process of Example 37 using the acid obtained in Preparation 16.

Elemental microanalysis: (%, theoretical: measured)
% C=72.13:71.39; % H=5.51:5.45; % N=11.22:10.75; % Cl=4.73:5.46

Example 73. 1-(5-Chloro-2-{[(3S)-3-[(4-methylpiperazin-1-yl)methyl]-3,4-dihydroisoquinolin-2(1H)-yl]carbonyl}phenyl)-N,N-bis(4-hydroxyphenyl)-1H-indole-3-carboxamide Elemental microanalysis: (%, theoretical: measured)
% C=71.11:70.47; % H=5.55:5.45; % N=9.64:9.44

Example 74. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(4-methylphenyl)-1H-indole-3-carboxamide Elemental microanalysis: (%, theoretical: measured)
% C=72.96:72.95; % H=5.84:5.74; % N=9.67:9.57

Example 75. 1-(5-Chloro-2-{[(3S)-3-[(4-methylpiperazin-1-yl)methyl]-3,4-dihydroisoquinolin-2(1H)-yl]carbonyl}phenyl)-N-(4-fluorophenyl)-N-(4-hydroxyphenyl)-1H-indole-3-carboxamide Elemental microanalysis: (%, theoretical: measured)
% C=70.92:70.28; % H=5.4:5.29; % N=9.62:9.44

Example 76. 1-(5-Chloro-2-{[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-1H-indole-3-carboxamide Elemental microanalysis: (%, theoretical: measured)
% C=69.35:69.01; % H=5.28:5.16; % N=9.4:9.17; % Cl=9.52:9.74

Example 77. 1-(5-Chloro-4-fluoro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-(1-methyl-1H-indol-5-yl)-1H-pyrrole-3-carboxamide Hydrochloride Elemental microanalysis: (%, theoretical:measured)
% C=63.12:63.39; % H=5.42:5.16; % N=10.27:10.04; % Cl=13.12.21; % Cl—=8.67:7

Example 78. 1-(5-Chloro-4-fluoro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1-methyl-1H-indol-5-yl)-1H-indole-3-carboxamide Hydrochloride Elemental microanalysis: (%, theoretical:measured)
% C=64.68:64.96; % H=5.19:4.89; % N=9.84:9.63; % Cl=12.45:12.01; % Cl—=8.3:6.83

Example 79. 1-(5-Bromo-2-{[(3S)-3-[(4,4-difluoropiperidin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical:measured)
% C=64.78:63.92; % H=4.92:4.98; % N=8.99:8.97; % Br=10.26:10.8

Example 80. 1-(5-Bromo-2-{[(3S)-3-[(4-cyclopentylpiperazin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical:measured)
% C=68.06:66.99; % H=5.84:5.75; % N=10.35:10.1; % Br=9.84:9.81

Example 81. N-(3-Chloro-4-hydroxyphenyl)-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical: measured)
% C=64.13:64.93; % H=5.15:4.92; % N=9.55:9.57; % Cl=12.08:11; % Cl—=8.06:6.45

Example 82. N-(3-Chloro-4-hydroxyphenyl)-N-(1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical: measured)
% C=63.78:64.52; % H=5:4.87; % N=9.7:9.72; % Cl=12.28:11.49; % Cl—=8.19:6.77

Example 83. N,N-bis(4-Hydroxyphenyl)-5-methyl-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical: measured)
% C=70.37:70.32; % H=5.91:5.77; % N=10.01:9.91

Example 84. N-(4-Fluorophenyl)-N-(4-hydroxyphenyl)-5-methyl-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical: measured)
% C=70.17:68.82; % H=5.74:5.5; % N=9.98:9.81
High-resolution mass spectroscopy (ESI+):
Empirical formula: $C_{41}H_{40}FN_5O_5$
[M+H]$^+$ calculated: 702.3092
[M+H]$^+$ measured: 702.3096

Example 85. N-(4-Chlorophenyl)-N-(4-hydroxyphenyl)-5-methyl-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical: measured)
% C=68.56:68.13; % H=5.61:5.53; % N=9.75:9.66

Example 86. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical:measured)
% C=70.72:70.45; % H=5.79:5.69; % N=11.78:11.56; % Cl=4.97:5.5

Example 87. N-(4-Hydroxyphenyl)-N-(1H-indol-5-yl)-5-methyl-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical: measured)

Example 88. 5-Chloro-N-(4-hydroxyphenyl)-N-(1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=69.64:69.34; % H=5.21:5.21; % N=10.59:10.45

Example 89. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-(1-methyl-1H-indol-5-yl)-1H-pyrrole-3-carboxamide Elemental microanalysis: (%, theoretical:measured)
% C=71.01:69.93; % H=5.96:5.84; % N=11.56:11.2
High-resolution mass spectroscopy (ESI+):
Empirical formula: $C_{43}H_{43}{}^{35}ClN_6O_3$
[M+H]$^+$ calculated: 727.3163
[M+H]$^+$ measured: 727.3126

Example 90. N-(4-Hydroxyphenyl)-5-methyl-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical:measured)
% C=71.72:69.98; % H=6.02:6.02; % N=11.41:11.05

High-resolution mass spectroscopy (ESI+):
Empirical formula: $C_{44}H_{44}N_6O_5$
[M+H]$^+$ calculated: 737.3451
[M+H]$^+$ measured: 737.3444

Example 91. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-5-methyl-N-(4-methylphenyl)-1H-pyrrole-3-carboxamide Elemental microanalysis: (%, theoretical:measured)
% C=71.55:71.06; % H=6.15:6.08; % N=10.18:10.02

Example 92. 1-(3,5-Dichloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide The title compound is synthesised in accordance with the process of Example 12 using in Step A the acid obtained in Preparation 17, the (3S)-3-[(4-methyl-1-piperazinyl)methyl]-1,2,3,4-tetrahydroisoquinoline obtained in Preparation 3' and the compound of Preparation 5".

Elemental microanalysis: (%, theoretical:measured)
% C=67.47:67.28; % H=5.39:5.84; % N=11.24:10.07; % Cl=9.48:9.21

Example 93. 1-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1-methyl-1H-indol-5-yl)-1H-indole-3-carboxamide Elemental microanalysis: (%, theoretical:measured)
% C=72.38:71.93; % H=5.68:5.94; % N=11.01:10.28

Example 94. 1-(6-{[(3S)-3-[(Dimethylamino)methyl]-3,4-dihydroisoquinolin-2(1H)-yl]carbonyl}-1,3-benzodioxol-5-yl)-N-(4-hydroxyphenyl)-5-methyl-N-(1-methyl-1H-indol-5-yl)-1H-pyrrole-3-carboxamide Hydrochloride Elemental microanalysis: (%, theoretical:measured)
% C=68.56:68.21; % H=5.61:5.43; % N=9.75:9.56; % Cl=4.94:5.41; % Cl—=4.94:5.17

Example 95. 1-(5-Chloro-2-{[(3S)-3-[(dimethylamino)methyl]-3,4-dihydroisoquinolin-2(1H)-yl]carbonyl}phenyl)-N-(4-hydroxyphenyl)-5-methyl-N-(1-methyl-1H-indol-5-yl)-1H-pyrrole-3-carboxamide Hydrochloride Elemental microanalysis: (%, theoretical:measured)
% C=67.79:67.07; % H=5.55:5.34; % N=9.88:9.58; % Cl=10.01:10.09; % Cl—=5:5.41

Example 96. N-(4-Hydroxyphenyl)-5-methyl-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide Elemental microanalysis: (%, theoretical:measured)
% C=72.29:72.01; % H=6.21:6.05; % N=10.04:9.95

Example 97. N-(3-Fluoro-4-hydroxyphenyl)-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Hydrochloride Elemental microanalysis: (%, theoretical:measured)
% C=65.35:65.8; % H=5.25:5.15; % N=9.73:9.57; % Cl—=8.21:6.82

Example 98. N-(4-Methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-(piperidin-4-yl)-1H-indole-3-carboxamide Bis-Hydrochloride Step A: tert-Butyl 4-[(4-methylphenyl){[1-(6-{[(3S)-3-[(4-methylpiperazin-1-yl)methyl]-3,4-dihydroisoquinolin-2(1H)-yl]carbonyl}-1,3-benzodioxol-5-yl)-1H-indol-3-yl]-carbonyl}amino]piperidine-1-carboxylate The title compound is synthesised in accordance with Steps A-B of the process of Example 31 using the acid obtained in Preparation 14 and the compound of Preparation 19".

Step B: N-(4-Methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-(piperidin-4-yl)-1H-indole-3-carboxamide Bis-Hydrochloride Trifluoroacetic acid (0.5 mL; 6 mmol) is added to a solution of starting material (615 mg; 0.74 mmol) in methylene chloride (7 mL). After stirring for 17 hours at ambient temperature, the reaction mixture is poured over a mixture composed of an aqueous sodium bicarbonate solution and dichloromethane. The aqueous phase is extracted with dichloromethane and then dried over MgSO$_4$, concentrated to dryness and the residue is purified by chromatography over silica gel (CH$_2$Cl$_2$/MeOH gradient) to provide the free base in the form of a white powder. This compound is dissolved in CH$_2$Cl$_2$ and then treated at ambient temperature with a 1M HCl solution in ether (2 mL; 2 mmol). The solution is then dried and the residue is lyophilised.

Elemental microanalysis: (%, theoretical:measured)
% C=63.35:63.51; % H=6.16:6.04; % N=10.07:10.14; % Cl=12.75:11.53; % Cl—=12.75:11.92

Example 99, N-(1-Ethyl-1H-indol-5-yl)-N-(4-hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide Elemental microanalysis: (%, theoretical:measured)
% C=73.26:72.93; % H=5.89:5.74; % N=10.68:10.69

Example 100. N-(4-Hydroxyphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-N-[1-(propan-2-yl)-1H-indol-5-yl]-1H-indole-3-carboxamide Elemental microanalysis: (%, theoretical:measured)
% C=73.48:74.43; % H=6.04:5.81; % N=10.49:10.71

Example 101. 1-(5-Bromo-2-{[(3S)-3-[(4-methyl-piperazin-1-yl)carbonyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical:measured)
% C=65.37:65.39; % H=5.09:4.89; % N=10.89:10.67; % Br=10.35:10.47

Example 102. 1-(5-Bromo-2-{[(3S)-3-[(4-cyclobutylpiperazin-1-yl)methyl]-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical: measured)
% C=67.75:67.81; % H=5.69:5.63; % N=10.53:10.32; % Br=10.02:9.89

Example 103. N-(2,3-Dihydro-1H-indol-5-yl)-N-(4-hydroxyphenyl)-5-methyl-1-(6-{[(3S)-3-[(4-methyl-piperazin-1-yl)methyl]-3,4-dihydroisoquinolin-2(1H)-yl]carbonyl}-1,3-benzodioxol-5-yl)-1H-pyrrole-3-carboxamide Hydrochloride Elemental microanalysis: (%, theoretical: measured)
% C=64.74:63.93; % H=5.81:6.29; % N=10.53:8.92; % Cl=8.89:10.68; % Cl⁻=8.89:10.58

Example 104. 1-(5-Bromo-2-{[(3S)-3-(pyrrolidin-1-ylmethyl)-3,4-dihydroisoquinolin-2(1H)-yl]carbonyl}phenyl)-N-(4-hydroxyphenyl)-N-(1H-indol-5-yl)-5-methyl-1H-pyrrole-3-carboxamide Elemental microanalysis: (%, theoretical: measured)
% C=67.58:67.45; % H=5.26:5.09; % N=9.61:9.36; % Br=10.97:10.84

Example 105. N-(4-Hydroxyphenyl)-5-methyl-N-(1-methyl-1H-indol-5-yl)-1-(6-{[(3S)-3-(pyrrolidin-1-ylmethyl)-3,4-dihydroisoquinolin-2(1H)-yl]carbonyl}-1,3-benzodioxol-5-yl)-1H-pyrrole-3-carboxamide Hydrochloride Elemental microanalysis: (%, theoretical:measured)
% H=5.69:5.51; % N=9.41:9.2; % Cl=4.76:5.06; % Cl⁻=4.76:4.8; % C=69.39:69.24

Example 106. N-(4-Hydroxyphenyl)-5-methyl-N-(4-methylphenyl)-1-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Hydrochloride Elemental microanalysis: (%, theoretical: measured)
% C=68.28:67.63; % H=5.73:5.65; % N=7.77:7.53; % Cl⁻=4.92:4.81

Example 107. N-(4-Hydroxyphenyl)-5-methyl-1-(6-{[(3S)-3-(morpholin-4-ylmethyl)-3,4-dihydroisoquinolin-2(1H)-yl]carbonyl}-2,3-dihydro-1H-inden-5-yl)-N-phenyl-1H-pyrrole-3-carboxamide Hydrochloride Elemental microanalysis: (%, theoretical: measured)
% C=71.73:71.34; % H=6.16:6.15; % N=7.97:7.87; % Cl⁻=5.04:4.73

Example 108. N-(4-Hydroxyphenyl)-5-methyl-1-(6-{[(3S)-3-(morpholin-4-ylmethyl)-3,4-dihydroisoquinolin-2(1H)-yl]carbonyl}-1,3-benzodioxol-5-yl)-N-phenyl-1H-pyrrole-3-carboxamide Hydrochloride Elemental microanalysis: (%, theoretical:measured)
% C=67.93:68.17; % H=5.56:5.43; % N=7.92:8.09; % Cl⁻=5.01:4.77

Example 109. N-(4-Hydroxyphenyl)-5-methyl-N-(1-methyl-1H-indol-5-yl)-1-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Hydrochloride Elemental microanalysis: (%, theoretical: measured)
% C=67.93:66.48; % H=5.57:5.52; % N=9.21:9.24; % Cl⁻=4.66:5.67

High-resolution mass spectroscopy (ESI+):
Empirical formula: $C_{43}H_{41}N_5O_6$
$[M+H]^+$ calculated: 724.3135
$[M+H]^+$ measured: 724.3073

Example 110. N-(2,3-Dihydro-1H-indol-5-yl)-N-(4-hydroxyphenyl)-5-methyl-1-(6-{[(3S)-3-(morpholin-4-ylmethyl)-3,4-dihydroisoquinolin-2(1H)-yl]carbonyl}-2,3-dihydro-1H-inden-5-yl)-1H-pyrrole-3-carboxamide Hydrochloride Elemental microanalysis: (%, theoretical: measured)
% C=67.69:67.78; % H=6.07:6.04; % N=8.97:9.39; % Cl=9.08:7.96; % Cl⁻=9.08:8.09

Example 111. N-(4-Hydroxyphenyl)-5-methyl-1-(6-{[(3R)-3-methyl-3,4-dihydroisoquinolin-2(1H)-yl]carbonyl}-1,3-benzodioxol-5-yl)-N-(1-methylpiperidin-4-yl)-1H-pyrrole-3-carboxamide Hydrochloride Elemental microanalysis: (%, theoretical:measured)
% C=67.23:66.34; % H=6.11:6.01; % N=8.71:8.72; % Cl⁻=5.51:5.67

Example 112. N-(4-Hydroxyphenyl)-5-methyl-1-(6-{[(3R)-3-methyl-3,4-dihydroisoquinolin-2(1H)-yl]carbonyl}-1,3-benzodioxol-5-yl)-N-[3-(4-methylpiperazin-1-yl)phenyl]-1H-pyrrole-3-carboxamide Hydrochloride Elemental microanalysis: (%, theoretical:measured)
% C=68.37:68.91; % H=5.88:5.34; % N=9.72:9.78; % Cl⁻=4.92:5.24

Example 113. N-(4-Hydroxyphenyl)-1-(6-{[(3S)-3-(morpholin-4-ylmethyl)-3,4-dihydroisoquinolin-2(1H)-yl]carbonyl}-1,3-benzodioxol-5-yl)-N-phenyl-4,5,6,7-tetrahydro-1H-indole-3-carboxamide Hydrochloride The title compound is synthesised in accordance with the process of Example 12 using in Step A the acid obtained in Preparation 19 and the (3S)-3-(4-morpholinylmethyl)-1,2,3,4-tetrahydroisoquinoline obtained in Preparation 2'.
Elemental microanalysis: (%, theoretical:measured)
% C=69.11:68.82; % H=5.8:5.8; % N=7.5:7.45; % Cl⁻=4.74:4.46
High-resolution mass spectroscopy (ESI+):
Empirical formula: $C_{43}H_{42}N_4O_6$

[M+H]⁺ calculated: 711.3183
[M+H]⁺ measured: 711.3140

Example 114. N-(4-Hydroxyphenyl)-5-methyl-N-(2-methyl-2,3-dihydro-1H-isoindol-5-yl)-1-(6-{[(3R)-3-methyl-3,4-dihydroisoquinolin-2(1H)-yl]carbonyl}-1,3-benzodioxol-5-yl)-1H-pyrrole-3-carboxamide Hydrochloride Elemental microanalysis: (%, theoretical:measured)
% C=69.17:68.95; % H=5.51:5.33; % N=8.27:8.05; % Cl—=5.24:5.23

Example 115. N-(4-Hydroxyphenyl)-5-methyl-N-(1-methyl-2,3-dihydro-1H-indol-5-yl)-1-(6-{[(3R)-3-methyl-3,4-dihydroisoquinolin-2(1H)-yl]carbonyl}-1,3-benzodioxol-5-yl)-1H-pyrrole-3-carboxamide Hydrochloride Elemental microanalysis: (%, theoretical:measured)
% C=69.17:69.32; % H=5.51:5.27; % N=8.27:8.48; % Cl—=5.24:5.18

Example 116. N-(4-Hydroxyphenyl)-5-methyl-1-(6-{[(3R)-3-methyl-3,4-dihydroisoquinolin-2(1H)-yl]carbonyl}-1,3-benzodioxol-5-yl)-N-{1-[2-(morpholin-4-yl)ethyl]-1H-indol-5-yl}-1H-pyrrole-3-carboxamide Hydrochloride Elemental microanalysis: (%, theoretical:measured)
% C=68.25:67.87; % H=5.73:5.42; % N=9.04:8.8; % Cl—=4.58:4.81

Example 117. N-(4-Hydroxyphenyl)-5-methyl-N-(1-methyl-1H-indol-5-yl)-1-(6-{[(3S)-3-(morpholin-4-ylmethyl)-3,4-dihydroisoquinolin-2(1H)-yl]carbonyl}-2,3-dihydro-1H-inden-5-yl)-1H-pyrrole-3-carboxamide Hydrochloride Elemental microanalysis: (%, theoretical:measured)
% C=71.46:70.88; % H=6.13:5.89; % N=9.26:9.12; % Cl—=4.69:4.37

Example 118. N-(4-Hydroxyphenyl)-5-methyl-N-(1-methyl-1H-indol-5-yl)-1-(5-{[(3S)-3-(morpholin-4-ylmethyl)-3,4-dihydroisoquinolin-2(1H)-yl]carbonyl}-2,3-dihydro-1-benzofuran-6-yl)-1H-pyrrole-3-carboxamide The title compound is synthesised in accordance with the process of Example 12 using in Step A the acid obtained in Preparation 20 and the (3S)-3-(4-morpholinylmethyl)-1,2,3,4-tetrahydroisoquinoline obtained in Preparation 2' and the suitable $NR_3R_4$ amine.
Elemental microanalysis: (%, theoretical:measured)
% C=73.21:72.64; % H=6:6.03; % N=9.7:9.57

Example 119. N-(4-Hydroxyphenyl)-5-methyl-N-(1-methyl-1H-indol-5-yl)-1-(5-{[(3S)-3-(morpholin-4-ylmethyl)-3,4-dihydroisoquinolin-2(1H)-yl]carbonyl}-1-benzofuran-6-yl)-1H-pyrrole-3-carboxamide Hydrochloride The title compound is synthesised in accordance with the process of Example 12 using in Step A the acid obtained in Preparation 21, the (3S)-3-(4-morpholinylmethyl)-1,2,3,4-tetrahydroisoquinoline obtained in Preparation 2' and the suitable $NR_3R_4$ amine.
Elemental microanalysis: (%, theoretical:measured)
% C=69.88:69.87; % H=5.6:5.29; % N=9.26:9.18; % Cl—=4.69:4.44

Example 120. N-(4-Hydroxyphenyl)-5-methyl-1-(6-{[(3S)-3-[2-(morpholin-4-yl)ethyl]-3,4-dihydroisoquinolin-2(1H)-yl]carbonyl}-1,3-benzodioxol-5-yl)-N-phenyl-1H-pyrrole-3-carboxamide Hydrochloride Elemental microanalysis: (%, theoretical:measured)
% C=68.28:67.77; % H=5.73:5.59; % N=7.77:7.69; % Cl—=4.92:5

Example 121. 1-{2-[(3S)-3-(Aminomethyl)-1,2,3,4-tetrahydroisoquinoline-2-carbonyl]-phenyl}-N,N-dibutyl-1H-indazole-3-carboxamide The compound of Preparation 6d is treated in accordance with the procedure described in Example 126.
LC/MS ($C_{33}H_{39}N_5O_2$) 538 [M+H]⁺; RT 2.33 (Method A)
High-resolution mass spectroscopy (ESI+):
Empirical formula: $C_{33}H_{39}N_5O_2$
[M+H]⁺ calculated: 538.3177
[M+H]⁺ measured: 538.3169

Example 122. 1-{2-[(3S)-3-(Aminomethyl)-1,2,3,4-tetrahydroisoquinoline-2-carbonyl]phenyl}-N,N-diphenyl-1H-indazole-3-carboxamide The compound of Preparation 6e is treated in accordance with the procedure described in Example 126, and the product so obtained is purified by chromatography over silica gel according to a gradient from dichloromethane to a 94:6 dichloromethane/methanol mixture.
LC/MS ($C_{37}H_{31}N_5O_2$) 578 [M+H]⁺; RT 1.15 (Method B)
High-resolution mass spectroscopy (ESI+):
Empirical formula: $C_{37}H_{31}N_5O_2$
[M+H]⁺ calculated: 578.2551
[M+H]⁺ measured: 578.2548

Example 123. 1-{2-[(3S)-3-(Aminomethyl)-1,2,3,4-tetrahydroisoquinoline-2-carbonyl]-phenyl}-N,N-diphenyl-1H-indole-3-carboxamide The procedure is the same as in Steps A and C of Example 131, replacing the compound obtained in Preparation 3d with the compound obtained in Preparation 3f.
LC/MS ($C_{38}H_{32}N_4O_2$) 577 [M+H]⁺; RT 2.24 (Method A)
High-resolution mass spectroscopy (ESI+):
Empirical formula: $C_{38}H_{32}N_4O_2$
[M+H]⁺ calculated: 577.2598
[M+H]⁺ measured: 577.2600

Example 124. 1-{2-[(3S)-3-(Aminomethyl)-1,2,3,4-tetrahydroisoquinoline-2-carbonyl]-phenyl}-6-(benzyloxy)-N,N-diphenyl-1H-indazole-3-carboxamide The compound of Preparation 6c is treated in accordance with the procedure as described in Example 126 and then purified by chromatography over silica gel according to a gradient from dichloromethane to a methanol (5%)/dichloromethane mixture.
LC/MS ($C_{44}H_{37}N_5O_3$) 684 [M+H]⁺; RT 2.45 (Method A)
High-resolution mass spectroscopy (ESI+):

Empirical formula: $C_{44}H_{37}N_5O_3$
[M+H]$^+$ calculated: 684.2969
[M+H]$^+$ measured: 684.2982

Example 125. 1-{2-[(3S)-3-(Aminomethyl)-1,2,3,4-tetrahydroisoquinoline-2-carbonyl]-phenyl}-6-hydroxy-N,N-diphenyl-1H-indazole-3-carboxamide The compound obtained in Example 124 (30 mg, 0.04 mmol) is dissolved in dichloromethane (5 ml), cooled to −78° C. under nitrogen, and then treated with boron trichloride (1M, 0.02 ml, 0.2 mmol). The reaction mixture is allowed to warm to ambient temperature again and is stirred for 3 hours. The reaction mixture is inactivated with methanol, neutralised with triethylamine and concentrated. The residue is extracted with ethyl acetate and washed with water, dried over magnesium sulphate, filtered and concentrated. The crude material is purified by chromatography in dichloromethane, a 95:5 dichloromethane/methanol mixture, then a 94:6 dichloromethane/methanol mixture.

LC/MS ($C_{37}H_{31}N_5O_3$) 594 [M+H]$^+$; RT 2.15 (Method A)
High-resolution mass spectroscopy (ESI+):
Empirical formula: $C_{37}H_{31}N_5O_3$
[M+H]$^+$ calculated: 594.2500
[M+H]$^+$ measured: 594.2526

Example 126. 1-{2-[(3S)-3-(Aminomethyl)-1,2,3,4-tetrahydroisoquinoline-2-carbonyl]-phenyl}-6-methoxy-N,N-diphenyl-1H-indazole-3-carboxamide Step A: tert-Butyl N-{[(3S)-2-{2-[3-(diphenylcarbamoyl)-6-methoxy-1H-indazol-1-yl]benzoyl}-1,2,3,4-tetrahydroisoquinolin-3-yl]methyl}carbamate The compound of Preparation 6g (39 mg, 0.08 mmol) in dichloromethane (8 ml) and N,N-dimethylformamide (1 drop) is cooled to 0° C. under nitrogen, and then 2M oxalyl chloride (14 µl, 0.17 mmol) is added and the reaction mixture is stirred for 1 hour before being concentrated in vacuo. N-Boc-aminomethyl THIQ (44.2 mg, 0.17 mmol) and triethylamine (60 µl, 0.4 mmol) dissolved in dichloromethane (5 ml) are cooled to 0° C. under nitrogen, and then the acid chloride in dichloromethane is added dropwise and the reaction mixture is stirred at ambient temperature overnight. The reaction mixture is distributed according to its solubility between dichloromethane and water, and the organic phases are separated, dried over magnesium sulphate, filtered and concentrated. The crude material is purified by chromatography over silica gel according to a gradient from isohexane to a 1:1 isohexane/ethyl acetate mixture to provide a gum.

LC/MS ($C_{43}H_{41}N_5O_5$) 608 [M-Boc]$^+$; RT 2.78 (Method A)

Step B: 1-{2-[(3S)-3-(Aminomethyl)-1,2,3,4-tetrahydroisoquinoline-2-carbonyl]phenyl}-6-methoxy-N,N-diphenyl-1H-indazole-3-carboxamide A solution of the compound obtained in Step A (58 mg, 0.08 mmol) in 4M HCl is stirred at ambient temperature for 1 hour in dioxane (3 ml). The reaction mixture is neutralised with 2M NaOH and the product is extracted with ethyl acetate, dried over magnesium sulphate, filtered and concentrated. The product is purified by application to a SCX column, washing with methanol and eluting with a 1:1 methanol/7N ammonia in methanol mixture. A final purification is carried out by preparative HPLC.

LC/MS ($C_{38}H_{33}N_5O_3$) 608 [M+H]$^+$; RT 2.27 (Method A)
High-resolution mass spectroscopy (ESI+):
Empirical formula: $C_{38}H_{33}N_5O_3$
[M+H]$^+$ calculated: 608.2656
[M+H]$^+$ measured: 608.2650

Example 127. 1-{2-[(3S)-3-(Aminomethyl)-1,2,3,4-tetrahydroisoquinoline-2-carbonyl]-phenyl}-6-hydroxy-N,N-diphenyl-1H-indole-3-carboxamide Step A: tert-Butyl N-{[(3S)-2-{2-[6-(benzyloxy)-3-(diphenylcarbamoyl)-1H-indol-1-yl]benzoyl}-1,2,3,4-tetrahydroisoquinolin-3-yl]methyl}carbamate The compound obtained in Preparation 3b (238 mg, 0.44 mmol) in dichloromethane (8 ml) and a drop of N,N-dimethylformamide is cooled to 0° C. and then oxalyl chloride (0.07 ml, 0.44 mmol) is added. The reaction mixture is stirred for one hour and then concentrated in vacuo. This material is added in the form of a suspension/solution in dichloromethane (5 ml) to a solution of tert-butyl N-[(3S)-1,2,3,4-tetrahydroisoquinolin-3-ylmethyl]-carbamate (232 mg, 0.88 mmol) obtained in Preparation 1' and triethylamine (0.31 ml, 2.2 mmol) in 5 ml of dichloromethane, the whole is cooled to 0° C. and the reaction mixture is stirred for approximately 16 hours under nitrogen. The reaction mixture is extracted with ethyl acetate, washed with water, dried over magnesium sulphate, filtered and evaporated and purified by chromatography over silica gel according to a gradient from isohexane to a 1:1 isohexane/ethyl acetate mixture to provide an oil.

LC/MS ($C_{50}H_{46}N_4O_5$) 783 [M+H]$^+$; RT 2.86 (Method A)

Step B: 1-{2-[(3S)-3-(Aminomethyl)-1,2,3,4-tetrahydroisoquinoline-2-carbonyl]phenyl}-6-hydroxy-N,N-diphenyl-1H-indole-3-carboxamide The product obtained in Step A (155 mg, 0.20 mmol) is dissolved in dichloromethane (8 ml) and cooled to −78° C. under nitrogen, and then an excess of boron trichloride solution is added and the reaction mixture is allowed to warm to ambient temperature again over a period of 2 hours. The reaction mixture is inactivated by adding methanol, neutralised by adding triethylamine, evaporated and distributed according to its solubility between ethyl acetate and water. The organic phase is dried over magnesium sulphate, the solvent is removed in vacuo and the crude product is purified first by chromatography over a silica gel column, eluting with dichloromethane to a 95:5 dichloromethane/methanol mixture, and then by preparative HPLC to provide the product in the form of a solid.

LC/MS ($C_{38}H_{32}N_4O_3$) 593 [M+H]$^+$; RT 1.06 (Method A)
High-resolution mass spectroscopy (ESI+):
Empirical formula: $C_{38}H_{32}N_4O_3$
[M+H]$^+$ calculated: 593.2547
[M+H]$^+$ measured: 593.2550

Example 128. Methyl 2-[(1-{2-[(3S)-3-(aminomethyl)-1,2,3,4-tetrahydroisoquinoline-2-carbonyl]phenyl}-3-(diphenylcarbamoyl)-1H-indazol-6-yl)oxy]acetate Step A: Ethyl 2-[(1-{2-[(3S)-3-({[(tert-butoxy)carbonyl]amino}methyl)-1,2,3,4-tetrahydroisoquinoline-2-carbonyl]phenyl}-3-(diphenylcarbamoyl)-1H-indazol-6-yl)oxy]-acetate The compound of Step B of Example 133 (175 mg, 0.25 mmol) is dissolved in acetone (10 ml), and then potassium carbonate (46 mg, 0.33 mmol) and ethyl 2-bromoacetate (36 µl, 0.33 mmol) are added and the reaction mixture is heated at reflux under nitrogen overnight. The reaction mixture is concentrated, extracted with ethyl acetate and washed with water, and the organic phases are dried over magnesium sulphate, filtered and concentrated. The crude material is purified by chromatography according to a gradient from isohexane to a 1:1 isohexane/ethyl acetate mixture to provide a gum.

LC/MS ($C_{46}H_{45}N_5O_7$) 680.3 [M-Boc]$^+$; RT 2.77 (Method A)

Step B: Methyl 2-[(1-{2-[(3S)-3-(aminomethyl)-1,2,3,4-tetrahydroisoquinoline-2-carbonyl]phenyl}-3-(diphenylcarbamoyl)-1H-indazol-6-yl)oxy]acetate The compound obtained in Step A (102 mg, 0.13 mmol) is dissolved in dichloromethane (4 ml); 1 ml of trifluoroacetic acid is added, and the reaction mixture is stirred at ambient temperature for 1 hour. The reaction mixture is neutralised with triethylamine, concentrated and the residue is extracted with ethyl acetate and washed with a saturated sodium bicarbonate solution. The organic phases are dried over magnesium sulphate, filtered and applied to a SCX column, which is washed with methanol, and the compounds are eluted with a 3:1 methanol/7N ammonia in methanol solution. The products are purified further by chromatography over silica gel in dichloromethane, to a 98:2 dichloromethane/methanol mixture, then 96:4 dichloromethane/methanol, then 9:1 dichloromethane/methanol to yield the deprotected compound of the trans-ester type (Example 128) and the fully deprotected compound (Example 129).

LC/MS ($C_{40}H_{35}N_5O_5$) 666 [M+H]$^+$; RT 2.26 (Method A)
High-resolution mass spectroscopy (ESI+):
Empirical formula: $C_{40}H_{35}N_5O_5$
[M+H]$^+$ calculated: 666.2711
[M+H]$^+$ measured: 666.2745

Example 129. 2-[(1-{2-[(3S)-3-(Aminomethyl)-1,2,3,4-tetrahydroisoquinoline-2-carbonyl]phenyl}-3-(diphenylcarbamoyl)-1H-indazol-6-yl)oxy]acetic Acid The compound of Example 129 is isolated as a secondary product starting from Step B of Example 128.
High-resolution mass spectroscopy (ESI+):
Empirical formula: $C_{39}H_{33}N_5O_5$
[M+H]$^+$ calculated: 652.2554
[M+H]$^+$ measured: 652.2584

Example 130. 1-{2-[(3S)-3-(Aminomethyl)-1,2,3,4-tetrahydroisoquinoline-2-carbonyl]phenyl}-N-[4-(benzyloxy)phenyl]-N-phenyl-1H-indole-3-carboxamide Trifluoroacetic acid (0.5 ml) is added to a solution of the compound obtained in Step A of Preparation 131 (50 mg, 0.06 mmol) in dichloromethane (3 ml) and the reaction mixture is stirred at ambient temperature for approximately 16 hours. The reaction mixture is diluted with water, rendered alkaline with a 2M aqueous NaOH solution, and the product is extracted with dichloromethane. The organic phases are dried over magnesium sulphate, filtered and evaporated, and the crude material is purified by chromatography over silica gel according to a gradient from dichloromethane to a methanol (5%)/dichloromethane mixture to provide the product in the form of a solid.

LC/MS ($C_{45}H_{38}N_4O_3$) 683 [M+H]$^+$; RT 2.44 (Method A)
High-resolution mass spectroscopy (ESI+):
Empirical formula: $C_{45}H_{38}N_4O_3$
[M+H]$^+$ calculated: 683.3017
[M+H]$^+$ measured: 683.2997

Example 131. 1-{2-[(3S)-3-(Aminomethyl)-1,2,3,4-tetrahydroisoquinoline-2-carbonyl]phenyl}-N-(4-hydroxyphenyl)-N-phenyl-1H-indole-3-carboxamide

Step A: tert-Butyl N-{[(3S)-2-[2-(3-{[4-(benzyloxy)phenyl](phenyl)carbamoyl}-1H-indol-1-yl)benzoyl]-1,2,3,4-tetrahydroisoquinolin-3-yl]methyl}carbamate Triethylamine (0.16 ml, 1.18 mmol), HOBT (100 mg, 0.65 mmol), EDAC (125 mg, 0.65 mmol) and tert-butyl N-[(3S)-1,2,3,4-tetrahydroisoquinolin-3-ylmethyl]carbamate (186 mg, 0.71 mmol) obtained in Preparation 1' are added to a solution of the acid obtained in Preparation 3d (318 mg, 0.59 mmol) in tetrahydrofuran (5 ml), and the reaction mixture is stirred at ambient temperature for approximately 16 hours. The reaction mixture is diluted with ethyl acetate, washed with water, and the organic phases are dried over magnesium sulphate, filtered and evaporated. The crude material is purified by chromatography over silica gel according to a gradient from isohexane to a 1:1 ethyl acetate/isohexane mixture to provide the product in the form of a solid.

LC/MS ($C_{50}H_{46}N_4O_5$) 783 [M+H]$^+$; RT 2.92 (Method A)

Step B: tert-Butyl N-{[(3S)-2-(2-{3-[(4-hydroxyphenyl)(phenyl)carbamoyl]-1H-indol-1-yl}benzoyl)-1,2,3,4-tetrahydroisoquinolin-3-yl]methyl}carbamate Catalytic 10% palladium on carbon is added to a solution of the material obtained in Step A (210 mg, 0.268 mmol) in ethanol (10 ml), evacuated and washed with nitrogen, and the reaction mixture is stirred by oscillation under hydrogen at ambient temperature for approximately 72 hours, a further quantity of catalytic 10% palladium on carbon being added during that time. The reaction mixture is filtered through Celite, washed with methanol and evaporated to provide an oil. The product is used for the following step without being purified further.

LC/MS ($C_{43}H_{40}N_4O_5$) 693 [M+H]$^+$; RT 2.68 (Method A)

Step C: 1-{2-[(3S)-3-(Aminomethyl)-1,2,3,4-tetrahydroisoquinoline-2-carbonyl]phenyl}-N-(4-hydroxyphenyl)-N-phenyl-1H-indole-3-carboxamide Trifluoroacetic acid (0.5 ml) is added to a solution of the compound obtained in Step B (200 mg, 0.29 mmol) in dichloromethane (5 ml) and the reaction mixture is stirred at ambient temperature for 2 hours. The reaction mixture is diluted with water, rendered alkaline with 2M NaOH and the product is extracted with dichloromethane. The organic extracts are dried over magnesium sulphate, filtered and evaporated, and the crude material is purified by chromatography over silica gel according to a gradient from dichloromethane to a methanol (10%)/dichloromethane mixture to provide the product in the form of a powder.

LC/MS ($C_{38}H_{32}N_4O_3$) 593 [M+H]$^+$; RT 2.12 (Method A)
High-resolution mass spectroscopy (ESI+):
Empirical formula: $C_{38}H_{32}N_4O_3$
[M+H]$^+$ calculated: 593.2547
[M+H]$^+$ measured: 593.2545

Example 132. 1-{6-[(3S)-3-(Aminomethyl)-1,2,3,4-tetrahydroisoquinoline-2-carbonyl]-2H-1,3-benzodioxol-5-yl}-N,N-diphenyl-1H-indazole-3-carboxamide

Step A: tert-Butyl N-{[(3S)-2-{6-[3-(diphenylcarbamoyl)-1H-indazol-1-yl]-2H-1,3-benzodioxole-5-carbonyl}-1,2,3,4-tetrahydroisoquinolin-3-yl]methyl}carbamate Triethylamine (0.26 ml, 1.88 mmol), HOBT (158 mg, 1.03 mmol) and EDAC (197 mg, 1.03 mmol), and then the compound of Preparation 1' (247 mg, 0.94 mmol), are added to a solution of the acid obtained in Step A of Preparation 6a (450 mg, 0.94 mmol) in tetrahydrofuran (5 ml). The reaction mixture is stirred at ambient temperature over the weekend, after which a further quantity of triethylamine (0.13 ml, 0.94 mmol), HOBT (79 mg, 0.52 mmol) and EDAC (99 mg, 0.5 mmol) is added and stirring of the reaction mixture is continued overnight. The reaction mixture is diluted with ethyl acetate and washed with water and with a saturated sodium bicarbonate solution. The organic phases are dried over magnesium sulphate, filtered and evaporated and the crude material is purified by chromatography over silica gel according to a gradient from isohexane to a 1:1 ethyl acetate/isohexane mixture to provide the product in the form of an oil.

LC/MS ($C_{43}H_{39}N_5O_6$) 622 [M-Boc]$^+$ observed; RT 2.77 (Method A)

Step B: 1-{6-[(3S)-3-(Aminomethyl)-1,2,3,4-tetrahydroisoquinoline-2-carbonyl]-2H-1,3-benzodioxol-5-yl}-N,N-diphenyl-1H-indazole-3-carboxamide Trifluoroacetic acid (0.5 ml) is added to a solution of the compound obtained in Step A (288 mg, 0.4 mmol) in dichloromethane (3 ml). The reaction mixture is stirred at ambient temperature for 1 hour. The reaction mixture is diluted with water and rendered alkaline with 2M NaOH. The organic phases are extracted with dichloromethane, dried over magnesium sulphate, filtered and evaporated and the crude material is purified by chromatography over silica gel according to a gradient from dichloromethane to a methanol (5%)/dichloromethane mixture.

LC/MS ($C_{38}H_{31}N_5O_4$) 622 [M–H]$^+$ observed; RT 2.27 (Method A)

High-resolution mass spectroscopy (ESI+):

Empirical formula: $C_{38}H_{31}N_5O_4$

[M+H]$^+$ calculated: 622.2449

[M+H]$^+$ measured: 622.2457

Example 133. 1-{2-[(3S)-3-(Aminomethyl)-1,2,3,4-tetrahydroisoquinoline-2-carbonyl]-phenyl}-3-(diphenylcarbamoyl)-1H-indazole-6-carboxylic Acid

Step A: tert-Butyl N-{[(3S)-2-{2-[3-(diphenylcarbamoyl)-6-hydroxy-1H-indazol-1-yl]benzoyl}-1,2,3,4-tetrahydroisoquinolin-3-yl]methyl}carbamate The compound obtained in Preparation 6h is treated in accordance with the procedure described in Step A of Example 132.

Step B: tert-Butyl N-{[(3S)-2-{2-[3-(diphenylcarbamoyl)-6-(trifluoromethane-sulphonyloxy)-1H-indazol-1-yl]benzoyl}-1,2,3,4-tetrahydroisoquinolin-3-yl]methyl}-carbamate The compound of Step A (170 mg, 0.25 mmol) is dissolved in dichloromethane (10 ml), cooled to 0° C. under nitrogen, and then triethylamine (0.28 ml, 2 mmol) and triflic anhydride (62 al, 0.37 mmol) are added, before the whole is stirred at ambient temperature for 1 hour. The reaction mixture is diluted with dichloromethane and washed with water, dried over magnesium sulphate, filtered and concentrated. The crude material is purified by chromatography over silica gel according to a gradient from isohexane to a 3:2 isohexane/ethyl acetate mixture to provide a gum.

LC/MS ($C_{43}H_{38}N_5O_7F_3S$) 726.2 [M-Boc]$^+$ observed; RT 2.87 (Method A)

Step C: 1-{2-[(3S)-3-({[(tert-Butoxy)carbonyl]amino}methyl)-1,2,3,4-tetrahydroisoquinoline-2-carbonyl]phenyl}-3-(diphenylcarbamoyl)-1H-indazole-6-carboxylic Acid DPPP (9 mg, 0.022 mmol) is added to a solution of the compound obtained in Step B (92 mg, 0.11 mmol) in a N,N-dimethylformamide/water mixture (9 ml:3 ml) and the mixture so obtained is degassed with nitrogen. Palladium(II) acetate (2.5 mg, 0.011 mmol) is added, and then degassing is carried out. The reaction mixture is then washed with carbon monoxide, and triethylamine (30 al, 0.22 mmol) is then added before the whole is heated to 80° C. over a period of 3 hours, under a CO atmosphere. The reaction mixture is concentrated, the residue is extracted with ethyl acetate and washed with dilute HCl. The organic phases are dried over magnesium sulphate, filtered and concentrated and applied to a PE-AX column, washed with methanol, and the product is eluted with a 9:1 dichloromethane/formic acid mixture to provide a solid.

LC/MS ($C_{43}H_{39}N_5O_6$) 622 [M-Boc]$^+$ observed; RT 2.67 (Method A)

Step D: 2-[3-(Diphenylcarbamoyl)-6-hydroxy-1H-indazol-1-yl]benzoic Acid

The compound of Step C is treated in accordance with the process described in Step B of Example 132.

LC/MS ($C_{38}H_{31}N_5O_4$) 622 [M+H]$^+$; RT 2.17 (Method A)

High-resolution mass spectroscopy (ESI+):

Empirical formula: $C_{38}H_{31}N_5O_4$

[M+H]$^+$ calculated: 622.2449

[M+H]$^+$ measured: 622.2439

Example 134. 1-{2-[(3S)-3-(Aminomethyl)-1,2,3,4-tetrahydroisoquinoline-2-carbonyl]-4-(benzyloxy)-5-methoxyphenyl}-N,N-diphenyl-1H-indazole-3-carboxamide Triethylamine (0.06 ml, 0.46 mmol), HOBT (39 mg, 0.253 mmol) and EDAC (49 mg, 0.253 mmol), and then the compound of Preparation 1' (60 mg, 0.23 mmol), are added to a solution of the acid obtained in Preparation 6i (130 mg, 0.23 mmol) in tetrahydrofuran (3 ml). The reaction mixture is stirred at ambient temperature for 7 hours and then diluted with ethyl acetate before being washed with water and with a saturated sodium bicarbonate solution. The organic phases are dried over magnesium sulphate, filtered and evaporated and the crude material is purified by chromatography over silica gel according to a gradient from isohexane to a 1:1 ethyl acetate/isohexane mixture to provide the product in the form of a solid.

The deprotection which follows is carried out in accordance with Step B of Example 132.

LC/MS ($C_{45}H_{39}N_5O_4$) 714 [M+H]$^+$; RT 2.47 (Method A)
High-resolution mass spectroscopy (ESI+):
Empirical formula: $C_{45}H_{39}N_5O_4$
[M+H]$^+$ calculated: 714.3075
[M+H]$^+$ measured: 714.3077

Example 135. 1-{2-[(3S)-3-(Aminomethyl)-1,2,3,4-tetrahydroisoquinoline-2-carbonyl]-4-hydroxy-5-methoxyphenyl}-N,N-diphenyl-1H-indazole-3-carboxamide Catalytic 10% palladium on carbon is added to a solution of the compound of Example 134 (146 mg, 0.18 mmol) in ethanol (5 ml); the mixture is degassed and washed with nitrogen. The reaction mixture is stirred under hydrogen, at ambient temperature, overnight. The reaction mixture is filtered through a Celite cartridge, washed with methanol and concentrated. The product is used in the following step as described in Step B of Example 132 without being purified further.

LC/MS ($C_{38}H_{33}N_5O_4$) 624 [M+H]$^+$; RT 2.23 (Method A)
High-resolution mass spectroscopy (ESI+):
Empirical formula: $C_{38}H_{33}N_5O_4$
[M+H]$^+$ calculated: 624.2605
[M+H]$^+$ measured: 624.2607

Example 136. 1-{2-[(3S)-3-(Aminomethyl)-1,2,3,4-tetrahydroisoquinoline-2-carbonyl]-phenyl}-5-hydroxy-N,N-diphenyl-1H-indazole-3-carboxamide The procedure is as described in Step A of Example 134 using the compound of Preparation 6j. The product so obtained is deprotected in accordance with the process described in Example 135.

LC/MS ($C_{37}H_{31}N_5O_3$) 594 [M+H]$^+$; RT 2.15 (Method A)
High-resolution mass spectroscopy (ESI+):
Empirical formula: $C_{37}H_{31}N_5O_3$
[M+H]$^+$ calculated: 594.2500
[M+H]$^+$ measured: 594.2482

Example 137. 1-{2-[(3S)-3-(Aminomethyl)-1,2,3,4-tetrahydroisoquinoline-2-carbonyl]-4-nitrophenyl}-N,N-diphenyl-1H-indazole-3-carboxamide The procedure is the same as that described for Example 132, replacing the compound of Preparation 6a in Step A with the compound of Preparation 6b.

LC/MS ($C_{37}H_{30}N_6O_4$) 623 [M+H]$^+$; RT 2.25 (Method A)
High-resolution mass spectroscopy (ESI+):
Empirical formula: $C_{37}H_{30}N_6O_4$
[M+H]$^+$ calculated: 623.2401
[M+H]$^+$ measured: 623.2380

Example 138. 1-{4-Amino-2-[(3S)-3-(aminomethyl)-1,2,3,4-tetrahydroisoquinoline-2-carbonyl]phenyl}-N,N-diphenyl-1H-indazole-3-carboxamide Step A: tert-Butyl N-{[(3S)-2-{5-amino-2-[3-(diphenylcarbamoyl)-1H-indazol-1-yl]-benzoyl}-1,2,3,4-tetrahydroisoquinolin-3-yl]methyl}carbamate Zinc (327 mg, 5 mmol) and ammonium chloride (267.5 mg, 5 mmol) are added to a solution of the compound obtained in Step A of Example 137 (360 mg, 0.5 mmol) in methanol (10 ml) and the reaction mixture is heated at reflux for 10 minutes under nitrogen. The reaction mixture is cooled to ambient temperature, filtered through Celite, washed with hot methanol and concentrated. The residue is extracted with ethyl acetate and washed with brine, dried over magnesium sulphate, filtered and concentrated. The material is used without being purified further.

LC/MS ($C_{42}H_{40}N_6O_4$) 593.3 [M-Boc]$^+$; RT 2.66 (Method A)

Step B: 1-{4-Amino-2-[(3S)-3-(aminomethyl)-1,2,3,4-tetrahydroisoquinoline-2-carbonyl]phenyl}-N,N-diphenyl-1H-indazole-3-carboxamide The compound obtained in Step A is deprotected in accordance with the procedure of Step B of Example 132 and then purified over a SCX column, the compound being eluted in a 4:1 methanol/7N ammonia in methanol mixture.

LC/MS ($C_{37}H_{32}N_6O_2$) 593 [M+H]$^+$; RT 2.15 (Method A)
High-resolution mass spectroscopy (ESI+):
Empirical formula: $C_{37}H_{32}N_6O_2$
[M+H]$^+$ calculated: 593.2660
[M+H]$^+$ measured: 593.2676

Example 139. 1-{2-[(3S)-3-(Aminomethyl)-1,2,3,4-tetrahydroisoquinoline-2-carbonyl]-5-hydroxyphenyl}-6-hydroxy-N,N-diphenyl-1H-indazole-3-carboxamide The procedure is as in the process of Preparation 6a, replacing the compound of Preparation 5a with the compound of Preparation 5c and using methyl 2-bromo-4-methoxybenzoate. The procedure described in Step B of Preparation 6b and then the process described in Step A of Example 132 are then applied.

The compound is dissolved in dichloromethane (3 ml), cooled to 0° C., and then boron tribromide (1M in dichloromethane, 0.4 ml, 0.4 mmol) is added and the reaction mixture is stirred at ambient temperature under nitrogen overnight. The reaction mixture is cooled to 0° C. and inactivated with methanol. The crude material is purified by preparative HPLC.

LC/MS ($C_{37}H_{31}N_5O_4$) 610 [M+H]$^+$; RT 2.08 (Method A)
High-resolution mass spectroscopy (ESI+):
Empirical formula: $C_{37}H_{31}N_5O_4$
[M+H]$^+$ calculated: 610.2449
[M+H]$^+$ measured: 610.2458

Example 140. 1-{2-[(3S)-3-(Aminomethyl)-1,2,3,4-tetrahydroisoquinoline-2-carbonyl]-4-(methylamino)phenyl}-N,N-diphenyl-1H-indazole-3-carboxamide Step A: tert-Butyl N-{[(3S)-2-{2-[3-(diphenylcarbamoyl)-1H-indazol-1-yl]-5-(methyl-amino)benzoyl}-1,2,3,4-tetrahydroisoquinolin-3-yl]methyl}carbamate A 37% formaldehyde solution (12.4 al, 0.09 mmol) and then triacetoxy borohydride (54 mg, 0.255 mmol) and, after 5 minutes, 2 drops of acetic acid are added to the compound prepared in Step A of Example 138 (59 mg, 0.09 mmol) in dichloromethane (5 ml), and then the reaction mixture is stirred at ambient temperature overnight under nitrogen. The reaction mixture is distributed according to its solubility between dichloromethane and brine, dried over magnesium sulphate, filtered and evaporated. The crude mixture of mono- and di-alkylated products is purified by chromatography over silica gel in isohexane, to a 1:1 isohexane/ethyl acetate mixture, then in a 3:2 isohexane/ethyl acetate mixture.

Compound 1: LC/MS ($C_{43}H_{42}N_6O_4$) 607.3 [M-Boc]$^+$; RT 2.7 (Method A)

Compound 2: LC/MS ($C_{44}H_{44}N_6O_4$) 621.3 [M-Boc]$^+$; RT 2.78 (Method A)

Step B: 1-{2-[(3S)-3-(Aminomethyl)-1,2,3,4-tetrahydroisoquinoline-2-carbonyl]-4-(methylamino)phenyl}-N,N-diphenyl-1H-indazole-3-carboxamide The compound obtained in Step A is deprotected in accordance with the procedure of Step B of Example 132 and then purified over a SCX column, the compound being eluted in 7N ammonia in methanol.

LC/MS ($C_{38}H_{34}N_6O_2$) 607 [M+H]$^+$; RT 2.23 (Method A)
High-resolution mass spectroscopy (ESI+):
Empirical formula: $C_{38}H_{34}N_6O_2$
[M+H]$^+$ calculated: 607.2816
[M+H]$^+$ measured: 607.2788

Example 141. 1-{2-[(3S)-3-(Aminomethyl)-1,2,3,4-tetrahydroisoquinoline-2-carbonyl]-4-(dimethylamino)phenyl}-N,N-diphenyl-1H-indazole-3-carboxamide Compound 2 obtained in Step A of Example 140 is deprotected in accordance with the procedure of Step B of Example 132 and then purified over a SCX column, the compound being eluted in 7N ammonia in methanol.

LC/MS ($C_{39}H_{36}N_6O_2$) 621 [M+H]$^+$; RT 2.31 (Method A)
High-resolution mass spectroscopy (ESI+):
Empirical formula: $C_{39}H_{36}N_6O_2$
[M+H]$^+$ calculated: 621.2973
[M+H]$^+$ measured: 621.2955

Example 142. 1-{2-[(3S)-3-(Aminomethyl)-1,2,3,4-tetrahydroisoquinoline-2-carbonyl]-4-(benzylamino)phenyl}-N,N-diphenyl-1H-indazole-3-carboxamide The compound is prepared in accordance with the procedure described in Step A of Example 140, using benzaldehyde, and then it is deprotected in accordance with the procedure of Step B of Example 132 and purified over a SCX column, the compound being eluted in a 4:1 methanol/7N ammonia in methanol solution.

LC/MS ($C_{44}H_{38}N_6O_2$) 683 [M+H]$^+$; RT 2.37 (Method A)
High-resolution mass spectroscopy (ESI+):
Empirical formula: $C_{44}H_{38}N_6O_2$
[M+H]$^+$ calculated: 683.3129
[M+H]$^+$ measured: 683.3127

Example 143. 1-{2-[(3S)-3-[(Dimethylamino)methyl]-1,2,3,4-tetrahydroisoquinoline-2-carbonyl]phenyl}-N-(4-hydroxyphenyl)-N-phenyl-1H-indole-3-carboxamide Step A: N-[4-(Benzyloxy)phenyl]-1-{2-[(3S)-3-[(dimethylamino)methyl]-1,2,3,4-tetrahydroisoquinoline-2-carbonyl]phenyl}-N-phenyl-1H-indole-3-carboxamide The procedure is the same as in the process of Step A of Example 131, replacing the compound of Preparation 1' with the compound of Preparation 12'.

LC/MS ($C_{47}H_{42}N_4O_3$) 711 [M+H]$^+$; RT 2.44 (Method A)

Step B: 1-{2-[(3S)-3-[(Dimethylamino)methyl]-1,2,3,4-tetrahydroisoquinoline-2-carbonyl]phenyl}-N-(4-hydroxyphenyl)-N-phenyl-1H-indole-3-carboxamide Catalytic 10% palladium on carbon is added to a solution of the compound obtained in Step A (200 mg, 0.28 mmol) in ethanol (10 ml), which is degassed with nitrogen. The reaction mixture is stirred under hydrogen at ambient temperature for approximately 16 hours. The reaction mixture is filtered through Celite and washed with ethanol, the solvent is evaporated off and the crude material is purified by chromatography over silica gel according to a gradient from dichloromethane to a methanol (5%)/dichloromethane mixture to provide the product in the form of a solid.

LC/MS ($C_{40}H_{36}N_4O_3$) 621 [M+H]$^+$; RT 2.09 (Method A)
High-resolution mass spectroscopy (ESI+):
Empirical formula: $C_{40}H_{36}N_4O_3$
[M+H]$^+$ calculated: 621.2860
[M+H]$^+$ measured: 621.2850

Example 144. 1-{2-[(3S)-3-(Aminomethyl)-1,2,3,4-tetrahydroisoquinoline-2-carbonyl]-4-(2-phenoxyacetamido)phenyl}-N,N-diphenyl-1H-indazole-3-carboxamide Step A: tert-Butyl N-{[(3S)-2-{2-[3-(diphenylcarbamoyl)-1H-indazol-1-yl]-5-(2-phenoxy-acetamido)benzoyl}-1,2,3,4-tetrahydroisoquinolin-3-yl]methyl}carbamate DIPEA (40 al, 0.225 mmol) and then 2-phenoxyacetyl chloride (25 al, 0.18 mmol) are added to a solution of the compound obtained in Step A of Example 138 (104 mg, 0.15 mmol) in dichloromethane (5 ml) and the reaction mixture is stirred at ambient temperature overnight under nitrogen. The reaction mixture is diluted with dichloromethane and washed with water, dried over magnesium sulphate, filtered and concentrated, before being purified by chromatography over silica gel according to a gradient from isohexane to a 2:1 ethyl acetate/isohexane mixture to provide the product in the form of a solid.

LC/MS ($C_{50}H_{46}N_6O_6$) 727.3 [M-Boc]$^+$; RT 2.79 (Method A)

Step B: 1-{2-[(3S)-3-(Aminomethyl)-1,2,3,4-tetrahydroisoquinoline-2-carbonyl]-4-(2-phenoxyacetamido)phenyl}-N,N-diphenyl-1H-indazole-3-carboxamide The compound obtained in Step A is deprotected in accordance with the procedure of Step B of Example 132 and then purified over a SCX column, the compound being eluted in a 4:1 methanol/7N ammonia mixture.

LC/MS ($C_{45}H_{38}N_6O_4$) 727 [M+H]$^+$; RT 2.33
High-resolution mass spectroscopy (ESI+):
Empirical formula: $C_{45}H_{38}N_6O_4$
[M+H]$^+$ calculated: 727.3027
[M+H]$^+$ measured: 727.3004

Example 145. 1-{2-[(3S)-3-(Aminomethyl)-1,2,3,4-tetrahydroisoquinoline-2-carbonyl]-4-hydroxy-5-methoxyphenyl}-N-(4-hydroxyphenyl)-N-phenyl-1H-indole-3-carboxamide The procedure is the same as in the process of Example 131, replacing the compound of Preparation 3d with the compound of Preparation 3a.

LC/MS ($C_{39}H_{34}N_4O_5$) 639 [M+H]$^+$; RT 2.03 (Method A)
High-resolution mass spectroscopy (ESI+):
Empirical formula: $C_{39}H_{34}N_4O_5$
[M+H]$^+$ calculated: 639.2602
[M+H]$^+$ measured: 639.2619

Example 146. 1-{2-[(3S)-3-(Aminomethyl)-1,2,3,4-tetrahydroisoquinoline-2-carbonyl]-5-methoxyphenyl}-N-(4-hydroxyphenyl)-N-phenyl-1H-indole-3-carboxamide The procedure is the same as in the process of Example 131, replacing the compound obtained in Preparation 3d with the compound obtained in Preparation 3e.
LC/MS ($C_{39}H_{34}N_4O_4$) 623 [M+H]$^+$; RT 2.12 (Method A)
High-resolution mass spectroscopy (ESI+):
Empirical formula: $C_{39}H_{34}N_4O_4$
[M+H]$^+$ calculated: 623.2653
[M+H]$^+$ measured: 623.2632

Example 147. 1-{2-[(3S)-3-(Aminomethyl)-1,2,3,4-tetrahydroisoquinoline-2-carbonyl]-5-methoxyphenyl}-N,N-diphenyl-1H-indole-3-carboxamide The procedure is the same as in Steps A and C of Example 131, replacing the compound obtained in Preparation 3d with the compound obtained in Preparation 3g and purifying the final product by preparative HPLC.
LC/MS ($C_{39}H_{34}N_4O_3$) 607 [M+H]$^+$; RT 1.14 (Method A)
High-resolution mass spectroscopy (ESI+):
Empirical formula: $C_{39}H_{34}N_4O_3$
[M+H]$^+$ calculated: 607.2704
[M+H]$^+$ measured: 607.2687

Example 148. 1-{2-[(3S)-3-(Aminomethyl)-1,2,3,4-tetrahydroisoquinoline-2-carbonyl]-phenyl}-N-(4-hydroxyphenyl)-N-phenyl-1H-indazole-3-carboxamide Step A: 1-{2-[(3S)-3-(Aminomethyl)-1,2,3,4-tetrahydroisoquinoline-2-carbonyl]phenyl}-N-[4-(benzyloxy)phenyl]-N-phenyl-1H-indazole-3-carboxamide The compound obtained in Preparation 6f is treated in accordance with procedure of Step A of Example 132 and then subsequently deprotected in accordance with the procedure of Step B of Example 132.

Step B: 1-{2-[(3S)-3-(Aminomethyl)-1,2,3,4-tetrahydroisoquinoline-2-carbonyl]phenyl}-N-(4-hydroxyphenyl)-N-phenyl-1H-indazole-3-carboxamide Catalytic 10% palladium on carbon is added to a solution of the compound (43 mg, 0.06 mmol) in methanol (4 ml) and the reaction mixture is washed with nitrogen. The reaction mixture then evacuated, filled with hydrogen and stirred under a hydrogen atmosphere for 2.5 hours. A further quantity of 10% palladium on carbon is added and stirring of the reaction mixture is continued for a further 3 hours. The reaction mixture is filtered through a Celite cartridge, washed with methanol and then concentrated in vacuo to provide a solid, which is purified by flash chromatography over silica gel according to a gradient from dichloromethane to a methanol (10%)/dichloromethane mixture, before being purified further by SCX. The column is pre-washed with methanol before application of the compound in dichloromethane, followed by successive washing with dichloromethane, methanol and elution with a 1:4 ammonia in methanol/methanol mixture.
LC/MS ($C_{37}H_{31}N_5O_3$) 594 [M+H]$^+$; RT 2.11 (Method A)
High-resolution mass spectroscopy (ESI+):
Empirical formula: $C_{37}H_{31}N_5O_3$
[M+H]$^+$ calculated: 594.2500
[M+H]$^+$ measured: 594.2475

Example 149. 1-{2-[(3S)-3-(Aminomethyl)-1,2,3,4-tetrahydroisoquinoline-2-carbonyl]-4-[2-(phenylsulphanyl)acetamido]phenyl}-N,N-diphenyl-1H-indazole-3-carboxamide The procedure is the same as that described in Example 144, using 2-(phenylsulphanyl)-acetyl chloride in Step A and then deprotecting the resulting compound in accordance with the procedure described in Step B of Example 132.
LC/MS ($C_{45}H_{38}N_6O_3S$) 743 [M+H]$^+$; RT 2.39 (Method A)
High-resolution mass spectroscopy (ESI+):
Empirical formula: $C_{45}H_{38}N_6O_3S$
[M+H]$^+$ calculated: 743.2799
[M+H]$^+$ measured: 743.2772

Example 150. 1-{2-[(3S)-3-(Aminomethyl)-1,2,3,4-tetrahydroisoquinoline-2-carbonyl]-5-methoxyphenyl}-N,N-diphenyl-1H-indazole-3-carboxamide The procedure is as in the process of Preparation 6a, replacing 6-bromo-2H-1,3-benzodioxole-5-carboxylic acid with 2-iodo-4-methoxybenzoic acid. The process described in Step A of Example 132 is then applied.
The compound so obtained (0.18 g, 0.25 mmol) is then dissolved in anhydrous dichloromethane (5 ml) under nitrogen and cooled to 0° C., treated dropwise with boron trichloride (0.09 ml, 1 mmol) and allowed to warm to ambient temperature again overnight. The reaction mixture is then cooled to 0° C. and treated with boron tribromide (0.09 ml, 1 mmol), and then a further 0.18 ml after 4 hours. The reaction mixture is inactivated with methanol, concentrated under reduced pressure, taken up in ethyl acetate and washed with water. The organic phases are dried over magnesium sulphate, filtered and concentrated to provide an oil, which is purified by flash chromatography according to a gradient from dichloromethane to a methanol (10%)/dichloromethane mixture.
LC/MS ($C_{38}H_{33}N_5O_3$) 608.2 [M+H]$^+$; RT 2.25 (Method A)
High-resolution mass spectroscopy (ESI+):
Empirical formula: $C_{38}H_{33}N_5O_3$
[M+H]$^+$ calculated: 608.2656
[M+H]$^+$ measured: 608.2639

Example 151. 1-{2-[(3S)-3-[(Dimethylamino)methyl]-1,2,3,4-tetrahydroisoquinoline-2-carbonyl]phenyl}-N,N-diphenyl-1H-indole-3-carboxamide Example 152. 1-{4-Amino-2-[(3S)-3-(aminomethyl)-1,2,3,4-tetrahydroisoquinoline-2-carbonyl]-5-methoxyphenyl}-N,N-diphenyl-1H-indazole-3-carboxamide Step A: tert-Butyl N-{[(3S)-2-{2-[3-(diphenylcarbamoyl)-1H-indazol-1-yl]-5-hydroxy-4-methoxybenzoyl}-1,2,3,4-tetrahydroisoquinolin-3-yl]methyl}carbamate The procedure is as in the process of Preparation 6a, replacing 6-bromo-2H-1,3-benzodioxole-5-carboxylic acid with 5-(benzyloxy)-2-bromo-4-methoxybenzoic acid. The process described in Step A of Example 132 is then applied.

The compound so obtained (367 mg, 0.45 mmol) is dissolved in ethyl acetate (10 ml) and degassed, and then catalytic 10% palladium on carbon is added. The reaction mixture is degassed and then stirred under a hydrogen atmosphere, at ambient temperature, overnight. The reaction mixture is filtered through Celite, washed with ethyl acetate and then concentrated to provide a solid, which is used in the following step without being purified further.

LC/MS ($C_{44}H_{42}N_4O_6$) 723.3 [M+H]$^+$; RT 2.68 (Method A)

Step B: tert-Butyl N-{[(3S)-2-{2-[3-(diphenylcarbamoyl)-1H-indazol-1-yl]-4-methoxy-5-(trifluoromethanesulphonyloxy)benzoyl}-1,2,3,4-tetrahydroisoquinolin-3-yl]methyl}-carbamate Triethylamine (0.14 ml, 1 mmol) is added to a solution of the compound obtained in Step A (236 mg, 0.33 mmol) in dichloromethane (10 ml). The reaction mixture is cooled to 0° C. under nitrogen, and then triflic anhydride (82.3 al, 0.49 mmol) is added, before the whole is stirred at ambient temperature under nitrogen for 5 hours. The reaction mixture is diluted with dichloromethane, washed with water, dried over magnesium sulphate, filtered and concentrated. The crude material is purified by chromatography over silica gel according to a gradient from isohexane to a 6:4 isohexane/ethyl acetate mixture to provide the product in the form of a gum.

LC/MS ($C_{44}H_{40}N_5O_8F_3S$) no m/z observed; RT 2.85 (Method A)

Step C: tert-Butyl N-{[(3S)-2-{2-[3-(diphenylcarbamoyl)-1H-indazol-1-yl]-5-[(diphenyl-methylidene)amino]-4-methoxybenzoyl}-1,2,3,4-tetrahydroisoquinolin-3-yl]methyl}-carbamate Diphenylmethanimine (22.4 µl, 0.13 mmol), palladium (II) acetate (4.04 mg, 0.018 mmol), BINAP (11.2 mg, 0.018 mmol) and caesium carbonate (58.6 mg, 0.18 mmol) are suspended in toluene (1 ml), and then a solution of the compound obtained in Step B (76 mg, 0.09 mmol) in toluene (4 ml) is added. The reaction mixture is degassed with nitrogen for 5 minutes and then subjected to microwaves for 1.5 hours at 150° C. Further diphenylmethanimine (22.4 al, 0.13 mmol) is added, and the reaction mixture is subjected to microwaves for 6 hours. The reaction mixture is concentrated, extracted with ethyl acetate and washed with brine, dried over magnesium sulphate, filtered and concentrated. The crude material is purified by chromatography in isohexane, to a 2:1 isohexane/ethyl acetate mixture, 2:1 isohexane/ethyl acetate, then 1:1 isohexane/ethyl acetate, to provide the product in the form of a solid.

LC/MS ($C_{56}H_{50}N_6O_5$) 787.3 [M-Boc]$^+$; RT 2.91 (Method A)

Step D: 1-{4-Amino-2-[(3S)-3-(aminomethyl)-1,2,3,4-tetrahydroisoquinoline-2-carbonyl]-5-methoxyphenyl}-N,N-diphenyl-1H-indazole-3-carboxamide Trifluoroacetic acid (0.5 ml) is added to the compound obtained Step C (4 mg, 0.005 mmol) in dichloromethane (3 ml) and the reaction mixture is stirred at ambient temperature. After 30 minutes, further trifluoroacetic acid (0.5 ml) is added, followed by several drops of 2N HCl after a further 30 minutes. After 15 minutes, the reaction mixture is rendered alkaline with 2N NaOH and the organic phase is separated off, dried over magnesium sulphate, filtered and evaporated. The crude material is purified by chromatography over silica gel in dichloromethane, to a 9:1 dichloromethane/methanol mixture.

LC/MS ($C_{38}H_{34}N_6O_3$) 623 [M+H]$^+$; RT 2.17 (Method A)
High-resolution mass spectroscopy (ESI+):
Empirical formula: $C_{38}H_{34}N_6O_3$
[M+H]$^+$ calculated: 623.2765
[M+H]$^+$ measured: 623.2768

Example 153. 1-{6-[(3S)-3-(Aminomethyl)-1,2,3,4-tetrahydroisoquinoline-2-carbonyl]-2H-1,3-benzodioxol-5-yl}-N-(4-hydroxyphenyl)-N-phenyl-1H-indole-3-carboxamide The procedure is the same as in the process of Example 131, replacing the compound obtained in Preparation 3d with the compound obtained in Preparation 3h.

LC/MS ($C_{39}H_{32}N_4O_5$) 637 [M+H]$^+$; RT 2.11 (Method A)

Example 154. 1-{2-[(3S)-3-(Aminomethyl)-1,2,3,4-tetrahydroisoquinoline-2-carbonyl]-5-methoxy-4-(3-phenoxyazetidin-1-yl)phenyl}-N,N-diphenyl-1H-indole-3-carboxamide

Step A: tert-Butyl N-{[(3S)-2-{5-(benzyloxy)-2-[3-(diphenylcarbamoyl)-1H-indol-1-yl]-4-methoxybenzoyl}-1,2,3,4-tetrahydroisoquinolin-3-yl]methyl}carbamate The procedure is the same as in the process of Step A of Example 131, replacing the compound of Preparation 3d with the compound of Preparation 3t.

Step B: tert-Butyl N-{[(3S)-2-{2-[3-(diphenylcarbamoyl)-1H-indol-1-yl]-4-methoxy-5-(trifluoromethanesulphonyloxy)benzoyl}-1,2,3,4-tetrahydroisoquinolin-3-yl]methyl}-carbamate Trifluoroacetic anhydride (85.5 µl, 0.51 mmol) is added to a solution of the compound obtained in Step A (245 mg, 0.34 mmol) and triethylamine (0.14 ml, 1.02 mmol) in dichloromethane (15 ml), cooled to 0° C., and the reaction mixture is stirred at ambient temperature under nitrogen. After 1 hour, the reaction mixture is distributed according to its solubility between dichloromethane and water, dried over magnesium sulphate, filtered and concentrated, before being purified by chromatography over silica gel according to a gradient from isohexane to a 6:4 isohexane/ethyl acetate mixture to provide the product in the form of an oil.

LC/MS ($C_{45}H_{41}N_4O_8F_3S$) no m/z observed; RT 2.87 (Method A)

Step C: tert-Butyl N-{[(3S)-2-{2-[3-(diphenylcarbamoyl)-1H-indol-1-yl]-4-methoxy-5-(3-phenoxyazetidin-1-yl)benzoyl}-1,2,3,4-tetrahydroisoquinolin-3-yl]methyl}carbamate A solution of the compound obtained in Step B (58 mg, 0.07 mmol) in tetrahydrofuran (2 ml), degassed with nitrogen, is added to a mixture of sodium tert-butanolate (19.8 mg, 0.2 mmol), 3-phenoxyazetidine hydrochloride (18.9 mg, 0.1 mmol) and bis(tri-tert-butylphosphine)palladium(0) (3.47 mg, 0.01 mmol) and the reaction mixture is heated by microwave irradiation for 30 minutes at 120° C. The reaction mixture is distributed according to its solubility between ethyl acetate and water, dried over magnesium sulphate, filtered and concentrated, before being purified by chromatography over silica gel according to a gradient from isohexane to a 1:1 isohexane/ethyl acetate mixture.

Step D: 1-{2-[(3S)-3-(Aminomethyl)-1,2,3,4-tetrahydroisoquinoline-2-carbonyl]-5-methoxy-4-(3-phenoxyazetidin-1-yl)phenyl}-N,N-diphenyl-1H-indole-3-carboxamide The procedure is the same as in the process of Step C of Example 131.
LC/MS ($C_{48}H_{43}N_5O_4$) 754 [M+H]$^+$; RT 2.5 (Method A)
High-resolution mass spectroscopy (ESI+):
Empirical formula: $C_{48}H_{43}N_5O_4$
[M+H]$^+$ calculated: 754.3388
[M+H]$^+$ measured: 754.3376

Example 155. N-(4-Hydroxyphenyl)-1-{2-[(3S)-3-[(4-methylpiperazin-1-yl)methyl]-1,2,3,4-tetrahydroisoquinoline-2-carbonyl]phenyl}-N-phenyl-1H-indole-3-carboxamide Step A: N-[4-(Benzyloxy)phenyl]-1-{2-[(3S)-3-[(4-methylpiperazin-1-yl)methyl]-1,2,3,4-tetrahydroisoquinoline-2-carbonyl]phenyl}-N-phenyl-1H-indole-3-carboxamide The procedure is the same as in the process of Step A of Example 131, replacing the compound of Preparation 1' with the compound of Preparation 3'.

Step B: N-(4-Hydroxyphenyl)-1-{2-[(3S)-3-[(4-methylpiperazin-1-yl)methyl]-1,2,3,4-tetrahydroisoquinoline-2-carbonyl]phenyl}-N-phenyl-1H-indole-3-carboxamide Boron trichloride (1M in dichloromethane, 0.03 ml) is added to a solution of the compound prepared in Step A (122 mg, 0.16 mmol) in dichloromethane (3 ml), cooled to 0° C. under nitrogen. The reaction mixture is allowed to warm to ambient temperature again and is stirred for 2 days, during which period 2 successive additions of aliquot amounts of 0.15 ml of boron trichloride are made. The reaction mixture is inactivated with methanol, concentrated, and the residue is purified by column chromatography in dichloromethane, to a methanol (5%)/dichloromethane mixture.
LC/MS ($C_{43}H_{41}N_5O_3$) 676 [M+H]$^+$; RT 2.15 (Method A)
High-resolution mass spectroscopy (ESI+):
Empirical formula: $C_{43}H_{41}N_5O_3$
[M+H]$^+$ calculated: 676.3282
[M+H]$^+$ measured: 676.3259

Example 156. 1-{2-[(3S)-3-(Aminomethyl)-1,2,3,4-tetrahydroisoquinoline-2-carbonyl]-5-chlorophenyl}-N-(4-hydroxyphenyl)-N-phenyl-1H-indole-3-carboxamide Step A: tert-Butyl N-{[(3S)-2-[2-(3-{[4-(benzyloxy)phenyl](phenyl)carbamoyl}-1H-indol-1-yl)-4-chlorobenzoyl]-1,2,3,4-tetrahydroisoquinolin-3-yl]methyl}carbamate The compound obtained in Preparation 3i (0.48 g, 0.84 mmol) is dissolved in 10 ml of anhydrous dichloromethane. Oxalyl chloride (0.63 ml, 1.26 mmol) is added, followed by several drops of N,N-dimethylformamide, and the reaction mixture is stirred at ambient temperature for approximately 16 hours. The reaction mixture is concentrated to dryness and then dissolved again in 10 ml of anhydrous dichloromethane, cooled to 0° C., and triethylamine (0.21 ml, 1.53 mmol) is added, followed by the compound obtained in Preparation 1' (0.24 g, 0.92 mmol), and the reaction mixture is stirred for 1.5 hours. The reaction mixture is distributed according to its solubility between dichloromethane and water, and the organic phase is washed with brine, dried over magnesium sulphate and concentrated. The crude material is purified by chromatography over a silica column, eluting with isohexane to ethyl acetate to provide the product in the form of an oil.
LC/MS ($C_{50}H_{45}N_4O_5Cl$) 817 [M+H]$^+$; RT 2.96 (Method A)

Step B: 1-{2-[(3S)-3-(Aminomethyl)-1,2,3,4-tetrahydroisoquinoline-2-carbonyl]-5-chlorophenyl}-N-(4-hydroxyphenyl)-N-phenyl-1H-indole-3-carboxamide A solution of boron trichloride (0.21 ml, 2.4 mmol) is added, dropwise, to a solution of the compound obtained in Step A (0.20 g, 0.24 mmol) in anhydrous dichloromethane (5 ml), under nitrogen and cooled 0° C. The reaction mixture is then allowed to warm to temperature again and is stirred for approximately 16 hours. The solution is cooled to 0° C. and further boron trichloride solution is added (0.21 ml, 2.4 mmol). After 6 hours, the reaction mixture is cooled, and then boron tribromide (0.23 ml, 2.4 mmol) is added. The reaction mixture is again allowed to warm to ambient temperature and is stirred for approximately 16 hours. Two other 0.23 ml portions of boron tribromide solution are added, cooling for a further 7 hours. The reaction mixture is inactivated with methanol, concentrated and then distributed according to its solubility between ethyl acetate and water. The organic phases are dried over magnesium sulphate, filtered and concentrated. The crude product is purified by chromatography over silica using a gradient from dichloromethane to a methanol (20%)/dichloromethane mixture, and then further purification by preparative HPLC is carried out.
LC/MS ($C_{38}H_{31}N_4O_3Cl$) 627 [M+H]$^+$; RT 107 (Method B)
High-resolution mass spectroscopy (ESI+):
Empirical formula: $C_{38}H_{31}N_4O_3Cl$
[M+H]$^+$ calculated: 627.2157
[M+H]$^+$ measured: 627.2178

Example 157. 1-{2-[(3S)-3-(Aminomethyl)-1,2,3,4-tetrahydroisoquinoline-2-carbonyl]-4-[2-(phenylsulphanyl)acetamido]phenyl}-N-(4-hydroxyphenyl)-N-phenyl-1H-indole-3-carboxamide Step A: 2-(3-{[4-(Benzyloxy)phenyl](phenyl)carbamoyl}-1H-indol-1-yl)-5-nitrobenzoic Acid To a solution of the compound obtained in Preparation 2a (175 mg, 0.42 mmol) in N,N-dimethylformamide (10 mL) there are added potassium carbonate (87 mg, 0.63 mmol) and methyl 2-fluoro-5-nitrobenzoate (93 mg, 0.5 mmol) and the reaction mixture is stirred at 110° C. under nitrogen. Further potassium carbonate (29 mg, 0.21 mmol) and methyl 2-fluoro-5-nitrobenzoate (46.5 mg, 0.25 mmol) are added and the temperature is increased to 130° C. The reaction mixture is stirred overnight. It is then concentrated and extracted with ethyl acetate, washed with 1M HCl and the organic phases are dried over magnesium sulphate, filtered and concentrated. The crude residue is purified by chromatography according to a gradient from dichloromethane to a methanol (10%)/dichloromethane mixture to yield an oil.

LC/MS ($C_{35}H_{25}N_3O_6$) 584.2 [M+H]$^+$; RT 2.69 (Method A)

Step B: tert-Butyl N-{[(3S)-2-[5-amino-2-(3-{[4-(benzyloxy)phenyl](phenyl)carbamoyl}-1H-indol-1-yl)benzoyl]-1,2,3,4-tetrahydroisoquinolin-3-yl]methyl}carbamate The compound obtained in Step A is treated in accordance with the procedure of Step A of Example 131. The compound so obtained (300 mg, 0.36 mmol) is dissolved in methanol (10 mL). There are added thereto zinc (235 mg, 3.6 mmol) and ammonium chloride (193 mg, 3.6 mmol). The reaction mixture is refluxed for 5 minutes under nitrogen and allowed to cool to ambient temperature. It is filtered over Celite, washed with hot ethanol and then concentrated. The residue is taken up in ethyl acetate and washed with a saturated sodium bicarbonate solution, dried over magnesium sulphate, filtered and concentrated to yield a solid, which is used further in the following step without being purified.

LC/MS ($C_{50}H_{47}N_5O_5$) 798.4 [M+H]$^+$; RT 2.83

Step C: tert-Butyl N-{[(3S)-2-[2-(3-{[4-(benzyloxy)phenyl](phenyl)carbamoyl})-1H-indol-1-yl)-5-[2-(phenylsulphanyl)acetamido]benzoyl]-1,2,3,4-tetrahydroisoquinolin-3-yl]-methyl}carbamate To a solution of the compound obtained in Step B (304 mg, 0.38 mmol) in dichloromethane (10 mL) and DIPEA (0.1 mL, 0.6 mmol) there is added 2-(phenylsulphanyl)acetyl chloride (68 µL, 0.46 mmol), and the reaction mixture is stirred at ambient temperature overnight. The reaction mixture is distributed according to its solubility between dichloromethane and brine, dried over magnesium sulphate, filtered and concentrated. The crude material is purified by chromatography in isohexane, to a 6:4 ethyl acetate/isohexane mixture, followed by a 2:1 ethyl acetate/isohexane mixture to yield the title product in the form of a solid.

LC/MS ($C_{58}H_{53}N_5O_6S$) no m/z observed; RT 2.93 (Method A)

Step D: 1-{2-[(3S)-3-(Aminomethyl)-1,2,3,4-tetrahydroisoquinoline-2-carbonyl]-4-[2-(phenylsulphanyl)acetamido]phenyl}-N-(4-hydroxyphenyl)-N-phenyl-1H-indole-3-carboxamide The compound obtained in Step C is treated in accordance with the procedure of Step C of Example 131. The compound so obtained (100 mg, 0.12 mmol) is dissolved in dichloromethane (10 mL), cooled to −78° C. Boron trichloride (1M, 0.6 mL, 0.6 mmol) is added thereto. The reaction mixture is allowed to warm to ambient temperature again and is stirred for 4 hours. It is inactivated with methanol, neutralised with triethylamine and washed with brine. The organic phases are dried over magnesium sulphate, filtered and concentrated. The residue obtained is purified by chromatography over silica gel according to a gradient from dichloromethane to a methanol (8%)/dichloromethane mixture. The product obtained is dissolved in ethyl acetate and washed with dilute HCl, dried over magnesium sulphate, filtered and concentrated.

LC/MS ($C_{46}H_{39}N_5O_4S$) 758.2 [M+H]$^+$; RT 1.83

Example 158. 1-{6-[(3S)-3-(Aminomethyl)-1,2,3,4-tetrahydroisoquinoline-2-carbonyl]-2-(2-methylpropyl)-2H-1,3-benzodioxol-5-yl}-N-(4-hydroxyphenyl)-N-phenyl-1H-indole-3-carboxamide The procedure is the same as in the process of Example 131, replacing the compound obtained in Preparation 3d with the compound obtained in Preparation 3j. The product is isolated in the form of a mixture of diastereoisomers.

LC/MS ($C_{43}H_{40}N_4O_5$) 693 [M+H]$^+$; RT 2.39 (Method A)
High-resolution mass spectroscopy (ESI+):
Empirical formula: $C_{43}H_{40}N_4O_5$
[M+H]$^+$ calculated: 693.3071
[M+H]$^+$ measured: 693.3096

Example 159. 1-{5-Chloro-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide

Step A: N-[4-(Benzyloxy)phenyl]-1-{5-chloro-2-[(3S)-3-[(4-methylpiperazin-1-yl)-methyl]-1,2,3,4-tetrahydroisoquinoline-2-carbonyl]phenyl}-N-phenyl-1H-indole-3-carboxamide The procedure is the same as in the process of Step A of Example 131, replacing the compound obtained in Preparation 3d with the compound obtained in Preparation 3i and replacing the compound obtained in Preparation 1' with the compound obtained in Preparation 3'.

Step B: 1-{5-Chloro-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide The compound obtained in Step A (0.39 g, 0.48 mmol) is dissolved in anhydrous dichloromethane (10 ml) and cooled to 0° C. A solution of boron tribromide (0.45 ml, 4.8 mmol) is added dropwise and the reaction mixture is allowed to warm to ambient temperature again before being stirred for approximately 16 hours. A further solution of boron tribromide of 0.23 ml is added at 0° C. and the reaction mixture is allowed to warm to ambient temperature again. After 4 hours, the reaction mixture is inactivated with methanol, concentrated and then distributed according to its solubility between ethyl acetate, minimal methanol and brine. The aqueous phase is extracted with dichloromethane, and the combined organic extracts are dried over magnesium sulphate and concentrated in vacuo. The crude material is first purified by flash chromatography over a silica gel column using a gradient from dichloromethane to a methanol (10%)/dichloromethane mixture and is then purified further by preparative HPLC (pH 4).

LC/MS ($C_{43}H_{40}N_5O_3Cl$) 710 [M+H]$^+$; RT 1.14 (Method B)
High-resolution mass spectroscopy (ESI+):
Empirical formula: $C_{43}H_{40}N_5O_3Cl$
[M+H]$^+$ calculated: 710.2892
[M+H]$^+$ measured: 710.2923

Example 160. 1-{4,5-Dimethoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 3d with the compound of Preparation 3k and replacing the compound of Preparation 1' with the compound of Preparation 3'. Deprotection is carried out in accordance with the procedure of Step B of Example 155.

LC/MS ($C_{45}H_{45}N_5O_5$) 736 [M+H]$^+$; RT 2.17 (Method A)

High-resolution mass spectroscopy (ESI+):

Empirical formula: $C_{45}H_{45}N_5O_5$

[M+H]$^+$ calculated: 736.3493

[M+H]$^+$ measured: 736.3465

Example 161. 1-{2-[(3S)-3-(Aminomethyl)-1,2,3,4-tetrahydroisoquinoline-2-carbonyl]-4,5-dimethoxyphenyl}-N-(4-hydroxyphenyl)-N-phenyl-1H-indole-3-carboxamide The procedure is the same as in the process of Example 131, replacing the compound of Preparation 3d with the compound of Preparation 3k.

LC/MS ($C_{40}H_{36}N_4O_5$) 653 [M+H]$^+$; RT 2.11 (Method A)

High-resolution mass spectroscopy (ESI+):

Empirical formula: $C_{40}H_{36}N_4O_5$

[M+H]$^+$ calculated: 653.2758

[M+H]$^+$ measured: 653.2754

Example 162. 1-{2-[(3S)-3-(Aminomethyl)-1,2,3,4-tetrahydroisoquinoline-2-carbonyl]-5-methoxy-4-[2-(phenylsulphanyl)acetamido]phenyl}-N-(4-hydroxyphenyl)-N-phenyl-1H-indole-3-carboxamide

Step A: 2-(3-{[4-(Benzyloxy)phenyl](phenyl)carbamoyl}-1H-indol-1-yl)-4-methoxy-5-nitrobenzoic Acid The procedure is analogous to that of Preparation 3a, using 4-chloro-2-fluoro-5-nitrobenzoic acid. The compound so obtained (162 mg, 0.26 mmol) in methanol (3 mL) is added to a solution of sodium methoxide (0.1 mL) in methanol (2 mL), and the reaction mixture is refluxed under nitrogen overnight. The reaction mixture is diluted with ethyl acetate, neutralised with 2M HCl, and then the organic phases are washed with water, dried over magnesium sulphate, filtered and concentrated to provide a gum, which is used without being purified further.

LC/MS ($C_{36}H_{27}N_3O_7$) 612 [M−H]$^−$; RT 2.7 (Method A)

Step B: tert-Butyl N-{[(3S)-2-(5-amino-2-{3-[(4-hydroxyphenyl)(phenyl)carbamoyl]-1H-indol-1-yl}-4-methoxybenzoyl)-1,2,3,4-tetrahydroisoquinolin-3-yl]methyl}carbamate The compound obtained in Step A is treated in accordance with the procedure of Step C of Example 166 using the compound of Preparation 1'. The compound so obtained (92 mg, 0.11 mmol) is dissolved in ethyl acetate (10 mL) and purged under nitrogen. A catalytic amount of 10% palladium on carbon is then added. The reaction mixture is degassed and then stirred under a hydrogen atmosphere for 2 days. The reaction mixture is filtered over Celite, washed with hot ethyl acetate, concentrated and purified by chromatography over silica gel according to a gradient from dichloromethane to a methanol (3%)/dichloromethane mixture to provide a solid.

LC/MS ($C_{44}H_{43}N_5O_6$) 738.3 [M+H]$^+$; RT 2.59 (Method A)

Step C: 4-(N-Phenyl-1-{2-[(3S)-3-({[(tert-butoxy)carbonyl]amino}methyl)-1,2,3,4-tetrahydroisoquinoline-2-carbonyl]-5-methoxy-4-[2-(phenylsulphanyl)acetamido]-phenyl}-1H-indole-3-amido)phenyl 2-(phenylsulphanyl)acetate To a solution of the compound obtained in Step B (44 mg, 0.06 mmol) in dichloromethane (4 mL) there are added DIPEA (0.04 mL, 0.24 mmol) and 2-(phenylsulphanyl)acetyl chloride (33.4 mg, 0.18 mmol), and the reaction mixture is stirred at ambient temperature, under nitrogen, over a weekend. The reaction mixture is diluted with dichloromethane, washed with water, dried over magnesium sulphate, filtered and concentrated. The crude product is purified by chromatography over silica gel according to a gradient from isohexane to a 6:4 ethyl acetate/isohexane mixture.

LC/MS ($C_{60}H_{55}N_5O_8S_2$) no m/z observed; RT 2.72 (Method A)

Step D: 1-{2-[(3S)-3-(Aminomethyl)-1,2,3,4-tetrahydroisoquinoline-2-carbonyl]-5-methoxy-4-[2-(phenylsulphanyl)acetamido]phenyl}-N-(4-hydroxyphenyl)-N-phenyl-1H-indole-3-carboxamide Trifluoroacetic acid (1 mL) is added to a solution of the compound obtained in Step C (45 mg, 0.04 mmol) in dichloromethane (5 mL), and the reaction mixture is stirred at ambient temperature for 1 hour. The reaction mixture is rendered alkaline with 2M NaOH and stirred for 15 minutes. The reaction mixture is extracted with dichloromethane, dried over magnesium sulphate, filtered and concentrated. The intermediate product is purified by chromatography over silica gel according to a gradient from dichloromethane to a methanol (5%)/dichloromethane mixture. The product is then re-suspended in tetrahydrofuran (4 mL) and 2M NaOH (2 mL) and stirred for 2 hours at ambient temperature. The reaction mixture is extracted with dichloromethane, dried over magnesium sulphate, filtered and concentrated, and then purified by chromatography over silica gel according to a gradient from dichloromethane to a methanol (10%)/dichloromethane mixture.

LC/MS ($C_{47}H_{41}N_5O_5S$) 788 [M+H]$^+$; RT 2.29 (Method A)

High-resolution mass spectroscopy (ESI+):

Empirical formula: $C_{47}H_{41}N_5O_5S$

[M+H]$^+$ calculated: 788.2901

[M+H]$^+$ measured: 788.2939

Example 163. N-(4-Hydroxyphenyl)-1-{2-[(3S)-3-[(4-methylpiperazin-1-yl)methyl]-1,2,3,4-tetrahydroisoquinoline-2-carbonyl]-4-[2-(phenylsulphanyl)acetamido]phenyl}-N-phenyl-1H-indole-3-carboxamide

Step A: 5-Amino-2-{3-[(4-hydroxyphenyl)(phenyl)carbamoyl]-1H-indol-1-yl}benzoic Acid The compound obtained in Step A of Example 157 (180 mg, 0.31 mmol) in ethyl acetate (10 mL) is degassed with nitrogen. A catalytic amount of 10% palladium on carbon is added thereto. The reaction mixture is degassed and then stirred under a hydrogen atmosphere overnight. Further catalyst is added, and the reaction mixture is stirred under a hydrogen atmosphere for a further 2 days at 28° C. Catalyst is again added, and the reaction mixture is stirred under a hydrogen atmosphere for a further one day. The incomplete reaction is filtered over Celite, washed with hot ethyl acetate and concentrated. The crude material is purified by chromatography over silica gel according to a gradient from dichloromethane to a methanol (15%)/dichloromethane mixture, followed by DMAW 240 to provide the desired compound (Compound 2) as well as a small amount of compound whose aniline is still protected (O-Bn group) (Compound 1).

Compound 1 LC/MS ($C_{35}H_{27}N_3O_4$) 554.2 [M+H]$^+$; RT 2.6 (Method A)

Compound 2 LC/MS ($C_{28}H_{21}N_3O_4$) 464.2 [M+H]$^+$; RT 2.22 (Method A)

Step B: 2-{3-[Phenyl(4-{[2-(phenylsulphanyl)acetyl]oxy}phenyl)carbamoyl]-1H-indol-1-yl}-5-[2-(phenylsulphanyl)acetamido]benzoic Acid Compound 2 obtained in Step A is treated in accordance with the procedure described in Step C of Example 162. The compound so obtained is purified over a PE-AX column, washed with dichloromethane and eluted in a formic acid (10%)/dichloromethane mixture to yield a gum.

LC/MS ($C_{44}H_{33}N_3O_6S_2$) 764.2 [M+H]$^+$; RT 2.75 (Method A)

Step C: 4-(N-Phenyl-1-{2-[(3S)-3-[(4-methylpiperazin-1-yl)methyl]-1,2,3,4-tetrahydroisoquinoline-2-carbonyl]-4-[2-(phenylsulphanyl)acetamido]phenyl}-1H-indole-3-amido)phenyl 2-(phenylsulphanyl)acetate The compound obtained in Step B is treated in accordance with the procedure described in Step C of Example 166 using Preparation 3' and purified by chromatography over silica gel according to a gradient from dichloromethane to a methanol (5%)/dichloromethane mixture. The compound is used in the following step without being purified further.

LC/MS ($C_{59}H_{54}N_6O_5S_2$) 991.4 [M+H]$^+$; RT 2.16 (Method A)

Step D: N-(4-Hydroxyphenyl)-1-{2-[(3S)-3-[(4-methylpiperazin-1-yl)methyl]-1,2,3,4-tetrahydroisoquinoline-2-carbonyl]-4-[2-(phenylsulphanyl)acetamido]phenyl}-N-phenyl-1H-indole-3-carboxamide 2M NaOH (1.5 mL) is added to a solution of the compound obtained in Step C (19 mg, 0.02 mmol) in tetrahydrofuran (1.5 mL) and the reaction mixture is stirred at ambient temperature for 1 hour and then for a further 1 hour at 32° C. The reaction mixture is distributed according to its solubility between ethyl acetate and water, and the organic phases are dried over magnesium sulphate, filtered and concentrated. The crude product is purified by chromatography over silica gel according to a gradient from dichloromethane to a methanol (5%)/dichloromethane mixture.

LC/MS ($C_{51}H_{48}N_6O_4S$) 841.4 [M+H]$^+$; RT 1.87 (Method A)

Example 164. N-(4-Hydroxyphenyl)-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide Dihydrochloride

Step A: N-[4-(Benzyloxy)phenyl]-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide The procedure is the same as in the process of Step A of Example 131, replacing the compound of Preparation 3d with the compound of Preparation 3h and replacing the compound of Preparation 1' with the compound of Preparation 3'.

Step B: N-(4-Hydroxyphenyl)-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide Dihydrochloride The compound obtained in Step A (1.44 g, 1.79 mmol) is dissolved in anhydrous dichloromethane (15 ml) and cooled to 0° C. under nitrogen, and then boron trichloride (1M, 3.6 ml, 3.58 mmol) is added and the reaction mixture is allowed to warm to ambient temperature again before being stirred for approximately 16 hours. The reaction mixture is cooled to 0° C., inactivated with methanol and then concentrated. The residue is dissolved in dichloromethane, washed with a saturated aqueous sodium bicarbonate solution, dried over magnesium sulphate and evaporated. The crude material is purified by chromatography over silica gel according to a gradient from dichloromethane to a methanol (10%)/dichloromethane mixture to provide a foam. The material is dissolved in hot isopropyl alcohol (5 ml), and the resulting solution is stirred vigorously while an excess of HCl (2M in ether, 4 ml) is added dropwise. The resulting pulp is stirred for 5 minutes and then filtered and washed with ether to provide the product in the form of a solid.

LC/MS ($C_{44}H_{41}N_5O_5$) 720.3 [M+H]$^+$; RT 2.19 (Method A)

High-resolution mass spectroscopy (ESI+):
Empirical formula: $C_{44}H_{41}N_5O_5$
[M+H]$^+$ calculated: 720.3180
[M+H]$^+$ measured: 720.3151

Example 165. 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide Dihydrochloride

Step A: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-[4-(benzyloxy)phenyl]-N-phenyl-1H-indole-3-carboxamide HBTU (531 mg, 1.4 mmol) and DIPEA (0.49 ml, 2.8 mmol), and then (3S)-3-[(4-methylpiperazin-1-yl)methyl]-1,2,3,4-tetrahydroisoquinoline (343 mg, 1.4 mmol) obtained in Preparation 3', are added to a solution of the acid obtained in Preparation 3a (944 mg, 1.4 mmol) in N,N-dimethylformamide (10 ml). The reaction mixture is stirred at ambient temperature for 3 hours and then diluted with water, and the resulting precipitate is filtered and washed with water, dissolved in dichloromethane and washed with a saturated sodium bicarbonate solution. The organic phases are dried over magnesium sulphate, filtered and evaporated, and the crude material is purified by chromatography over silica gel according to a gradient from dichloromethane to a methanol (5%)/dichloromethane mixture to provide the product in the form of a gum.

LC/MS ($C_{58}H_{55}N_5O_5$) no m/z observed; RT 2.63 (Method A)

Step B: 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide Ammonium formate (793 mg, 12.6 mmol) and then 10% palladium on carbon (130 mg) are added to a solution of the product obtained in Step A (1.14 g, 1.26 mmol) in methanol (20 ml) and the reaction mixture is heated at reflux under nitrogen for 2.5 hours. The reaction mixture is allowed to cool to ambient temperature and is filtered through Celite, washed with methanol and concentrated in vacuo. The material is dissolved in dichloromethane, washed with water and then dried over magnesium sulphate, filtered and evaporated. The crude product is purified by chromatography over silica gel according to a gradient from dichloromethane to a methanol (10%)/dichloromethane mixture to provide the product in the form of a foam.

LC/MS ($C_{44}H_{43}N_5O_5$) 722 [M+H]$^+$; RT 2.17 (Method A)

Step C: 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide Dihydrochloride 2M HCl in ether (3.70 ml, 7.4 mmol) is added to a solution of the compound obtained in Step B (535 mg, 0.74 mmol) in isopropyl alcohol (5 ml). The resulting suspension is diluted with ether (5 ml) and then cooled to 0° C. over a period of 30 minutes before being filtered. The solid is washed with cold ether and dried in vacuo.

LC/MS ($C_{44}H_{43}N_5O_5$) 722 [M+H]$^+$; RT 2.16 (Method A)
High-resolution mass spectroscopy (ESI+):
Empirical formula: $C_{44}H_{43}N_5O_5$
[M+H]$^+$ calculated: 722.3337
[M+H]$^+$ measured: 722.3344

Example 166. N-(4-Hydroxyphenyl)-1-{2-[(3S)-3-(4-methylpiperazine-1-carbonyl)-1,2,3,4-tetrahydroisoquinoline-2-carbonyl]phenyl}-N-phenyl-1H-indole-3-carboxamide Step A: tert-Butyl (3S)-3-(4-methylpiperazine-1-carbonyl)-1,2,3,4-tetrahydroisoquinoline-2-carboxylate To a solution of (3S)-2-[(tert-butoxy)carbonyl]-1,2,3,4-tetrahydroisoquinoline-3-carboxylic acid (15 g, 54.1 mmol) in N,N-dimethylformamide (600 mL) under nitrogen there are added DIPEA (11.3 mL, 65 mmol), N-methylpiperazine (12 mL, 108 mmol) and then HBTU (24.6 g, 65 mmol) in portions, and the reaction mixture is stirred at ambient temperature for 16 hours. The mixture is concentrated in vacuo, diluted with a saturated NaHCO$_3$ solution and extracted with ethyl acetate. The organic phases are washed with a saturated NaHCO$_3$ solution and with brine and are then dried over magnesium sulphate, filtered and concentrated in vacuo. The crude material is applied in the dry state to a silica column and eluted with isohexane, ethyl acetate and then a 19:1 ethyl acetate:7M ammonia in methanol mixture to provide the product in the form of a solid.

LC/MS ($C_{20}H_{29}N_3O_3$) 360 [M+H]$^+$; RT 1.83 (Method A)

Step B: (3S)-3-(4-Methylpiperazine-1-carbonyl)-1,2,3,4-tetrahydroisoquinoline

To a solution of the compound obtained in Step A (19.68 g, 54.75 mmol) in dichloromethane there is slowly added trifluoroacetic acid (42.2 mL, 547.5 mmol) at ambient temperature and then the reaction mixture is heated to 40° C., stirred for 6 hours and then cooled to ambient temperature and again stirred for 16 hours. The reaction mixture is then concentrated in vacuo, diluted in water, cooled to 0° C. and rendered alkaline to pH=12 with concentrated NH$_4$OH. The aqueous phase is extracted with ethyl acetate and the organic phases are dried over magnesium sulphate, filtered and concentrated in vacuo. The crude material is applied in the dry state to a silica column and eluted with isohexane, ethyl acetate and then a 19:1 ethyl acetate:7M ammonia in methanol mixture, and finally a 9:1 ethyl acetate:7M ammonia in methanol mixture. The product is dissolved again in dichloromethane and washed with a 5% NH$_4$OH solution, with brine, and then dried over magnesium sulphate, filtered and concentrated in vacuo, to yield a glass.

LC/MS ($C_{15}H_{21}N_3O$) 260 [M+H]$^+$; RT 0.18 (Method A)

Step C: N-[4-(Benzyloxy)phenyl]-1-{2-[(3S)-3-(4-methylpiperazine-1-carbonyl)-1,2,3,4-tetrahydroisoquinoline-2-carbonyl]phenyl}-N-phenyl-1H-indole-3-carboxamide To a solution of the compound obtained in accordance with Preparation 3a, using 2-iodobenzoic acid (135 mg, 251 µmol) in N,N-dimethylformamide (4 mL) there are added DIPEA (52 µL, 301 µmol), the compound obtained in Step B (71.5 mg, 275.7 µmol) followed by HBTU (114 mg, 300.8 µmol), and the reaction mixture is stirred at ambient temperature for 16 hours. The reaction mixture is diluted with a saturated NaHCO$_3$ solution and extracted with ethyl acetate. The organic phases are then washed with brine, dried over magnesium sulphate, filtered and concentrated in vacuo. The crude material is applied in the dry state to a silica column and eluted with isohexane, ethyl acetate, and then with a 19:1 ethyl acetate:methanol mixture and then a 19:1 ethyl acetate:7M ammonia in methanol mixture to yield a foam.

LC/MS ($C_{50}H_{45}N_5O_4$) 780 [M+H]$^+$; RT 2.5 (Method A)

Step D: N-(4-Hydroxyphenyl)-1-{2-[(3S)-3-(4-methylpiperazine-1-carbonyl)-1,2,3,4-tetrahydroisoquinoline-2-carbonyl]phenyl}-N-phenyl-1H-indole-3-carboxamide The compound obtained in Step C (146 mg, 187 µmol) is dissolved in methanol. There are added thereto ammonium formate (118 mg, 1.87 mmol) and 10% palladium on carbon (106 mg, 18.7 µmol) and the reaction mixture is refluxed under nitrogen for 3 hours. It is then diluted with brine and extracted with ethyl acetate. The organic phases are washed with water, dried over magnesium sulphate, filtered over Celite and concentrated in vacuo.

The crude material is applied in the dry state to a silica column and eluted with isohexane, ethyl acetate, and then with a 19:1 ethyl acetate:7M ammonia in methanol mixture, and finally with a 9:1 ethyl acetate:7M ammonia in methanol mixture.

LC/MS ($C_{43}H_{39}N_5O_4$) 690 [M+H]$^+$; RT 2.17 (Method A)
High-resolution mass spectroscopy (ESI+):
Empirical formula: $C_{43}H_{39}N_5O_4$
[M+H]$^+$ calculated: 690.3075
[M+H]$^+$ measured: 690.3063

Example 167. 1-{5-Chloro-4-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 3d with the compound of Preparation 3l and replacing the compound of Preparation 1' with the compound of Preparation 3'. The deprotection is carried out in accordance with the procedure of Example 155.

LC/MS ($C_{44}H_{42}N_5O_4Cl$) 740.4 [M+H]$^+$; RT 1.85 (Method A)
High-resolution mass spectroscopy (ESI+):
Empirical formula: $C_{44}H_{42}N_5O_4Cl$
[M+H]$^+$ calculated: 740.2998
[M+H]$^+$ measured: 740.2977

Example 168. N-(4-Hydroxyphenyl)-1-{5-methoxy-2-[(3S)-3-[(4-methylpiperazin-1-yl)methyl]-1,2,3,4-tetrahydroisoquinoline-2-carbonyl]phenyl}-N-phenyl-1H-indole-3-carboxamide Dihydrochloride The procedure is the same as in the process of Example 164, replacing the compound obtained in Preparation 3h with the compound obtained in Preparation 3e.

LC/MS ($C_{44}H_{43}N_5O_4$) 706 [M+H]$^+$; RT 1.75 (Method A)
High-resolution mass spectroscopy (ESI+):
Empirical formula: $C_{44}H_{43}N_5O_4$
[M+H]$^+$ calculated: 706.3388
[M+H]$^+$ measured: 706.3415

Example 169. N-(4-Hydroxyphenyl)-1-{5-methoxy-2-[(3S)-3-(piperidin-1-ylmethyl)-1,2,3,4-tetrahydroisoquinoline-2-carbonyl]phenyl}-N-phenyl-1H-indole-3-carboxamide Hydrochloride The procedure is the same as in the process of Example 164, replacing the compound obtained in Preparation 3h with the compound obtained in Preparation 3e and replacing the compound of Preparation 3' with the compound of Preparation 11'.

LC/MS ($C_{44}H_{42}N_4O_4$) 691 [M+H]$^+$; RT 2.25 (Method A)
High-resolution mass spectroscopy (ESI+):
Empirical formula: $C_{44}H_{42}N_4O_4$
[M+H]$^+$ calculated: 691.3279
[M+H]$^+$ measured: 691.3256

Example 170. N-(4-Hydroxyphenyl)-1-{7-[(3S)-3-[(4-methylpiperazin-1-yl)methyl]-1,2,3,4-tetrahydroisoquinoline-2-carbonyl]-2,3-dihydro-1,4-benzodioxin-6-yl}-N-phenyl-1H-indole-3-carboxamide The compound is prepared in accordance with the procedure of Preparation 3a, using 7-bromo-2,3-dihydro-1,4-benzodioxine-6-carboxylic acid and placing the whole in a microwave apparatus at 150° C. for 40 minutes. The procedure described in Step C of Example 166 is then applied using the compound of Preparation 3'. The material is purified by chromatography over silica gel in dichloromethane, to a 5% methanol/dichloromethane mixture, and finally deprotected in accordance with the procedure of Step D of Example 166 and purified by chromatography over silica gel in dichloromethane, to an 8% methanol/dichloromethane mixture.

LC/MS ($C_{45}H_{43}N_5O_5$) 734 [M+H]$^+$; RT 2.2 (Method A)
High-resolution mass spectroscopy (ESI+):
Empirical formula: $C_{45}H_{43}N_5O_5$
[M+H]$^+$ calculated: 734.3337
[M+H]$^+$ measured: 734.3323

Example 171. 1-{5-Chloro-2-[(3S)-3-(piperidin-1-ylmethyl)-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 3d with the compound of Preparation 3i and replacing the compound of Preparation 1' with the compound of Preparation 11'. The deprotection is carried out in accordance with the procedure of Step B of Example 155.

LC/MS ($C_{43}H_{39}N_4O_3Cl$) 695 [M+H]$^+$; RT 2.31 (Method A)
High-resolution mass spectroscopy (ESI+):
Empirical formula: $C_{43}H_{39}N_4O_3Cl$
[M+H]$^+$ calculated: 695.2783
[M+H]$^+$ measured: 695.2771

Example 172. 1-{2-[(3S)-3-(Hydroxymethyl)-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 1' with (3S)-1,2,3,4-tetrahydroisoquinolin-3-ylmethanol. The deprotection is carried out in accordance with the procedure of Step B of Example 155.

LC/MS ($C_{38}H_{31}N_3O_4$) 594 [M+H]$^+$; RT 2.47 (Method A)
High-resolution mass spectroscopy (ESI+):
Empirical formula: $C_{38}H_{31}N_3O_4$
[M+H]$^+$ calculated: 594.2387
[M+H]$^+$ measured: 594.2368

Example 173. N-(4-Hydroxyphenyl)-N-phenyl-1-{2-[(3S)-3-(piperidin-1-ylmethyl)-1,2,3,4-tetrahydroisoquinoline-2-carbonyl]phenyl}-1H-indole-3-carboxamide The procedure is the same as in the process of Step A of Example 131, replacing the compound of Preparation 1' with the compound of Preparation 11'. The deprotection is carried out in accordance with the procedure of Step B of Example 155.

LC/MS ($C_{43}H_{40}N_4O_3$) 661 [M+H]$^+$; RT 2.21 (Method A)
High-resolution mass spectroscopy (ESI+):
Empirical formula: $C_{43}H_{40}N_4O_3$
[M+H]$^+$ calculated: 661.3173
[M+H]$^+$ measured: 661.3156

Example 174. N-(4-Hydroxyphenyl)-N-phenyl-1-{6-[(3S)-3-(piperidin-1-ylmethyl)-1,2,3,4-tetrahydroisoquinoline-2-carbonyl]-2H-1,3-benzodioxol-5-yl}-1H-indole-3-carboxamide The procedure is the same as in the process of Example 164, replacing the compound of Preparation 3' with the compound of Preparation 11'.

LC/MS ($C_{44}H_{40}N_4O_5$) 705 [M+H]$^+$; RT 2.24 (Method A)
High-resolution mass spectroscopy (ESI+):
Empirical formula: $C_{44}H_{40}N_4O_5$
[M+H]$^+$ calculated: 705.3071
[M+H]$^+$ measured: 705.3041

Example 175. 1-{2-[(3S)-3-[(Dimethylamino) methyl]-1,2,3,4-tetrahydroisoquinoline-2-carbonyl]-5-methoxyphenyl}-N-(4-hydroxyphenyl)-N-phenyl-1H-indole-3-carboxamide The procedure is the same as in the process of Example 164, replacing the compound obtained in Preparation 3h with the compound obtained in Preparation 3e and replacing the compound of Preparation 3' with the compound of Preparation 12'.
LC/MS ($C_{44}H_{38}N_4O_4$) 651 [M+H]$^+$; RT 2.18 (Method A)
High-resolution mass spectroscopy (ESI+):
Empirical formula: $C_{41}H_{38}N_4O_4$
[M+H]$^+$ calculated: 651.2966
[M+H]$^+$ measured: 651.2941

Example 176. 1-{4-Hydroxy-5-methoxy-2-[(3S)-3-(piperidin-1-ylmethyl)-1,2,3,4-tetrahydroisoquinoline-2-carbonyl]phenyl}-N-(4-hydroxyphenyl)-N-phenyl-1H-indole-3-carboxamide Hydrochloride The procedure is the same as in the process of Example 165, replacing the (3S)-3-[(4-methylpiperazin-1-yl)methyl]-1,2,3,4-tetrahydroisoquinoline obtained in Preparation 3' with the (3S)-3-(piperidin-1-ylmethyl)-1,2,3,4-tetrahydroisoquinoline obtained in Preparation 11'.
LC/MS ($C_{44}H_{42}N_4O_5$) 707 [M+H]$^+$; RT 2.17 (Method A)
High-resolution mass spectroscopy (ESI+):
Empirical formula: $C_{44}H_{42}N_4O_5$
[M+H]$^+$ calculated: 707.3228
[M+H]$^+$ measured: 707.3206

Example 177. 1-{6-[(3S)-3-[(4-Methylpiperazin-1-yl)methyl]-1,2,3,4-tetrahydroisoquinoline-2-carbonyl]-2H-1,3-benzodioxol-5-yl}-N,N-diphenyl-1H-indole-3-carboxamide Dihydrochloride The procedure is the same as in the process of Example 164, replacing the compound obtained in Preparation 3h with the compound obtained in Preparation 3p.
LC/MS ($C_{44}H_{41}N_5O_4$) 704 [M+H]$^+$; RT 2.33 (Method A)
High-resolution mass spectroscopy (ESI+):
Empirical formula: $C_{44}H_{41}N_5O_4$
[M+H]$^+$ calculated: 704.3231
[M+H]$^+$ measured: 704.3245

Example 178. 1-{5-Chloro-2-[(3S)-3-[(4-methylpiperazin-1-yl)methyl]-1,2,3,4-tetrahydroisoquinoline-2-carbonyl]phenyl}-N,N-diphenyl-1H-indole-3-carboxamide Dihydrochloride The procedure is the same as in the process of Example 164, replacing the compound obtained in Preparation 3h with the compound obtained in Preparation 3q.
LC/MS ($C_{43}H_{40}N_5O_2$) 694 [M+H]$^+$; RT 2.89 (Method A)
High-resolution mass spectroscopy (ESI+):
Empirical formula: $C_{43}H_{40}N_5O_2Cl$
[M+H]$^+$ calculated: 694.2943
[M+H]$^+$ measured: 694.2918

Example 179. 1-{5-Chloro-2-[(3S)-3-[(dimethylamino)methyl]-1,2,3,4-tetrahydroisoquinoline-2-carbonyl]phenyl}-N-(4-hydroxyphenyl)-N-phenyl-1H-indole-3-carboxamide Hydrochloride The procedure is the same as in the process of Example 164, replacing the compound obtained in Preparation 3h with the compound obtained in Preparation 3i and replacing the compound of Preparation 3' with the compound of Preparation 12'.
LC/MS ($C_{40}H_{35}N_4O_3Cl$) 655 [M+H]$^+$; RT 2.3 (Method A)
High-resolution mass spectroscopy (ESI+):
Empirical formula: $C_{40}H_{35}N_4O_3Cl$
[M+H]$^+$ calculated: 655.2470
[M+H]$^+$ measured: 655.2446

Example 180. 1-{6-[(3S)-3-[(Dimethylamino)methyl]-1,2,3,4-tetrahydroisoquinoline-2-carbonyl]-2H-1,3-benzodioxol-5-yl}-N-(4-hydroxyphenyl)-N-phenyl-1H-indole-3-carboxamide Hydrochloride The procedure is the same as in the process of Example 164, replacing the compound of Preparation 3' with the compound of Preparation 12'.
LC/MS ($C_{41}H_{36}N_4O_5$) 665 [M+H]$^+$; RT 2.16 (Method. A)
High-resolution mass spectroscopy (ESI+):
Empirical formula: $C_{41}H_{36}N_4O_5$
[M+H]$^+$ calculated: 665.2758
[M+H]$^+$ measured: 665.2756

Example 181. 1-{4-Hydroxy-5-methoxy-2-[(3S)-3-[(4-methylpiperazin-1-yl)methyl]-1,2,3,4-tetrahydroisoquinoline-2-carbonyl]phenyl}-N,N-diphenyl-1H-indole-3-carboxamide Dihydrochloride The procedure is the same as in the process of Example 165, replacing the compound of Preparation 3a used in Step A with the compound of Preparation 3c; which gives the product in the form of a solid.
LC/MS ($C_{44}H_{43}N_5O_4$) 706 [M+H]$^+$; RT 1.78 (Method. A)
High-resolution mass spectroscopy (ESI+):
Empirical formula: $C_{44}H_{43}N_5O_4$
[M+H]$^+$ calculated: 706.3388
[M+H]$^+$ measured: 706.3398

Example 182. 1-{2,2-Difluoro-6-[(3S)-3-[(4-methylpiperazin-1-yl)methyl]-1,2,3,4-tetrahydroisoquinoline-2-carbonyl]-2H-1,3-benzodioxol-5-yl}-N-(4-hydroxyphenyl)-N-phenyl-1H-indole-3-carboxamide Step A: Methyl 6-bromo-2H-1,3-benzodioxole-5-carboxylate Concentrated sulphuric acid is added dropwise over a period of ca 1 minute to a stirred suspension of 6-bromo-1,3-benzodioxole-5-carboxylic acid (10.29 g, 0.04 mol) in methanol. The mixture is brought to reflux and stirred overnight. The reaction mixture is allowed to cool to ambient temperature, and precipitation occurs. Ice is added to the mixture, and stirring is carried out until the ice has melted. The mixture is then filtered and washed with a water-methanol mixture (2:1). The solid is dried by aspiration to yield a powder.
LC/MS ($C_9H_7O_4Br$) no m/z observed; RT 1.22 (Method B)

Step B: Methyl 2-bromo-4,5-dihydroxybenzoate

Boron trichloride (1 M in dichloromethane; 15.5 mL, 0.02 mol) is added in portions over a period of 5 minutes to a stirred solution of the compound obtained in Step A (2 g, 7.72 mmol) in anhydrous dichloromethane (20 mL), cooled to 0° C. under nitrogen, and then the reaction mixture is allowed to warm to ambient temperature again overnight. The reaction mixture is poured slowly over methanol (20 mL), with stirring, cooled with ice and then stirred over 1 weekend. The solvent is removed in vacuo and the residue is dissolved in a dichloromethane/methanol mixture, dried over magnesium sulphate, filtered, concentrated and dried in vacuo to yield a solid. The product is used directly in the following step without being purified further.

LC/MS ($C_8H_7O_4Br$) 245 [M−H]$^-$; RT 0.94 (Method B)

Step C: Methyl 2-bromo-4,5-bis(methoxymethoxy)benzoate $P_2O_5$ (1.15 g, 8.1 mmol) is added to a solution of the compound obtained in Step B (200 mg, 0.81 mmol) in chloroform (5 mL) and dimethoxymethane (5 mL), cooled to 0° C. The reaction mixture is stirred under nitrogen for 5 minutes and then allowed to warm to ambient temperature again. At the end of 5 hours, the reaction mixture is cooled to 0° C. again and a further 200 mg of $P_2O_5$ are added. The reaction mixture is stirred overnight at ambient temperature. It is then poured over ice, extracted with ethyl acetate, dried over magnesium sulphate, filtered and concentrated. The crude material is purified by chromatography over silica gel according to a gradient from isohexane to a 2:1 isohexane/ethyl acetate mixture to provide an oil.

LC/MS ($C_{12}H_{15}O_6Br$) 337.1 [M+H]$^+$; RT 2.38 (Method A)

Step D: Methyl 2-(3-{[4-(benzyloxy)phenyl](phenyl)carbamoyl}-1H-indol-1-yl)-4,5-dihydroxybenzoate The compound obtained in Step C is treated in accordance with procedure of Preparation 3a and heated in a microwave apparatus at 160° C. for 2 hours. The resulting compound is taken up in 4M HCl in dioxane (4 mL) and stirred at ambient temperature under nitrogen for 1 hour. The reaction mixture is distributed according to its solubility between ethyl acetate and a 2N NaOH solution and then the organic phases are dried over magnesium sulphate, filtered and concentrated to provide a solid, which is used in the following step without being purified further.

LC/MS ($C_{36}H_{28}N_2O_6$) 585.4 [M+H]$^+$; RT 2.69 (Method A)

Step E: Methyl 6-(3-{[4-(benzyloxy)phenyl](phenyl)carbamoyl}-1H-indol-1-yl)-2,2-difluoro-2H-1,3-benzodioxole-5-carboxylate To a solution of the compound obtained in Step D (90 mg, 0.15 mmol) in N,N-dimethylformamide (3 mL) there is added dibromodifluoromethane (70 µL, 0.77 mmol) followed by caesium carbonate (147 mg, 0.45 mmol), and the reaction mixture is heated in a microwave apparatus at 150° C. for 10 minutes. The reaction mixture is distributed according to its solubility between ethyl acetate and water, dried over magnesium sulphate, filtered and concentrated, before being purified by chromatography over silica gel according to a gradient from isohexane to a 3:1 isohexane/ethyl acetate mixture to yield an oil.

LC/MS ($C_{37}H_{26}N_2O_6F_2$) 633.3 [M+H]$^+$; RT 2.94 (Method A)

Step F: 6-(3-{[4-(Benzyloxy)phenyl](phenyl)carbamoyl}-1H-indol-1-yl)-2,2-difluoro-2H-1,3-benzodioxole-5-carboxylic Acid 2N NaOH (1 mL, 2 mmol) is added to a solution of the compound obtained in Step E (39 mg, 0.06 mmol) in tetrahydrofuran (1 mL) and ethanol (1 mL), and the reaction mixture is stirred at ambient temperature for 2 hours. It is distributed according to its solubility between ethyl acetate and water, dried over magnesium sulphate, filtered and concentrated to yield a gum, which is used in the following step without being purified further.

LC/MS ($C_{36}H_{24}N_2O_6F_2$) 619.3 [M+H]$^+$; RT 2.84 (Method A)

Step G: 1-{2,2-Difluoro-6-[(3S)-3-[(4-methylpiperazin-1-yl)methyl]-1,2,3,4-tetrahydroisoquinoline-2-carbonyl]-2H-1,3-benzodioxol-5-yl}-N-(4-hydroxyphenyl)-N-phenyl-1H-indole-3-carboxamide The compound obtained in Step F is treated in accordance with the procedure of Step C of Example 166 using the compound of Preparation 3' and is purified over silica gel in dichloromethane to a methanol (5%)/dichloromethane mixture and is finally deprotected in accordance with the procedure of Step D of Example 166, the reaction taking place slowly over 7 days and requiring several further additions of 10% palladium on carbon, ammonium formate and ethanol. The final product is purified by chromatography over silica gel in dichloromethane to a methanol (6%)/dichloromethane mixture.

LC/MS ($C_{44}H_{39}N_5O_5F_2$) 756 [M+H]$^+$; RT 2.33 (Method A)

High-resolution mass spectroscopy (ESI+):
Empirical formula: $C_{44}H_{39}N_5O_5F_2$
[M+H]$^+$ calculated: 756.2992
[M+H]$^+$ measured: 756.2985

Example 183. 1-{4,5-Dihydroxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 1' with the compound of Preparation 3' and replacing the compound of Preparation 3d with the compound of Preparation 3r. The deprotection is carried out in accordance with the procedure of Step B of Example 155.

LC/MS ($C_{43}H_{41}N_5O_5$) 708 [M+H]$^+$; RT 2.07 (Method A)
High-resolution mass spectroscopy (ESI+):
Empirical formula: $C_{43}H_{41}N_5O_5$
[M+H]$^+$ calculated: 708.3180
[M+H]$^+$ measured: 708.3194

Example 184. N-(4-Hydroxyphenyl)-1-{6-[(3S)-3-(morpholin-4-ylmethyl)-1,2,3,4-tetrahydroisoquinoline-2-carbonyl]-2H-1,3-benzodioxol-5-yl}-N-phenyl-1H-indole-3-carboxamide Hydrochloride The procedure is the same as in the process of Example 164, replacing the compound of Preparation 3' with the compound of Preparation 2'.

LC/MS (C₄₃H₃₈N₄O₆) 707 [M+H]⁺; RT 2.24 (Method A)
High-resolution mass spectroscopy (ESI+):
Empirical formula: C₄₃H₃₈N₄O₆
[M+H]⁺ calculated: 707.2864
[M+H]⁺ measured: 707.2870

Example 185. 1-{2-Ethyl-7-[(3S)-3-[(4-methylpiperazin-1-yl)methyl]-1,2,3,4-tetrahydroisoquinoline-2-carbonyl]-2,3-dihydro-1,4-benzodioxin-6-yl}-N-(4-hydroxyphenyl)-N-phenyl-1H-indole-3-carboxamide The procedure is the same as in the process of Step A of Example 131, replacing the compound of Preparation 1' with the compound of Preparation 3' and replacing the compound of Preparation 3d with the compound of Preparation 3m. The deprotection is carried out in accordance with the procedure of Step B of Example 155.

LC/MS (C₄₇H₄₇N₅O₅) 762 [M+H]⁺; RT 1.84 (Method A)
High-resolution mass spectroscopy (ESI+):
Empirical formula: C₄₇H₄₇N₅O₅
[M+H]⁺ calculated: 762.3650
[M+H]⁺ measured: 762.3614

Example 186. 1-{5-Chloro-2-[(3S)-3-(morpholin-4-ylmethyl)-1,2,3,4-tetrahydroisoquinoline-2-carbonyl]phenyl}-N-(4-hydroxyphenyl)-N-phenyl-1H-indole-3-carboxamide Hydrochloride The procedure is the same as in the process of Example 164, replacing the compound obtained in Preparation 3h with the compound obtained in Preparation 3q and replacing the compound of Preparation 3' with the compound of Preparation 2'.

LC/MS (C₄₂H₃₇N₄O₄·HCl) 697 [M+H]⁺; RT 2.38 (Method A)
High-resolution mass spectroscopy (ESI+):
Empirical formula: C₄₂H₃₇N₄O₄Cl
[M+H]⁺ calculated: 697.2576
[M+H]⁺ measured: 697.2569

Example 187. N-Cyclohexyl-1-{4-hydroxy-5-methoxy-2-[(3S)-3-[(4-methylpiperazin-1-yl)methyl]-1,2,3,4-tetrahydroisoquinoline-2-carbonyl]phenyl}-N-phenyl-1H-indole-3-carboxamide Dihydrochloride

Step A: 5-(Benzyloxy)-4-methoxy-2-[3-(methoxycarbonyl)-1H-indol-1-yl]benzoic acid A solution of 5-(benzyloxy)-2-bromo-4-methoxybenzoic acid (7.5 g, 22.24 mmol), methyl indole-3-carboxylate (3.9 g, 22.24 mmol) and potassium carbonate (6.15 g, 44.48 mmol) in N,N-dimethylformamide (60 ml) is degassed by bubbling nitrogen through. Copper iodide (490 mg, 2.22 mmol) is added and the reaction mixture is stirred at 90° C. under nitrogen for approximately 16 hours. The reaction mixture is cooled to ambient temperature, diluted with water and acidified with 2M aqueous HCl. The resulting precipitate is filtered off, washed with water and then suspended in dichloromethane and washed with brine. The organic phases are dried over magnesium sulphate, filtered and evaporated and the crude material is purified by chromatography over silica gel according to a gradient from dichloromethane to a methanol (5%)/dichloromethane mixture to provide the product in the form of a powder.

LC/MS (C₂₅H₂₁NO₆) 432 [M+H]⁺; RT 2.62 (Method A)

Step B: Methyl 1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-carboxylate DIPEA (4.7 ml, 27 mmol) and HBTU (2 g, 5.4 mmol) and then the compound obtained in Preparation 3' (1.92 g, 5.4 mmol) are added to a solution of the acid obtained in Step A (2.3 g, 5.4 mmol) in N,N-dimethylformamide (20 ml) and the reaction mixture is stirred at ambient temperature for approximately 72 hours. The reaction mixture is diluted with dichloromethane, washed with water, with a saturated sodium bicarbonate solution and then dried over magnesium sulphate, filtered and evaporated. The crude material is purified by chromatography over silica gel according to a gradient from dichloromethane to a methanol (5%)/dichloromethane mixture to provide the product in the form of a foam.

LC/MS (C₄₀H₄₂N₄O₅) 659 [M+H]⁺; RT 2.31 (Method A)

Step C: Sodium 1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-carboxylate A 2M aqueous NaOH solution (10 ml) is added to a solution of the ester obtained in Step B (2.18 g, 3.31 mmol) in methanol (20 ml) and tetrahydrofuran (10 ml) and the suspension is stirred at 50° C. for 7 hours. The reaction mixture is cooled to ambient temperature and concentrated and the residue is dissolved in ethyl acetate, dried over magnesium sulphate, filtered and evaporated to provide a solid.

LC/MS (C₃₉H₃₉N₄O₅·Na) 645 [M+H]⁺; RT 1.77 (Method A) [mass of the acid-type parent molecule]

Step D: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-carbonyl Chloride A 2M solution of oxalyl chloride in dichloromethane (1.77 ml, 3.54 mmol) and then several drops of N,N-dimethylformamide are added to a solution of the compound prepared in Step C (1.18 g, 1.77 mmol) in anhydrous dichloromethane (15 ml) and the reaction mixture is stirred under nitrogen at ambient temperature for approximately 16 hours. The solvent is removed to give a solid.

LC/MS (C₃₉H₃₉N₄O₄Cl) 659 [M+H]⁺; RT 1.85 [methyl ester for the deactivation of the methanol is observed]

Step E: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-cyclohexyl-N-phenyl-1H-indole-3-carboxamide N-Cyclohexylaniline (145 mg, 0.83 mmol) and pyridine (305 μl, 3.77 mmol) are added to a solution of the acid chloride obtained in Step D (500 mg, 0.75 mmol) in anhydrous dichloromethane (6 ml) cooled to 0° C. under nitrogen, and the reaction mixture is allowed to warm to ambient temperature again. The reaction mixture is stirred for approximately 16 hours, after which a further 70 mg of N-cyclohexylaniline (0.4 mmol) are added and stirring of the reaction mixture is continued at ambient temperature. The reaction mixture is cooled, diluted with dichloromethane and washed in succession with water, with 2M NaOH and with brine. The organic phases are dried over magnesium sulphate, filtered and evaporated and the crude material is purified by chromatography over silica gel according to a gradient from dichloromethane to a methanol (5%)/dichloromethane mixture to provide a gum.

LC/MS ($C_{51}H_{55}N_5O_4$) 802 [M+H]$^+$; RT 2.58 (Method A)

Step F: N-Cyclohexyl-1-{4-hydroxy-5-methoxy-2-[(3S)-3-[(4-methylpiperazin-1-yl)-methyl]-1,2,3,4-tetrahydroisoquinoline-2-carbonyl]phenyl}-N-phenyl-1H-indole-3-carboxamide Ammonium formate (150 mg, 2.2 mmol) and catalytic 10% palladium on carbon are added to a solution of the compound obtained in Step E (180 mg, 0.22 mmol) in methanol (10 ml). The reaction mixture is heated at reflux under nitrogen for 1 hour. The reaction mixture is cooled to ambient temperature, filtered through Celite, washed with methanol and concentrated. The crude material is purified by chromatography over silica gel according to a gradient from dichloromethane to a methanol (10%)/dichloromethane mixture to provide the product in the form of a solid.

LC/MS ($C_{44}H_{49}N_5O_4$) 712 [M+H]$^+$; RT 1.35 (Method B)

Step G: N-Cyclohexyl-1-{4-hydroxy-5-methoxy-2-[(3S)-3-[(4-methylpiperazin-1-yl)-methyl]-1,2,3,4-tetrahydroisoquinoline-2-carbonyl]phenyl}-N-phenyl-1H-indole-3-carboxamide Dihydrochloride 2M HCl in ether (0.35 ml, 0.7 mmol) is added to a solution of the compound obtained in Step F (100 mg, 0.14 mmol) in isopropyl alcohol (2 ml). The solution is diluted with ether (10 ml) and the resulting suspension is stirred for 30 minutes and then allowed to concentrate. The residue is triturated with ether, filtered, washed with a further quantity of ether, and the solid is dried in vacuo.

LC/MS ($C_{44}H_{49}N_5O_4$) 712 [M+H]$^+$; RT 2.37 (Method A)
High-resolution mass spectroscopy (ESI+):
Empirical formula: $C_{44}H_{49}N_5O_4$
[M+H]$^+$ calculated: 712.3857
[M+H]$^+$ measured: 712.3828

Example 188. 1-[(2S)-2-[(Benzyloxy)methyl]-7-[(3S)-3-[(4-methylpiperazin-1-yl)-methyl]-1,2,3,4-tetrahydroisoquinoline-2-carbonyl]-2,3-dihydro-1,4-benzodioxin-6-yl]-N-(4-hydroxyphenyl)-N-phenyl-1H-indole-3-carboxamide Step A: Methyl 2-bromo-4,5-dihydroxybenzoate Boron tribromide (1M, 11.62 mL, 122.6 mmol) is added to a solution of methyl 2-bromo-4,5-dimethoxybenzoate (5.62 g, 20.43 mmol) in dichloromethane (60 mL), cooled to −78° C., under nitrogen. The reaction mixture is allowed to warm to ambient temperature again and is stirred overnight. The reaction mixture is poured over 500 mL of cold methanol with stirring and is then concentrated and distributed according to its solubility between ethyl acetate and water. The organic phases are dried over magnesium sulphate, filtered and concentrated to provide a solid.

LC/MS ($C_8H_7O_4Br$) 247 [M+H]$^+$; RT 1.82 (Method A)

Step B: Methyl (3S)-7-bromo-3-(hydroxymethyl)-2,3-dihydro-1,4-benzodioxine-6-carboxylate To a solution of the compound obtained in Step A (1 g, 4.05 mmol) in N,N-dimethylformamide (16 mL) there is added 4-methylbenzyl (2R)-oxiran-2-ylmethanesulphonate (1.11 g, 4.86 mmol) followed by potassium carbonate (1.12 g, 8.1 mmol), and the reaction mixture is heated in a microwave apparatus at 120° C. for 20 minutes. The reaction mixture is concentrated and distributed according to its solubility between ethyl acetate and water, and the organic phases are dried over magnesium sulphate, filtered and concentrated. The crude product is purified by chromatography over silica gel in isohexane to a 1:1 ethyl acetate/isohexane mixture to provide an oil.

LC/MS ($C_{11}H_{11}O_5Br$) no m/z observed; RT 1.62 (Method A)

Step C: Methyl (3S)-3-[(benzyloxy)methyl]-7-bromo-2,3-dihydro-1,4-benzodioxine-6-carboxylate To a solution of the compound obtained in Step B (1.04 g, 3.44 mmol) in N,N-dimethylformamide (15 mL) under nitrogen there are added 60% sodium hydride (165 mg, 4.13 mmol), and, after 15 minutes, benzyl bromide (0.49 mL, 4.13 mmol), and the reaction mixture is stirred at 50° C. for 4 hours. It is then concentrated and distributed according to its solubility between ethyl acetate and water. The organic phases are dried over magnesium sulphate, filtered and concentrated. The crude product is purified by chromatography over silica gel in isohexane to a 7:1 ethyl acetate/isohexane mixture to provide an oil.

LC/MS ($C_{18}H_{17}O_5Br$) 393.1 [M+H]$^+$; RT 2.72 (Method A)

Step D: (3S)-3-[(Benzyloxy)methyl]-7-bromo-2,3-dihydro-1,4-benzodioxine-6-carboxylic Acid 2M NaOH (3 mL, 6 mmol) is added to a solution of the compound obtained in Step C (0.5 g, 1.28 mmol) dissolved in a methanol/tetrahydrofuran mixture (1.5 mL:1.5 mL), and the reaction mixture is stirred at 50° C. for 2 hours. The reaction mixture is concentrated, diluted in water and acidified with 2M HCl, extracted with ethyl acetate, dried over magnesium sulphate, filtered and concentrated to provide a solid.

LC/MS ($C_{17}H_{15}O_5Br$) 379 [M+H]$^+$; RT 2.48 (Method A)

Step E: Methyl 1-[(2S)-2-[(benzyloxy)methyl]-7-[(3S)-3-[(4-methylpiperazin-1-yl)-methyl]-1,2,3,4-tetrahydroisoquinoline-2-carbonyl]-2,3-dihydro-1,4-benzodioxin-6-yl]-1H-indole-3-carboxylate The compound obtained in Step D is treated in accordance with the procedure of Step A of Preparation 3d and heated in a microwave apparatus at 130° C. for 40 minutes before being purified by chromatography over silica gel according to a gradient from dichloromethane to a methanol (5%)/dichloromethane mixture. The compound obtained is then treated in accordance with the procedure of Step C of Example 166 using the compound of Preparation 3' and purified by chromatography over silica gel according to a gradient from dichloromethane to a methanol (5%)/dichloromethane mixture to provide an oil.

LC/MS ($C_{42}H_{44}N_4O_6$) 701.4 [M+H]$^+$; RT 2.42 (Method A)

Step F: 1-[(2S)-2-[(Benzyloxy)methyl]-7-[(3S)-3-[(4-methylpiperazin-1-yl)methyl]-1,2,3,4-tetrahydroisoquinoline-2-carbonyl]-2,3-dihydro-1,4-benzodioxin-6-yl]-1H-indole-3-carboxylic Acid The compound obtained in Step E (301 mg, 0.43 mmol) in THF (1.5 mL) and methanol (1.5 mL) is stirred with 2M NaOH (3 mL, 6 mmol) and then heated at 50° C. overnight. The reaction mixture is concentrated, taken up in water and acidified with 2M HCl to pH=4, and the product is extracted with ethyl acetate. The organic phases are dried over magnesium sulphate, filtered and concentrated to provide a solid.
LC/MS ($C_{41}H_{42}N_4O_6$) 697.3 [M+H]$^+$; RT 2.3 (Method A)

Step G: 1-[(2S)-2-[(Benzyloxy)methyl]-7-[(3S)-3-[(4-methylpiperazin-1-yl)methyl]-1,2,3,4-tetrahydroisoquinoline-2-carbonyl]-2,3-dihydro-1,4-benzodioxin-6-yl]-N-{4-[(tert-butyldimethylsilyl)oxy]phenyl}-N-phenyl-1H-indole-3-carboxamide The compound obtained in Step F (207 mg, 0.3 mmol) in dichloromethane (5 mL) is cooled to 0° C., under nitrogen. Oxalyl chloride (2M, 0.45 mL, 0.9 mmol) and 1 drop of N,N-dimethylformamide are added thereto. After 3 hours, the reaction mixture is concentrated and then co-evaporated twice more with dichloromethane. The residue is re-suspended in dichloromethane (5 mL) and stirred under nitrogen. A solution of 4-[(tert-butyldimethylsilyl)oxy]-N-phenylaniline (135 mg, 0.45 mmol) and pyridine (0.036 mL, 0.45 mmol) in a minimum volume of dichloromethane is added thereto, and the reaction mixture is stirred overnight. The reaction, which is incomplete, is inactivated with 2M NaOH and the organic phase is separated off by means of a phase separator and then concentrated, applied to a PE-AX column and then eluted with dichloromethane followed by a formic acid (5%)/dichloromethane mixture. The material obtained is subjected to azeotropic distillation with toluene and then used in the following step without being purified further.
LC/MS ($C_{59}H_{65}N_5O_6Si$) 968.5 [M+H]$^+$; RT 2.81 (Method A)

Step H: 1-[(2S)-2-[(Benzyloxy)methyl]-7-[(3S)-3-[(4-methylpiperazin-1-yl)methyl]-1,2,3,4-tetrahydroisoquinoline-2-carbonyl]-2,3-dihydro-1,4-benzodioxin-6-yl]-N-(4-hydroxyphenyl)-N-phenyl-1H-indole-3-carboxamide To the compound obtained in Step G (103 mg, 0.11 mmol) in THF (3 mL) there are added ethylenediamine (21.4 μL, 0.32 mmol) and TBAF (1M in tetrahydrofuran, 0.32 mL, 0.32 mmol), and the reaction mixture is heated in a microwave apparatus at 120° C. for 20 minutes. The reaction mixture is concentrated and distributed according to its solubility between ethyl acetate and a saturated sodium bicarbonate solution, and then the organic phases are dried over magnesium sulphate, filtered and concentrated. The crude product is purified by preparative HPLC chromatography.
LC/MS ($C_{53}H_{51}N_5O_6$) 854.4 [M+H]$^+$; RT 1.35 (Method B)

Example 189. 1-{3-Chloro-4-hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-phenyl-1H-indole-3-carboxamide The procedure is the same as in the process of Step A of Example 131, replacing the compound of Preparation 1' with the compound of Preparation 3' and replacing the compound of Preparation 3d with the compound of Preparation 3n. The deprotection is carried out in accordance with the procedure of Step B of Example 155.
LC/MS ($C_{44}H_{42}N_5O_5Cl$) 756.3 [M+H]$^+$; RT 2.14 (Method A)
High-resolution mass spectroscopy (ESI+):
Empirical formula: $C_{44}H_{42}N_5O_5Cl$
[M+H]$^+$ calculated: 756.2947
[M+H]$^+$ measured: 756.2948

Example 190. N-(4-Fluorophenyl)-1-{4-hydroxy-5-methoxy-2-[(3S)-3-[(4-methylpiperazin-1-yl)methyl]-1,2,3,4-tetrahydroisoquinoline-2-carbonyl]phenyl}-N-phenyl-1H-indole-3-carboxamide Dihydrochloride The procedure is the same as in the process of Example 164, replacing the compound obtained in Preparation 3h with the compound obtained in Preparation 3u.
LC/MS ($C_{44}H_{42}N_5O_4F$) 724 [M+H]$^+$; RT 2.26 (Method A)
High-resolution mass spectroscopy (ESI+):
Empirical formula: $C_{44}H_{42}N_5O_4F$
[M+H]$^+$ calculated: 724.3294
[M+H]$^+$ measured: 724.3301

Example 191. N,N-Dibutyl-1-{4-hydroxy-5-methoxy-2-[(3S)-3-[(4-methylpiperazin-1-yl)methyl]-1,2,3,4-tetrahydroisoquinoline-2-carbonyl]phenyl}-1H-indole-3-carboxamide Dihydrochloride The procedure is the same as in the process of Example 187, replacing the N-cyclohexylaniline used in Step E with dibutylamine.
LC/MS ($C_{40}H_{51}N_5O_4$) 666 [M+H]$^+$; RT 2.31 (Method A)
High-resolution mass spectroscopy (ESI+):
Empirical formula: $C_{40}H_{51}N_5O_4$
[M+H]$^+$ calculated: 666.4014
[M+H]$^+$ measured: 666.3987

Example 192. N,N-Dibutyl-1-{2-[(3S)-3-[(4-methylpiperazin-1-yl)methyl]-1,2,3,4-tetrahydroisoquinoline-2-carbonyl]-4-nitrophenyl}-1H-indole-3-carboxamide The compound of Preparation 3' (173 mg, 0.7 mmol), DIPEA (0.22 ml, 1.28 mmol) and HBTU (291 mg, 0.77 mmol) are added to the compound of Preparation 3s (280 mg, 0.64 mmol) in N,N-dimethylformamide and the reaction mixture is stirred at ambient temperature for 16 hours. The reaction mixture is concentrated in vacuo, diluted with a saturated aqueous NaHCO$_3$ solution and extracted with ethyl acetate. The organic extracts are washed in succession with a saturated aqueous NaHCO$_3$ solution and with brine, dried over magnesium sulphate and concentrated in vacuo. The crude material is applied in the dry state to a 20 g silica column and eluted with isohexane, then with ethyl acetate, then with a 19:1 mixture and then a 9:1 mixture of ethyl acetate/methanol to provide the product.
LC/MS ($C_{39}H_{48}N_6O_4$) 665 [M+H]$^+$; RT 2.41 (Method A)
High-resolution mass spectroscopy (ESI+):
Empirical formula: $C_{39}H_{48}N_6O_4$
[M+H]$^+$ calculated: 665.3810
[M+H]$^+$ measured: 665.3817

Example 193. 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-methylphenyl)-N-phenyl-1H-indole-3-carboxamide The procedure is the same as in the process of Step A of Example 131, replacing the compound of Preparation 1' with the compound of Preparation 3' and replacing the compound of Preparation 3d with the compound of Preparation 3v. The deprotection is carried out in accordance with the procedure of Step B of Example 155.
LC/MS ($C_{45}H_{45}N_5O_4$) 720 [M+H]$^+$; RT 2.28 (Method A)
High-resolution mass spectroscopy (ESI+):
Empirical formula: $C_{45}H_{45}N_5O_4$
[M+H]$^+$ calculated: 720.3544
[M+H]$^+$ measured: 720.3520

Example 194. N-Butyl-1-{4-hydroxy-5-methoxy-2-[(3S)-3-[(4-methylpiperazin-1-yl)-methyl]-1,2,3,4-tetrahydroisoquinoline-2-carbonyl]phenyl}-N-phenyl-1H-indole-3-carboxamide Dihydrochloride The procedure is the same as in the process of Example 187, replacing the N-cyclohexylaniline used in Step E with N-butylaniline.
LC/MS ($C_{42}H_{47}N_5O_4$.2HCl) 686.4 [M+H]$^+$; RT 2.28 (Method A)
High-resolution mass spectroscopy (ESI+):
Empirical formula: $C_{42}H_{47}N_5O_4$
[M+H]$^+$ calculated: 686.3701
[M+H]$^+$ measured: 686.3672

Example 195. 5-Fluoro-N-(4-hydroxyphenyl)-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide The procedure is the same as in the process of Step A of Example 131, replacing the compound of Preparation 1' with the compound of Preparation 3' and replacing the compound of Preparation 3d with the compound of Preparation 3o. The deprotection is carried out in accordance with the procedure of Step B of Example 155.
LC/MS ($C_{44}H_{40}N_5O_5F$) 738 [M+H]$^+$; RT 2.22 (Method A)
High-resolution mass spectroscopy (ESI+):
Empirical formula: $C_{44}H_{40}N_5O_5F$
[M+H]$^+$ calculated: 738.3086
[M+H]$^+$ measured: 738.3066

Example 196. 1-{4-Amino-2-[(3S)-3-[(4-methylpiperazin-1-yl)methyl]-1,2,3,4-tetrahydroisoquinoline-2-carbonyl]phenyl}-N,N-dibutyl-1H-indole-3-carboxamide 10% palladium on carbon is added to a solution of the compound obtained in Example 192 (294 mg, 0.44 mmol) in tetrahydrofuran (15 ml), degassed with nitrogen, and then the whole is stirred by oscillation under a hydrogen atmosphere at ambient temperature for 20 hours, after which the reaction mixture is treated with a further quantity of 10% palladium on carbon and is heated again to 45° C. over a period of 4 hours under a hydrogen atmosphere. The reaction mixture is cooled to ambient temperature, filtered through Celite, which is then washed with tetrahydrofuran, and the combined organic phases are concentrated in vacuo. The crude material is applied in the dry state to a 20 g silica column and eluted with dichloromethane, then with a 19:1, 15:1 and then 9:1 mixture of dichloromethane/methanol, then with a 19:1 and then 15:1 mixture of ethyl acetate:7M ammonia in methanol to provide the product.
LC/MS ($C_{39}H_{50}N_6O_2$) 635 [M+H]$^+$; RT 2.31 (Method A)
High-resolution mass spectroscopy (ESI+):
Empirical formula: $C_{39}H_{50}N_6O_2$
[M+H]$^+$ calculated: 635.4068
[M+H]$^+$ measured: 635.4056

Example 197. 6-Fluoro-N-(4-hydroxyphenyl)-1-{6-[(3S)-3-[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide The procedure is in accordance with Step A of Preparation 2a, using methyl 6-fluoro-1H-indole-3-carboxylate, and then in accordance with the procedure of Step B, the reaction mixture being heated at 50° C., followed by the procedure of Step C. The compound obtained is then treated in accordance with the procedure of Preparation 3a using 6-bromo-2H-1,3-benzodioxole-5-carboxylic acid and heated in a microwave apparatus at 130° C. for 2 hours, before being purified by chromatography over silica gel according to a gradient from dichloromethane to a methanol (10%)/dichloromethane mixture. The compound is then treated in accordance with the procedure of Step C of Example 166 using the compound of Preparation 3', and purified by chromatography over silica gel in dichloromethane, to a methanol (5%)/dichloromethane mixture, and finally deprotected in accordance with the procedure of Step D of Example 166 and purified by chromatography over silica gel in dichloromethane, to a methanol (8%)/dichloromethane mixture.
LC/MS ($C_{44}H_{40}N_5O_5F$) 738 [M+H]$^+$; RT 2.1 (Method A)
High-resolution mass spectroscopy (ESI+):
Empirical formula: $C_{44}H_{40}N_5O_5F$
[M+H]$^+$ calculated: 738.3086
[M+H]$^+$ measured: 738.3077

Example 198. 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(1H-indol-5-yl)-N-phenyl-1H-indole-3-carboxamide Step A: tert-Butyl 5-{N-phenyl-1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-amido}-1H-indole-1-carboxylate The procedure is the same as in the process of Example 204, replacing the 4-[(tert-butyldimethylsilyl)oxy]-N-cyclohexylaniline used in Step B with the tert-butyl 5-(phenylamino)-1H-indole-1-carboxylate of Preparation 3".
LC/MS ($C_{58}H_{58}N_6O_6$) 935 [M+H]$^+$; RT 2.64 (Method. A)

Step B: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-(1H-indol-5-yl)-N-phenyl-1H-indole-3-carboxamide Trifluoroacetic acid (2 ml) is added to a solution of the compound obtained in Step A (2.18 g, 2.33 mmol) in dichloromethane (20 ml). The reaction mixture is stirred at ambient temperature for 5 hours and is then diluted with dichloromethane and water before being rendered alkaline with 2M aqueous NaOH. The organic phase is separated off and washed with brine, dried over magnesium sulphate, filtered and evaporated. The crude material is purified by chromatography over silica gel according to a gradient from dichloromethane to a methanol (5%)/dichloromethane mixture to provide a foam.

LC/MS ($C_{53}H_{50}N_6O_4$) 835 [M+H]$^+$; RT 2.41 (Method A)

Step C: 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(1H-indol-5-yl)-N-phenyl-1H-indole-3-carboxamide Ammonium formate (775 mg, 12.3 mmol) and 10% palladium on carbon (catalytic) are added to a solution of the compound obtained in Step B (1.03 g, 1.23 mmol) in methanol (15 ml) and the reaction mixture is heated to 80° C. under nitrogen over a period of 6 hours, following which a further portion of ammonium formate (775 mg, 12.3 mmol) and of 10% palladium on carbon (catalytic) is added and heating of the reaction mixture is continued for 16 hours. The reaction mixture is allowed to cool to ambient temperature and is then filtered through Celite, washed with methanol and the solvent is removed by evaporation. The crude material is dissolved in dichloromethane and washed with water, and then the organic phases are dried over magnesium sulphate, filtered and evaporated. The crude product is purified by chromatography over silica gel according to a gradient from dichloromethane to a methanol (10%)/ammonia/dichloromethane mixture.

LC/MS ($C_{46}H_{44}N_6O_4$) 745.4 [M+H]$^+$; RT 2.19
High-resolution mass spectroscopy (ESI+):
Empirical formula: $C_{46}H_{44}N_6O_4$
[M+H]$^+$ calculated: 745.3497
[M+H]$^+$ measured: 745.3465

Example 199. N,N-Dibutyl-1-{2-[(3S)-3-[(4-methylpiperazin-1-yl)methyl]-1,2,3,4-tetrahydroisoquinoline-2-carbonyl]-4-[2-(phenylsulphanyl)acetamido]phenyl}-1H-indole-3-carboxamide DIPEA (45 al, 0.26 mmol) is added to a solution of the compound obtained in Example 196 (82 mg, 0.13 mmol) in dichloromethane (4 ml), cooled to 0° C. under nitrogen, and then 2-(phenylsulphanyl)acetyl chloride (21 al, 0.14 mmol) is added slowly. Once the addition is complete, the reaction mixture is stirred at 0° C. for 15 minutes and is then heated to ambient temperature again and stirred for 3 hours. The reaction mixture is treated with a further quantity of DIPEA (45 al) and of acid chloride (21 al) and the whole is stirred for a further 16 hours. The reaction mixture is diluted with a 5% aqueous ammonium hydroxide solution and extracted with ethyl acetate. The organic extracts are then washed in succession with a 5% aqueous ammonium hydroxide solution and with brine before being dried over magnesium sulphate and concentrated in vacuo. Purification takes place by preparative HPLC (pH 9).

LC/MS ($C_{47}H_{56}N_6O_3S$) 785 [M+H]$^+$; RT 2.5 (Method A)
High-resolution mass spectroscopy (ESI+):
Empirical formula: $C_{47}H_{56}N_6O_3S$
[M+H]$^+$ calculated: 785.4207
[M+H]$^+$ measured: 785.4183

Example 200. N,N-Dibutyl-1-{2-[(3S)-3-[(4-methylpiperazin-1-yl)methyl]-1,2,3,4-tetrahydroisoquinoline-2-carbonyl]-4-(2-phenoxyacetamido)phenyl}-1H-indole-3-carboxamide The procedure is the same as in the process of Example 199, replacing 2-(phenylsulphanyl)acetyl chloride with 2-phenoxyacetyl chloride.

LC/MS ($C_{47}H_{56}N_6O_4$) 769 [M+H]$^+$; RT 2.49 (Method A)
High-resolution mass spectroscopy (ESI+):
Empirical formula: $C_{47}H_{56}N_6O_4$
[M+H]$^+$ calculated: 769.4436
[M+H]$^+$ measured: 769.4446

Example 201. N-(4-Fluorophenyl)-1-{4-hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-1H-indole-3-carboxamide Dihydrochloride The procedure is the same as in the process of Example 204, replacing the 4-[(tert-butyldimethylsilyl)oxy]-N-cyclohexylaniline used in Step B with 4-[(tert-butyldimethylsilyl)oxy]-N-(4-fluorophenyl)aniline.

LC/MS ($C_{44}H_{42}N_5O_5F$) 740 [M+H]$^+$; RT 2.15 (Method A)
High-resolution mass spectroscopy (ESI+):
Empirical formula: $C_{44}H_{42}N_5O_5F$
[M+H]$^+$ calculated: 740.3243
[M+H]$^+$ measured: 740.3213

Example 202. 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-(1H-indol-5-yl)-1H-indole-3-carboxamide

Step A: tert-Butyl 5-(N-{4-[(tert-butyldimethylsilyl)oxy]phenyl}-1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-amido)-1H-indole-1-carboxylate The procedure is the same as in the process of Example 204, replacing the 4-[(tert-butyldimethylsilyl)oxy]-N-cyclohexylaniline used in Step B with the tert-butyl 5-({4-[(tert-butyldimethylsilyl)oxy]phenyl}amino)-1H-indole-1-carboxylate of Preparation 5".

LC/MS ($C_{64}H_{72}N_6O_7Si$) 533 [M+2H]$^{2+}$; RT 2.85 (Method A)

Step B: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-(4-hydroxyphenyl)-N-(1H-indol-5-yl)-1H-indole-3-carboxamide Potassium hydroxide (1M, 2.1 ml, 2.1 mmol) is added to a solution of the material obtained in Step A (1.49 g, 1.4 mmol) in methanol (20 ml) and the reaction mixture is stirred at ambient temperature for ca 16 hours. The reaction mixture is concentrated and the residue is taken up in dichloromethane and washed with dilute HCl. The organic phases are dried over magnesium sulphate, filtered and evaporated. The residue is again dissolved in dichloromethane (20 ml), and trifluoroacetic acid (3 ml) is added thereto. The reaction mixture is stirred at ambient temperature for ca 72 hours. The residue is taken up in dichloromethane and neutralised with 2M aqueous NaOH. The organic phases are separated off and washed with water, dried over magnesium sulphate, filtered and evaporated. The crude product is purified by chromatography over silica gel according to a gradient from dichloromethane to a methanol (10%)/dichloromethane mixture to provide the product in the form of a solid.
LC/MS ($C_{53}H_{50}N_6O_5$) 851 [M+H]$^+$; RT 2.31 (Method A)

Step C: 1-{4-Hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-N-(1H-indol-5-yl)-1H-indole-3-carboxamide The procedure is the same as in the process of Step D of Example 204, and purification is carried out by preparative HPLC.
LC/MS ($C_{46}H_{44}N_6O_5$) 761.2 [M+H]$^+$; RT 1.12 (Method B)
High-resolution mass spectroscopy (ESI+):
Empirical formula: $C_{46}H_{44}N_6O_5$
[M+H]$^+$ calculated: 761.3446
[M+H]$^+$ measured: 761.3429

Example 203. N-Butyl-1-{4-hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-1H-indole-3-carboxamide Dihydrochloride The procedure is the same as in the process of Example 204, replacing the 4-[(tert-butyldimethylsilyl)oxy]-N-cyclohexylaniline of Preparation 4a with the 4-(benzyloxy)-N-butylaniline of Preparation 4b.
LC/MS ($C_{42}H_{47}N_5O_5$) 702.4 [M+H]$^+$; RT 2.19 (Method A)
High-resolution mass spectroscopy (ESI+):
Empirical formula: $C_{42}H_{47}N_5O_5$
[M+H]$^+$ calculated: 702.3650
[M+H]$^+$ measured: 702.3623

Example 204. N-Cyclohexyl-1-{4-hydroxy-5-methoxy-2-[(3S)-3-[(4-methylpiperazin-1-yl)methyl]-1,2,3,4-tetrahydroisoquinoline-2-carbonyl]phenyl}-N-(4-hydroxyphenyl)-1H-indole-3-carboxamide Dihydrochloride Step A: Lithium 1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-carboxylate LiOH (1M, 7.28 ml, 7.28 mmol) is added to a solution of the ester obtained in Step B of Example 187 (4 g, 6.07 mmol) in dioxane (30 ml) and the reaction mixture is heated at reflux for ca 16 hours. A further quantity of LiOH (1M, 9.1 ml) is added to the reaction mixture, which is then heated at reflux for ca 16 hours. The reaction mixture is allowed to cool to ambient temperature, the solvent is removed in vacuo, and the residue is subjected to azeotropic distillation with toluene to provide a solid, which is used for the following step without being purified further.
LC/MS ($C_{39}H_{39}N_4O_5$.Li) 645 [M+H]$^+$; RT 2.23 (Method A) [mass of the acid-type parent molecule]

Step B: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-{4-[(tert-butyldimethylsilyl)oxy]phenyl}-N-cyclohexyl-1H-indole-3-carboxamide Thionyl chloride (0.22 ml, 3.08 mmol) is added to a solution of the lithium salt obtained in Step A (1 g, 1.54 mmol) in anhydrous dichloromethane (16 ml) cooled to 0° C. under nitrogen. The reaction mixture is allowed to warm to ambient temperature again and is stirred for 2 hours before further thionyl chloride (0.11 ml, 1.54 mmol) is added, and stirring is then carried out for ca 16 hours. The solvent is removed and the residue is suspended in dichloromethane again and evaporated once more. Co-evaporation with dichloromethane is repeated twice more before azeotropic distillation with toluene to obtain a solid, which is dissolved in anhydrous dichloromethane (10 ml). A solution of the aniline obtained in Preparation 4a (640 mg, 2.07 mmol) and of pyridine (0.2 ml, 2.31 mmol) in dichloromethane (6 ml) is added, and the solution is stirred at ambient temperature under nitrogen for 4 hours. The reaction mixture is diluted with dichloromethane and washed in succession with water, with a saturated sodium bicarbonate solution and with brine. The organic phases are dried over magnesium sulphate, filtered and evaporated, and the crude material is purified by chromatography over silica gel according to a gradient from dichloromethane to a methanol (5%)/dichloromethane mixture to provide the product in the form of a foam.
LC/MS ($C_{57}H_{69}N_5O_5Si$) 932 [M+H]$^+$; RT 2.79 (Method A)

Step C: 1-[4-(Benzyloxy)-5-methoxy-2-[(3S)-3-[(4-methylpiperazin-1-yl)methyl]-1,2,3,4-tetrahydroisoquinoline-2-carbonyl]phenyl]-N-cyclohexyl-N-(4-hydroxyphenyl)-1H-indole-3-carboxamide Aqueous potassium hydroxide (1M, 1.22 ml, 1.22 mmol) is added to a solution of the material obtained in Step B (758 mg, 0.81 mmol) in methanol (10 ml) and the reaction mixture is stirred at ambient temperature for 3 hours. The reaction mixture is concentrated and the aqueous phase is acidified (slightly) with 2M aqueous HCl, and the product is extracted with ethyl acetate, dried over magnesium sulphate, filtered and evaporated. The crude product is used for the following step without being purified further.
LC/MS ($C_{51}H_{55}N_5O_5$) 818 [M+H]$^+$; RT 2.39 (Method A)

Step D: N-Cyclohexyl-1-{4-hydroxy-5-methoxy-2-[(3S)-3-[(4-methylpiperazin-1-yl)-methyl]-1,2,3,4-tetrahydroisoquinoline-2-carbonyl]phenyl}-N-(4-hydroxyphenyl)-1H-indole-3-carboxamide Ammonium formate (510 mg, 8.1 mmol) and 10% palladium on carbon (catalytic) are added to a solution of the compound obtained in Step C (665 mg, 0.81 mmol) in methanol (15 ml) and the reaction mixture is heated at reflux under nitrogen for 2 days, during which time 2 further portions of ammonium formate (510 mg, 8.1 mmol) and of 10% palladium on carbon (catalytic) are added. The reaction mixture is allowed to cool to ambient temperature. It is then filtered through Celite, washed with methanol, and the solvent is removed by evaporation. The crude material is purified by preparative HPLC (pH 4), and then the purified material is dissolved in dichloromethane and washed with water and with a saturated sodium bicarbonate solution, before being dried over magnesium sulphate.

Step E: N-Cyclohexyl-1-{4-hydroxy-5-methoxy-2-[(3S)-3-[(4-methylpiperazin-1-yl)-methyl]-1,2,3,4-tetrahydroisoquinoline-2-carbonyl]phenyl}-N-(4-hydroxyphenyl)-1H-indole-3-carboxamide Dihydrochloride HCl in ether (2M, 1.13 mL, 2.25 mmol) is added to a solution of the compound obtained in Step D (330 mg, 0.45 mmol) in isopropanol (5 mL). The solution so obtained is diluted in ether (5 mL) and stirred at ambient temperature for 20 minutes. The solid is then filtered off, washed with ether and dried in vacuo.

LC/MS ($C_{44}H_{49}N_5O_5$) 728 [M+H]$^+$; RT 2.21 (Method A)
High-resolution mass spectroscopy (ESI+):
Empirical formula: $C_{44}H_{49}N_5O_5$
[M+H]$^+$ calculated: 728.3806
[M+H]$^+$ measured: 728.3786

Example 205. N-(4-Hydroxyphenyl)-1-{5-methoxy-2-[(3S)-3-[(4-methylpiperazin-1-yl)methyl]-1,2,3,4-tetrahydroisoquinoline-2-carbonyl]phenyl}-N-(1-methyl-1H-indol-5-yl)-1H-indole-3-carboxamide Step A: 4-Methoxy-2-[3-(methoxycarbonyl)-1H-indol-1-yl]benzoic Acid Methyl indole-3-carboxylate (2 g, 11.42 mmol), potassium carbonate (2.32 g, 16.8 mmol) and 2-iodo-4-methoxybenzoic acid (3.17 g, 11.42 mmol) are combined under nitrogen and suspended in N,N-dimethylformamide (30 ml), degassed with nitrogen, and then copper iodide (217 mg, 1.14 mmol) is added. The reaction mixture is heated to 80° C. under nitrogen over a period of ca 16 hours. The reaction mixture is allowed to cool to ambient temperature. It is then diluted with water and acidified with 2M aqueous HCl. The organic phases are extracted with dichloromethane and washed with water, dried over magnesium sulphate, filtered and evaporated. The crude material is purified by chromatography over silica gel according to a gradient from isohexane to a 1:1 isohexane/ethyl acetate mixture to provide the product in the form of an oil.

LC/MS ($C_{18}H_{15}NO_5$) 326 [M+H]$^+$; RT 2.36 (Method A)

Step B: Methyl 1-{5-methoxy-2-[(3S)-3-[(4-methylpiperazin-1-yl)methyl]-1,2,3,4-tetrahydroisoquinoline-2-carbonyl]phenyl}-1H-indole-3-carboxylate DIPEA (8.25 ml, 47.35 mmol) and HBTU (2.6 g, 7 mmol) and then the compound of Preparation 3' (3 g, 8.52 mmol) are added to a solution of the acid obtained in Step A (3.08 g, 9.47 mmol) in N,N-dimethylformamide (30 ml) and the reaction mixture is stirred at ambient temperature for ca 16 hours. The reaction mixture is diluted with dichloromethane and washed in succession with water and with a saturated sodium bicarbonate solution. The organic phases are dried over magnesium sulphate, filtered and evaporated, and the crude material is purified by chromatography over silica gel according to a gradient from dichloromethane to a methanol (10%)/dichloromethane mixture to provide the product in the form of an oil.

LC/MS ($C_{33}H_{36}N_4O_4$) 553 [M+H]$^+$; RT 2.14 (Method A)

Step C: Lithium 1-{5-methoxy-2-[(3S)-3-[(4-methylpiperazin-1-yl)methyl]-1,2,3,4-tetrahydroisoquinoline-2-carbonyl]phenyl}-1H-indole-3-carboxylate The procedure is the same as in the process of Step A of Example 204, replacing methyl 1-[4-(benzyloxy)-5-methoxy-2-[(3S)-3-[(4-methylpiperazin-1-yl)methyl]-1,2,3,4-tetrahydroisoquinoline-2-carbonyl]phenyl]-1H-indole-3-carboxylate with the compound of Step B.

LC/MS ($C_{32}H_{33}N_4O_4$.Li) 539 [M+H]$^+$; RT 2.04 (Method A) [mass for the acid-type parent molecule]

Step D: 1-{5-Methoxy-2-[(3S)-3-[(4-methylpiperazin-1-yl)methyl]-1,2,3,4-tetrahydroisoquinoline-2-carbonyl]phenyl}-1H-indole-3-carbonyl Chloride Thionyl chloride (0.14 ml, 1.98 mmol) is added to a solution of the lithium salt obtained in Step C (540 mg, 0.99 mmol) in anhydrous dichloromethane (10 ml) cooled to 0° C. under nitrogen. The reaction mixture is allowed to warm to ambient temperature again and is stirred for 5 hours before a further quantity of thionyl chloride (0.035 ml, 0.5 mmol) is added, and then stirring is carried out for ca 16 hours. The solvent is removed and the residue is suspended in dichloromethane again and evaporated once more. Co-evaporation with dichloromethane is repeated twice more before azeotropic distillation with toluene, to obtain a solid, which is used for the following step without being purified further.

LC/MS ($C_{32}H_{33}N_4O_3Cl$) 553 [M+H]$^+$; RT 2.13 (Method A) [methyl ester obtained by inactivation of the methanol is observed]

Step E: N-{4-[(tert-Butyldimethylsilyl)oxy]phenyl}-1-{5-methoxy-2-[(3S)-3-[(4-methylpiperazin-1-yl)methyl]-1,2,3,4-tetrahydroisoquinoline-2-carbonyl]phenyl}-N-(1-methyl-1H-indol-5-yl)-1H-indole-3-carboxamide A solution of the aniline obtained in Preparation 4c (348 mg, 0.99 mmol) and of pyridine (0.13 ml, 1.5 mmol) in dichloromethane (8 ml) is added to a solution of the acid chloride obtained in Step D (550 mg, 0.99 mmol) in dichloromethane (10 ml) under nitrogen, and the reaction mixture is stirred at ambient temperature for ca 72 hours. The reaction mixture is diluted with dichloromethane and washed in succession with water, with a saturated sodium bicarbonate solution and with brine. The organic phases are dried over magnesium sulphate, filtered and evaporated, and the crude material is purified by chromatography over silica gel according to a gradient from dichloromethane to a methanol (10%)/dichloromethane mixture to provide the product in the form of a solid.

LC/MS ($C_{53}H_{60}N_6O_4Si$) 873 [M+H]$^+$; RT 2.67 (Method A)

Step F: N-(4-Hydroxyphenyl)-1-{5-methoxy-2-[(3S)-3-[(4-methylpiperazin-1-yl)methyl]-1,2,3,4-tetrahydroisoquinoline-2-carbonyl]phenyl}-N-(1-methyl-1H-indol-5-yl)-1H-indole-3-carboxamide Potassium hydroxide (1M, 0.78 ml, 0.78 mmol) is added to a solution of the material obtained in Step E (451 mg, 0.52 mmol) in methanol (10 ml) and the reaction mixture is stirred at ambient temperature overnight. The solvent is removed and the residue is dissolved in dichloromethane and washed with water (plus several drops of 2M HCl), dried over magnesium sulphate, filtered and evaporated. The crude product is purified by chromatography over silica gel according to a gradient from dichloromethane to a methanol (10%)/dichloromethane mixture and is then triturated with ether, filtered and dried in vacuo to provide a powder.

LC/MS ($C_{47}H_{46}N_6O_4$) 759 [M+H]$^+$; RT 2.2 (Method A)
High-resolution mass spectroscopy (ESI+):
Empirical formula: $C_{47}H_{46}N_6O_4$
[M+H]$^+$ calculated: 759.3653
[M+H]$^+$ measured: 759.3628

Example 206. N-(4-Hydroxyphenyl)-5-methyl-N-(1-methyl-1H-pyrrolo[2,3-b]pyridin-5-yl)-1-(6-{[(3S)-3-(morpholin-4-ylmethyl)-3,4-dihydroisoquinolin-2(1H)-yl]-carbonyl}-1,3-benzodioxol-5-yl)-1H-pyrrole-3-carboxamide Hydrochloride Elemental microanalysis: % measured (theoretical)
% C=66.28 (66.27);% H=5.08 (5.43);% N=10.70 (11.04); % Cl—5.41 (4.66)
High-resolution mass spectroscopy (ESI+):
Empirical formula: $C_{42}H_{40}N_6O_6$
[M+H]$^+$ calculated: 725.3082
[M+H]$^+$ measured: 725.3089

Example 207. N-(4-Hydroxyphenyl)-N-(1-methyl-1H-pyrrolo[2,3-b]pyridin-5-yl)-1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indole-3-carboxamide Hydrochloride The title compound is synthesised in accordance with the process of Example 12 using in Step A the acid obtained in Preparation 19, the (3S)-3-(4-morpholinylmethyl)-1,2,3,4-tetrahydroisoquinoline obtained in Preparation 2', and the N-(4-{[tert-butyl(dimethyl)silyl]oxy}phenyl)-1-methyl-1H-pyrrolo[2,3-b]pyridin-5-amine obtained in Preparation 24".
Elemental microanalysis: % measured (theoretical)
% C=67.26 (67.45);% H=5.73 (5.66);% N=10.22 (10.49); % Cl—4.70 (4.42)
High-resolution mass spectroscopy (ESI+/FIA):
Empirical formula: $C_{45}H_{44}N_6O_6$
[M+H]$^+$ calculated: 765.3395
[M+H]$^+$ measured: 765.3398

Example 208. Disodium 4-[(1-methyl-1H-pyrrolo[2,3-b]pyridin-5-yl){[1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indol-3-yl]carbonyl}amino]phenyl Phosphate Step A: Dibenzyl 4-[(1-methyl-1H-pyrrolo[2,3-b]pyridin-5-yl){[1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indol-3-yl]carbonyl}amino]phenyl Phosphate To a suspension of 80 mg of sodium hydride (2 mmol) in 8 mL of anhydrous THF there are added, in portions and at 0° C., 719 mg (0.9 mmol) of the compound of Example 207. After stirring for 30 minutes at 0° C. and for 30 minutes at ambient temperature, tetrabenzyl pyrophosphate (580 mg; 1 mmol) is added at 0° C. and the reaction mixture is stirred overnight at ambient temperature. After evaporation of the solvent, the crude reaction mixture is diluted with dichloromethane (40 mL), washed with a saturated NaHCO$_3$ solution and then with a saturated NaCl solution. The organic phase is then dried over MgSO$_4$, filtered, concentrated to dryness and purified by chromatography over silica gel (CH$_2$Cl$_2$/MeOH gradient). The title product is then obtained in the form of a solid.

Step B: Disodium 4-[(1-methyl-1H-pyrrolo[2,3-b]pyridin-5-yl){[1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indol-3-yl]carbonyl}amino]phenyl Phosphate To a solution of the product obtained in Step A (395 mg; 0.39 mmol) in methanol (6 mL) there are added 40 mg of 10% Pd/C, and then the reaction mixture is placed under a hydrogen atmosphere (1 bar) for 2 hours. After filtering off the catalyst and concentrating to dryness, the crude reaction mixture is dissolved in methanol (5 mL) and treated with 0.8 mL of 1N sodium hydroxide solution. The solvents are then evaporated off and the crude reaction mixture is purified by chromatography over OASIS® phase (acetonitrile/H$_2$O gradient) to obtain a solid.

Example 209. 1-(5-Chloro-2-{[(3S)-3-(morpholin-4-ylmethyl)-3,4-dihydroisoquinolin-2(1H)-yl]carbonyl}phenyl)-N-(4-hydroxyphenyl)-4,5-dimethyl-N-(1-methyl-1H-pyrrolo[2,3-b]pyridin-5-yl)-1H-pyrrole-3-carboxamide Hydrochloride Step A: Methyl 1-(5-chloro-2-{[(3S)-3-(morpholin-4-ylmethyl)-3,4-dihydroisoquinolin-2(1H)-yl]carbonyl}phenyl)-4,5-dimethyl-1H-pyrrole-3-carboxylate The compound is obtained in accordance with the protocol of Step A of Example 8 using in Step A the acid obtained in Preparation 22 and the (3S)-3-(4-morpholinylmethyl)-1,2,3,4-tetrahydroisoquinoline obtained in Preparation 2'.
$^1$H NMR (400 MHz, dmso-d6) δ ppm: 9.85 (sl, OH), 7.77 (d, 1H), 7.72 (d, 1H), 7.63 (s, 1H), 7.45-6.81 (m, 4H), 6.88 (m, 1H), 5.27 (m, 1H), 4.51/4.28 (m, 2H), 4/3.69 (m, 4H), 3.61-3.01 (m, 6H), 3.55 (m, 3H), 2.57 (s, 2H), 1.79 (m, 6H)
IR (ATR) cm$^{-1}$: 1698 ν aromatic —C=O ester, 1639 ν —C=O amide Step B: Lithium 1-(5-chloro-2-{[(3S)-3-(morpholin-4-ylmethyl)-3,4-dihydroisoquinolin-2(1H)-yl]carbonyl}phenyl)-4,5-dimethyl-1H-pyrrole-3-carboxylate The compound is obtained in accordance with the protocol of Step B of Example 8 starting from the compound obtained in the preceding step.
$^1$H NMR (500 MHz, dmso-d6) δ ppm: 7.72-7.56 (m, 3H), 7.66 (m, 1H), 7.4-6.92 (m, 4H), 4.85/3.72 (m, 1H), 4.82/4.31/4.24/4.14 (m, 2H), 3.5 (m, 4H), 2.99/2.85/2.67/2.52 (m, 2H), 2.62-1.94 (m, 6H), 2.14/2.07/2.02/1.78/1.74 (m, 6H)
IR (ATR) cm$^{-1}$: 2575 ν —OH, 1696-1670 ν —C=O, 1626 ν —C=O, 1595 ν Ar, 1230-1180-1114 ν —C—O—C, 867-833-743 ν —CH—Ar Step C: N-(4-{[tert-Butyl(dimethyl)silyl]oxy}phenyl)-1-(5-chloro-2-{[(3S)-3-(morpholin-4-ylmethyl)-3,4-dihydroisoquinolin-2(1H)-yl]carbonyl}phenyl)-4,5-dimethyl-N-(1-methyl-1H-pyrrolo[2,3-b]pyridin-5-yl)-1H-pyrrole-3-carboxamide The compound is obtained in accordance with the protocol of Step C of Example 8, replacing the compound of Preparation 1" with the compound of Preparation 24".
LC/MS [M+H]$^+$=717.45+719.45 for 717.30+719.30 theoretical Step D: 1-(5-Chloro-2-{[(3S)-3-(morpholin-4-ylmethyl)-3,4-dihydroisoquinolin-2(1H)-yl]carbonyl}phenyl)-N-(4-hydroxyphenyl)-4,5-dimethyl-N-(1-methyl-1H-pyrrolo[2,3-b]pyridin-5-yl)-1H-pyrrole-3-carboxamide Hydrochloride The compound obtained in the preceding step (1.16 g, 1.38 mmol) is dissolved directly in 15 mL of THF. 1M TBAF in solution in THF (1.51 ml, 1.51 mmol) is added dropwise by means of a syringe. The reaction mixture is then stirred at ambient temperature for 12 hours. The progress of the reaction is monitored by LC-MS. The solution is diluted with dichloromethane, washed with a saturated NaHCO$_3$ solution and then with water. The organic phase is dried over magnesium sulphate, filtered and then evaporated to dryness. The compound is purified over a silica gel column using dichloromethane and ethanol as solvents to provide the free base.

450 mg of the product so obtained are dissolved in 5 mL of ethanol, and 4 mL of a 1M solution of hydrochloric acid in ether are added slowly; the corresponding hydrochloride precipitates. It is filtered off, washed with ether and lyophilised in an acetonitrile:water mixture. 470 mg of hydrochloride are obtained in the form of a white powder.

$^1$H NMR (500 MHz, dmso-d6) δ ppm: 11.46 (sl, NH), 9.5 (sl, OH), 8.14 (m, 1H), 7.99 (m, 1H), 7.63/7.51 (m, 1H), 7.63 (m, 1H), 7.51 (m, 1H), 7.33-6.99 (m, 6H), 6.8-6.6 (m, 2H), 6.7/6.62 (m, 2H), 6.41 (m, 1H), 5.23 (m, 1H), 4.82/4.11 (m, 2H), 4.03/3.88 (m, 4H), 3.8 (m, 3H), 3.73/3.4/3.13/3.01 (m, 4H), 3.28/3.15 (m, 2H), 2.78/2.65 (m, 2H), 1.93-1.56 (m, 6H)

IR (ATR) cm$^{-1}$: 2000 to 3500 ν —NH$^+$/OH, 1628 ν —C=O, 1260-1230-1186 ν —C—O—C, 830-736 ν —CH—Ar

High-resolution mass spectroscopy (ESI+/FIA):
Empirical formula: C$_{42}$H$_{41}$ClN$_6$O$_4$
[M+H]$^+$ calculated: 729.2951
[M+H]$^+$ measured: 759.2949
(isotope ratios consistent with one chlorine atom)

Example 210. 1-(5-Chloro-2-{[(3S)-3-(morpholin-4-ylmethyl)-3,4-dihydroisoquinolin-2(1H)-yl]carbonyl}phenyl)-N-(4-hydroxyphenyl)-4,5-dimethyl-N-(1-methyl-2,3-dihydro-1H-pyrrolo[2,3-b]pyridin-5-yl)-1H-pyrrole-3-carboxamide Hydrochloride The free base of the compound of Example 209 (490 mg, 0.671 mmol) is dissolved in 6.5 mL of acetic acid. Sodium cyanoborohydride (370 mg, 5.90 mmol) is added in three portions. The reaction mixture is stirred at ambient temperature for 70 hours. The progress of the reaction is monitored by LC-MS. The reaction mixture is evaporated and then co-evaporated with toluene. The compound so obtained is purified over a silica gel column using dichloromethane and ethanol as solvents. This compound is then dissolved in 5 mL of ethanol, and 4 mL of a 1M solution of hydrochloric acid in ether are added slowly; the hydrochloride precipitates. It is filtered off, washed with ether and lyophilised in an acetonitrile/water mixture. The hydrochloride is obtained in the form of a white powder.

$^1$H NMR (500 MHz, dmso-d6) δ ppm: 11.6 (sl, 1H), 8.16 (m, 1H), 7.67 (m, 1H), 7.55-7.01 (m, 11H), 6.91 (m, 1H), 6.65 (m, 1H), 5.21 (m, 1H), 4.82/4.14 (m, 2H), 4.14-3.81 (m, 4H), 3.85-2.94 (m, 4H), 3.27/3.15 (m, 2H), 3.11 (m, 3H), 3.09 (m, 2H), 2.62 (m, 2H), 2.03/1.78/1.63 (m, 6H)

IR (ATR) cm$^{-1}$: 2000 to 3500 ν NH$^+$/OH, 1628 ν —C=O, 1361 ν —C—O—C, 1264 ν —CH—Ar

High-resolution mass spectroscopy (ESI+/FIA):
Empirical formula: C$_{42}$H$_{43}$ClN$_6$O$_4$
[M+H]$^+$ calculated: 731.3107
[M+H]$^+$ measured: 731.3111

Example 211. 1-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxy-phenyl)-4,5-dimethyl-1H-pyrrole-3-carboxamide Hydrochloride Step A: N-(4-{[tert-Butyl(dimethyl)silyl]oxy}phenyl)-1-(5-chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-4,5-dimethyl-1H-pyrrole-3-carboxamide The compound is obtained in accordance with the protocols of Steps A-C of Example 209, replacing in Step C the compound of Preparation 24" with the compound of Preparation 26".

$^1$H NMR (500 MHz, dmso-d6) δ ppm: 7.67 (m, 1H), 7.62/7.6 (m, 1H), 7.44 (m, 1H), 7.39 (m, 1H), 7.25-6.95 (m, 4H), 6.9 (m, 2H), 6.78/6.63 (m, 1H), 6.74/6.68/6.61 (m, 2H), 5.03/4.79/3.56 (m, 1H), 4.88/4.32/4.22/4.03 (m, 2H), 3.64-3.41 (m, 4H), 3.59 (s, 3H), 2.97/2.82/2.7/2.63 (m, 2H), 2.56-1.92 (m, 6H), 2.1-1.68 (m, 9H), 0.88 (m, 9H), 0.1 (s, 6H)

IR (ATR) cm$^{-1}$: 2211 ν —CN, 1637, ν —C=O, 1253 ν —C—O—C—, 910 ν —Si—O—C—, 837 ν —Si—C—, 782-744 ν —CH—Ar

Step B: 1-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-4,5-dimethyl-1H-pyrrole-3-carboxamide Hydrochloride The compound of Step A (440 mg, 0.530 mmol) is dissolved in 10 mL of tetrahydrofuran, and tetrabutylammonium fluoride (580 µL, 1M in THF, 0.580 mmol) is added dropwise. The reaction mixture is stirred at ambient temperature for 1 hour. A saturated aqueous hydrogen carbonate solution is then added to the mixture, which is extracted 3 times with dichloromethane. The organic phase is dried over magnesium sulphate, filtered and then evaporated to dryness. The compound so obtained is purified over a silica gel column using dichloromethane and ethanol+0.1% ammonia as solvents. The desired compound is obtained in the form of a white powder. The latter is dissolved in 5 mL of ethanol, and 4 mL of a 1M solution of hydrochloric acid in ether are added slowly; the hydrochloride precipitates. It is filtered off, washed with ether and lyophilised in an acetonitrile/water mixture.

$^1$H NMR (500 MHz, dmso-d6) δ ppm: 11.3 (sl, 1H), 9.4 (s, 1H), 8.1 (sl, 1H), 7.65 (d, 1H), 7.4 (s, 1H), 7.3-6.7 (several m, 7H), 6.7 (m, 2H), 6.5-5.5 (sl, 1? H), 5.2 (m, 1H), 4.75/4.1 (m+m, 1+1H), 4/3.9 (m+m, 2+2H), 3.75/3.15 (m+m, 1+1H), 3.6 (s, 3H), 3.4/3 (m+m, 1+1H), 3.3/3.15 (m+m, 1+1H), 2.75-2.5 (m, 2H), 2.1-1.55 (several s, 9H)

IR (ATR) cm$^{-1}$: 3373 ν —OH, 2700-2200 ν —NH+, 2211 ν —CN, 1625 ν —C=O

High-resolution mass spectroscopy (ESI+/FIA):
Empirical formula: C$_{41}$H$_{41}$ClN$_6$O$_4$
[M+H]$^+$ calculated: 717.2951
[M+H]$^+$ measured: 717.2941

Pharmacological Study

Example A: Inhibition of Bcl-2 by the Fluorescence Polarisation Technique

Method A:

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of $2.50 \times 10^{-8}$ M, is mixed with a fluorescent peptide (Fluorescein-REIGAQLRRMADDLNAQY), at a final concentration of $1.50 \times 10^{-8}$ M in a buffer solution ($NaPO_4$ 20 mM, NaCl 50 mM, EDTA 1 mM, pH 7.4), in the presence or absence of increasing concentrations of test compounds. After incubation for 2 hours, the fluorescence polarisation is measured.

Method B:

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of $2.50 \times 10^{-8}$ M, is mixed with a fluorescent peptide (Fluorescein-REIGAQLRRMADDLNAQY), at a final concentration of $1.00 \times 10^{-8}$ M in a buffer solution (Hepes 10 mM, NaCl 150 mM, Tween20 0.05%, pH 7.4), in the presence or absence of increasing concentrations of test compounds. After incubation for 2 hours, the fluorescence polarisation is measured.

The results are expressed in $IC_{50}$ (the concentration of compound that inhibits fluorescence polarisation by 50%) and are presented in Table 1 below. The $IC_{50}$s of Bcl-2 inhibition obtained using method B are underlined.

The results show that the compounds of the invention inhibit interaction between the Bcl-2 protein and the fluorescent peptide described hereinbefore.

Example B: In Vitro Cytotoxicity

The cytotoxicity studies were carried out on the RS4;11 leukaemia tumour line.

The cells are distributed onto microplates and exposed to the test compounds for 48 hours. The cell viability is then quantified by a colorimetric assay, the Microculture Tetrazolium Assay (*Cancer Res.*, 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Bcl-2 inhibition (fluorescence polarisation test) and of cytotoxicity for RS4; 11 cells

| | $IC_{50}$ (nM) Bcl-2 FP | $IC_{50}$ (nM) MTT RS4; 11 |
|---|---|---|
| Example 5 | 212.7 | 2590 |
| Example 6 | 50.5 | 915 |
| Example 10 | 145.8 | 2220 |
| Example 12 | 120.4 | 1810 |
| Example 13 | 16.2 | 462.0 |
| Example 14 | 24.8 | 1270.0 |
| Example 15 | 22.1 | 759.0 |
| Example 16 | 29.6 | 656.0 |
| Example 17 | 11.4 | 1010.0 |
| Example 18 | 44.6 | 1130.0 |
| Example 19 | 245.0 | 2360 |
| Example 20 | 74.3 | 900.0 |
| Example 21 | 24.6 | 256 |
| Example 22 | 10.7 | 142.0 |
| Example 23 | 26.1 | 445.0 |
| Example 24 | 15.6 | 140.0 |
| Example 25 | 87.6 | 1100.0 |
| Example 26 | 7.5 | 171.0 |
| Example 27 | 20.5 | 479.0 |
| Example 28 | 8.0 | 378.0 |
| Example 29 | 44.6 | 1010.0 |
| Example 31 | 5.5 | 71.4 |
| Example 32 | 3.5 | 63.7 |
| Example 33 | 4.4 | 199.0 |
| Example 34 | 7.7 | 133.0 |
| Example 35 | 3.5 | 68.9 |
| Example 36 | 1110.5 | 2420.0 |
| Example 37 | 3.8 | 47.1 |
| Example 38 | 238.2 | 1780.0 |
| Example 39 | 12.5 | 263.0 |
| Example 40 | 7.8 | 167.0 |
| Example 41 | 3.7 | 52.2 |
| Example 42 | 23.1 | 353.0 |
| Example 43 | 7.2 | 101.0 |
| Example 44 | 6.8 | 164.0 |
| Example 45 | 6.7 | 36.5 |
| Example 46 | 8.4 | 93.4 |
| Example 47 | 9.2 | 50.3 |
| Example 48 | 10.5 | 93.9 |
| Example 49 | 13.1 | 136.0 |
| Example 50 | 7.4 | 301.0 |
| Example 51 | 6.9 | 155.0 |
| Example 52 | 5.4 | 77.3 |
| Example 53 | 9.0 | 207.0 |
| Example 54 | <u>20</u> | 103 |
| Example 55 | 57.2 | 1020.0 |
| Example 56 | 5.0 | 135.0 |
| Example 57 | 13.4 | 267.0 |
| Example 58 | 20.5 | 190.0 |
| Example 59 | 19.2 | 206.0 |
| Example 60 | 206.4 | 89.5 |
| Example 61 | 7.7 | 204.0 |
| Example 62 | 7.5 | 205.0 |
| Example 63 | 168.3 | 1510.0 |
| Example 64 | 295.6 | 1360.0 |
| Example 65 | 5.1 | 130.0 |
| Example 66 | 6.6 | 148.0 |
| Example 67 | 5.9 | 101.0 |
| Example 68 | 79.7 | 856.0 |
| Example 69 | 9.0 | 67.6 |
| Example 70 | 2.9 | 63.8 |
| Example 71 | 8.3 | 196.0 |
| Example 72 | 4.5 | 43.4 |
| Example 73 | 3.9 | 51.4 |
| Example 74 | 4.2 | 162.0 |
| Example 75 | 7.1 | 184.0 |
| Example 76 | 8.7 | 151.0 |
| Example 77 | 4.9 | 207.0 |
| Example 78 | 3.7 | 81.4 |
| Example 79 | 85.5 | 344.0 |
| Example 80 | 6.8 | 120.0 |
| Example 81 | 83.8 | 652.0 |
| Example 82 | 17.6 | 373.0 |
| Example 83 | 3.7 | 350.0 |
| Example 84 | 6.7 | 146.0 |
| Example 85 | 3.7 | 129.0 |
| Example 86 | 5.4 | 67.7 |
| Example 87 | 4.4 | 138.0 |
| Example 88 | 19.6 | 541.0 |
| Example 89 | 4.2 | 59.8 |
| Example 90 | 3.6 | 76.6 |
| Example 91 | 5.3 | 172.0 |
| Example 92 | 9.6 | 202.0 |
| Example 93 | 3.3 | 75.4 |
| Example 94 | 7.9 | 118.0 |
| Example 95 | 6.4 | 264.0 |

TABLE 1-continued

IC$_{50}$ of Bcl-2 inhibition (fluorescence polarisation test) and of cytotoxicity for RS4; 11 cells

| | IC$_{50}$ (nM) Bcl-2 FP | IC$_{50}$ (nM) MTT RS4; 11 |
|---|---|---|
| Example 96 | 3.9 | 157.0 |
| Example 97 | 6.1 | 73.2 |
| Example 98 | 45.1% @10 μM | 1880.0 |
| Example 99 | 4.8 | 41.7 |
| Example 100 | 6.9 | 43.4 |
| Example 101 | 99.1 | 1880.0 |
| Example 102 | 8.4 | 108.0 |
| Example 103 | 17.4 | 523.0 |
| Example 104 | 18.8 | 383.0 |
| Example 105 | 13.6 | 202.0 |
| Example 106 | 19.6 | 521.0 |
| Example 107 | 44.0 | 150.0 |
| Example 108 | 35.5 | 544.0 |
| Example 109 | 4.4 | 116.0 |
| Example 110 | 8.1 | 291.0 |
| Example 112 | 11.8 | 281.0 |
| Example 113 | 19.2 | 203.0 |
| Example 114 | 23.7 | 726.0 |
| Example 115 | 14.5 | 272.0 |
| Example 116 | 12.1 | 131.0 |
| Example 117 | 7.6 | 193.0 |
| Example 118 | 5.9 | 114.0 |
| Example 119 | 28.4 | 96.4 |
| Example 120 | _15_ | 367.0 |
| Example 121 | 447.5 | 8770 |
| Example 122 | 53.3 | 2290 |
| Example 123 | 90 | 2370 |
| Example 131 | 18.9 | 469 |
| Example 132 | 31.7 | 1860 |
| Example 133 | 841.4 | ND |
| Example 134 | 72.1% @22.2 μM | 2100 |
| Example 135 | 10.4 | 461 |
| Example 138 | 52.2 | 2020 |
| Example 140 | 25.0 | 1840 |
| Example 141 | 56.7 | 2280 |
| Example 142 | 70.6 | 2290 |
| Example 143 | 71.5 | 533 |
| Example 144 | 35.0 | 1380 |
| Example 145 | 12.2 | 1180 |
| Example 146 | 17.2 | 346 |
| Example 147 | 22.5 | 966 |
| Example 148 | 28.3 | 1170 |
| Example 149 | 21.6 | 340 |
| Example 150 | 51.0 | 1320 |
| Example 152 | 217.5 | 2160 |
| Example 153 | 285.8 | 237 |
| Example 155 | 13.2 | 246 |
| Example 156 | 11.7 | 450 |
| Example 157 | 16.1 | 487 |
| Example 158 | 54.1 | 834 |
| Example 159 | 10.2 | 191 |
| Example 163 | 22.8 | 292 |
| Example 164 | 7.8 | 132 |
| Example 165 | 3.2 | 179 |
| Example 167 | 37.4 | 984 |
| Example 168 | 11.4 | 188 |
| Example 169 | 107.9 | 854 |
| Example 170 | 16.8 | 177 |
| Example 171 | 71.8 | 1050 |
| Example 172 | 4.2 | 1200 |
| Example 173 | 167.9 | 2040 |
| Example 174 | 41.2 | 402 |
| Example 175 | 25.1 | 460 |
| Example 176 | 6.2 | 225 |
| Example 177 | 18.8 | 568 |
| Example 178 | 17.5 | 812 |
| Example 179 | 18.1 | 886 |
| Example 180 | 11.0 | 210 |
| Example 181 | 6.9 | 205 |
| Example 182 | 110.7 | 1850 |
| Example 183 | 8.3 | ND |
| Example 184 | 14.1 | 154 |
| Example 185 | 17.3 | 422 |
| Example 186 | 23.5 | 626 |
| Example 187 | 21.6 | 1990 |
| Example 188 | 16.8 | 68 |
| Example 190 | 13.6 | 645 |
| Example 193 | 5.6 | 499 |
| Example 194 | 6.7 | 534 |
| Example 195 | 31.1 | 507 |
| Example 197 | 9.8 | 328 |
| Example 198 | 3.4 | 616 |
| Example 199 | 57.7 | 2360 |
| Example 200 | 154.8 | 2080 |
| Example 201 | 3.1 | 124 |
| Example 202 | 4.4 | 798 |
| Example 203 | 10.0 | 454 |
| Example 204 | 4.7 | 780 |
| Example 205 | 4.3 | 123 |
| Example 206 | _16.7_ | 72.4 |
| Example 207 | _20.3_ | 22.2 |
| Example 209 | _4.1_ | 62.9 |
| Example 210 | _3.1_ | 64.7 |
| Example 211 | _3.7_ | 46.9 |

Note:
The IC$_{50}$s of Bcl-2 inhibition obtained using method B are underlined.
ND: not determined For partial inhibitors, the percentage fluorescence polarisation inhibition for a given concentration of the test compound is indicated. Accordingly, 45.1% @10 μM means that 45.1% fluorescence polarisation inhibition is observed for a concentration of test compound equal to 10 μM.

Example C: Induction of Caspase Activity In Vivo

The ability of the compounds of the invention to activate caspase 3 is evaluated in a xenograft model of RS4;11 leukaemia cells.

$1\times10^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities: the activity for the treated mice divided by the activity for the control mice.

The results show that the compounds of the invention are capable of inducing apoptosis in RS4;11 tumour cells in vivo.

Example D: Quantification of the Cleaved Form of Caspase 3 In Vivo

The ability of the compounds of the invention to activate caspase 3 is evaluated in a xenograft model of RS4;11 leukaemia cells.

$1\times10^7$ RS4;11 cells are grafted sub-cutaneously into immunosuppressed mice (SCID strain). 25 to 30 days after the graft, the animals are treated orally with the various compounds. After treatment, the tumour masses are recovered (after a time period T) and lysed, and the cleaved (activated) form of caspase 3 is quantified in the tumour lysates.

This quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of the invention are capable of inducing apoptosis in RS4;11 tumour cells in vivo.

TABLE 2

Caspase activation factors (cleaved caspase 3 MSD test in the tumours of treated mice versus control mice) in vivo, after treatment by the oral route (exact doses in brackets)

| Compound tested | Time period after which the tumour is removed (T) | Activation factor ± SEM (versus control) |
|---|---|---|
| Example 184 | 16 h | 15.1 (100 mg/kg) |
| Example 207 | 2 h | 14.6 ± 4.4 (25 mg/kg) |
| Example 210 | 2 h | 36.3 ± 13.3 (125 mg/kg) |
| Example 211 | 2 h | 94.7 ± 9.8 (25 mg/kg) |

Example E: Anti-Tumour Activity In Vivo

The anti-tumour activity of the compounds of the invention is evaluated in a xenograft model of RS4;11 leukaemia cells.

$1 \times 10^7$ RS4;11 cells are grafted sub-cutaneously into immunosuppressed mice (SCID strain). 25 to 30 days after the graft, when the tumour mass has reached about 150 mm$^3$, the mice are treated orally with the various compounds in two different regimes (daily treatment for five days per week for two weeks, or two treatments weekly for two weeks). The tumour mass is measured twice weekly from the start of treatment.

The results obtained accordingly show that the compounds of the invention are capable of inducing significant tumour regression during the treatment period.

Example F: Pharmaceutical Composition: Tablets

| 1000 tablets containing a dose of 5 mg of a compound selected from Examples 1 to 211 | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A method of treating leukemia in a subject in need thereof, comprising administration of a compound of formula (I):

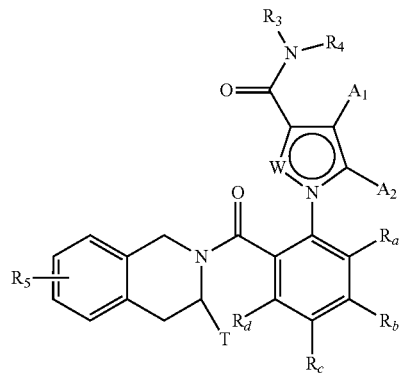

wherein:
W represents a group C-$A_3$ or a nitrogen atom;
$A_1$, $A_2$ and $A_3$ each independently of the others, represent a hydrogen or halogen atom, a linear or branched polyhalo-($C_1$-$C_6$)alkyl, a linear or branched ($C_1$-$C_6$)alkyl group or a cycloalkyl, or $A_1$ and $A_2$, together with the carbon atoms carrying them, form a cycloalkyl or a benzo ring, these two groups being optionally substituted by a halogen atom, a linear or branched ($C_1$-$C_6$)alkyl group, a linear or branched polyhalo-($C_1$-$C_6$)alkyl group, a hydroxy group, a linear or branched ($C_1$-$C_6$)alkoxy group or —COOH, with the proviso that W represents a group C-$A_3$ when $A_1$ and $A_2$ independently of one another represent a hydrogen or halogen atom, a linear or branched polyhalo-($C_1$-$C_6$)alkyl, a linear or branched ($C_1$-$C_6$)alkyl group or a cycloalkyl;
T represents a hydrogen atom, a linear or branched ($C_1$-$C_6$)alkyl group optionally substituted by one to three halogen atoms, a group ($C_1$-$C_4$)alkyl-$NR_1R_2$, or a group ($C_1$-$C_4$)alkyl-$OR_6$;
$R_1$ and $R_2$ independently of one another represent a hydrogen atom or a linear or branched ($C_1$-$C_6$)alkyl group,
or $R_1$ and $R_2$ form with the nitrogen atom carrying them a heterocycloalkyl;
$R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl moiety is linear or branched, a heterocycloalkyl group, an aryl group or a heteroaryl group, wherein one or more carbon atoms of the preceding groups, or carbon atoms of their possible substituents, may be deuterated;
$R_4$ represents an aryl group, a heteroaryl group, a cycloalkyl group or a linear or branched ($C_1$-$C_6$) alkyl group, wherein one or more carbon atoms of the preceding groups, or carbon atoms of their possible substituents, may be deuterated;
$R_5$ represents a hydrogen or halogen atom, a linear or branched ($C_1$-$C_6$)alkyl group, or a linear or branched ($C_1$-$C_6$)alkoxy group;
$R_6$ represents a hydrogen atom or a linear or branched ($C_1$-$C_6$)alkyl group;
$R_a$, $R_b$, $R_c$ and $R_d$, each independently of the others, represent a hydrogen, a linear or branched ($C_1$-$C_6$) alkyl group, a linear or branched ($C_2$-$C_6$)alkenyl group, a linear or branched ($C_2$-$C_6$)alkynyl group, an aryl group, a heteroaryl group, a halogen atom, a linear or branched $(C_1-C_6)$alkoxy group, a hydroxy group, a linear or branched polyhalo-$(C_1-C_6)$alkyl group, a trifluoromethoxy group, $-NR_7R_7'$, nitro, $R_7-CO-(C_0-C_6)$alkyl-, $R_7-CO-NH-(C_0-C_6)$alkyl-, $NR_7R_7'-CO-(C_0-C_6)$alkyl-, $NR_7R_7'-CO-$ alkyl$(C_0-C_6)-O-$, $R_7-NH-CO-NH-(C_0-C_6)$alkyl-, $R_7-O-CO-NH-(C_0-C_6)$alkyl-, a heterocycloalkyl group, or the substituents of one of the pairs $(R_a,R_b)$, $(R_b,R_c)$ or $(R_c,R_d)$ form together with the carbon atoms carrying them a ring composed of from 5 to 7 ring members, optionally having one to 2 hetero atoms selected from the group consisting of oxygen and sulphur, wherein one or more carbon atoms of the ring defined hereinbefore may be deuterated oar substituted by from one to 3 groups selected from the group consisting of halogen and linear or branched $(C_1-C_6)$alkyl, $R_7$ and $R_7'$, each independently of the other, represent a hydrogen, a linear or branched $(C_1-C_6)$alkyl group, a linear or branched $(C_2-C_6)$alkenyl group, a linear or branched $(C_2-C_6)$alkynyl group, an aryl group or a heteroaryl group, or $R_7$ and $R_7'$ form together with the nitrogen atom carrying them a heterocycle composed of from 5 to 7 ring members;

wherein when the compound of formula (I) contains a hydroxyl group, the latter may be optionally substituted by one of the following groups: $-PO(OM)(OM')$, $-PO(OM)(O^-M_1^+)$, $-PO(O^-M_1^+)(O^-M_2^+)$, $-PO(O^-)(O^-)M_3^{2+}$, $-PO(OM)(O[CH_2CH_2O]_nCH_3)$, or $-PO(O^-M_1^+)(O[CH_2CH_2O]_nCH_3)$, wherein M and M' independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl or a heterocycloalkyl, both composed of from 5 to 6 ring members, while $M_1^+$ and $M_2^+$ independently of one another represent a pharmaceutically acceptable monovalent cation, $M_3^{2+}$ represents a pharmaceutically acceptable divalent cation, and n is an integer from 1 to 5;

wherein

"aryl" means a phenyl, naphthyl, biphenyl or indenyl group,

"heteroaryl" means any mono- or bi-cyclic group composed of from 5 to 10 ring members, having at least one aromatic moiety and from 1 to 4 hetero atoms selected from the group consisting of oxygen, sulphur and nitrogen, "cycloalkyl" means any mono- or bi-cyclic, non-aromatic, carbocyclic group having from 3 to 10 ring members, "heterocycloalkyl" means any mono- or bi-cyclic, non-aromatic group composed of from 3 to 10 ring members and having from 1 to 3 hetero atoms selected from the group consisting of oxygen, sulphur, SO, $SO_2$ and nitrogen;

wherein the aryl, heteroaryl, cycloalkyl and heterocycloalkyl groups defined above and the alkyl, alkenyl, alkynyl and alkoxy groups may be optionally substituted by 1 to 3 groups selected from the group consisting of optionally substituted, linear or branched $(C_1-C_6)$alkyl, $(C_3-C_6)$spiro, optionally substituted linear or branched $(C_1-C_6)$alkoxy, $(C_1-C_6)$alkyl-S—, hydroxy, oxo (or N-oxide where appropriate), nitro, cyano, $-COOR'$, $-OCOR'$, $NR'R''$, linear or branched polyhalo-$(C_1-C_6)$alkyl, trifluoromethoxy, $(C_1-C_6)$alkylsulphonyl, halogen, optionally substituted aryl, heteroaryl, aryloxy, arylthio, cycloalkyl, heterocycloalkyl optionally substituted by one or more halogen atoms or alkyl groups, wherein R' and R", each independently of the other, represent a hydrogen atom or an optionally substituted, linear or branched $(C_1-C_6)$alkyl group, its enantiomers and diastereoisomers, and addition salts thereof with a pharmaceutically acceptable acid or base, alone or in combination with one or more pharmaceutically acceptable excipients.

2. The method according to claim 1, wherein $R_4$ represents a phenyl substituted in the para-position by a group of the formula $-OPO(OM)(OM')$, $-OPO(OM)(O^-M_1^+)$, $-OPO(O^-M_1^+)(O^-M_2^+)$, $-OPO(O^-)(O^-)M_3^{2+}$, $-OPO(OM)(O[CH_2CH_2O]_nCH_3)$, or $-OPO(O^-M_1^+)(O[CH_2CH_2O]_nCH_3)$, wherein M and M' independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl or a heterocycloalkyl, both composed of from 5 to 6 ring members, while $M_1^+$ and $M_2^+$ independently of one another represent a pharmaceutically acceptable monovalent cation, $M_3^{2+}$ represents a pharmaceutically acceptable divalent cation, and n is an integer from 1 to 5, wherein the phenyl group may be optionally substituted by one or more halogen atoms.

3. The method according to claim 1, wherein W represents a group C—H, and $A_1$ and $A_2$ represent a hydrogen atom and a methyl group, respectively.

4. The method according to claim 1, wherein W represents a group C—H, and $A_1$ and $A_2$, together with the carbon atoms carrying them, form a cyclohexenyl or a benzo ring optionally substituted by a halogen atom.

5. The method according to claim 1, wherein W represents a nitrogen atom, and $A_1$ and $A_2$, together with the carbon atoms carrying them, form a benzo ring.

6. The method according to claim 1, wherein T represents a group selected from the group consisting of methyl, aminomethyl, dimethylaminomethyl, morpholinylmethyl, (4-methyl-1-piperazinyl)methyl, (3aR,6aS)-hexahydrocyclopenta[c]pyrrol-2(1H)-ylmethyl, (4,4-difluoropiperidin-1-yl)methyl, (4-cyclopentyl-piperazin-1-yl)methyl, (4-cyclobutylpiperazin-1-yl)methyl, pyrrolidin-1-ylmethyl, piperidin-1-ylmethyl and 2-(morpholin-4-yl)ethyl.

7. The method according to claim 1, wherein $R_a$, $R_b$, $R_c$ and $R_d$, each independently of the others, represent a hydrogen, a linear or branched $(C_1-C_6)$alkyl group, a linear or branched $(C_2-C_6)$alkenyl group, a linear or branched $(C_2-C_6)$alkynyl group, an aryl group, a heteroaryl group, a halogen atom, a linear or branched $(C_1-C_6)$alkoxy group, a hydroxy group, a linear or branched polyhalo-$(C_1-C_6)$alkyl group, a trifluoromethoxy group, $-NR_7R_7'$, nitro, or the substituents of one of the pairs $(R_a,R_b)$, $(R_b,R_c)$ or $(R_c,R_d)$ form together with the carbon atoms carrying them a ring composed of from 5 to 7 ring members, optionally having one to 2 hetero atoms selected from the group consisting of oxygen and sulphur, wherein one or more carbon atoms of the ring defined hereinbefore may be deuterated or substituted by from one to 3 groups selected from the group consisting of halogen and linear or branched $(C_1-C_6)$alkyl.

8. The method according to claim 7, wherein $R_a$ and $R_d$ each represent a hydrogen atom and $(R_b,R_c)$, together with the carbon atoms carrying them, form one of the following groups: optionally substituted 1,3-dioxolane; optionally substituted 1,4-dioxane; cyclopentane; tetrahydrofuran; 2,3-dihydrofuran; or $R_a$, $R_c$ and $R_d$ each represent a hydrogen atom and $R_b$ represents a hydroxy group, a methoxy group, a halogen atom, a trifluoromethyl group or a trifluoromethoxy group.

9. The method according to claim 7, wherein one to two of the groups $R_a$, $R_b$, $R_c$, $R_d$ represent a halogen atom, while the others represent a hydrogen.

10. The method according to claim 1, wherein: $R_a$ and $R_d$ each represent a hydrogen atom; $R_b$ represents hydrogen, halogen, hydroxy or methoxy; and $R_c$ represents hydroxy, methoxy, amino, 3-phenoxyazetidine, 2-(phenylsulphanyl) acetamide or 2-(phenoxy)acetamide.

11. The method according to claim 1, wherein $R_4$ represents a butyl, phenyl, 4-hydroxyphenyl, 4-methoxyphenyl, 4-methylphenyl, 3-chloro-4-hydroxyphenyl or 3-fluoro-4-hydroxyphenyl group.

12. The method according to claim 1, wherein $R_3$ represents an aryl or heteroaryl group.

13. The method according to claim 1, wherein $R_3$ represents a group selected from the group consisting of phenyl, 1H-indole, benzothiophene, benzofuran, 2,3-dihydro-1H-indole, 1H-indazole, 2,3-dihydro-1H-isoindole, 1H-pyrrolo[2,3-b]pyridine, phenoxyphenyl, 2,3-dihydro-1H-pyrrolo[2,3-b]pyridine, and 1H-pyrrole, which groups may be optionally substituted by one or more substituents selected from the group consisting of halogen, linear or branched $(C_1-C_6)$alkyl, trifluoromethoxy, 4-methylpiperazinyl, linear or branched $(C_1-C_6)$alkoxy, and cyano.

14. The method according to claim 1, wherein the compound of formula (I) is selected from the group consisting of:

N-(4-hydroxyphenyl)-1-{6-[(3S)-3-(morpholin-4-ylmethyl)-1,2,3,4-tetrahydroisoquinoline-2-carbonyl]-2H-1,3-benzodioxol-5-yl}-N-phenyl-1H-indole-3-carboxamide, N-(4-hydroxyphenyl)-N-(1-methyl-1H-pyrrolo[2,3-b]pyridin-5-yl)-1-(6-{[(3S)-3-(morpholin-4-ylmethyl)-3,4-dihydroisoquinolin-2(1H)-yl]carbonyl}-1,3-benzodioxol-5-yl)-4,5,6,7-tetrahydro-1H-indole-3-carboxamide, 1-(5-chloro-2-{[(3S)-3-(morpholin-4-ylmethyl)-3,4-dihydroisoquinolin-2(1H)-yl]carbonyl}phenyl)-N-(4-hydroxyphenyl)-4,5-dimethyl-N-(1-methyl-2,3-dihydro-1H-pyrrolo[2,3-b]pyridin-5-yl)-1H-pyrrole-3-carboxamide, 1-(5-chloro-2-{[3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-4,5-dimethyl-1H-pyrrole-3-carboxamide, N-(4-hydroxyphenyl)-N-(4-methylphenyl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide, N-(4-hydroxyphenyl)-N-(1H-indol-5-yl)-1-(6-{[(3 S)-3-[(4-methylpiperazin-1-yl)methyl]-3,4-dihydroisoquinolin-2(1H)-yl]carbonyl}-1,3-benzodioxol-5-yl)-1H-indole-3-carboxamide, N-(4-hydroxyphenyl)-N-(1-methyl-1H-indol-5-yl)-1-(6-{[(3S)-3-[(4-methylpiperazin-1-yl)methyl]-3,4-dihydroisoquinolin-2(1H)-yl]carbonyl}-1,3-benzodioxol-5-yl)-1H-indole-3-carboxamide, 1-(5-chloro-2-[(3S)-3-[(4-methylpiperazin-1-yl)methyl]-3,4-dihydroisoquinolin-2(1H)-yl]carbonyl}phenyl)-N-(4-chlorophenyl)-N-(4-hydroxyphenyl)-5-methyl-1H-pyrrole-3-carboxamide, 1-(5-chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1H-indole-3-carboxamide, N-(4-hydroxyphenyl)-1-{6-[(3S)-3[(4-methylpiperazin-1-yl)methyl]-1,2,3,4-tetrahydroisoquinoline-2-carbonyl]-2H-1,3-benzodioxol-5-yl}-N-phenyl-1H-indole-3-carboxamide, and enantiomers and diastereoisomers thereof, and addition salts thereof with a pharmaceutically acceptable acid or base.

15. The method according to claim 1, wherein the compound of formula (I) is administered as a pharmaceutical composition comprising the compound of formula (I) in combination with one or more pharmaceutically acceptable excipients.

16. The method according to claim 1, wherein the compound of formula (I) is administered in combination with an anti-cancer agent selected from the group consisting of genotoxic agents, mitotic poisons, anti-metabolites, proteasome inhibitors, kinase inhibitors and antibodies.

17. The method according to claim 1, wherein the compound of formula (I) is administered in combination with radiotherapy.

* * * * *

UNITED STATES PATENT AND TRADEMARK OFFICE
CERTIFICATE OF CORRECTION

PATENT NO. : 10,662,173 B2
APPLICATION NO. : 15/676154
DATED : May 26, 2020
INVENTOR(S) : Patrick Casara et al.

It is certified that error appears in the above-identified patent and that said Letters Patent is hereby corrected as shown below:

In the Claims

Column 123, Line 16: oar should read or.

Column 126, Line 17: 2-[(3S should read 2-{[(3S.
        Line 20: (35) should read (3S).

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*